(12) United States Patent
Fang et al.

(10) Patent No.: US 11,858,905 B1
(45) Date of Patent: Jan. 2, 2024

(54) CATHEPSIN L INHIBITORS

(71) Applicants: BIOFRONT THERAPEUTICS (BEIJING) CO., LTD., Beijing (CN); RK PHARMTECH (BEIJING) LTD., Beijing (CN)

(72) Inventors: Lichao Fang, Beijing (CN); Yayi Wang, Beijing (CN); Tianwei Ma, Beijing (CN); Ling Song, Beijing (CN); Zheng Huang, Beijing (CN); Jin-Kui Yang, Beijing (CN); Shuo Gu, Beijing (CN)

(73) Assignees: BIOFRONT THERAPEUTICS (BEIJING) CO., LTD., Beijing (CN); RK PHARMTECH (BEIJING) LTD., Beijing (CN)

( * ) Notice: Subject to any disclaimer, the term of this patent is extended or adjusted under 35 U.S.C. 154(b) by 0 days.

(21) Appl. No.: 18/194,609

(22) Filed: Mar. 31, 2023

Related U.S. Application Data

(60) Provisional application No. 63/478,502, filed on Jan. 5, 2023.

(51) Int. Cl.
| | | |
|---|---|---|
| *C07D 263/56* | (2006.01) |
| *C07D 413/12* | (2006.01) |
| *C07D 413/04* | (2006.01) |
| *C07D 231/56* | (2006.01) |
| *C07D 277/64* | (2006.01) |
| *A61P 31/14* | (2006.01) |
| *C07D 413/14* | (2006.01) |

(52) U.S. Cl.
CPC ............ *C07D 263/56* (2013.01); *A61P 31/14* (2018.01); *C07D 231/56* (2013.01); *C07D 277/64* (2013.01); *C07D 413/04* (2013.01); *C07D 413/12* (2013.01); *C07D 413/14* (2013.01)

(58) Field of Classification Search
CPC ...... C07D 263/56; C07D 231/56; A61P 31/14
See application file for complete search history.

(56) References Cited

U.S. PATENT DOCUMENTS

2022/0289732 A1* 9/2022 Fang ...................... A61P 35/00

* cited by examiner

*Primary Examiner* — Kamal A Saeed
(74) *Attorney, Agent, or Firm* — METIS IP LLC

(57) ABSTRACT

The present disclosure provides a plurality of the compounds. The compounds are capable of inhibiting Cathepsin L (CatL). A composition including at least one of these compounds is also provided. A method for treating or preventing one or more CatL-related diseases in a subject is further provided. The method may include administering the composition to the subject.

20 Claims, 38 Drawing Sheets
Specification includes a Sequence Listing.

CATHEPSIN L INHIBITORS

CROSS-REFERENCE TO RELATED APPLICATIONS

This application claims priority to Chinese Patent Application No. 202211702259.1 filed on Dec. 29, 2022, and U.S. Patent Application No. 63/478,502, filed on Jan. 5, 2023, the contents of each of which are incorporated herein by reference in their entirety.

SEQUENCE LISTING

The instant application contains a Sequence Listing which has been submitted electronically in XML format and is hereby incorporated by reference in its entirety. The XML file, created on Mar. 31, 2023, is named "Sequence list-20752-0002US00," and is 2,644 bytes in size.

TECHNICAL FIELD

The present disclosure generally relates to inhibitors of proteases, in particular, to inhibitors of Cathepsin L (CatL) and their pharmaceutical use for the treatment or prevention of CatL-related diseases.

BACKGROUND

Cathepsin is a protease with serine, cysteine, or aspartic acid residues as the nucleophiles, which is vital for digestion, coagulation, immune response, peptide synthesis, etc. There are generally three families of cathepsin: serine proteases (cathepsins A and G), aspartic proteases (cathepsin D and E), and eleven cysteine proteases (cathepsins B, C, F, H, K, L, O, S, V, X, and W). As a member of the cysteine protease family of cathepsin, CatL is involved in multiple physiological processes, including apoptosis, antigen processing, and extracellular matrix modeling. It is also implicated in pathological conditions, such as tumor invasion and metastasis, chronic inflammation, diabetes, cardiovascular disease, renal disease, bone disease, neurodegenerative diseases, as well as viral infection. Thus, it is desirable to develop novel CatL inhibitors for therapeutic uses in treating or preventing CatL-related diseases.

SUMMARY

According to an aspect of the present disclosure, a compound is provided. The compound may be represented by formula (I-a):

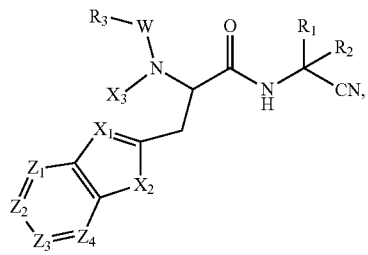

(I-a)

$R_1$ and $R_2$ may be independently selected from H, a —$CH_2$— group, and an alkyl group. $R_1$ and $R_2$ may be unconnected or connected via a single bond. W may be CO or $SO_2$. $R_3$ may be an alkyl group, a fluoroalkyl group, a cycloalkyl group, an alkoxy group, an aryl group, a heteroaryl group, or a heterocyclic group, and $R_3$ may be optionally substituted by one or more groups selected from halogen, a hydroxyl group, an alkyl group, a fluoroalkyl group, a cycloalkyl group, an aryl group, a heterocyclic group, and an alkoxy group. $X_1$ may be a CH group or N. $X_2$ may be O, S, or N—$R_4$, and $R_4$ may be selected from H, an alkyl group, an aryl group and a heterocyclic group. $X_3$ may be H, an alkyl group, a cycloalkyl group, an aryl group, a heteroaryl group, or a heterocyclic group, and $X_3$ may be optionally substituted by one or more groups selected from halogen, a hydroxyl group, an alkyl group, a fluoroalkyl group, a cycloalkyl group, and an alkoxy group. $Z_1$ may be a CH group, C—$R_5$, or N. $Z_2$ may be a CH group, C—$R_6$, or N. $Z_3$ may be a CH group, C—$R_7$, or N. $Z_4$ may be a CH group, C—$R_8$, or N. $R_5$-$R_8$ may be independently selected from H, halogen, a hydroxyl group, an alkyl group, a fluoroalkyl group, —CN, a cycloalkyl group, an alkoxy group, an aryl group, a heteroaryl group, and a heterocyclic group, and each of $R_5$-$R_8$ may be optionally substituted by one or more groups selected from halogen, a hydroxyl group, an alkyl group, a fluoroalkyl group, a cycloalkyl group, a heterocyclic group, a cycloalkyl group, an aryl group, and an alkoxy group.

According to another aspect of the present disclosure, a compound selected from Table 1 is provided. The Table 1 is shown in the "detailed description" section.

According to yet another aspect of the present disclosure, a method of treating a disease in a subject is provided. The method may include administering a composition to a subject suffering from the disease. The composition may include a compound represented by formula (I-a):

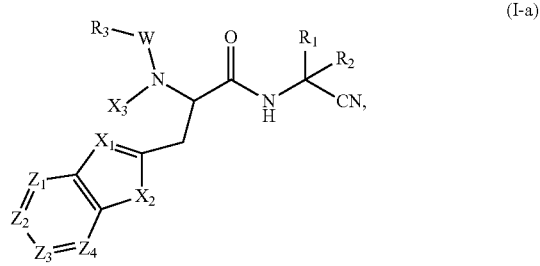

(I-a)

an isomer thereof, an enantiomer thereof, a diastereomer thereof, a racemate thereof, a solvate thereof, or a pharmaceutically acceptable salt thereof, in a pharmaceutically effective amount. $R_1$ and $R_2$ may be independently selected from H, a —$CH_2$— group, and an alkyl group. $R_1$ and $R_2$ may be unconnected or connected via a single bond. W may be CO or $SO_2$. $R_3$ may be an alkyl group, a fluoroalkyl group, a cycloalkyl group, an alkoxy group, an aryl group, a heteroaryl group, or a heterocyclic group, and $R_3$ may be optionally substituted by one or more groups selected from halogen, a hydroxyl group, an alkyl group, a fluoroalkyl group, a cycloalkyl group, an aryl group, a heterocyclic group, and an alkoxy group. $X_1$ may be a CH group or N. $X_2$ may be O, S, or N—$R_4$, and $R_4$ may be selected from H, an alkyl group, an aryl group and a heterocyclic group. $X_3$ may be H, an alkyl group, a cycloalkyl group, an aryl group, a heteroaryl group, or a heterocyclic group, and $X_3$ may be optionally substituted by one or more groups selected from halogen, a hydroxyl group, an alkyl group, a fluoroalkyl group, a cycloalkyl group, and an alkoxy group. $Z_1$ may be a CH group, C—$R_5$, or N. $Z_2$ may be a CH group, C—$R_6$, or N. $Z_3$ may be a CH group, C—$R_7$, or N. $Z_4$ may be a CH group, C—$R_8$, or N. $R_5$-$R_8$ may be independently selected from H, halogen, a hydroxyl group, an alkyl group, a fluoroalkyl group, —CN, a cycloalkyl group, an alkoxy group, an aryl group, a heteroaryl group, and a heterocyclic group, and each of $R_5$-$R_8$ may be optionally substituted by one or more groups selected from halogen, a hydroxyl group, an alkyl group, a fluoroalkyl group, a cycloalkyl group, a heterocyclic group, a cycloalkyl group, an aryl group, and an alkoxy group. The disease may include at least one of a severe acute respiratory syndrome (SARS), a coronavirus disease 19 (COVID-19), long-term effects of coronavirus (long COVID), post-acute sequelae of COVID-19 (PASC), respiratory syncytial virus (RSV) infection, ebola virus infection, middle east respiratory syndrome (MERS), herpes simplex virus infection, acute respiratory distress syndrome (ARDS), ARDS-induced multiple organ failures, acute kidney injury (AKI), liver injury, liver fibrosis, cancer, osteoporosis, inflammation, atherosclerosis, a renal disease, a bone disease, or diabetes.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein.

DETAILED DESCRIPTION

Figure 1:
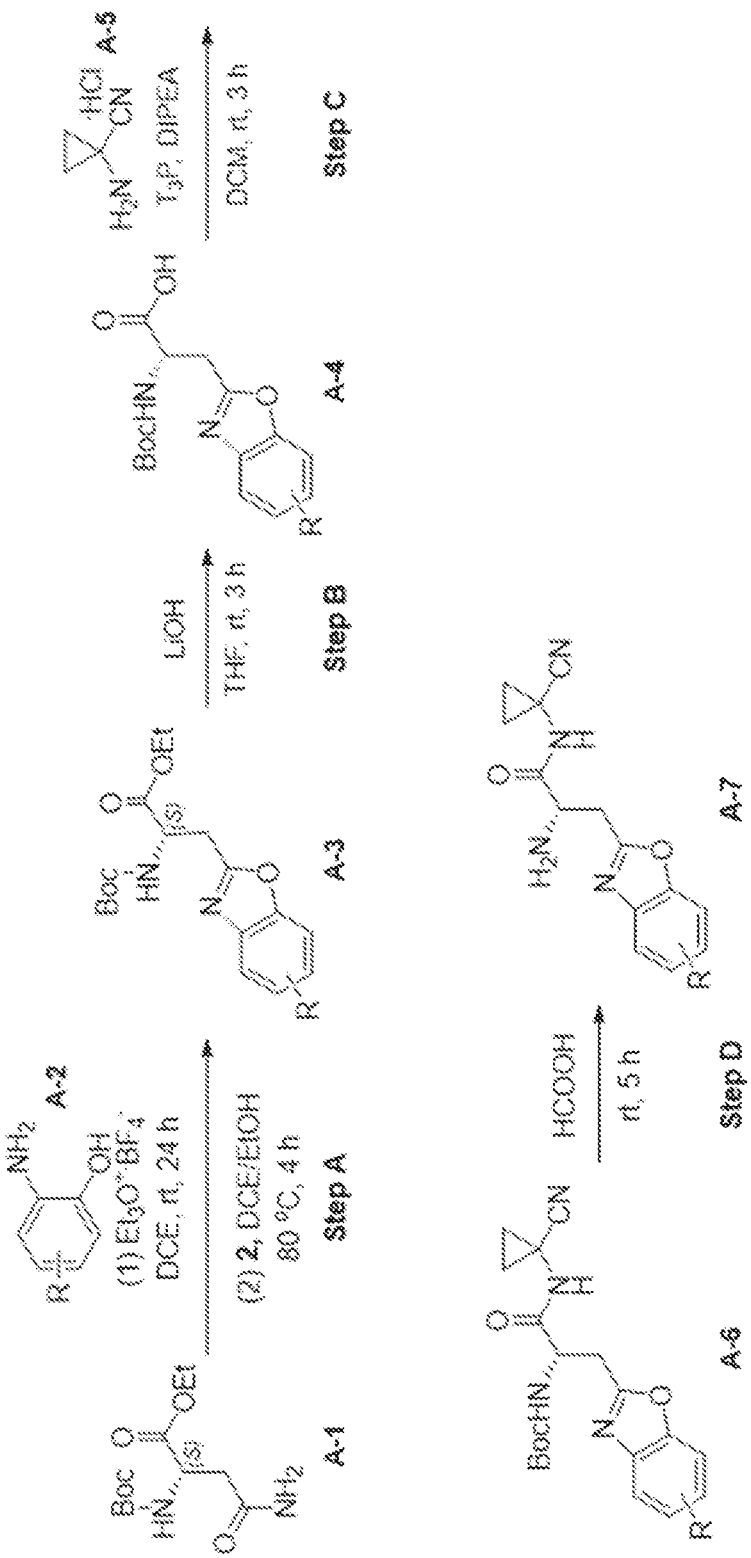
FIG. 1 is a schematic diagram illustrating an exemplary general procedure A for preparing a compound A-7 according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) is for the purpose of illustration and description only and are not intended to limit the scope of the present disclosure. It is understood that the drawings are not to scale.

According to an aspect of the present disclosure, a plurality of compounds are provided. The compounds are capable of inhibiting CatL and may be used for treating or preventing a CatL-related disease in a subject. As used herein, the term "inhibiting CatL" refers to decreasing the activity of CatL and/or the content of CatL in a local part (e.g., in vitro and/or in vivo). These compounds provided by the present disclosure are referred to as "Compounds" herein for convenience. In some embodiments, the Compounds may be represented by formula (I-a):

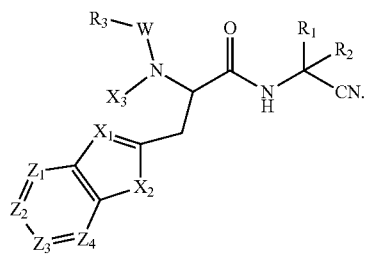

In some embodiments, in formula (I-a), W may be CO or $SO_2$. When W is CO, the Compounds may be represented by formula (I-b):

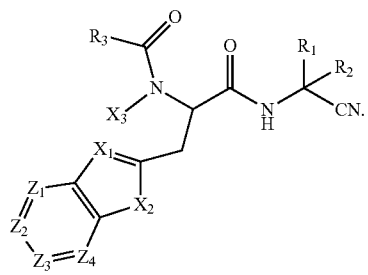

When W is $SO_2$, the Compounds may be represented by formula (I-c):

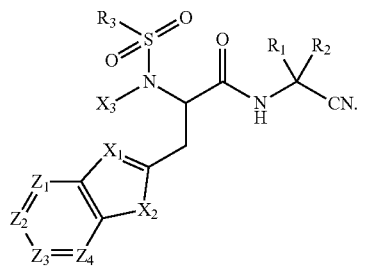

In some embodiments, $R_1$ and $R_2$ may be independently selected from H, a —$CH_2$-group, and an alkyl group. In some embodiments, $R_1$ and $R_2$ may be unconnected or connected via a single bond.

In some embodiments, $R_3$ may be an alkyl group, a fluoroalkyl group, a cycloalkyl group, an alkoxy group, an aryl group, a heteroaryl group, or a heterocyclic group, and $R_3$ may be optionally substituted by one or more groups selected from halogen, a hydroxyl group, an alkyl group, a fluoroalkyl group, a cycloalkyl group, an aryl group, a heterocyclic group, and an alkoxy group.

In some embodiments, X1 may be a CH group or N. In some embodiments, $X_2$ may be O, S, or N—$R_4$, and $R_4$ may be selected from H, an alkyl group, an aryl group, and a heterocyclic group.

In some embodiments, $X_3$ may be H, an alkyl group, a cycloalkyl group, an aryl group, a heteroaryl group, or a heterocyclic group, and $X_3$ may be optionally substituted by one or more groups selected from halogen, a hydroxyl group, an alkyl group, a fluoroalkyl group, a cycloalkyl group, and an alkoxy group.

In some embodiments, $Z_1$ may be a CH group, C—$R_5$, or N. In some embodiments, $Z_2$ may be a CH group, C—$R_6$, or N. In some embodiments, $Z_3$ may be a CH group, C—$R_7$, or N. In some embodiments, $Z_4$ may be a CH group, C—$R_8$, or N. In some embodiments, $R_5$-$R_8$ may be independently selected from H, halogen, a hydroxyl group, an alkyl group, a fluoroalkyl group, —CN, a cycloalkyl group, an alkoxy group, an aryl group, a heteroaryl group, and a heterocyclic group, and each of $R_5$-$R_8$ may be optionally substituted by one or more groups selected from halogen, a hydroxyl group, an alkyl group, a fluoroalkyl group, a cycloalkyl group, a heterocyclic group, a cycloalkyl group, an aryl group, and an alkoxy group.

In some embodiments, the Compounds may be represented by formula (II):

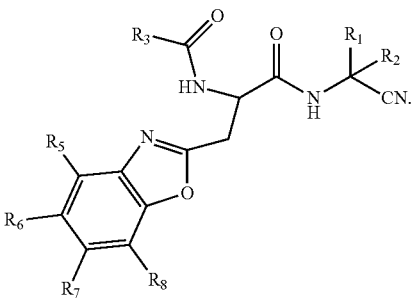

In some embodiments, the Compounds may be represented by formula (III):

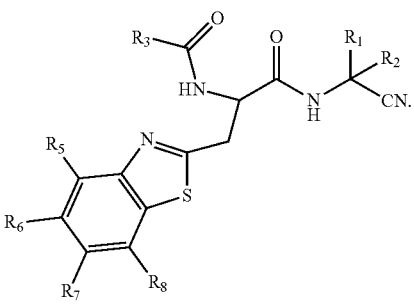

In some embodiments, the Compounds may be represented by formula (IV):

(IV)

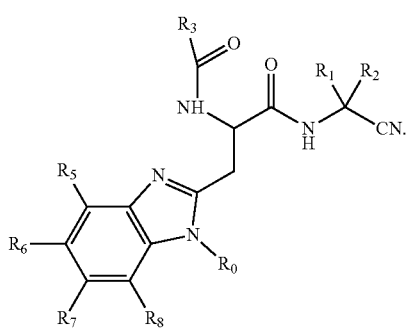

In some embodiments, R₀ may be H, an alkyl group, a cycloalkyl group, an aryl group, a heteroaryl group, or a heterocyclic group, and R₀ may be optionally substituted by one or more groups selected from halogen, a hydroxyl group, an alkyl group, a fluoroalkyl group, a cycloalkyl group, and an alkoxy group.

In some embodiments, the Compounds may be represented by formula (V):

(V)

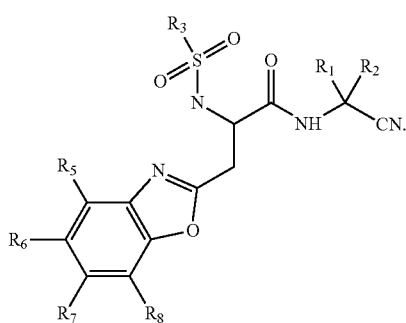

In some embodiments, at least one of R₅-R₈ is H. For example, R₅-R₈ are H.

In some embodiments, at least one of R₅-R₈ is halogen or —CN, and the other of R₅-R₈ are H.

In some embodiments, at least one of R₅-R₈ is a pyrazole group, which is optionally substituted by one or more groups selected from halogen, a hydroxyl group, an alkyl group, a fluoroalkyl group, a cycloalkyl group, an alkoxy group, an aryl group, a heteroaryl group, and a heterocyclic group, and the other of R₅-R₈ are H. For example, one of R₅-R₈ is a group represented by formula (VI-a):

(VI-a)

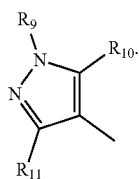

In some embodiments, R₉ may be H, an alkyl group, a cycloalkyl group, an aryl group, a heteroaryl group, or a heterocyclic group. In some embodiments, R₁₀ and R₁₁ may be independently selected from H, halogen, a hydroxyl group, an alkyl group, a fluoroalkyl group, a cycloalkyl group, an alkoxy group, an aryl group, a heteroaryl group, and a heterocyclic group. Formula (VI-a) may be connected with the benzoxazole group shown in formula (II), formula (III), formula (IV), or formula (V) at methyl. In such cases, the Compounds may be represented by, for example, formula (II-a), formula (II-b), formula (II-c), or formula (II-d):

(II-a)

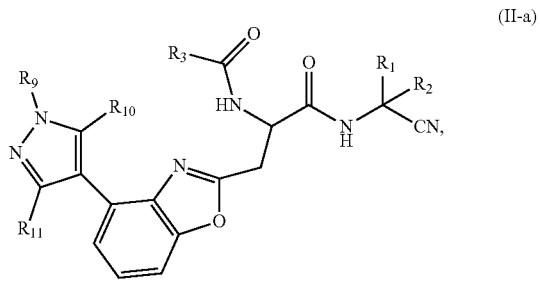

(II-b)

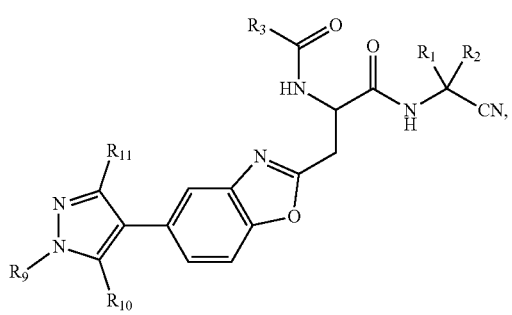

(II-c)

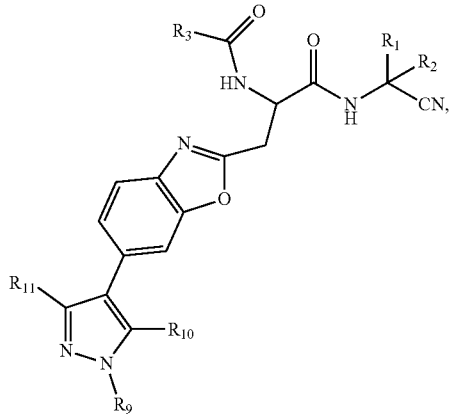

(II-d)

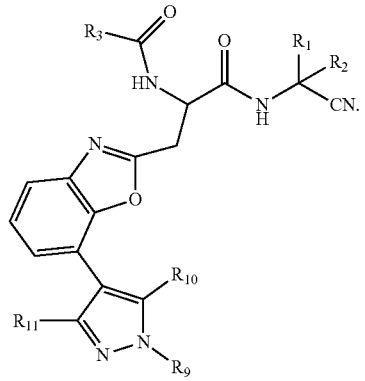

In some embodiments, R₅-R₁₀ are H, and the Compounds may be represented by, for example, formula (II-a1):

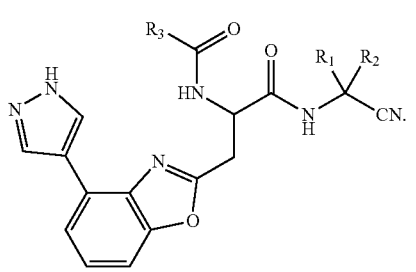
(II-a1)

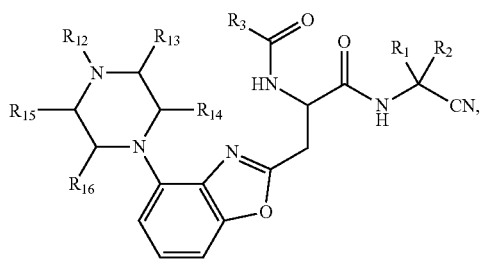
(II-e)

In some embodiments, at least one of $R_5$-$R_8$ is a cycloalkyl group or a heterocyclic group, which is optionally substituted by one or more groups selected from halogen, a hydroxyl group, an alkyl group, a fluoroalkyl group, a cycloalkyl group, an alkoxy group, an aryl group, a heteroaryl group, and a heterocyclic group, and the other of $R_5$-$R_8$ are H. For example, one of $R_5$-$R_8$ may be a group represented by formula (VI-b):

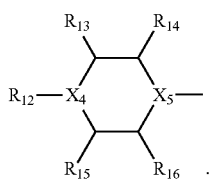
(VI-b)

In some embodiments, $X_4$ may be S, O, $SO_2$, N, C, or C-$L_1$. $L_1$ may be selected from H, halogen, a hydroxyl group, an alkyl group, a fluoroalkyl group, a cycloalkyl group, an alkoxy group, an aryl group, a heteroaryl group, and a heterocyclic group, and $L_1$ may be optionally substituted by one or more groups selected from halogen, a hydroxyl group, an alkyl group, a fluoroalkyl group, a cycloalkyl group, an aryl group, a heterocyclic group, and an alkoxy group. In some embodiments, $X_5$ may be N or C. In some embodiments, $R_{12}$ does not exist, or may be selected from H, halogen, a hydroxyl group, an alkyl group, a fluoroalkyl group, a cycloalkyl group, an alkoxy group, an aryl group, a heteroaryl group, and a heterocyclic group, and may be optionally substituted by one or more groups selected from halogen, a hydroxyl group, an alkyl group, a fluoroalkyl group, a cycloalkyl group, an aryl group, a heterocyclic group, and an alkoxy group. In some embodiments, $R_{13}$-$R_{16}$ may be independently selected from H, halogen, a hydroxyl group, an alkyl group, a fluoroalkyl group, a cycloalkyl group, an alkoxy group, an aryl group, a heteroaryl group, and a heterocyclic group, and each of $R_{13}$-$R_{16}$ may be optionally substituted by one or more groups selected from halogen, a hydroxyl group, an alkyl group, a fluoroalkyl group, a cycloalkyl group, an aryl group, a heterocyclic group, and an alkoxy group.

Formula (VI-b) may be connected with the benzoxazole group shown in formula (II), formula (III), formula (IV), or formula (V) at $X_5$. In some embodiments, X4 and X5 in Formula (VI-b) may be both N, and the Compounds may be represented by, for example, formula (II-e), formula (II-f), formula (II-g), or formula (II-h):

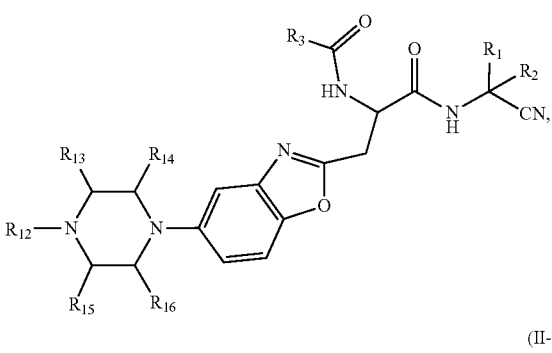
(II-f)

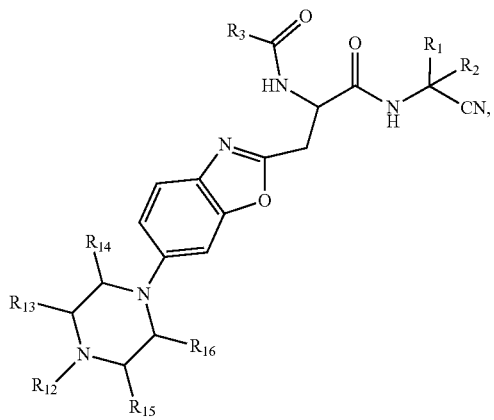
(II-g)

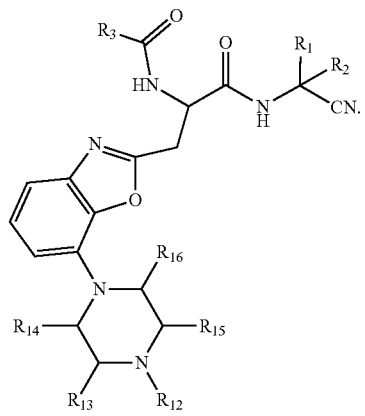
(II-h)

In some embodiments, in Formula (VI-b), X4 and X5 are both N, $R_{12}$ is a methyl group, and $R_{13}$-$R_{16}$ are H, in such cases, the Compounds may be represented by, for example, formula (II-g1):

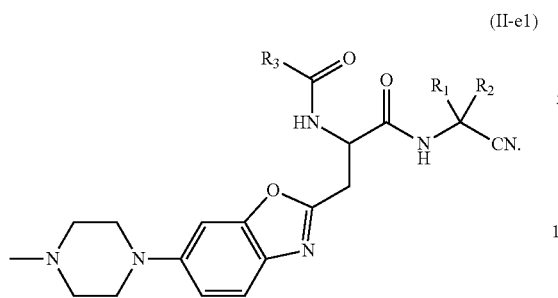
(II-e1)

As another example, one of $R_5$-$R_8$ may be a group represented by formula (VI-c):

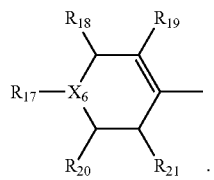
(VI-c)

In some embodiments, $X_6$ may be S, O, $SO_2$, N, C, or C-$L_2$. $L_2$ may be selected from H, halogen, a hydroxyl group, an alkyl group, a fluoroalkyl group, a cycloalkyl group, an alkoxy group, an aryl group, a heteroaryl group, and a heterocyclic group. $L_2$ may be optionally substituted by one or more groups selected from halogen, a hydroxyl group, an alkyl group, a fluoroalkyl group, a cycloalkyl group, an aryl group, a heterocyclic group, and an alkoxy group. In some embodiments, $R_{17}$ does not exist, or may be selected from H, halogen, a hydroxyl group, an alkyl group, a fluoroalkyl group, a cycloalkyl group, an alkoxy group, an aryl group, a heteroaryl group, and a heterocyclic group, and may be optionally substituted by one or more groups selected from halogen, a hydroxyl group, an alkyl group, a fluoroalkyl group, a cycloalkyl group, an aryl group, a heterocyclic group, and an alkoxy group. In some embodiments, $R_{18}$—$R_{21}$ may be independently selected from H, halogen, a hydroxyl group, an alkyl group, a fluoroalkyl group, a cycloalkyl group, an alkoxy group, an aryl group, a heteroaryl group, and a heterocyclic group, and each of $R_{18}$-$R_{21}$ may be optionally substituted by one or more groups selected from halogen, a hydroxyl group, an alkyl group, a fluoroalkyl group, a cycloalkyl group, an aryl group, a heterocyclic group, and an alkoxy group.

Formula (VI-c) may be connected with the benzoxazole group shown in formula (II), formula (III), formula (IV), or formula (V) at methyl. In some embodiments, $X_6$ in Formula (VI-c) may be N, and the Compounds may be represented by, for example, formula (II-i), (II-j), (II-k), or (II-l):

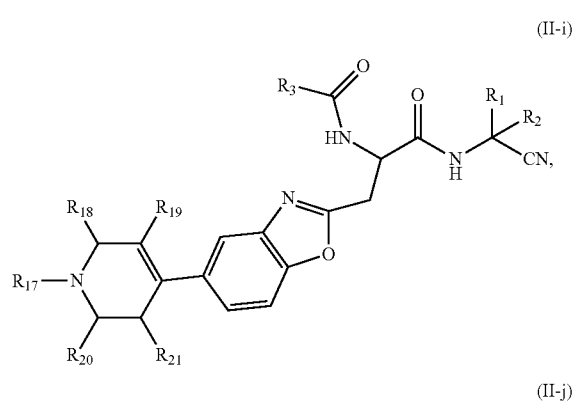
(II-i)

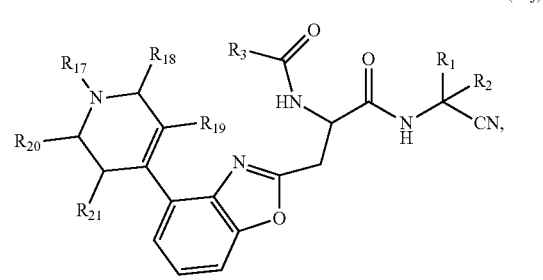
(II-j)

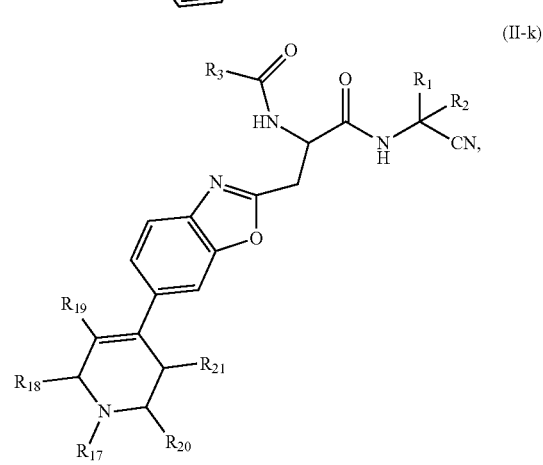
(II-k)

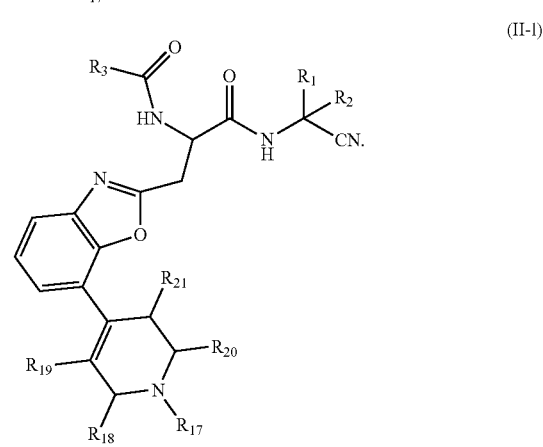
(II-l)

In some embodiments, in Formula (VI-c), $X_6$ is N, $R_{18}$-$R_{21}$ are H, and $R_{17}$ is a methyl group, —$CH_2$—$CHF_2$, or —$C_2H_4$—$OCH_3$, in such cases, the Compounds may be represented by, for example, formula (II-k1), formula (II-k2), and formula (II-k2),:

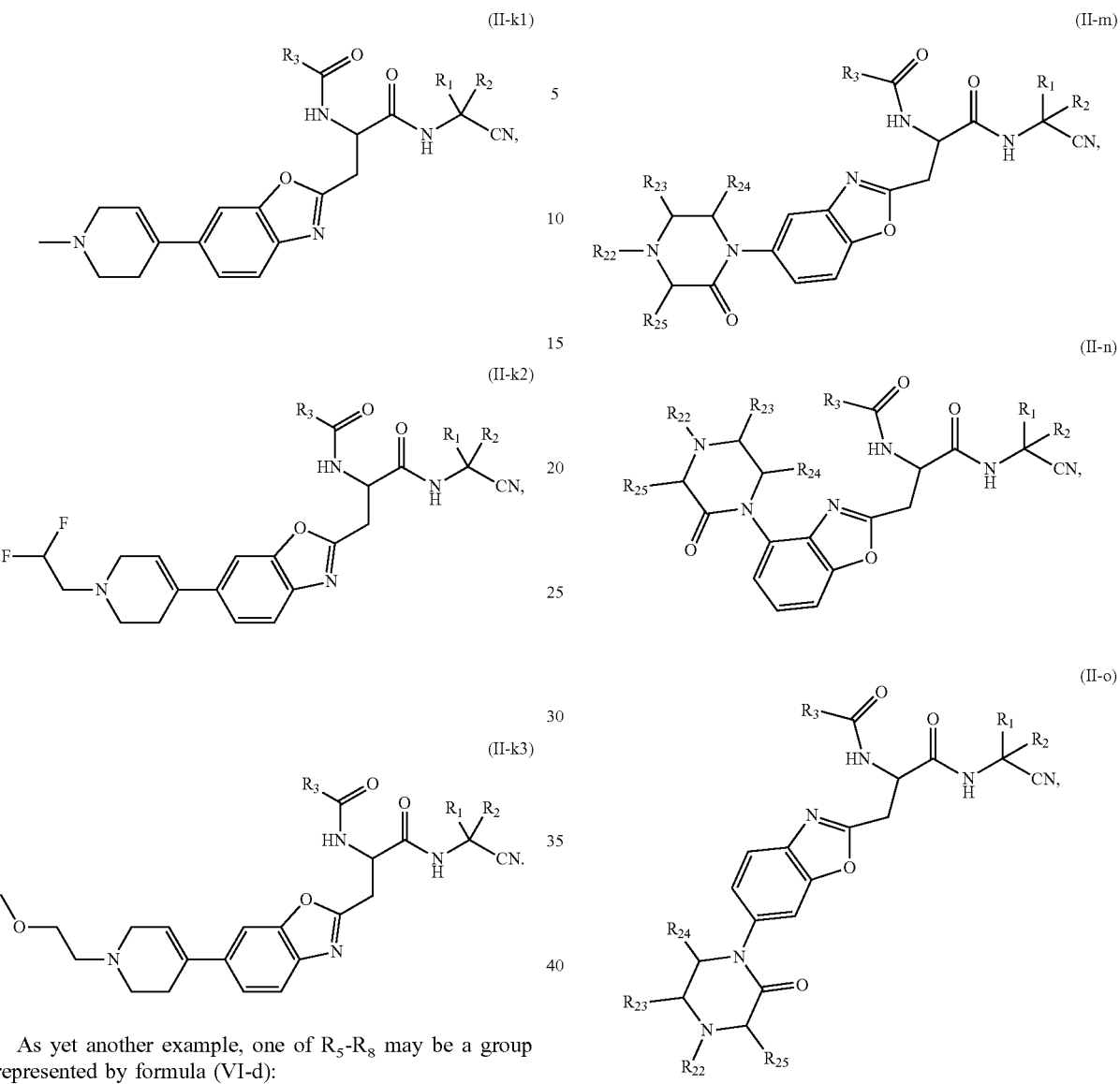

As yet another example, one of R₅-R₈ may be a group represented by formula (VI-d):

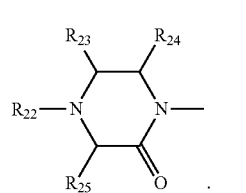

In some embodiments, $R_{22}$ may be H, an alkyl group, a cycloalkyl group, an aryl group, a heteroaryl group, or a heterocyclic group, and $R_{22}$ may be optionally substituted by one or more groups selected from halogen, a hydroxyl group, an alkyl group, a fluoroalkyl group, a cycloalkyl group, and an alkoxy group. In some embodiments, $R_{23}$-$R_{25}$ may be independently selected from H, halogen, a hydroxyl group, an alkyl group, a fluoroalkyl group, a cycloalkyl group, an alkoxy group, an aryl group, a heteroaryl group, and a heterocyclic group.

In such cases, the Compounds may be represented by, for example, formula (II-m), (II-n), (II-o), or (II-p):

In some embodiments, in Formula (VI-d), $R_{22}$ is a methyl group, and $R_{23}$—$R_{25}$ are H, in such cases, the Compounds may be represented by, for example, (11-01):

(II-o1)

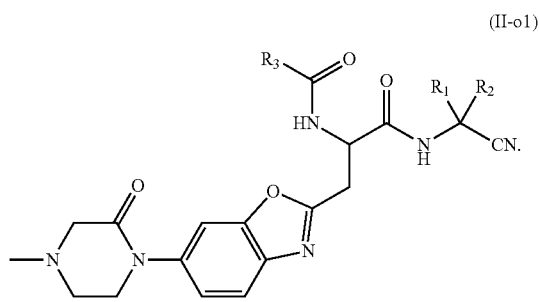

In some embodiments, at least one of $R_5$—$R_8$ is a heteroaryl group, which is optionally substituted by one or more groups selected from halogen, a hydroxyl group, an alkyl group, a fluoroalkyl group, a cycloalkyl group, an alkoxy group, an aryl group, a heteroaryl group, and a heterocyclic group, and the other of $R_5$-$R_8$ are H. For example, one of $R_5$—$R_8$ may be a group represented by formula (VI-e):

(VI-e)

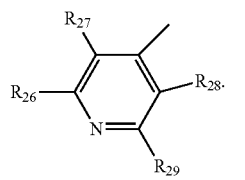

In some embodiments, $R_{26}$-$R_{29}$ may be independently selected from H, halogen, a hydroxyl group, an alkyl group, a fluoroalkyl group, a cycloalkyl group, an alkoxy group, an aryl group, a heteroaryl group, a heterocyclic group, and N—$R_{38}$, wherein $R_{38}$ may be selected from H, an alkyl group, an aryl group, a heterocyclic group, and a ketone group.

Formula (VI-e) may be connected with the benzoxazole group shown in formula (II), formula (III), formula (IV), or formula (V) at methyl. In such cases, the Compounds may be represented by, for example, formula (II-q), formula (II-r), formula (II-s), or formula (II-t):

(II-q)

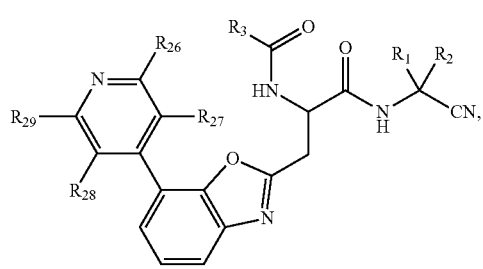

(II-r)

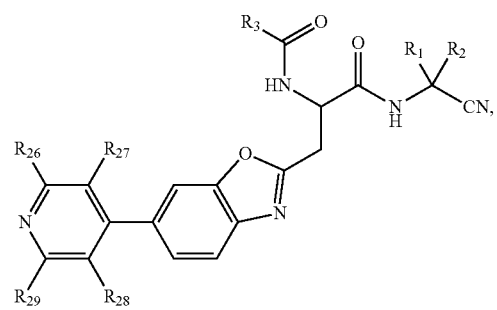

(II-s)

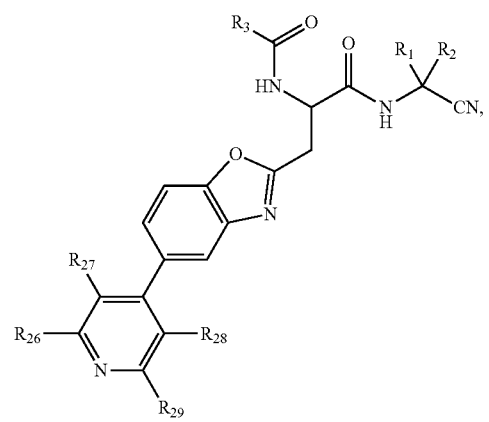

(II-t)

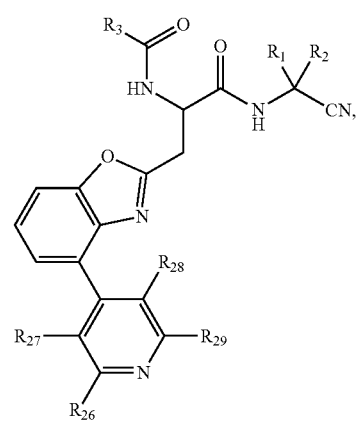

In some embodiments, in Formula (VI-e), $R_{27}$—$R_{29}$ are H, and $R_{26}$ is a methyl group, —$CHF_2$, or a cyclopropyl group, accordingly, the Compounds may be represented by, for example, formula (II-r1), formula (II-r2), and formula (II-r3):

(II-r1)

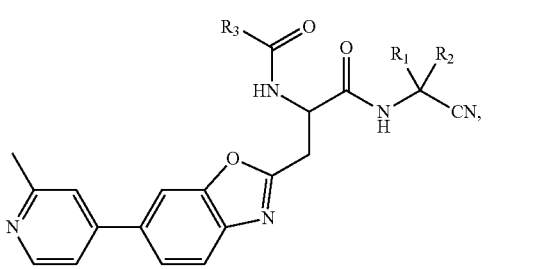

(II-r2)

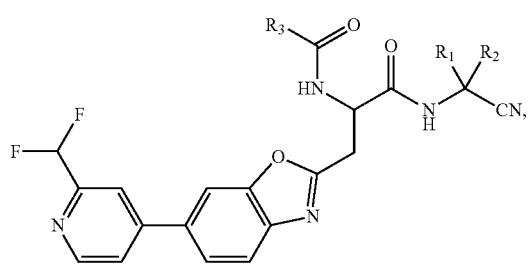

(II-r3)

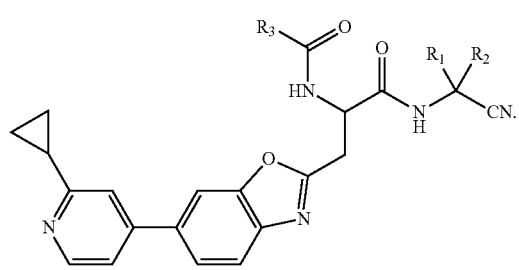

As another example, one of $R_5$-$R_8$ may be a group represented by formula (VI-f:

(VI-f)

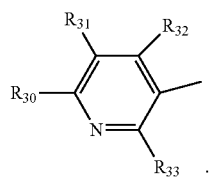

In some embodiments, $R_{30}$-$R_{33}$ may be independently selected from H, halogen, a hydroxyl group, an alkyl group, a fluoroalkyl group, a cycloalkyl group, an alkoxy group, an aryl group, a heteroaryl group, a heterocyclic group, and N—$R_{38}$, wherein $R_{38}$ may be selected from H, an alkyl group, an aryl group, a heterocyclic group, and a ketone group.

Formula (VI-f may be connected with the benzoxazole group shown in formula (II), formula (III), formula (IV), or formula (V) at methyl. In such cases, the Compounds may be represented by, for example, formula (II-u), formula (II-v), formula (II-w), or formula (II-x):

(II-u)

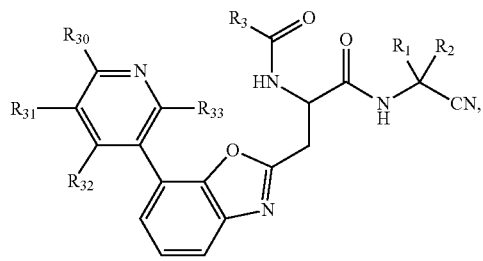

(II-v)

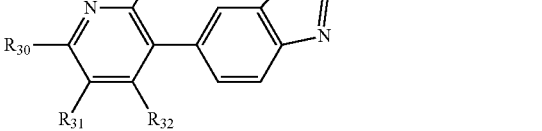

(II-w)

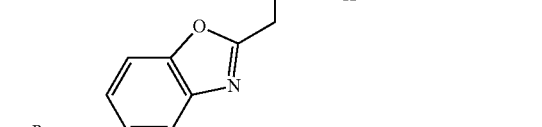

(II-x)

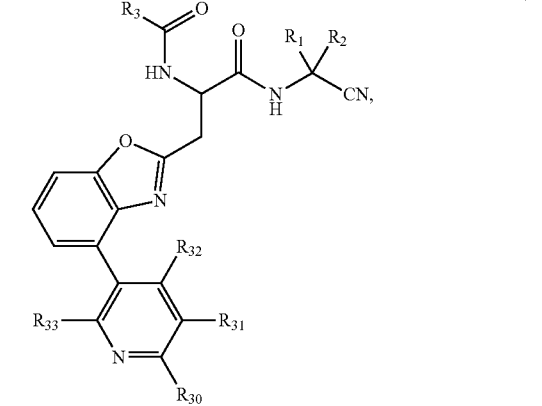

In some embodiments, in Formula (VI-f, $R_{31}$-$R_{33}$ are H, and $R_{30}$ is a methyl group, —NH$_2$, —NC$_2$H$_6$, —NHCOCH$_3$, or —NHCH$_3$, accordingly, the Compounds may be represented by, for example, formula (II-v1), formula (II-v2), formula (II-v3), formula (II-v4), and formula (II-v5):

(II-v1)

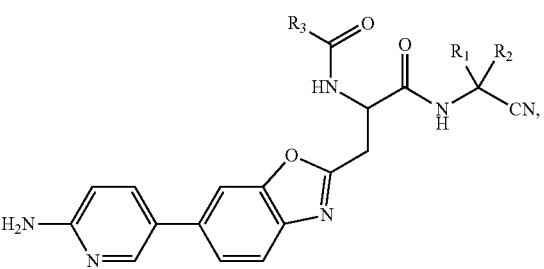

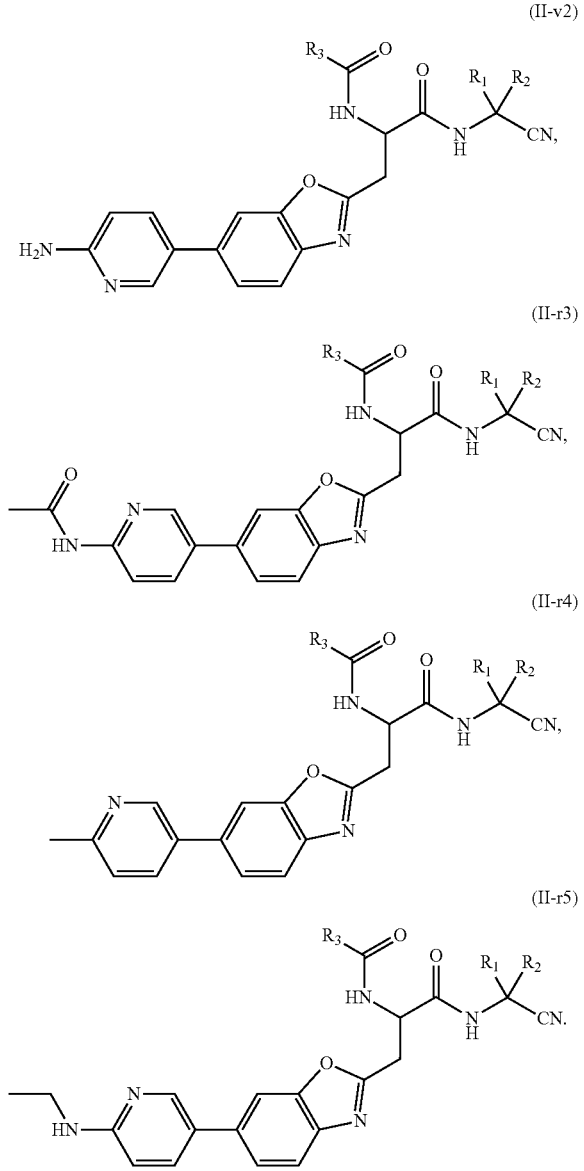

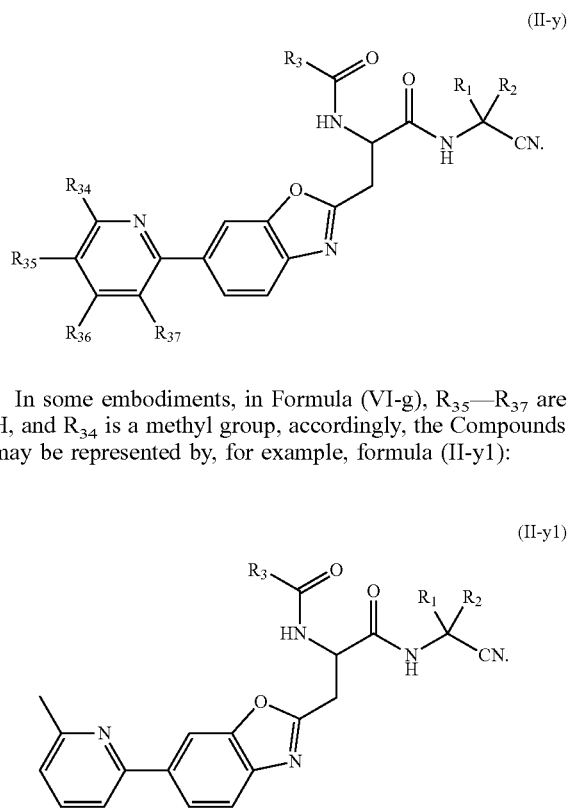

As yet another example, one of $R_5$—$R_8$ may be a group represented by formula (VI-g):

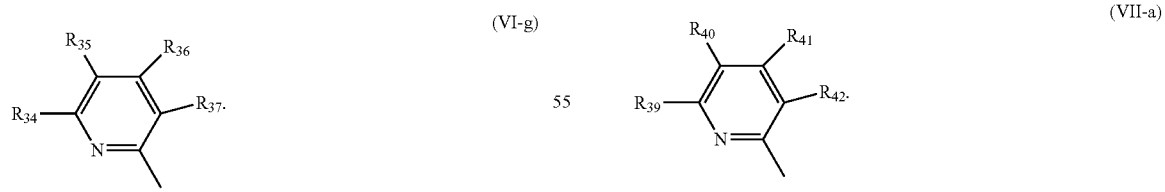

In some embodiments, $R_{34}$-$R_{37}$ may be independently selected from H, halogen, a hydroxyl group, an alkyl group, a fluoroalkyl group, a cycloalkyl group, an alkoxy group, an aryl group, a heteroaryl group, a heterocyclic group, and N—$R_{38}$, wherein $R_{38}$ may be selected from H, an alkyl group, an aryl group, a heterocyclic group, and a ketone group.

Formula (VI-g) may be connected with the benzoxazole group shown in formula (II), formula (III), formula (IV), or formula (V) at methyl. In such cases, the Compounds may be represented by, for example, formula (II-y):

In some embodiments, in Formula (VI-g), $R_{35}$—$R_{37}$ are H, and $R_{34}$ is a methyl group, accordingly, the Compounds may be represented by, for example, formula (II-y1):

In some embodiments, $R_3$ may be an aryl group, and $R_3$ may be optionally substituted by one or more groups selected from halogen, a cycloalkyl group, a fluoroalkyl group, a methyl group, an ethyl group, a propyl group, and a butyl group. For example, $R_3$ may be benzene halide.

In some embodiments, $R_3$ may be a heterocyclic group, and $R_3$ may be optionally substituted by one or more groups selected from halogen, a cycloalkyl group, a fluoroalkyl group, a methyl group, an ethyl group, a propyl group, and a butyl group. For example, $R_3$ is a group represented by formula (VII-a):

In some embodiments, $R_{39}$-$R_{42}$ may be independently selected from H, halogen, a hydroxyl group, an alkyl group, a fluoroalkyl group, a cycloalkyl group, an alkoxy group, an aryl group, a heteroaryl group, a heterocyclic group, and N—$R_{49}$, wherein $R_{49}$ is selected from H, an alkyl group, an aryl group, a heterocyclic group, and a ketone group. Formula (VII-a) may be connected with —CO— or —SO$_2$— shown in formula (II), formula (III), formula (IV), or formula (V) at methyl. In such cases, the Compounds may be represented by, for example, formula (II-aa):

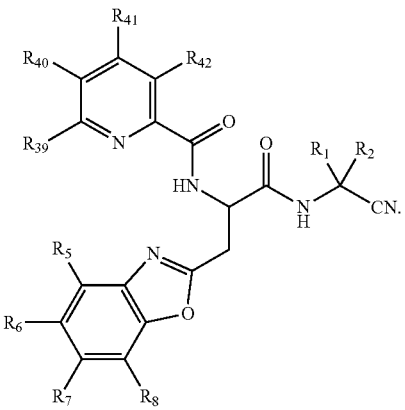

(II-aa)

In some embodiments, $R_{40}$-$R_{42}$ are H, and $R_{39}$ is a methyl group, accordingly, the Compounds may be represented by, for example, formula (II-aa1):

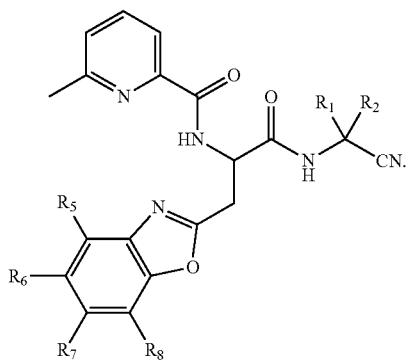

(II-aa1)

In some embodiments, $R_3$ may be selected from an imidazole group, a pyrrole group, a pyrazole group, a triazole, a piperidine group, a pyridine group, a pyrimidine group, and a pyridazine group, and $R_3$ may be optionally substituted by one or more groups selected from a cycloalkyl group, a fluoroalkyl group, a methyl group, and a tertiary butyl group. For example, $R_3$ is a group represented by formula (VII-b):

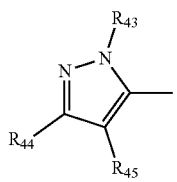

In some embodiments, $R_{43}$ may be H, an alkyl group, a cycloalkyl group, an aryl group, a heteroaryl group, or a heterocyclic group. In some embodiments, $R_{44}$ and $R_{45}$ may be independently selected from H, halogen, a hydroxyl group, an alkyl group, a fluoroalkyl group, a cycloalkyl group, an alkoxy group, an aryl group, a heteroaryl group, and a heterocyclic group, and each of $R_{44}$ and $R_{45}$ may be optionally substituted by one or more groups selected from halogen, a hydroxyl group, an alkyl group, a fluoroalkyl group, a cycloalkyl group, an aryl group, a heterocyclic group, and an alkoxy group. Formula (VII-b) may be connected with —CO— or —SO$_2$— shown in formula (II), formula (III), formula (IV), or formula (V) at methyl. In such cases, the Compounds may be represented by, for example, formula (II-bb):

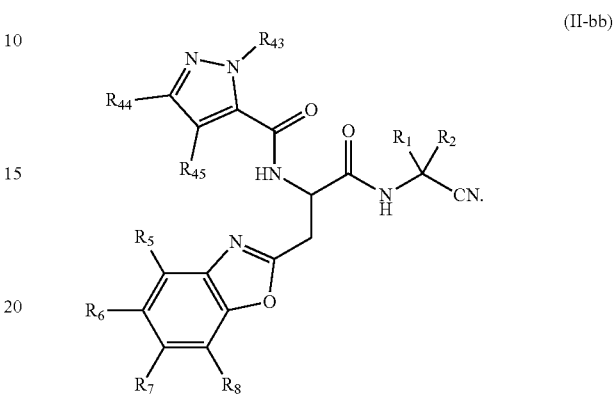

(II-bb)

In some embodiments, $R_{45}$ is H, $R_{43}$ is a methyl group, a cyclopropyl group, or

and $R_{44}$ is a tert-butyl group, a cyclopropyl group, or

As another example, $R_3$ is a group represented by formula (VII-c):

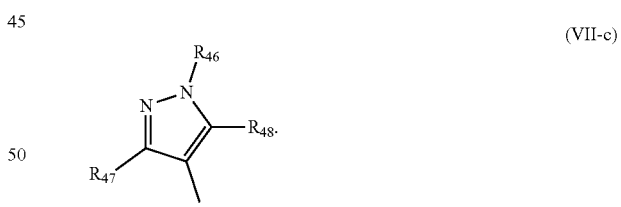

(VII-c)

In some embodiments, $R_{46}$ may be H, an alkyl group, a cycloalkyl group, an aryl group, a heteroaryl group, or a heterocyclic group. In some embodiments, $R_{47}$ and $R_{48}$ may be independently selected from H, halogen, a hydroxyl group, an alkyl group, a fluoroalkyl group, a cycloalkyl group, an alkoxy group, an aryl group, a heteroaryl group, and a heterocyclic group, and each of $R_{47}$ and $R_{48}$ is optionally substituted by one or more groups selected from halogen, a hydroxyl group, an alkyl group, a fluoroalkyl group, a cycloalkyl group, an aryl group, a heterocyclic group, and an alkoxy group. Formula (VII-c) may be connected with —CO— or —SO$_2$— shown in formula (II), formula (III), formula (IV), or formula (V) at methyl. In such cases, the Compounds may be represented by, for example, formula (II-cc):

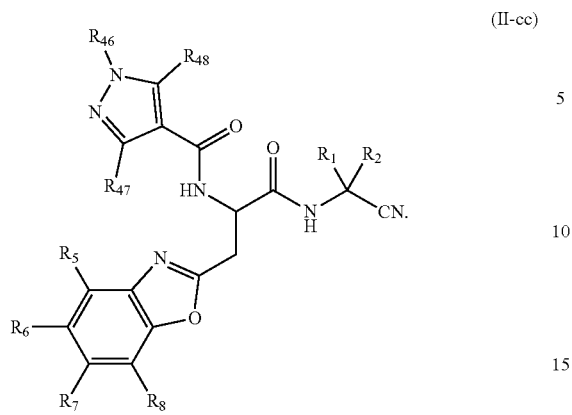

(II-cc)

In some embodiments, $R_{48}$ is H, $R_{46}$ is a methyl group, a —$CHF_2$, or —$CF_3$, and $R_{47}$ is a cyclopropyl group.

In some embodiments, $R_1$ and $R_2$ may be H. In some embodiments, $R_1$ and $R_2$ may be —$CH_2$— groups connected via a single bond.

Some exemplary compounds as CatL inhibitors provided by the present disclosure are shown in Table 1:

TABLE 1 exemplary compounds as CatL inhibitors

Compound 1

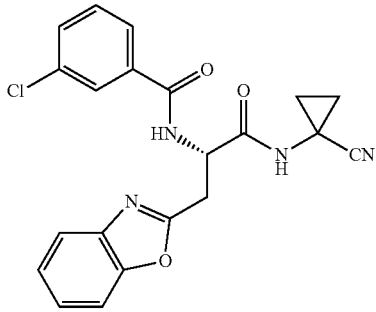 [SMILES: N#CC1(NC(=O)[C@H](Cc2nc3ccccc3o2)NC(=O)c2cccc(Cl)c2)CC1]

Compound 2

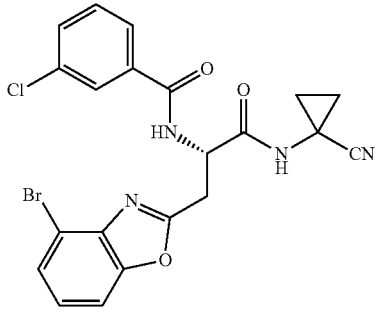 [SMILES: N#CC1(NC(=O)[C@H](Cc2nc3c(Br)cccc3o2)NC(=O)c2cccc(Cl)c2)CC1]

TABLE 1-continued
exemplary compounds as CatL inhibitors
Compound 3
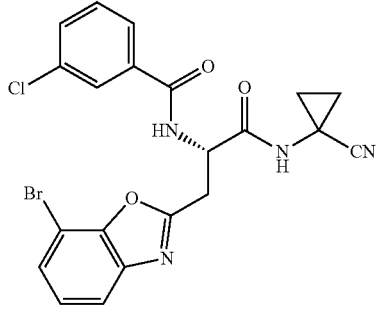
Compound 4
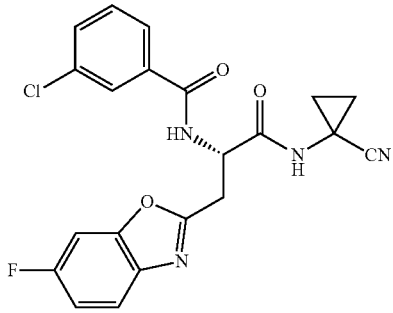 [SMILES: N#CC1(NC(=O)[C@H](Cc2nc3ccc(F)cc3o2)NC(=O)c2cccc(Cl)c2)CC1]
Compound 5
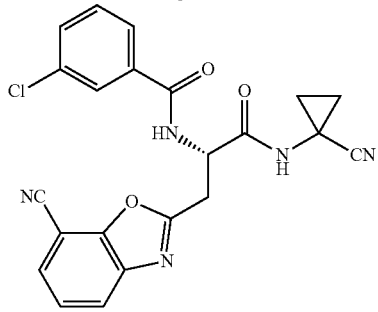
Compound 6
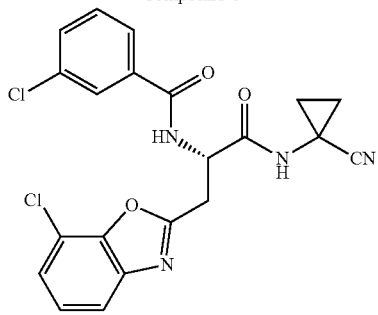

TABLE 1-continued
exemplary compounds as CatL inhibitors
Compound 7
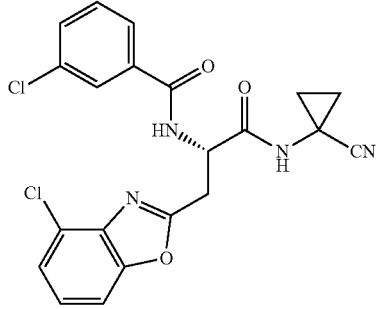
Compound 8
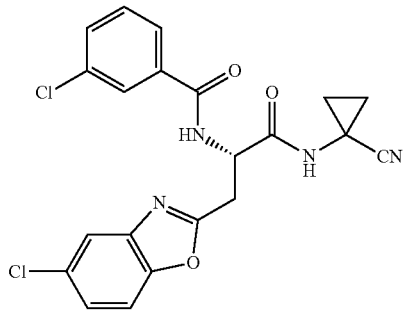 [SMILES: N#CC1(NC(=O)[C@H](Cc2nc3cc(Cl)ccc3o2)NC(=O)c2cccc(Cl)c2)CC1]
Compound 9
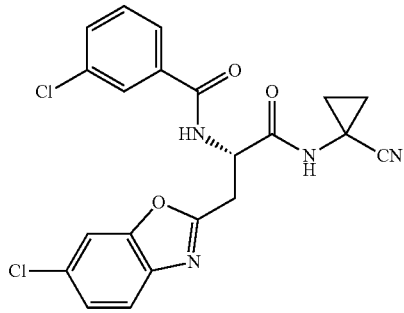 [SMILES: N#CC1(NC(=O)[C@H](Cc2nc3ccc(Cl)cc3o2)NC(=O)c2cccc(Cl)c2)CC1]
Compound 10
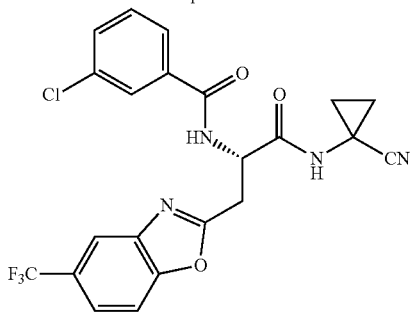

TABLE 1-continued
exemplary compounds as CatL inhibitors
Compound 11
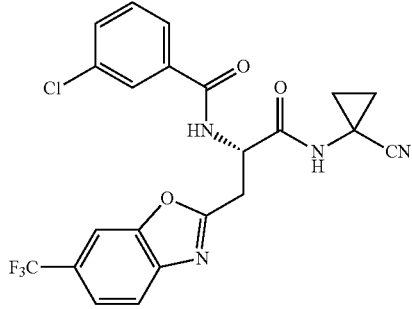 [SMILES: N#CC1(NC(=O)[C@H](Cc2nc3ccc(C(F)(F)F)cc3o2)NC(=O)c2cccc(Cl)c2)CC1]
Compound 12
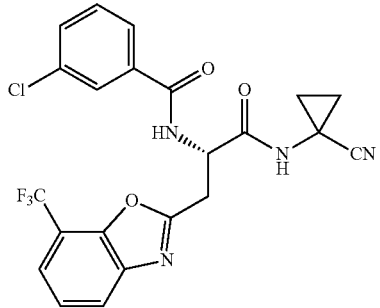 [SMILES: N#CC1(NC(=O)[C@H](Cc2nc3cccc(C(F)(F)F)c3o2)NC(=O)c2cccc(Cl)c2)CC1]
Compound 13
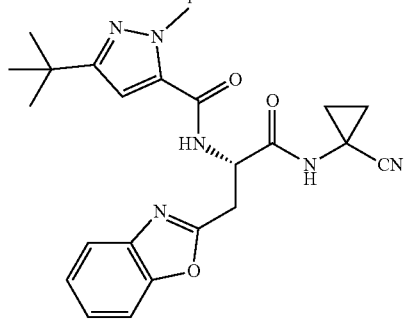
Compound 14
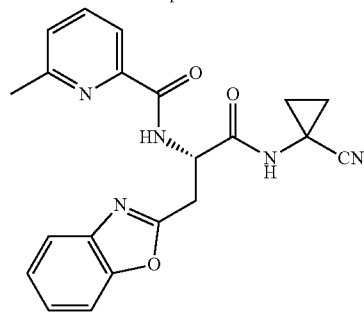

TABLE 1-continued
exemplary compounds as CatL inhibitors
Compound 15
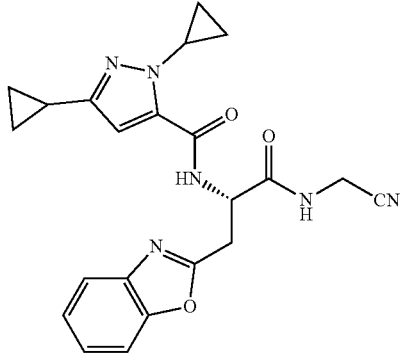 [SMILES: N#CCNC(=O)[C@H](Cc1nc2ccccc2o1)NC(=O)c1cc(C2CC2)nn1C1CC1]
Compound 16
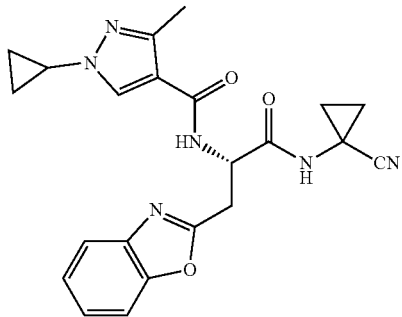 [SMILES: Cc1nn(C2CC2)cc1C(=O)N[C@@H](Cc1nc2ccccc2o1)C(=O)NC1(C#N)CC1]
Compound 17
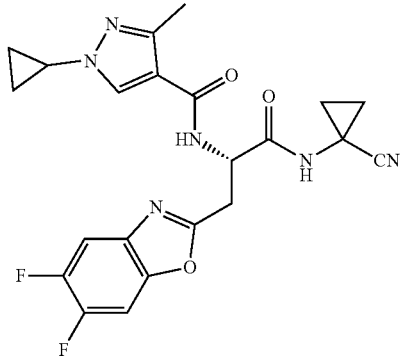 [SMILES: Cc1nn(C2CC2)cc1C(=O)N[C@@H](Cc1nc2cc(F)c(F)cc2o1)C(=O)NC1(C#N)CC1]
Compound 18
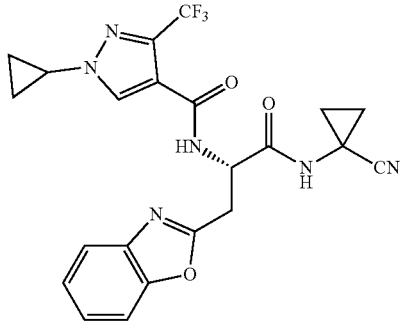 [SMILES: N#CC1(NC(=O)[C@H](Cc2nc3ccccc3o2)NC(=O)c2cn(C3CC3)nc2C(F)(F)F)CC1]

TABLE 1-continued
exemplary compounds as CatL inhibitors
Compound 19
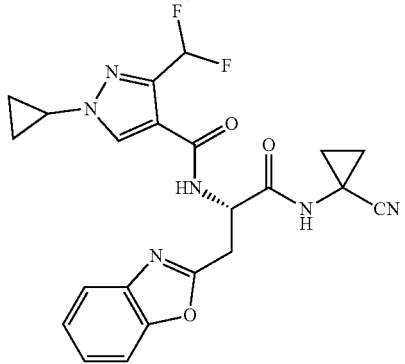 [SMILES: N#CC1(NC(=O)[C@H](Cc2nc3ccccc3o2)NC(=O)c2cn(C3CC3)nc2C(F)F)CC1]
Compound 20
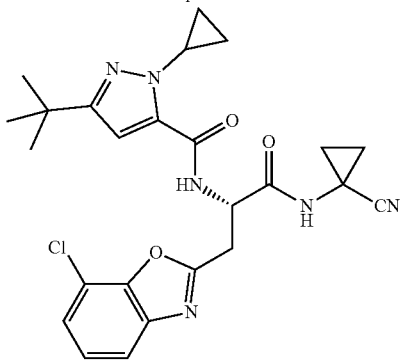
Compound 21
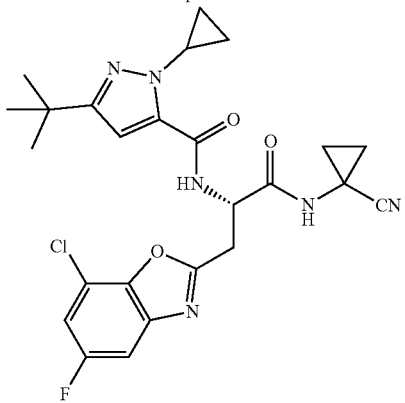

TABLE 1-continued
exemplary compounds as CatL inhibitors
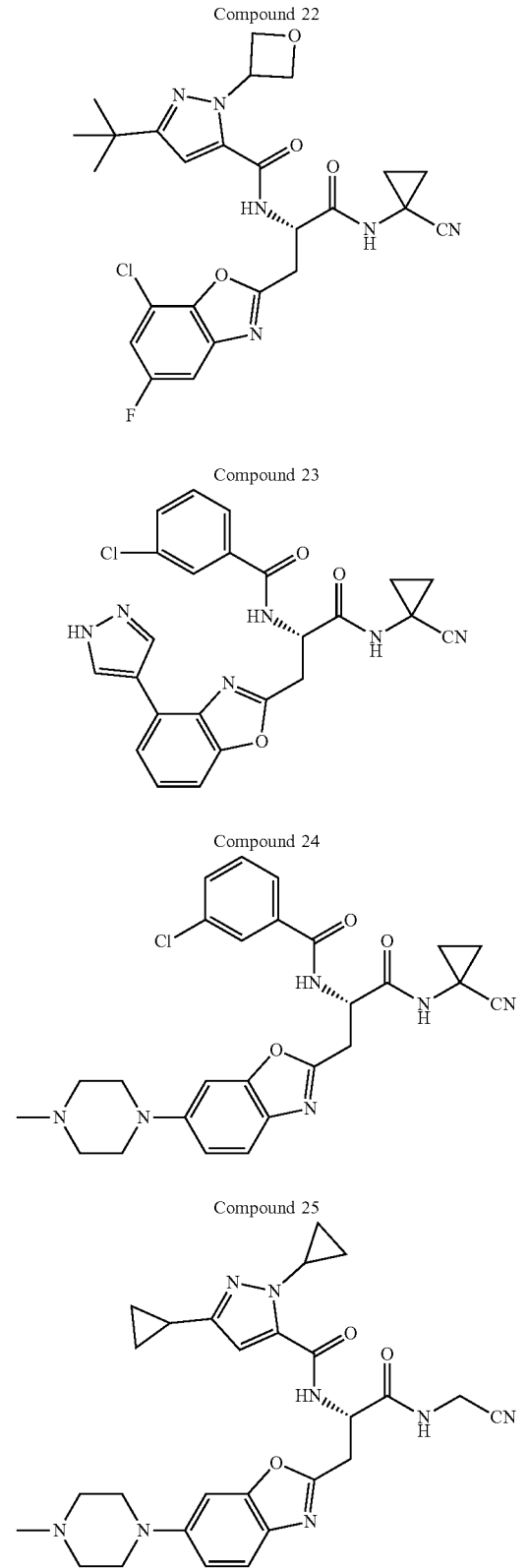
Compound 22
Compound 23
Compound 24
Compound 25

TABLE 1-continued
exemplary compounds as CatL inhibitors
Compound 26
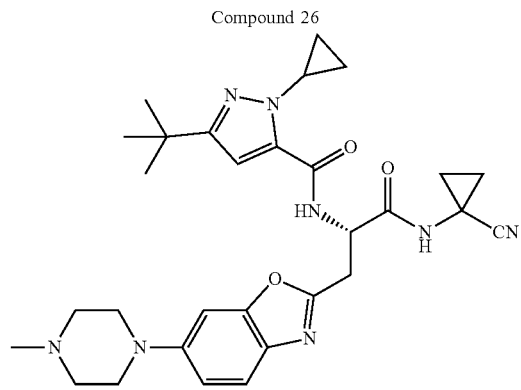
Compound 27
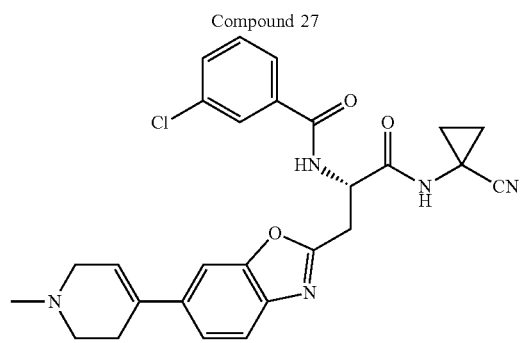
Compound 28
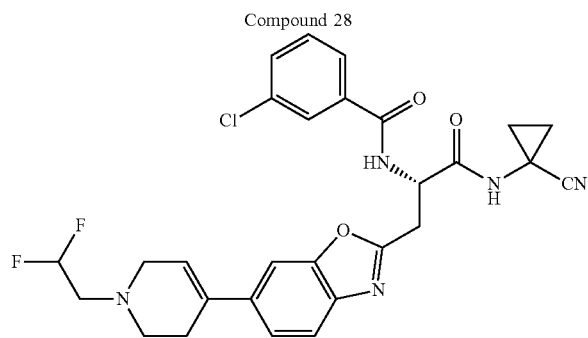
Compound 29
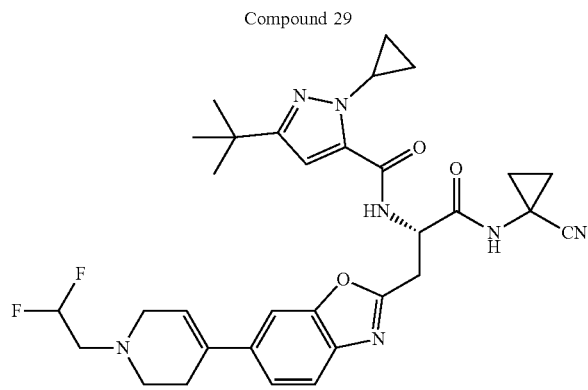

TABLE 1-continued
exemplary compounds as CatL inhibitors
Compound 30
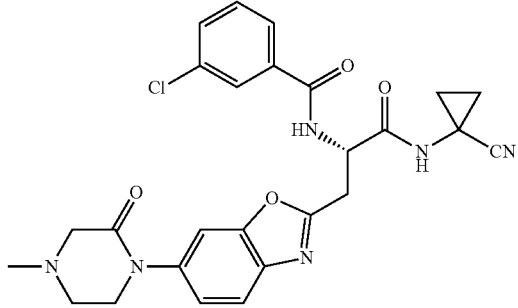 [SMILES: CN1CCN(c2ccc3nc(C[C@H](NC(=O)c4cccc(Cl)c4)C(=O)NC4(C#N)CC4)oc3c2)C(=O)C1]
Compound 31
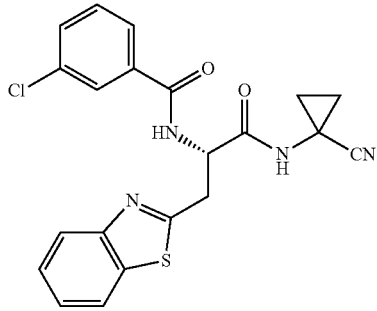
Compound 32
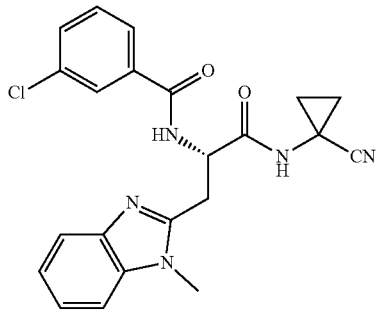 [SMILES: Cn1c(C[C@H](NC(=O)c2cccc(Cl)c2)C(=O)NC2(C#N)CC2)nc2ccccc21]
Compound 33
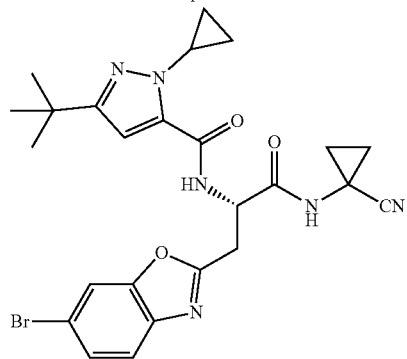

TABLE 1-continued
exemplary compounds as CatL inhibitors
Compound 34
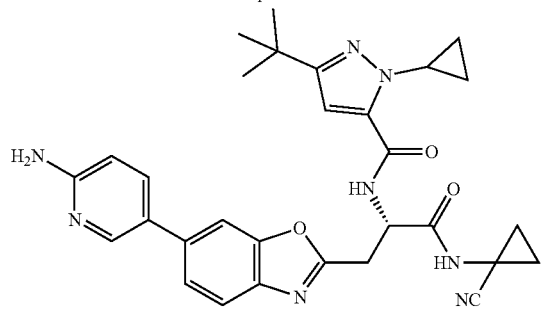
Compound 35
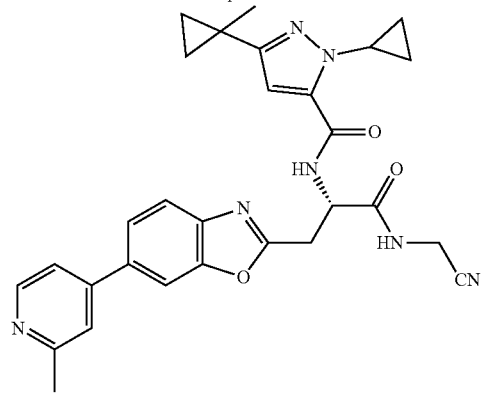
Compound 36
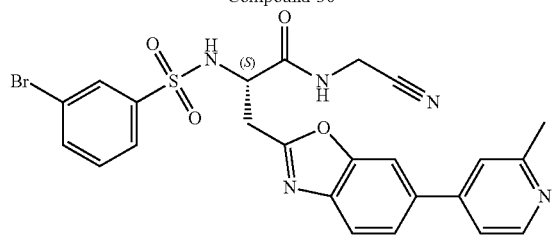
Compound 37
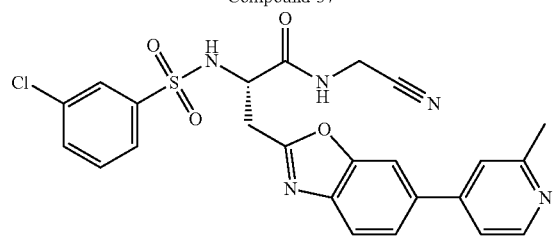

TABLE 1-continued
exemplary compounds as CatL inhibitors
Compound 38
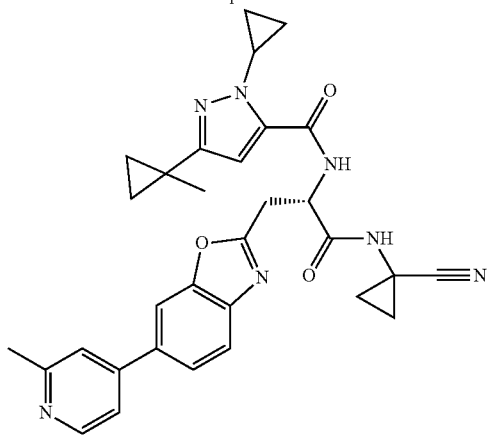
Compound 39
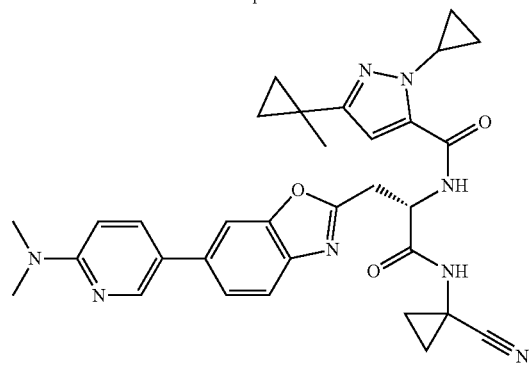
Compound 40
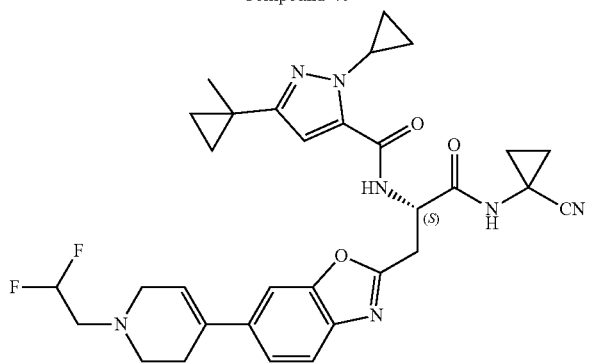
Compound 41
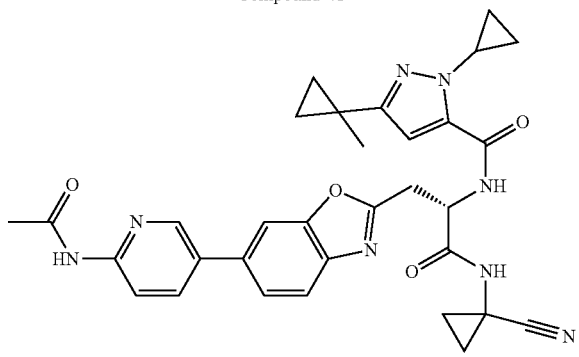

TABLE 1-continued
exemplary compounds as CatL inhibitors
Compound 42
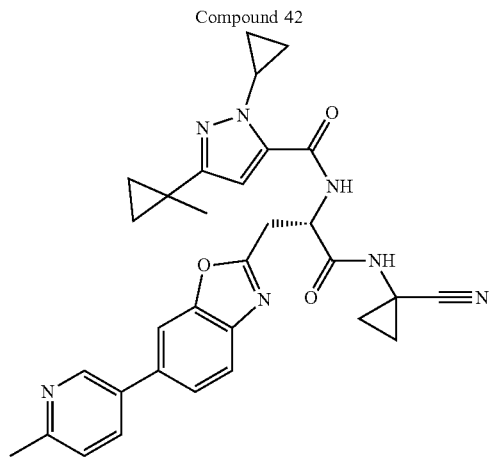
Compound 43
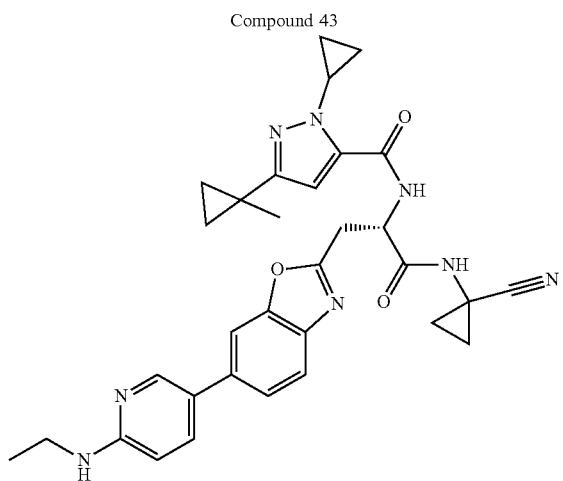
Compound 44
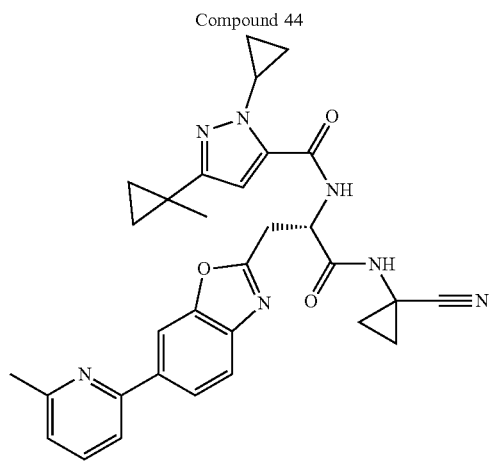

TABLE 1-continued
exemplary compounds as CatL inhibitors
Compound 45
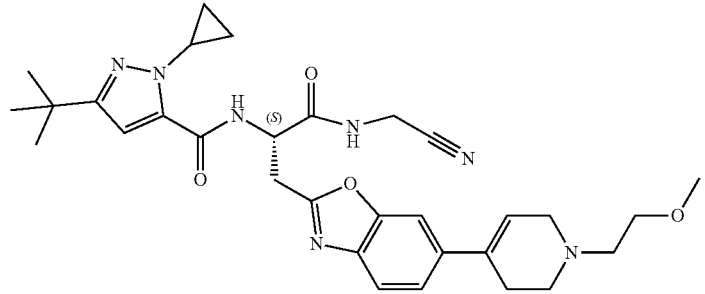
Compound 46
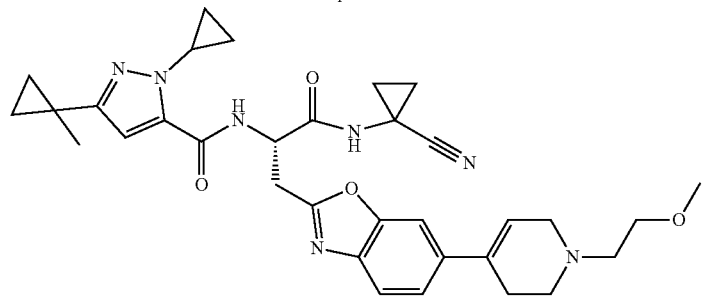
Compound 47
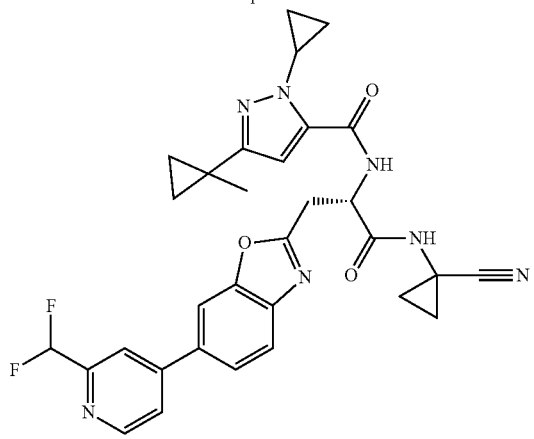
Compound 48
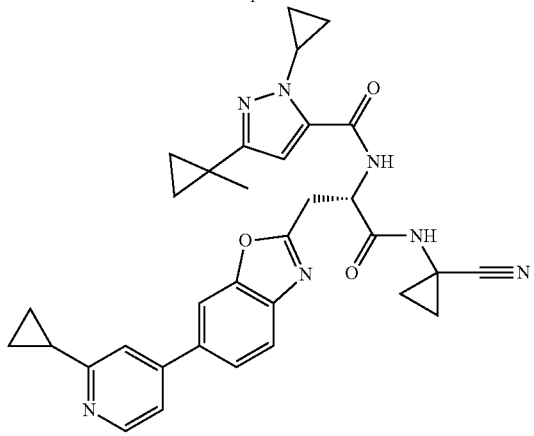

It should be noted that the Compounds listed above in Table 1 are provided merely for illustration purposes. Other Compounds represented by the formulas presented in the present disclosure (e.g., formula (I-a), formula (I-b), formula (I-c), formula (II), formula (III), formula (IV), and formula (V)) are also within the scope of the present disclosure.

According to another aspect of the present disclosure, a composition is provided. The composition may include at least one of the Compounds described previously, an isomer thereof, an enantiomer thereof, a diastereomer thereof, a racemate thereof, a solvate thereof, or a pharmaceutically acceptable salt thereof, in a pharmaceutically effective amount.

In some embodiments, the composition may further include a pharmaceutically acceptable carrier. For instance, the carrier may include a coating layer, a capsule, a microcapsule, a nano-capsule, or the like, or any combination thereof. It should be noted that the carrier may need to be non-toxic and may not have significant impacts on the activity of the key ingredients in the pharmaceutical composition (e.g., the Compounds described above). In some embodiments, the carrier may protect the key ingredients against some undesired conditions, such as oxidation, decomposition, or inactivation of the key ingredients. For instance, enzymes or relatively low-pH in the stomach may cause the decomposition or inactivation of the key ingredients. The carrier may help maintain or increase the efficacy of the pharmaceutical composition by protecting the key ingredients in the pharmaceutical composition. In some embodiments, the carrier may be used for the controlled release of the key ingredients. The controlled release may include but is not limited to slow release, sustained release, targeted release, or the like. For instance, the carrier may include hydrogel capsules, microcapsules, or nano-capsules made of collagen, gelatin, chitosan, alginate, polyvinyl alcohol, polyethylene oxide, starch, cross-linked starch, or the like, or any combination thereof. In some embodiments, the carrier may facilitate a controlled release of the key ingredients (e.g., at least one of the Compounds described previously) in the pharmaceutical composition.

In some embodiments, the composition may be administered to the subject via an oral administration, an injection administration, an inhalation administration, or a topical administration. In some embodiments, the injection administration may include subcutaneous injection, intramuscular injection, intravenous injection, or the like. In some embodiments, the injection administration may include the injection of the composition into a tumor or a region close to the tumor. In some embodiments, the injection administration may include injection of the composition into the kidney, liver, heart, thyroid, or joints. In some embodiments, the inhalation administration may include applying the composition dispersed via an aerosol spray, mist, or powder. In some embodiments, the topical administration may include applying the composition on the skin to attenuate cancer such as skin cancer, or lymphoma. In some embodiments, the topical administration may include vaginal administration, rectal administration, nasal administration, auricular administration, intramedullary administration, intra-articular administration, intra-pleural administration, or the like, or any combination thereof. In some embodiments, the composition may be administered to the subject via a combination of different means of administration. In some embodiments, the method may include administering the composition to the subject three times a day, two times a day, one time a day, once every two days, etc.

In some embodiments, a method of treating a disease in a subject is provided. The method may include administering the composition described earlier to the subject.

In some embodiments, the subject is a human. In some embodiments, the subject is a non-human animal. In some embodiments, the subject is male. In some embodiments, the subject is female. In some embodiments, the subject is suffering from a disease or pathological condition.

In some embodiments, the disease may be caused by a viral infection. The Compounds provided by the present disclosure exhibit remarkable anti-viral effects. Thus, the Compounds may be used for treating diseases related to virus infections.

For example, the disease may include a severe acute respiratory syndrome (SARS), severe acute respiratory syndrome coronavirus 1 (SARS-CoV-1) infection, severe acute respiratory syndrome coronavirus 2 (SARS-CoV-2) infection, or a coronavirus disease 19 (COVID-19). Merely by way of example, the Compounds may be used for treating the long-term effects of coronavirus (long COVID) or post-acute sequelae of COVID-19 (PASC). Severe acute respiratory syndrome coronavirus 2 (SARS-CoV-2) is a coronavirus that has caused the coronavirus disease 2019 (COVID-19) pandemics in the past three years. It imposes a great threat to public health and social-economical systems worldwide. To date, most COVID-19 treatments have been focused on targeting the viral spike protein (S protein) and viral proteases (mainly 3C-like protease and papain-like protease). These treatments have been proven to be effective in preventing SARS-CoV-2 infection and severe COVID-19 symptoms. However, more immune-evasive and contagious SARS-CoV-2 variants continue emerging and spreading around the world. This demands innovative strategies to develop new antiviral medicines to combat COVID-19.

As another example, the disease may include herpes simplex virus (HSV) infection. Infection with HSV, known as herpes, is common globally. Some medications are available to reduce the severity and frequency of symptoms, but they may not cure the infection. Cystatin C is a human cysteine proteinase inhibitor present in extracellular fluids. Cystatin C and a tripeptide derivative (Z-LVG-CHN2) that mimics its proteinase-binding center, were tested for possible antiviral activity against HSV type 1 and poliovirus type 1. (J Virol. 1990 February; 64(2): 941-943.) Thus, the compounds provided by the present disclosure may be used for treating HSV infection.

As yet another example, the disease may include respiratory syncytial virus (RSV) infection. Human RSV is a globally prevalent cause of lower respiratory tract infection in all age groups. RSV infection is frequently reported in infants, the elderly, and immunocompromised patients. RSV is highly contagious and can be fatal. There is no vaccine currently available to prevent RSV infection. Current antiviral drugs for the treatment of RSV infection have notable limitations. There is an urgent need to search for novel medicines that can meet clinical demands. RSV infection increases the expression and activity of several host proteases, including MMP and cathepsin families of proteases. The induced host protease response can facilitate RSV infection and may have a major role in disease progression. A selective cathepsin L inhibitor alone or in combination with the inhibition of additional host proteases has the potential to enhance RSV clearance and prevent RSV-induced airway hyperresponsiveness and allergic response. It was reported that, cathepsin inhibitor E64 or ribavirin prevented airway hyperresponsiveness and enhanced viral clearance in RSV infected mice. (Mucosal Immunol. 2015

January; 8(1): 161-175.) Thus, the Compounds provided by the present disclosure may be used for treating RSV infection.

As yet another example, the disease may include an ebola virus infection or a middle east respiratory syndrome (MERS).

In some embodiments, the disease may be Acute respiratory distress syndrome (ARDS), or ARDS-induced multiple organ failures (e.g., of lung, kidney, liver).

In some embodiments, the disease may be acute kidney injury (AKI). For example, the AKI may be caused by anti-cancer drugs, microbial infections, parasites, etc.

In some embodiments, the disease may be liver injury or liver fibrosis.

In some embodiments, the disease may be cancer.

In some embodiments, the disease may be osteoporosis.

In some embodiments, the disease may be inflammation.

In some embodiments, the disease may be atherosclerosis.

In some embodiments, the disease may be a renal disease or a bone disease.

In some embodiments, the disease may be diabetes.

In some embodiments, the method may include orally administering the composition to the subject, injecting the composition to the subject, or administering the composition to the subject via a topical administration.

According to another aspect of the present disclosure, a method of inhibiting cathepsin L in a subject is provided. The method may include administering the composition described earlier to the subject.

In some embodiments, administering the composition to the subject may include: orally administering the composition to the subject, inhaling the composition to the subject, injecting the composition to the subject, or administering the composition to the subject via a topical administration.

According to another aspect of the present disclosure, a use of the Compounds described earlier for inhibiting cathepsin L in a subject is provided. The use of the Compounds may include steps mentioned in the method for inhibiting CatL.

According to yet another aspect of the present disclosure, a use of at least one of the Compounds described earlier for preparing a composition for treating a disease in a subject is provided.

The present disclosure is further described according to the following examples, which should not be construed as limiting the scope of the present disclosure.

EXAMPLES

Abbreviations
Å=angstrom
Ac=acetyl
Ac$_2$O=acetic anhydride
Boc$_2$O=di-tert-butyl dicarbonate
DCM=dichloromethane
DIPEA=N,N-Diisopropylethylamine or N-ethyl-N-isopropyl-propan-2-amine
DMAP=dimethylamino pyridine
DMA=dimethyl acetamide
DME=dimethoxyethane
DMF=dimethylformamide
DMSO=dimethyl sulfoxide
EtOAc/EA=Ethyl Acetate
EtOH=ethanol
FA=formic acid
HATU=1-[Bis(dimethylamino)methylene]-1H-1,2,3-triazolo[4,5-b]pyridinium 3-oxide hexafluorophosphate
HOAc=acetic acid
KOAc=potassium acetate
LiHMDS=lithium bis(trimethylsilyl)amide
MeMgBr=methylmagnesium bromide
MeOH=methanol
NaOAc=sodium acetate
NBS=N-bromosuccinimide
Pd(dppf)$_2$Cl$_2$=[1,1'-Bis(diphenylphosphino)ferrocene]dichloropalladium(II)
PE=petroleum ether
PTSA=p-Toluenesulfonic acid monohydrate
rt=room (ambient) temperature
T3P=2,4,6-Tripropyl-1,3,5,2,4,6-trioxatriphosphorinane-2,4,6-trioxide
TEA=triethylamine
TFA=trifluoroacetic acid
THF=tetrahydrofuran
TsCl=p-toluene sulfonyl chloride
UV=ultra-violet
X-Phos=2-dicyclohexylphosphino-2',4',6'-triisopropylbiphenyl Example 1-Inhibition of CatL by the Compounds In Vitro Biological Data Human Cathepsin L (CatL) Enzymatic Assay Human cathepsin L enzymatic assay was performed in assay buffer (50 mM MES pH 5.5, 2.5 mM DTT, 0.5 mM EDTA) to assess the inhibition of human CatL by tested compounds. 60 μL of the compounds were added to 384-well dilution plate. The compound solution was diluted for 1:3 in succession in DMSO for each column for 10 pts. 0.05 μL diluted compound solution was added in each row to 384 assay plates (Corning 4514) using Echo (LABCYTE 655), each column containing 2 replicates. 5 μL working solution of human CatL enzyme (Abcam #ab81780) was added to 384-well assay plate, centrifuge 1000 rpm for 1 min. The mixture was incubated at 2500 for 15 min, then add 5 μL working solution of CatL substrate (Genscript #C$_{7360}$HB140_5) to initiate the reaction (CatL: 0.05 nM, Substrate: 500 nM). Incubate at 2500 for 30 min. Reading Ex370 nm and Em460 nm fluorescence signals with BMG CLARIO Star Plusaucu. Percent inhibition for each compound was calculated and IC$_{50}$ (half maximal inhibitory concentration) was fitted from non-linear regression by XLfit 5.5.0. The results of CatL enzymatic assays are shown in the following Table 2.

TABLE 2

IC$_{50}$ of Compounds 1-48 for inhibiting CatL

| Compound | Enzymatic inhibition IC$_{50}$ (nM) |
|---|---|
| 1 | 14.1 |
| 2 | 7.5 |
| 3 | 5.9 |
| 4 | 34.9 |
| 5 | 122 |
| 6 | 7.0 |
| 7 | 21.1 |
| 8 | 17.4 |
| 9 | 30.5 |
| 10 | 51.5 |
| 11 | 94.6 |
| 12 | 235 |
| 13 | 3.9 |
| 14 | 534 |
| 15 | 19.4 |

TABLE 2-continued

IC$_{50}$ of Compounds 1-48 for inhibiting CatL

| Compound | Enzymatic inhibition IC$_{50}$ (nM) |
|---|---|
| 16 | 139 |
| 17 | 201 |
| 18 | 50.7 |
| 19 | 44.6 |
| 20 | 4.2 |
| 21 | 8.2 |
| 22 | 5.3 |
| 23 | 361 |
| 24 | 9.7 |
| 25 | 36.7 |
| 26 | 1.4 |
| 27 | 8.5 |
| 28 | 12.3 |
| 29 | 1.3 |
| 30 | 124 |
| 31 | 11.7 |
| 32 | >1000 |
| 33 | 2.9 |
| 34 | 0.6 |
| 35 | 1.1 |
| 36 | 79.3 |
| 37 | 125 |
| 38 | 1.7 |
| 39 | 1.6 |
| 40 | 1.5 |
| 41 | 5.3 |
| 42 | 4.5 |
| 43 | 0.8 |
| 44 | 16.5 |
| 45 | 2.5 |
| 46 | 1.0 |
| 47 | 6.6 |
| 48 | 3.5 |

This example shows that compounds provided by the present disclosure may be used effectively as CatL inhibitors. According to the results, many of the compounds 1-48 exhibit remarkable inhibition capacities with respect to CatL. Specifically, the IC$_{50}$ of Compounds 1-4, 6-9, 13, 15, 19-22, 24-29, 31, and 44 for inhibiting CatL was less than 50 nM. Moreover, the IC$_{50}$ of Compounds 2, 3, 6, 13, 20-22, 24, 26, 27, 29, 33-35, 38-43, and 45-48 for inhibiting CatL was less than 10 nM.

Example 2-Pseudovirus Infection Assay

In order to infect the host, SARS-CoV-2 needs to enter host cells for viral replication. This depends on the proper cleavage and activation of the viral S protein by host cell proteases, primarily furin, TMPRSS2, and cathepsin L (also known as CatL or CTSL). TMPRSS2 and furin cleave viral S protein at different sites, priming the virus for entry into host cells. CatL then cleaves S protein into smaller fragments, promoting the fusion between virus and endosome membrane, allowing the release of the viral genome into host cells for viral replication. The CatL cleavage sites are highly conserved among all known SARS-CoV-2 variants. Therefore, the inhibition of CatL alone or in combination with the inhibition of additional host proteases will likely prevent the proper processing of S protein, and the infection of SARS-CoV-2 and its variants.

Pseudoviruses (PsVs) incorporated with S protein from SARS-CoV-2, or mutants were constructed using a reported procedure. For this VSV-based PsV system, the backbone was provided by VSV-G pseudotyped virus (G*ΔG-VSV) that packages expression cassettes for firefly luciferase instead of VSV-G in the VSV genome. For quantification of PsV, viral RNA was extracted by using the QIAamp Viral RNA Mini Kit (Cat. No. 52906, QIAGEN), and the reverse transcription was performed with RevertAid™ First Strand cDNA Synthesis Kit (Fermentas K1622) according to the manufacturer. The real-time qPCR was then performed on the LightCycler® 96 Real-Time PCR System (Roche) using SYBR Green I Master Mix reagent (Roche). The P protein gene of VSV virus was quantified and the viral copy number is calculated accordingly. The forward primers were: TCTCGTCTGGATCAGGCGG (SEQ ID NO: 1); the reverse primer is: TGCTCTTCCACTCCATCCTCTTGG (SEQ ID NO: 2). All PsVs were normalized to the same amount as previously described (See Zhao, M. M. et al. Novel cleavage sites identified in SARS-CoV-2 spike protein reveal the mechanism for cathepsin L-facilitated viral infection and treatment strategies. Cell Discovery. 8: 53-70 (2022)).

Vero E6 cells were maintained in high glucose Dulbecco's modified Eagle's medium (DMEM) (Sigma-Aldrich, St. Louis, MO, USA) supplemented with 10% fetal bovine serum (FBS, Gibco, Carlsbad, CA), 100 units/mL Penicillin-Streptomycin (Gibco). All the cells were maintained at 37 00 in a humidified atmosphere containing 95% air and 5% CO$_2$.

To assess the anti-viral effect of tested compounds, Vero E6 cells were seeded in 96-well cell culture plates, then co-treated with different concentrations of tested compounds and SARS-CoV-2 PsVs (100 μL of the normalized PsV was added to each well). After 24 h incubation at 3700, the activities of firefly luciferase were measured in cell lysates using luciferase substrate (PerkinElmer, BRITELITE PLUS 100 mL KIT, Cat. No. 6066761) following the manufacturer's instructions. Luciferase activity was quantified using a luminometer (Promega). The infection rate was calculated from a control reaction containing only vehicle. The results of pseudovirus infection assays are shown in the following Table 3.

TABLE 3

Results of compounds 1-48 in Pseudovirus infection assay

| Compound | % Infection rate at 500 nM | % Infection rate at 5 uM |
|---|---|---|
| 1 | 69 | 39 |
| 2 | 55 | 12 |
| 3 | 65 | 10 |
| 4 | 81 | 51 |
| 5 | 91 | 81 |
| 6 | 75 | 20 |
| 7 | 96 | 48 |
| 8 | 92 | 69 |
| 9 | 97 | 73 |
| 10 | 97 | 96 |
| 11 | 86 | 81 |
| 13 | 55 | 10 |
| 14 | 103 | 97 |
| 15 | 79 | 20 |
| 18 | 92 | 72.6 |
| 19 | 101 | 77.3 |
| 20 | 40 | 6.3 |
| 21 | 60 | 12 |
| 22 | 33 | 13 |
| 23 | 93 | 98 |
| 24 | 34 | 2 |
| 25 | 54 | 15 |
| 26 | 25 | 2.2 |
| 27 | 40 | 13 |
| 28 | 70 | 38 |
| 29 | 7.3 | 8.8 |
| 30 | 99 | 101 |
| 31 | 67 | 10 |
| 32 | 101 | 95 |

TABLE 3-continued

Results of compounds 1-48 in Pseudovirus infection assay

| Compound | % Infection rate at 500 nM | % Infection rate at 5 uM |
|---|---|---|
| 33 | 39 | 5.9 |
| 34 | 41 | 0.9 |
| 35 | 40 | 3.1 |
| 36 | 110 | 125 |
| 37 | 96 | 104 |
| 38 | 34 | 1.0 |
| 39 | 32 | 4.0 |
| 40 | 57 | 12 |
| 41 | 90 | 57.7 |
| 42 | 34 | 5.6 |
| 43 | 18 | 0.8 |
| 44 | 82 | 55.5 |
| 45 | 7.0 | 0.02 |
| 46 | 7.0 | 0.08 |
| 47 | 56 | 15.9 |
| 48 | 63 | 22.4 |

This example indicates that the Compounds provided by the present disclosure may effectively protect cells from viral infections and may be used for treating or preventing a disease related to viral infections (e.g., SARS-CoV-2). According to the results in Table 3, many of Compounds 1-48 are capable of protecting cells from pseudovirus infections in dose-dependent manners from 500 nM to 5 uM, and some Compounds (e.g., Compound 29, 45, 46) demonstrated nearly full protection at 500 nM.

Example 3-Preparation of Compounds 1-48

General Procedure A

The general procedure A for preparing a compound A-7 is illustrated in FIG. 1. As illustrated in FIG. 1, the general procedure A may include steps A-D.

Step A. Benzoxazole Ring Formation

Ethyl (tert-butoxycarbonyl)-L-asparaginate (A-1, 1 equiv.) was dissolved in 1,2-dichloroethane (0.2 M), $Et_3O^+$ $BF_4^-$ (1.2 equiv.) was added in portions under nitrogen. The resulting mixture was stirred for 24 h at RT (room temperature). A solution of (substituted) aminophenol (A-2, 1 equiv.) in 2 mL ethanol (2 M) was transferred into the solution through a syringe. The mixture was heated to 90° C. and stirred for 24 h. The reaction mixture was cooled to room temperature, saturated $NaHCO_3$ (aq.) was added, and then the aqueous layer was extracted with dichloromethane. The combined organic layer was washed with brine and dried over anhydrous $Na_2SO_4$. After filtration and concentration, the crude product was purified by chromatography (EtOAc in PE, 25% to 50%) to give the desired product A-3.

Step B. Ester Hydrolysis

A solution of ester A-3 (1 equiv.) in THF (0.1 M) and 1N LiOH (aq., 3 equiv.) was stirred for 3 h at rt. The reaction was adjusted to pH=7 by HCl (1 M) then extracted with DCM/MeOH (v/v, 10:1). The combined organic layer was separated, dried ($MgSO_4$) and concentration to obtain the desired product A-4.

Step C. Amide Coupling (C-Terminal)

To a stirred solution of acid A-4 (1 equiv.), 1-aminocyclopropane-1-carbonitrile hydrochloride A-5 (1.2 equiv.) and T3P (50 wt % EA solution, 1.1 equiv.) in DCM (0.2 M) was added DIPEA (4 equiv.). The reaction mixture was stirred under $N_2$ atmosphere at rt for 3 hrs. The reaction mixture was concentrated and purified by chromatography (EtOAc in PE, 40% to 100%) to give the desired product A-6.

Step D. N-Boc Deprotection

A solution of protected amine A-6 in HCOOH (0.4 M) was stirred at 25° C. for 5 h. The mixture was blown by nitrogen to dryness at 20° C., basified with saturated $NaHCO_3$ (aq.) and extracted with EA. The combined organic layer was concentrated to give the desired product A-7.

General Procedure B-1

Figure 2:
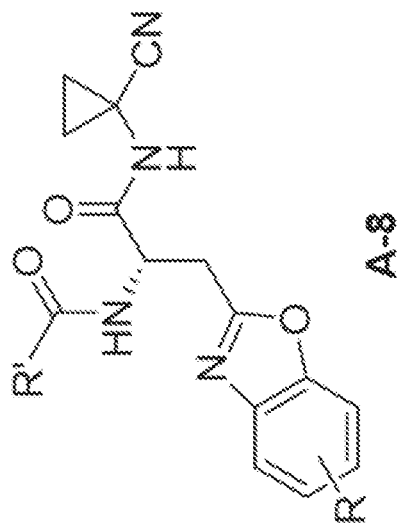
FIG. 2 is a schematic diagram illustrating an exemplary procedure B-1 for preparing a compound A-8 based on Compound A-7 according to some embodiments of the present disclosure.
Figure 2:
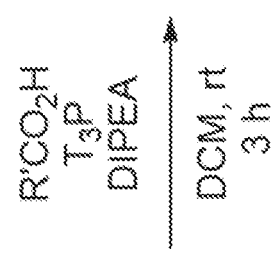
Figure 2:
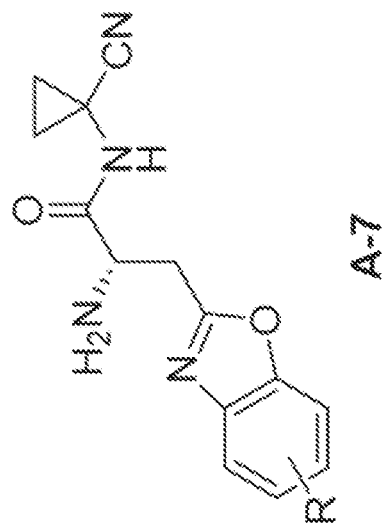

The general procedure B-1 for preparing a compound A-8 based on Compound A-7 is illustrated in FIG. 2.

A solution of amine A-7 (1 equiv.), acyl chloride (1.1 equiv.) and DIPEA (3 equiv.) in DCM (0.5 M) was stirred under at 25° C. for 2 hrs. The reaction mixture was concentrated, the residue was purified by prep-High Performance Liquid Chromatography (HPLC) [(Gemini-C18, 150×21.2 mm, 5um; ACN-$H_2O$ (0.1% FA); 15%-80%)] to give the desired product A-8.

General Procedure B-2

Figure 3:
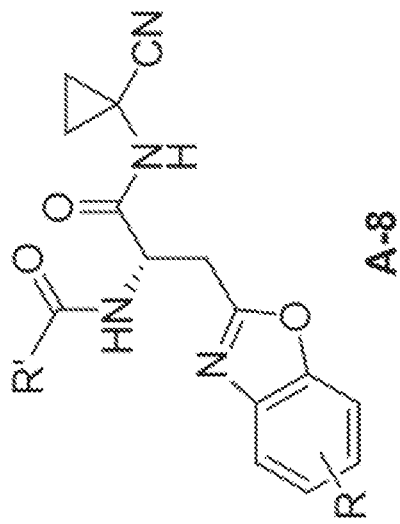
FIG. 3 is a schematic diagram illustrating an exemplary procedure B-2 for preparing Compound A-8 based on Compound A-7 according to some embodiments of the present disclosure.
Figure 3:
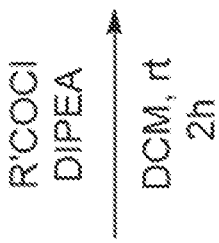

The general procedure B-2 for preparing Compound A-8 based on Compound A-7 is illustrated in FIG. 3.

To a stirred solution of amine A-7, acid (1.2 equiv.) and DIPEA (4 equiv.) in DCM (0.1 M) was added $T_3P$ (50 wt % DMF solution, 1.2 equiv.) dropwise. The reaction was stirred at 25° C. for 3 h. The reaction mixture was quenched with water and extracted with DCM. The combined organic layer was dried over $Na_2SO_4$ and concentrated under vacuum to give a crude product, which was purified by prep-HPLC [(Gemini-C18, 150×21.2 mm, 5 um; ACN-$H_2O$ (0.1% FA); 15%-80%)] to give the desired product A-8.

General Procedure B-3

Figure 4:
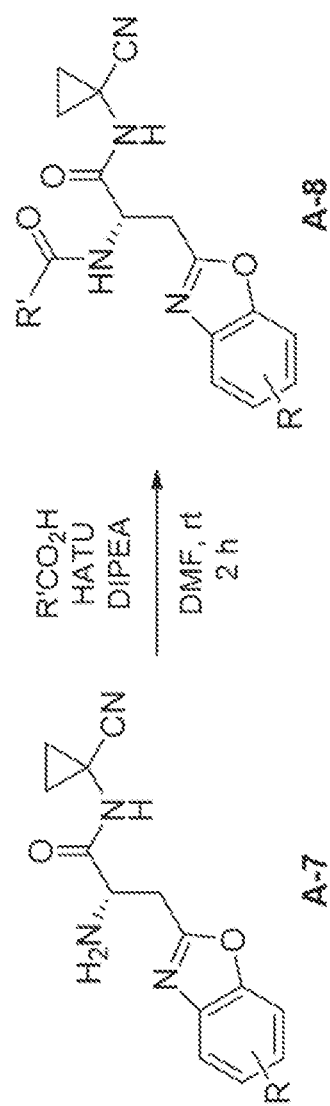
FIG. 4 is a schematic diagram illustrating an exemplary procedure B-3 for preparing Compound A-8 based on Compound A-7 according to some embodiments of the present disclosure.

The general procedure B-3 for preparing Compound A-8 based on Compound A-7 is illustrated in FIG. 4.

To a stirred solution of amine A-7 (70 mg, 0.2 mmol) in DMF (0.2 M) was added acid (1 equiv.), DIPEA (5 equiv.) and HATU (3 equiv.). The reaction mixture was stirred at rt under $N_2$ for 2 hrs. After the reaction completed, $H_2O$ was added to the reaction mixture, and then extracted with EA. The combined organic layer was washed with brine, dried over anhydrous $Na_2SO_4$. After filtration, the solution was concentrated under vacuum, and the residue was purified by prep-HPLC to give the desired product A-8.

Synthesis of Intermediates

Figure 5:
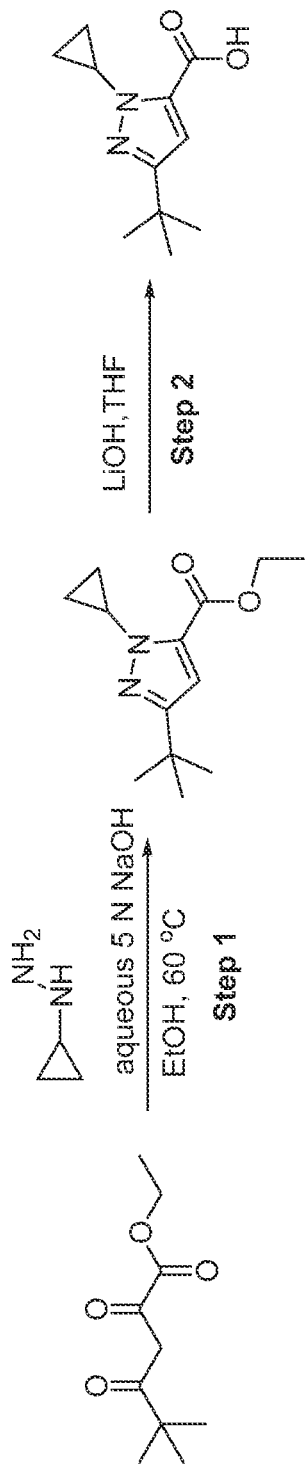
FIG. 5 is a schematic diagram illustrating an exemplary procedure for preparing Intermediate I-1 according to some embodiments of the present disclosure.

Preparation of Intermediate I-1: 3-(tert-butyl)-1-cyclopropyl-1H-pyrazole-5-carboxylic acid FIG. 5 is a schematic diagram illustrating an exemplary procedure for preparing Intermediate I-1 according to some embodiments of the present disclosure.

Step 1. Preparation of ethyl 3-(tert-butyl)-1-cyclopropyl-1H-pyrazole-5-carboxylate To a solution of cyclopropylhydrazine hydrochloride (1.5 g, 0.0138 mol) in EtOH (40 mL) was added 5 N aq. NaOH solution (3 mL) and stirred for 10 min at 0° C. Then the mixture was added to an ethanol solution of ethyl 5,5-dimethyl-2,4-dioxohexanoate (4.14 g, 0.02 mol). The resulting mixture was stirred at 60° C. for 16 hrs. The mixture was concentrated and the residue was purified by flash column (PE/EA=50:1) to give the product as colorless oil (1.79 g, 50.3%). Mass spectrometry was conducted on the resultant compound, and the test results are as follows: Mass(m/z): 237.1 $[M+H]^+$.

Step 2. Preparation of 3-(tert-butyl)-1-cyclopropyl-1H-pyrazole-5-carboxylic acid To a solution of ethyl 3-(tert-butyl)-1-cyclopropyl-1H-pyrazole-5-carboxylate (1.79 g, 7.6 mmol) in THF (18 mL), $H_2O$ (6 mL), and MeOH (6 mL) was added LiOH (3.19 g, 76 mmol) and stirred at RT for 5 hrs. The solvent was removed under reduced pressure. The residue was dissolved in $H_2O$ (20 mL) and adjusted to pH 7 by using 1 N aq. HCl. Then the mixture was extracted with DCM (100 mL×2). The combined organic layer was washed with brine (50 mL), then dried over anhydrous $Na_2SO_4$. After filtration, the solution was concentrated under vacuum to give the product as a light pink solid (1.45 g, 86%). Mass spectrometry was conducted on the resultant compound, and the test results are as follows: Mass(m/z): 209.1 [M+H]$^+$. $^1$H NMR (400 MHz, DMSO-$d_6$) δ 13.16 (s, 1H), 6.67 (s, 1H), 4.27 (d, J=3.8 Hz, 1H), 1.21 (s, 9H), 1.11-1.04 (m, 2H), 0.95 (dd, J=7.2, 2.4 Hz, 2H).

Figure 6:
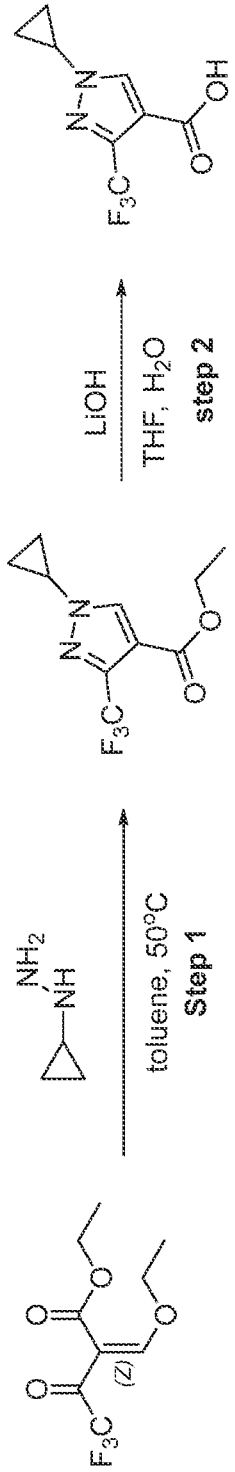
FIG. 6 is a schematic diagram illustrating an exemplary procedure for preparing Intermediate I-2 according to some embodiments of the present disclosure.

Preparation of Intermediate I-2: 1-cyclopropyl-3-(trifluoromethyl)-1H-pyrazole-4-carboxylic acid FIG. 6 is a schematic diagram illustrating an exemplary procedure for preparing Intermediate I-2 according to some embodiments of the present disclosure.

Step 1. Preparation of ethyl 1-cyclopropyl-3-(trifluoromethyl)-1H-pyrazole-4-carboxylate To a solution of ethyl (Z)-2-(ethoxymethylene)-4,4,4-trifluoro-3-oxobutanoate (2 g, 8.3 mmol) in toluene (20 mL) at 0° C. was added cyclopropylhydrazine hydrochloride (0.54 g, 4.9 mmol). The mixture was stirred at 50° C. under $N_2$ for 16 hrs. After completion, the mixture was concentrated under vacuum. The residue was purified by prep-TLC (PE:EA=4:1) to give the product as a white solid (500 mg, 22%). Mass spectrometry was conducted on the resultant compound, and the test results are as follows: Mass(m/z): 249.2 [M+H]$^+$.

Step 2. Preparation of 1-cyclopropyl-3-(trifluoromethyl)-1H-pyrazole-4-carboxylic acid A solution of ethyl 1-cyclopropyl-3-(trifluoromethyl)-1H-pyrazole-4-carboxylate (620 mg, 2.48 mmol) in 1 N aq. LiOH (5 mL) and THF(5 mL) was stirred at RT for 16 hours. The mixture was acidified to pH 3-4 with 5 N aqueous HCl and extracted with EA (20 mL×3). The combined organic layers were washed with brine (20 mL×2), and dried over $Na_2SO_4$. Then by filtration, the filtrate was concentrated to give the product as a white solid (447 mg, 70%). Mass spectrometry was conducted on the resultant compound, and the test results are as follows: Mass (m/z): 221.0 [M+H]$^+$.

Figure 7:
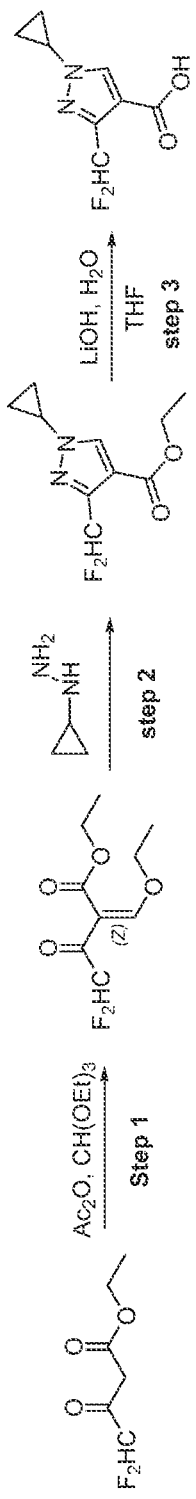
FIG. 7 is a schematic diagram illustrating an exemplary procedure for preparing Intermediate I-3 according to some embodiments of the present disclosure.

Preparation of Intermediate I-3: 1-cyclopropyl-3-(difluoromethyl)-1H-pyrazole-4-carboxylic acid FIG. 7 is a schematic diagram illustrating an exemplary procedure for preparing Intermediate I-3 according to some embodiments of the present disclosure.

Step 1. Preparation of ethyl (Z)-2-(ethoxymethylene)-4,4-difluoro-3-oxobutanoate A solution of ethyl 4,4-difluoro-3-oxobutanoate (5 g, 30 mmol) and (diethoxy methoxy) ethane (10 mL, 58 mmol) in acetic acid anhydride (30 mL) was stirred at 140° C. under $N_2$ for 6 hrs. After completion, the mixture was concentrated under vacuum to give the product as light-yellow oil (5 g, 74%). Mass spectrometry was conducted on the resultant compound, and the test results are as follows: Mass (m/z): Mass(m/z): 222.0 [M+H]$^+$.

Step 2. Preparation of ethyl 1-cyclopropyl-3-(difluoromethyl)pyrazole-4-carboxylate To a solution of ethyl (Z)-2-(ethoxymethylene)-4,4-difluoro-3-oxobutanoate (1.55 g, 0.45 mmol) in toluene (10 mL) at 0° C. was added cyclopropylhydrazine hydrochloride (0.46 g, 4.2 mmol). The mixture was stirred at 50° C. under $N_2$ for 16 hrs. After completion, the mixture was concentrated under vacuum. The residue was purified by prep-TLC (PE:EA=5:1) to give the product as a light-yellow solid (210 mg, 11%). Mass spectrometry was conducted on the resultant compound, and the test results are as follows: Mass(m/z): 231.0 [M+H]$^+$.

Step 3. Preparation of 1-cyclopropyl-3-(difluoromethyl)-1H-pyrazole-4-carboxylic acid A solution of ethyl 1-cyclopropyl-3-(trifluoromethyl)-1H-pyrazole-4-carboxylate (210 mg, 0.9 mmol) in 1 N aq. LiOH (2 mL) and THF (2 mL) was stirred at RT for 16 hours. The mixture was acidified to pH 3-4 with 5 N aqueous HCl and extracted with EA (20 mL×3). The combined organic layers were washed with brine (20 mL×2), and dried over $Na_2SO_4$. Then by filtration, the filtrate was concentrated to give the product as a white solid (150 mg, 77%). Mass spectrometry was conducted on the resultant compound, and the test results are as follows: Mass (m/z): 203.1 [M+H]$^+$.

Figure 8:
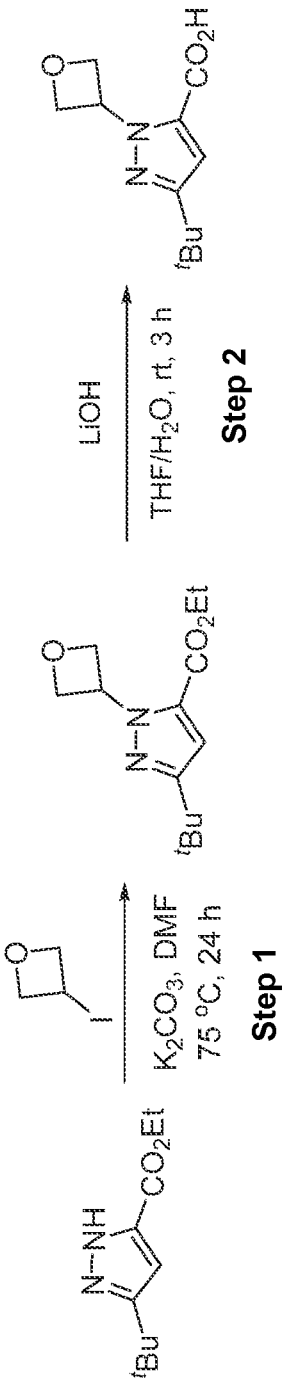
FIG. 8 is a schematic diagram illustrating an exemplary procedure for preparing Intermediate I-4 according to some embodiments of the present disclosure.

Preparation of Intermediate I-4: 3-(tert-butyl)-1-(oxetan-3-yl)-1H-pyrazole-5-carboxylic acid FIG. 8 is a schematic diagram illustrating an exemplary procedure for preparing Intermediate I-4 according to some embodiments of the present disclosure.

Step 1. Preparation of ethyl 3-(tert-butyl)-1-(oxetan-3-yl)-pyrazole-5-carboxylate To a solution of ethyl 3-(tert-butyl)-1H-pyrazole-5-carboxylate (1.6 g, 8 mmol) and $K_2CO_3$ (2.24 g, 16 mmol) in DMF (8 mL) was added 3-iodooxetane (1.3 mL, 12 mmol). The reaction was stirred at 75° C. for 24 hrs. The reaction mixture was quenched with ice water, and extracted with EtOAc (30 mL×3). The combined organic layer was washed with water (30 mL×3) and brine (30 mL), dried with anhydrous $Na_2SO_4$, filtered, and concentrated under reduced pressure. The residue was purified by flash chromatography (PE/EtOAc=4:1) to give the product as a white solid (1.9 g, 94%). Mass spectrometry was conducted on the resultant compound, and the test results are as follows: Mass(m/z): 253.2 [M+H]+.

Step 2. Preparation of 3-(tert-butyl)-1-(oxetan-3-yl)-pyrazole-5-carboxylic acid To a solution of ethyl 3-(tert-butyl)-1-(oxetan-3-yl)-pyrazole-5-carboxylate (500 mg, 2 mmol) in THF/$H_2O$ (5:1, 10 mL) was added LiOH.$H_2O$ (420 mg, 10 mmol). The reaction mixture was stirred at RT for 3 hrs. The reaction solution was adjusted pH to 5~6 by using 1N aq.HCl. Then the mixture was extracted with EtOAc (30 mL×2). The combined organic layer was washed with brine (30 mL), then dried over with anhydrous $Na_2SO_4$. The mixture was filtered, and the filtrate was concentrated under vacuum to afford desired product (400 mg, 89%) as a white solid. Mass spectrometry was conducted on the resultant compound, and the test results are as follows: Mass(m/z): 225.1 [M+H]$^+$.

Figure 9:
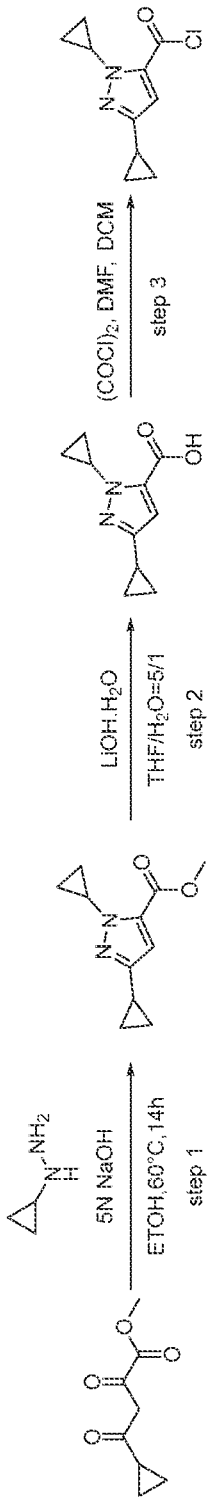
FIG. 9 is a schematic diagram illustrating an exemplary procedure for preparing Intermediate I-5 according to some embodiments of the present disclosure.

Preparation of Intermediate I-5: 1,3-dicyclopropyl-1H-pyrazole-5-carbonyl chloride FIG. 9 is a schematic diagram illustrating an exemplary procedure for preparing Intermediate I-5 according to some embodiments of the present disclosure.

Step 1. Preparation of methyl 1,3-dicyclopropyl-1H-pyrazole-5-carboxylate

To a solution of the cyclopropylhydrazine dihydrochloride (2813 mg, 19.4 mmol) in EtOH (50 mL) was added 5N NaOH (3 mL). After stirred for 10 min at 0° C. A solution of Methyl 4-cyclopropyl-2,4-dioxobutanoate (2200 mg, 12.9 mmol) in EtOH (50 mL) was added and the resulting mixture was stirred at 60° C. for 14 hrs. The solvent was removed under reduced pressure and the residue was purified by Combiflash column (PE/EA=0~ 50%) to give the product (800 mg, 27%) as colorless oil. Mass spectrometry was conducted on the resultant compound, and the test results are as follows: Mass(m/z): 206.9 [M+H]$^+$.

Step 2. Preparation of 1,3-dicyclopropyl-1H-pyrazole-5-carboxylic acid

To a solution of methyl 1,3-dicyclopropyl-1H-pyrazole-5-carboxylate (170 mg, 0.82 mmol) in THF/H$_2$O (5:1, 6 mL) was added LiOH·H$_2$O (346 mg, 8.2 mmol). The reaction mixture was stirred at RT for 4 hrs. The reaction solution was adjusted pH to 5~ 6 by using 1 N aq.HCl. Then the mixture was extracted with EA (20 mL×2). The combined organic layer was washed with brine (30 mL), then dried over with anhydrous Na$_2$SO$_4$. The mixture was filtered, and the filtrate was concentrated under vacuum to afford compound product (140 mg, 79.5%) as a white solid. Mass spectrometry was conducted on the resultant compound, and the test results are as follows: Mass(m/z): 193.1 [M+H]$^+$.

Step 3. Preparation of 1,3-dicyclopropyl-1H-pyrazole-5-carbonyl chloride

To a solution of the 1,3-dicyclopropyl-1H-pyrazole-5-carboxylic acid (140 mg, 0.73 mmol) in DCM (10 mL) was added oxalyl chloride (140 mg, 1.1 mmol) and DMF (0.05 ml). The reaction mixture was stirred at 0° C. for 1 hour. The solvent was removed under reduced pressure to afford crude product. Mass spectrometry was conducted on the resultant compound, and the test results are as follows: Mass(m/z): 207.1 [M−Cl+MeOH]$^+$.

Figure 10:
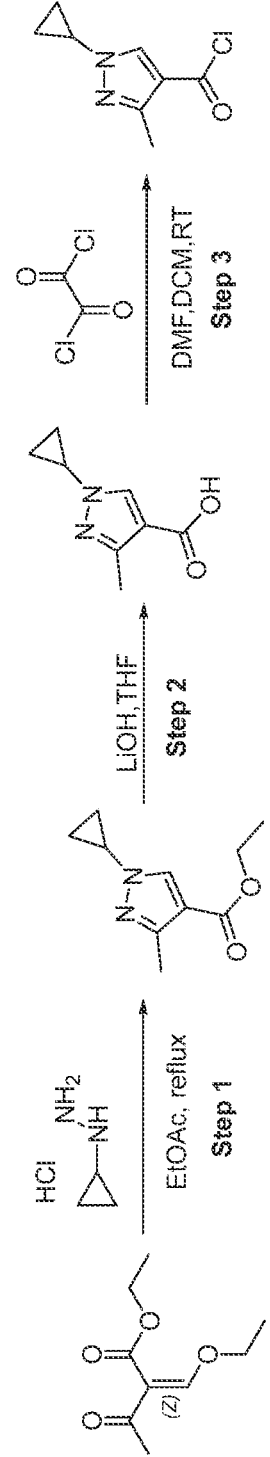
FIG. 10 is a schematic diagram illustrating an exemplary procedure for preparing Intermediate I-6 according to some embodiments of the present disclosure.

Preparation of Intermediate I-6: 1-cyclopropyl-3-methyl-1H-pyrazole-4-carbonyl chloride FIG. 10 is a schematic diagram illustrating an exemplary procedure for preparing Intermediate I-6 according to some embodiments of the present disclosure.

Step 1. Preparation of ethyl 1-cyclopropyl-3-methyl-1H-pyrazole-4-carboxylate

A solution of ethyl (Z)-2-(ethoxymethylene)-3-oxobutanoate (5 g, 0.02 mol) and cyclopropylhydrazine (1.94 g, 0.02 mol) in EA (50 mL) was stirred under reflux for 3 hours. The mixture was concentrated under reduced pressure and the residue was purified by flash column (PE/EA=5:1) to give the product as orange oil (0.53 g, 9.6%). Mass spectrometry was conducted on the resultant compound, and the test results are as follows: Mass(m/z): 195.1 [M+H]$^+$.

Step 2. Preparation of 1-cyclopropyl-3-methyl-1H-pyrazole-4-carboxylic acid

To a solution of ethyl 1-cyclopropyl-3-methyl-1H-pyrazole-4-carboxylate (0.53 g, 0.7 mmol) in 1N aq. LiOH (10 mL) and THF (10 mL). The reaction mixture was stirred for 24 hours at 25° C. After completion, the mixture was concentrated under vacuum. The residue was dissolved in water (10 mL), adjusted pH to 7 with 1N aq. HCl, and extracted with ethyl acetate (10 mL×2). The combined organic layer was washed with brine (10 mL), dried over Na$_2$SO$_4$, filtered, and concentrated under vacuum to give the product as a yellow solid (380 mg, 85.7%). Mass spectrometry was conducted on the resultant compound, and the test results are as follows: Mass(m/z): 167.2 [M+H]$^+$.

Step 3. Preparation of 1-cyclopropyl-3-methyl-1H-pyrazole-4-carbonyl chloride

To a solution of 1-cyclopropyl-3-methyl-1H-pyrazole-4-carboxylic acid (150 mg, 0.9 mmol) in DCM (2 mL) was added oxalic dichloride (103 mg, 0.8 mmol) and a drop of DMF. The reaction mixture was stirred at 25° C. for 16 hrs. The mixture are concentrated under vacuum to give the product as a yellow oil (150 mg, 81%). Mass spectrometry was conducted on the resultant compound, and the test results are as follows: Mass(m/z): 181.0 [M-Cl+MeOH]$^+$.

Figure 11:
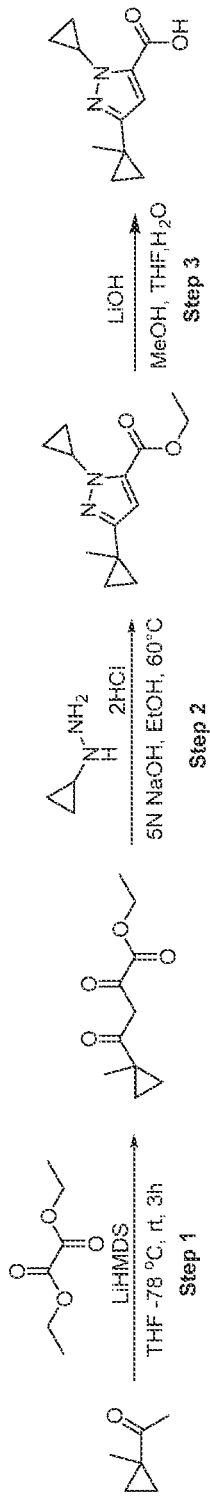
FIG. 11 is a schematic diagram illustrating an exemplary procedure for preparing Intermediate I-7 according to some embodiments of the present disclosure.

Preparation of Intermediate I-7: 2-cyclopropyl-5-(1-methylcyclopropyl)pyrazole-3-carboxylic acid FIG. 11 is a schematic diagram illustrating an exemplary procedure for preparing Intermediate I-7 according to some embodiments of the present disclosure.

Step 1. Preparation of ethyl 4-(1-methylcyclopropyl)-2,4-dioxobutanoate

To a mixture of 1-(1-methylcyclopropyl)ethenone (3.00 g, 30.6 mmol) and diethyl oxalate (4.47 g, 30.6 mmol) in THF (30.0 mL) was added LiHMDS (30.6 mL, 30.6 mmol). The reaction was stirred at −70° C. for 16 hrs. The reaction mixture was quenched with NH$_4$Cl solution (100 mL) at 0° C., then extracted with EA (100 mL×3). The combined organic layers were washed with brine (100 mL×3), dried over Na$_2$SO$_4$, and concentrated under reduced pressure. The residue was purified by flash column (PE: EA=0~50%) to give the desired product ethyl 4-(1-methylcyclopropyl)-2,4-dioxobutanoate as brown oil (2.80 g, 42%). Mass spectrometry was conducted on the resultant compound, and the test results are as follows: Mass(m/z): 199.1 [M+H]$^+$.

Step 2. Preparation of ethyl 2-cyclopropyl-5-(1-methylcyclopropyl)pyrazole-3-carboxylate A mixture of ethyl 4-(1-methylcyclopropyl)-2,4-dioxobutanoate cyclopropyl hydrazine (3.07 g, 21.1 mmol) in EtOH (10.0 mL) was adjusted pH to 10 with aq.NaOH (5N) at 0° C. Then the mixture was added to a solution of ethyl 4-(1-methylcyclopropyl)-2,4-dioxobutanoate (2.80 g, 14.1 mmol) in EtOH (20.0 mL) at 0° C. The reaction was stirred at 60° C. for 16 hrs. The reaction mixture was concentrated under reduced pressure. The residue was purified by flash column (PE:EA=0-5%) to give the product ethyl 2-cyclopropyl-5-(1-methylcyclopropyl)pyrazole-3-carboxylate as colorless oil (2.20 g, 60%). Mass spectrometry was conducted on the resultant compound, and the test results are as follows: Mass(m/z): 235.1 [M+H]$^+$.

Step 3. Preparation of 2-cyclopropyl-5-(1-methylcyclopropyl)pyrazole-3-carboxylic acid To a mixture of ethyl 2-cyclopropyl-5-(1-methyl cyclopropyl) pyrazole-3-carboxylate (2.20 g, 9.40 mmol) in THF/H$_2$O (3:1, 24.0 mL) was added LiOH (680 mg, 28.2 mmol). The reaction was stirred at RT for 16 hrs. The reaction mixture was concentrated under reduced pressure. The residue was diluted with water (50 mL), then adjusted pH to 4 with aq. HCl (2 M). The mixture was extracted with EA (100 mL×3), washed with brine (100 mL), dried over Na$_2$SO$_4$, and concentrated under reduced pressure to give the product 2-cyclopropyl-5-(1-methylcyclopropyl) pyrazole-3-carboxylic acid as a white solid (1.20 g, 55%). Mass spectrometry was conducted on the resultant compound, and the test results are as follows: Mass(m/z): 207.1 [M+H]$^+$.

Figure 12:
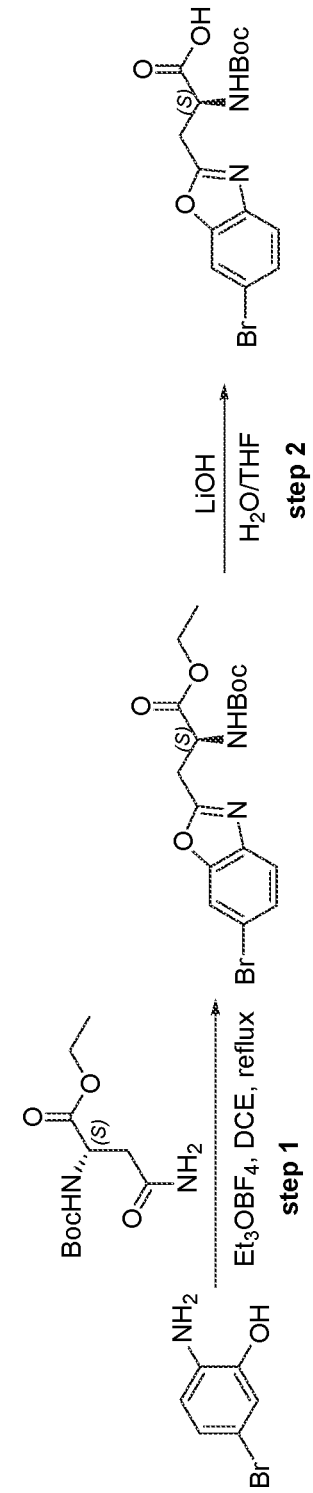
FIG. 12 is a schematic diagram illustrating an exemplary procedure for preparing Intermediate I-8 according to some embodiments of the present disclosure.

Preparation of Intermediate I-8: (S)-3-(6-bromobenzo[d]oxazol-2-yl)-2-((tert-butoxycarbonyl)amino)propanoic acid FIG. 12 is a schematic diagram illustrating an exemplary procedure for preparing Intermediate I-8 according to some embodiments of the present disclosure.

Step 1. Preparation of ethyl (S)-3-(6-bromobenzo[d]oxazol-2-yl)-2-((tert-butoxycarbonyl)amino)propanoate To a solution of ethyl (tert-butoxycarbonyl)-L-asparaginate (20.7 g, 79.78 mmol) in DCE (300 mL) was added Triethyloxonium tetrafluoroborate (15.1 g, 79.78 mmol). The reaction mixture was stirred at 25° C. under $N_2$ for 16 hrs. To the resulting mixture was added 2-amino-5-bromophenol (15 g, 79.78 mmol). The reaction mixture was stirred at 85° C. under $N_2$ for 16 hrs. The mixture was diluted with water (500 mL), and extracted with DCM (300 mL×2). The organic phase was evaporated, and the residue was purified by silica gel column chromatography (PE:EA=5:1) to give the product as a black oil (19 g, 46%). Mass spectrometry was conducted on the resultant compound, and the test results are as follows: Mass(m/z): 413.0 415.0[M+H]$^+$.

Step 2. Preparation of (S)-3-(6-bromobenzo[d]oxazol-2-yl)-2-((tert-butoxycarbonyl) amino)propanoic acid To a solution of ethyl (S)-3-(6-bromobenzo[d]oxazol-2-yl)-2-((tert-butoxycarbonyl)amino)propanoate (6 g, 14.52 mmol) in THF (45 mL) and $H_2O$ (15 mL) was added LiOH·$H_2O$ (914 mg, 21.78 mmol). The reaction mixture was stirred at 25° C. under $N_2$ for 2 hrs. The mixture was adjusted pH to 6~ 7 with 2 N aq.HCl. The mixture was washed with water (50 mL), and the mixture was extracted with EA (50 mL×3). The organic phase was washed with brine (50 mL×2), dried over $Na_2SO_4$, and evaporated to give the product as black oil (5.2 g, 74%). Mass spectrometry was conducted on the resultant compound, and the test results are as follows: Mass(m/z): 385.0 387.0[M+H]$^+$.

Figure 13:
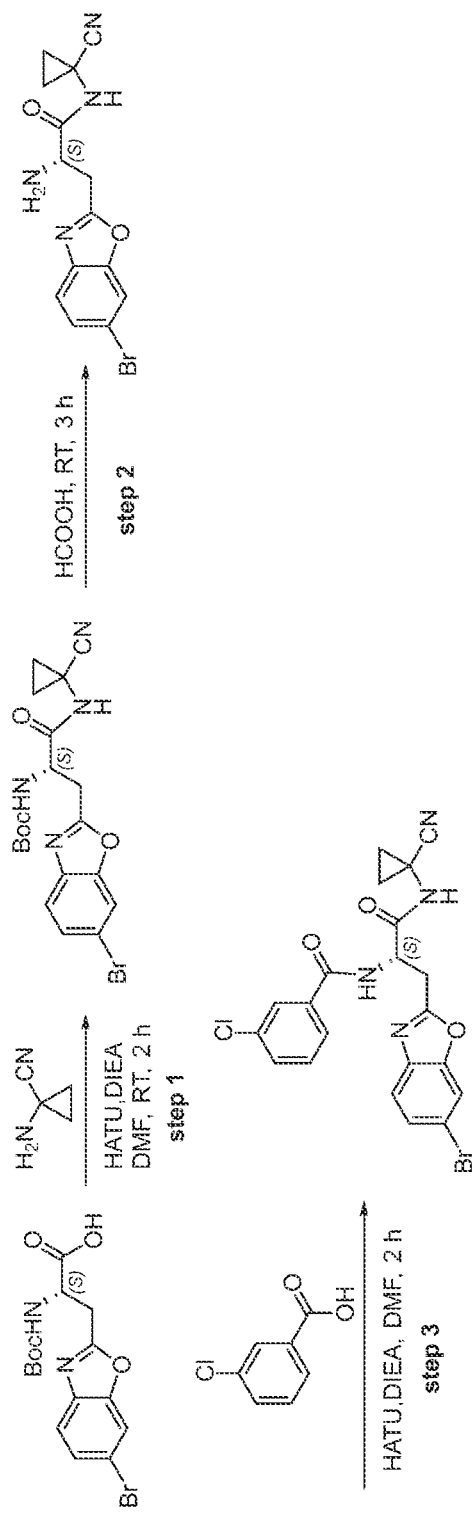
FIG. 13 is a schematic diagram illustrating an exemplary procedure for preparing Intermediate I-9 according to some embodiments of the present disclosure.

Preparation of Intermediate I-9: (2S)-3-(6-bromo-1,3-benzoxazol-2-yl)-2-[(3-chlorophenyl)formamido]-N-(1-cyanocyclopropyl)propanamide FIG. 13 is a schematic diagram illustrating an exemplary procedure for preparing Intermediate I-9 according to some embodiments of the present disclosure.

Step 1. Preparation of tert-butyl N-[(1S)-2-(6-bromo-1,3-benzoxazol-2-yl)-1-[(1-cyanocyclopropyl)carbamoyl]ethyl] carbamate To a solution of (2S)-3-(6-bromo-1,3-benzoxazol-2-yl)-2-{[(tert-butoxy) carbonyl]amino}propanoic acid (3.3 g, 0.0086 mol) in DMF (30 mL) was added DIEA (3.33 g, 0.0258 mol), HATU (4.10 g, 0.0129 mol), and 1-aminocyclopropane-1-carbonitrile (1.06 g, 0.0129 mol). The solution was stirred at 25° C. under $N_2$ for 2 hrs. Water (50 mL) was added, and the mixture was extracted with EA (40 mL×3). The combined organic layer was washed with brine (30 mL×3), then dried over with anhydrous $Na_2SO_4$. After filtration, the solution was concentrated under vacuum, and the crude product was purified by Combiflash (EA/PE=20%-25%) to afford tert-butyl N-[(1S)-2-(6-bromo-1,3-benzoxazol-2-yl)-1-[(1-cyanocyclopropyl)carbamoyl]ethyl]carbamate as a yellow solid (1.6 g, 39.53%). Mass spectrometry was conducted on the resultant compound, and the test results are as follows: Mass(m/z): 449.3 [M+H]$^+$.

Step 2. Preparation of (2S)-2-amino-3-(6-bromo-1,3-benzoxazol-2-yl)-N-(1-cyanocyclopropyl)propanamide A solution of tert-butyl N-[(1S)-2-(6-bromo-1,3-benzoxazol-2-yl)-1-[(1-cyanocyclopropyl)carbamoyl]ethyl]carbamate (1.6 g, 0.0036 mmol) in FA (10 mL) was stirred at 25° C. for 1 hr. The result was concentrated under vacuum to afford (2S)-2-amino-3-(6-bromo-1,3-benzoxazol-2-yl)-N-(1-cyanocyclopropyl)propanamide as a yellow solid (900 mg, 69%). Mass spectrometry was conducted on the resultant compound, and the test results are as follows: Mass (m/z): 349.1 [M+H]$^+$.

Step 3. Preparation of (2S)-3-(6-bromo-1,3-benzoxazol-2-yl)-2-[(3-chlorophenyl)formamido]-N-(1-cyanocyclopropyl)propanamide To a solution of (2S)-2-amino-3-(6-bromo-1,3-benzoxazol-2-yl)-N-(1-cyanocyclopropyl)propenamide (600 mg, 1.71 mmol) in DMF (6 mL) was added 3-chlorobenzoic acid (349 mg, 2.23 mmol), HATU (820 mg, 2.23 mmol), and DIEA (666 mg, 5.15 mmol). The solution was stirred at 25° C. under $N_2$ for 2 hrs. Water (50 mL) was added, and the mixture was extracted with EA (40 mL×3). The combined organic layer was washed with brine (30 mL×3), then dried over with anhydrous $Na_2SO_4$. After filtration, the solution was concentrated under vacuum, and the crude product was purified by Combiflash (EA/PE=25%-30%) to afford (2S)-3-(6-bromo-1,3-benzoxazol-2-yl)-2-[(3-chlorophenyl)formamido]-N-(1-cyanocyclopropyl)propanamide as a yellow solid (450 mg, 51%). Mass spectrometry was conducted on the resultant compound, and the test results are as follows: Mass(m/z): 487.2 [M+H]$^+$.

Example 3.1: Preparation of Compound 1 ((S)—N-(3-(benzo[d]oxazol-2-yl)-1-((1-cyanocyclopropyl)amino)-1-oxopropan-2-yl)-3-chlorobenzamide)

Figure 14:
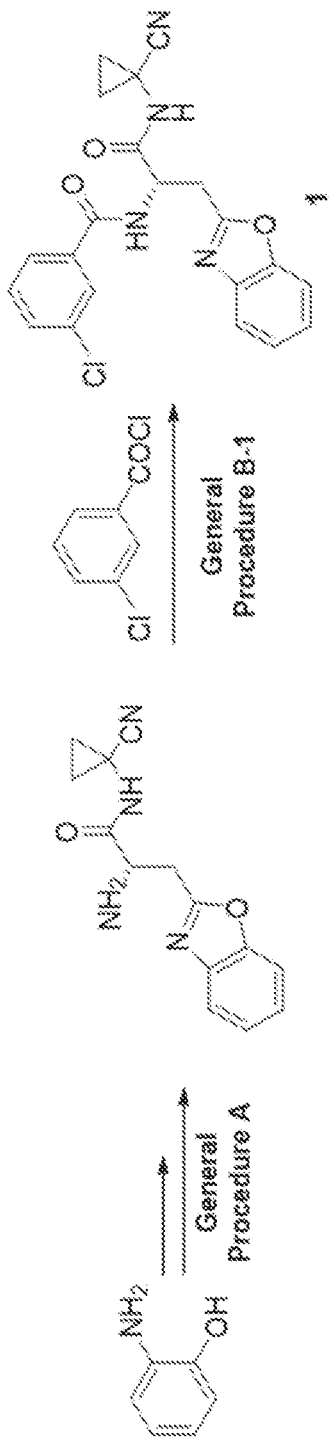
FIG. 14 is a schematic diagram illustrating an exemplary procedure for preparing Compound 1 according to some embodiments of the present disclosure.

FIG. 14 is a schematic diagram illustrating an exemplary procedure for preparing Compound 1 according to some embodiments of the present disclosure.

Following general procedure A, from 2-aminophenol, the (S)-2-amino-3-(benzo[d]oxazol-2-yl)-N-(1-cyanocyclopropyl)propenamide was obtained as a yellow solid. Mass spectrometry was conducted on the resultant compound, and the test results are as follows: Mass(m/z): 271.0 [M+H]$^+$.

Following general procedure B-1, from (S)-2-amino-3-(benzo[d]oxazol-2-yl)-N-(1-cyanocyclopropyl)propenamide (50 mg), the desired product Compound 1 was obtained as a white solid (25 mg, 33%). Mass spectrometry was conducted on the resultant compound, and the test results are as follows: Mass(m/z): 409.0 [M+H]$^+$. $^1$H NMR (400 MHz, CDCl$_3$) δ 8.34 (d, J=7.1 Hz, 1H), 8.17 (s, 1H), 7.87 (t, J=1.7 Hz, 1H), 7.74 (d, J=7.8 Hz, 1H), 7.68 (m, 1H), 7.54 (m, 2H), 7.42 (t, J=7.9 Hz, 1H), 7.36 (m, 2H), 5.16 (td, J=7.0, 4.4 Hz, 1H), 3.69 (dd, J=16.6, 4.3 Hz, 1H), 3.37 (dd, J=16.6, 6.9 Hz, 1H), 1.51 (m, 2H), 1.24 (m, 2H).

Example 3.2: Preparation of Compound 2 ((S)—N-(3-(4-bromobenzo[d]oxazol-2-yl)-1-((1-cyanocyclopropyl)amino)-1-oxopropan-2-yl)-3-chlorobenzamide)

Figures 15, 16:
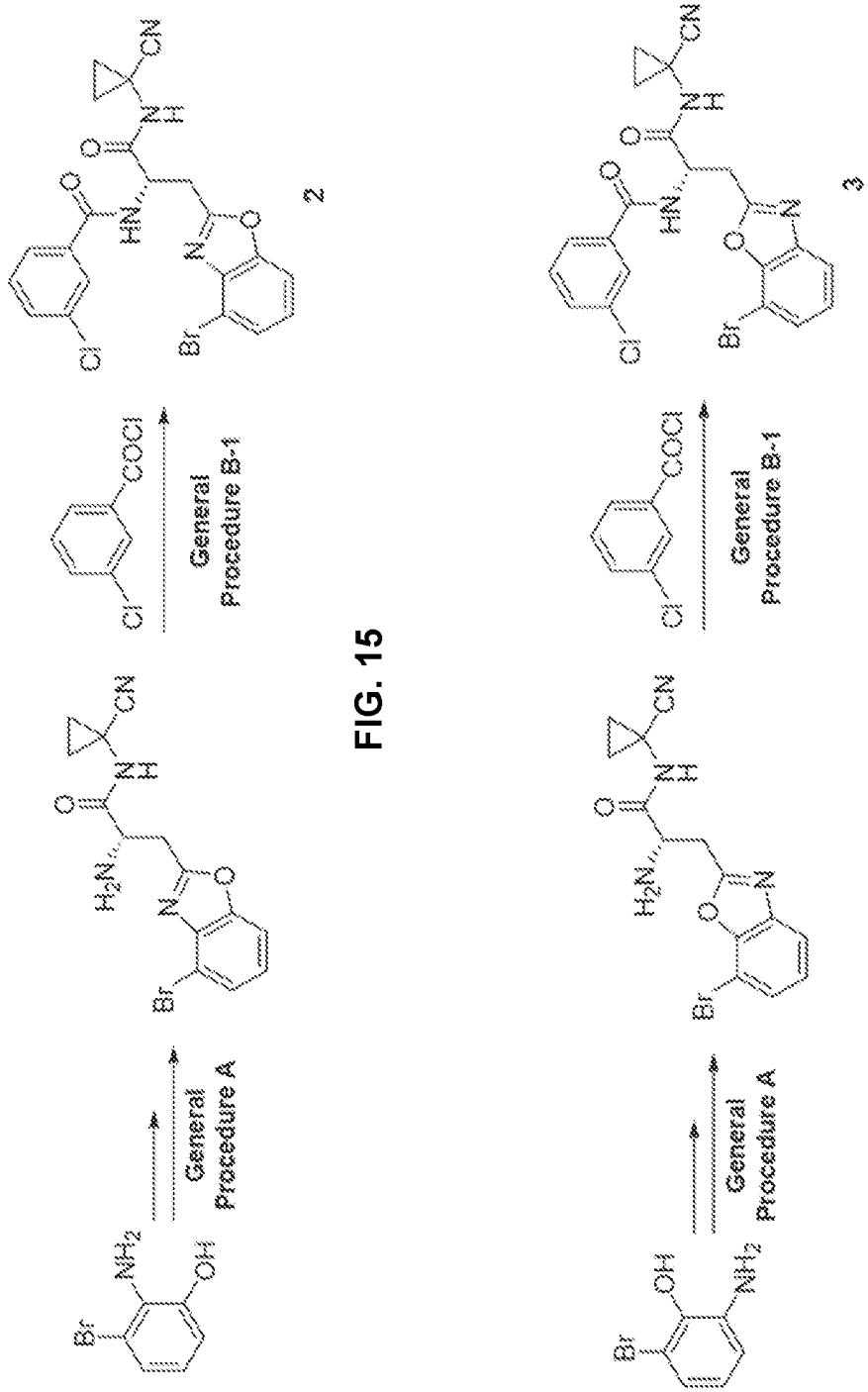
FIG. 15 is a schematic diagram illustrating an exemplary procedure for preparing Compound 2 according to some embodiments of the present disclosure.
FIG. 16 is a schematic diagram illustrating an exemplary procedure for preparing Compound 3 according to some embodiments of the present disclosure.

FIG. 15 is a schematic diagram illustrating an exemplary procedure for preparing Compound 2 according to some embodiments of the present disclosure.

Following general procedure A, from 2-amino-3-bromophenol, the (S)-2-amino-3-(4-bromobenzo[d]oxazol-2-yl)-N-(1-cyanocyclopropyl)propenamide was obtained as a yellow solid. Mass spectrometry was conducted on the resultant compound, and the test results are as follows: Mass(m/z): 349.02, 351.02 [M+H]$^+$ Following general procedure B-1, from (S)-2-amino-3-(4-bromobenzo[d]oxazol-2-yl)-N-(1-cyanocyclopropyl)propenamide (40 mg), the desired product Compound 2 was obtained as a white solid (4 mg, 7%). Mass spectrometry was conducted on the resultant compound, and the test results are as follows: Mass(m/z): 487.01, 489.01 [M+H]$^+$. 1H NMR (400 MHz, DMSO-d$_6$) δ 9.09 (s, 1H), 9.03 (d, J=7.9 Hz, 1H), 7.85 (t, J=1.8 Hz, 1H), 7.76-7.71 (m, 1H), 7.64 (dd, J=7.9, 0.9 Hz, 1H), 7.60-7.52 (m, 2H), 7.47 (t, J=7.9 Hz, 1H), 7.25 (t, J=8.0 Hz, 1H), 4.96-4.89 (m, 1H), 3.49 (dd, J=15.6, 5.6 Hz, 1H), 3.36 (d, J=8.9 Hz, 1H), 1.44 (m, 2H), 1.08 (m, 2H).

Example 3.3: Preparation of Compound 3 ((S)—N-(3-(7-bromobenzo[d]oxazol-2-yl)-1-((1-cyanocyclopropyl)amino)-1-oxopropan-2-yl)-3-chlorobenzamide)

FIG. 16 is a schematic diagram illustrating an exemplary procedure for preparing Compound 3 according to some embodiments of the present disclosure.

Following general procedure A, from 2-amino-6-bromophenol, the (S)-2-amino-3-(7-bromobenzo[d]oxazol-2-yl)-N-(1-cyanocyclopropyl)propenamide was obtained as a yellow solid. Mass spectrometry was conducted on the resultant compound, and the test results are as follows: Mass(m/z): 349.1 [M+H]$^+$ Following general procedure B-1, from 2-amino-6-bromo-phenol, the (S)-2-amino-3-(7-bromobenzo[d]oxazol-2-yl)-N-(1-cyanocyclopropyl)propenamide (35 mg), the desired product Compound 3 was obtained as a white solid (17.2 mg, 35%). Mass spectrometry was conducted on the resultant compound, and the test results are as follows: Mass(m/z): 486.8 [M+H]$^+$. $^1$H NMR (400 MHz, DMSO-d$_6$) δ 9.11 (s, 1H), 9.05 (d, J=7.9 Hz, 1H), 7.90 (t, J=1.8 Hz, 1H), 7.79 (d, J=7.8 Hz, 1H), 7.67 (m, 1H), 7.61 (m, 2H), 7.51 (t, J=7.9 Hz, 1H), 7.29 (t, J=8.0 Hz, 1H), 4.97 (td, J=8.5, 5.6 Hz, 1H), 3.54 (dd, J=15.6, 5.5 Hz, 1H), 3.39 (dd, J=12.5, 5.7 Hz, 1H), 1.48 (m, 2H), 1.13 (m, 2H).

Example 3.4: Preparation of Compound 4 ((S)-3-chloro-N-(1-((1-cyanocyclopropyl)amino)-3-(6-fluorobenzo[d]oxazol-2-yl)-1-oxopropan-2-yl)benzamide)

Figure 17:
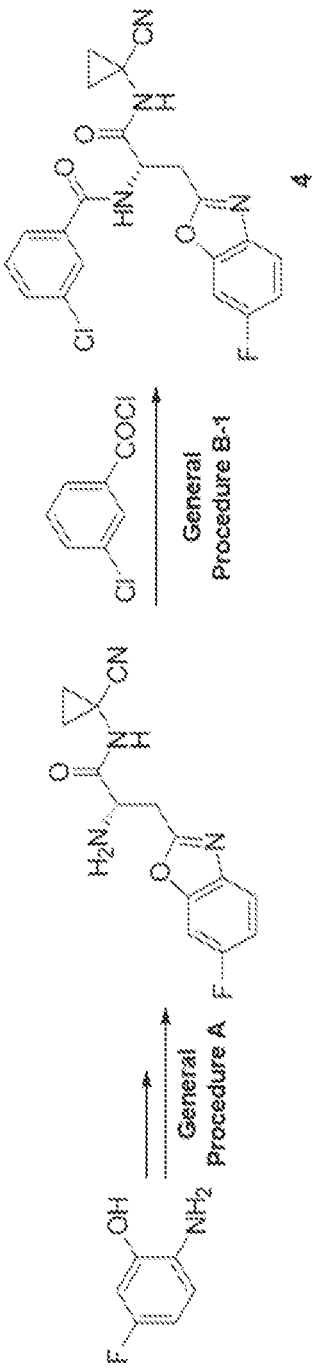
FIG. 17 is a schematic diagram illustrating an exemplary procedure for preparing Compound 4 according to some embodiments of the present disclosure.

FIG. 17 is a schematic diagram illustrating an exemplary procedure for preparing Compound 4 according to some embodiments of the present disclosure.

Following general procedure A, from 2-amino-5-fluorophenol, the (S)-2-amino-N-(1-cyanocyclopropyl)-3-(6-fluorobenzo[d]oxazol-2-yl)propenamide was obtained as a yellow solid. Mass spectrometry was conducted on the resultant compound, and the test results are as follows: Mass(m/z): 289.0 [M+H]$^+$ Following general procedure B-1, from (S)-2-amino-N-(1-cyanocyclopropyl)-3-(6-fluorobenzo[d]oxazol-2-yl)propenamide (60 mg), the desired product Compound 4 was obtained as a white solid (20.2 mg, 23%). Mass spectrometry was conducted on the resultant compound, and the test results are as follows: Mass(m/z): 427.0 [M+H]$^+$. $^1$H NMR (400 MHz, DMSO-d$_6$) δ 9.10 (s, 1H), 9.04 (d, J=7.9 Hz, 1H), 7.89 (s, 1H), 7.78 (d, J=7.8 Hz, 1H), 7.66 (m, 3H), 7.50 (d, J=7.9 Hz, 1H), 7.24-7.18 (m, 1H), 4.95 (dd, J=14.0, 8.3 Hz, 1H), 3.48 (dd, J=15.6, 5.9 Hz, 2H), 1.46 (t, J=6.0 Hz, 2H), 1.13-1.03 (m, 2H).

Example 3.5: Preparation of Compound 5 ((S)-3-chloro-N-(3-(7-cyanobenzo[d]oxazol-2-yl)-1-((1-cyanocyclopropyl)amino)-1-oxopropan-2-yl)benzamide)

Figure 18:
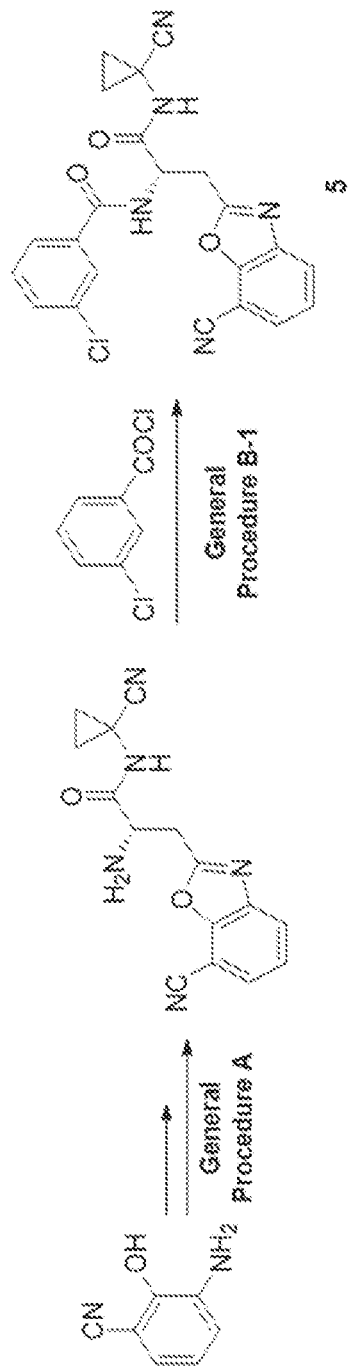
FIG. 18 is a schematic diagram illustrating an exemplary procedure for preparing Compound 5 according to some embodiments of the present disclosure.

FIG. 18 is a schematic diagram illustrating an exemplary procedure for preparing Compound 5 according to some embodiments of the present disclosure.

Following general procedure A, from 3-amino-2-hydroxybenzonitrile, the (S)-2-amino-3-(7-cyanobenzo[d]oxazol-2-yl)-N-(1-cyanocyclopropyl)propenamide was obtained as a light-yellow solid. Mass spectrometry was conducted on the resultant compound, and the test results are as follows: Mass(m/z): 296.0 [M+H]$^+$ Following general procedure B-1, from (S)-2-amino-3-(7-cyanobenzo[d]oxazol-2-yl)-N-(1-cyanocyclopropyl)propenamide (52 mg), the desired product Compound 5 was obtained as a white solid (12.5 mg, 16%). Mass spectrometry was conducted on the resultant compound, and the test results are as follows: Mass(m/z): 434.1 [M+H]$^+$. $^1$H NMR (400 MHz, DMSO-d$_6$) δ 9.09 (s, 1H), 9.04 (d, J=8.0 Hz, 1H), 8.02 (dd, J=8.0, 1.0 Hz, 1H), 7.87-7.80 (m, 2H), 7.74 (m, 1H), 7.62-7.56 (m, 1H), 7.48 (m, 2H), 4.95 (td, J=8.4, 5.8 Hz, 1H), 3.54 (dd, J=15.5, 5.8 Hz, 1H), 3.39 (dd, J=15.5, 8.7 Hz, 1H), 1.48-1.36 (m, 2H), 1.15-0.98 (m, 2H).

Example 3.6: Preparation of Compound 6 ((S)-3-chloro-N-(3-(7-chlorobenzo[d]oxazol-2-yl)-1-((1-cyanocyclopropyl)amino)-1-oxopropan-2-yl)benzamide)

Figure 19:
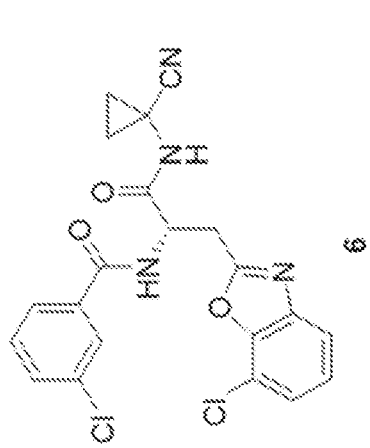
FIG. 19 is a schematic diagram illustrating an exemplary procedure for preparing Compound 6 according to some embodiments of the present disclosure.
Figure 19:
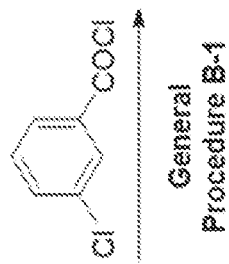
Figure 19:
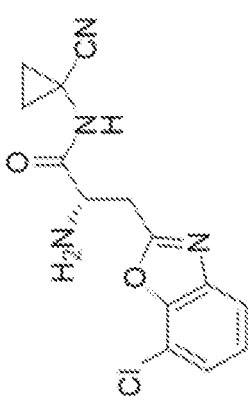
Figure 19:
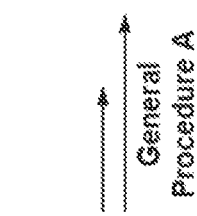
Figure 19:
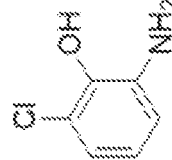

FIG. 19 is a schematic diagram illustrating an exemplary procedure for preparing Compound 6 according to some embodiments of the present disclosure.

Following general procedure A, from 2-amino-6-chlorophenol, the (S)-2-amino-3-(7-chlorobenzo[d]oxazol-2-yl)-N-(1-cyanocyclopropyl)propenamide was obtained as a yellow solid. Mass spectrometry was conducted on the resultant compound, and the test results are as follows: Mass(m/z): 305.0 [M+H]$^+$ Following general procedure B-1, from (S)-2-amino-3-(7-chlorobenzo[d]oxazol-2-yl)-N-(1-cyanocyclopropyl)propenamide (58 mg), the desired product Compound 6 was obtained as a white solid (68.9 mg, 82%). Mass spectrometry was conducted on the resultant compound, and the test results are as follows: Mass(m/z): 443.0 [M+H]$^+$. $^1$H NMR (400 MHz, DMSO-d$_6$) δ 9.11 (s, 1H), 9.06 (d, J=7.9 Hz, 1H), 7.89 (t, J=1.9 Hz, 1H), 7.79-7.77 (m, 1H), 7.67-7.64 (m, 1H), 7.64-7.61 (m, 1H), 7.51 (t, J=7.9 Hz, 1H), 7.48-7.46 (m, 1H), 7.35 (t, J=8.0 Hz, 1H), 5.01-4.90 (m, 1H), 3.58-3.49 (m, 1H), 3.45-3.36 (m, 1H), 1.52-1.41 (m, 2H), 1.20-1.05 (m, 2H).

Example 3.7: Preparation of Compound 7 ((S)-3-chloro-N-(3-(4-chlorobenzo[d]oxazol-2-yl)-1-((1-cyanocyclopropyl)amino)-1-oxopropan-2-yl)benzamide)

Figure 20:
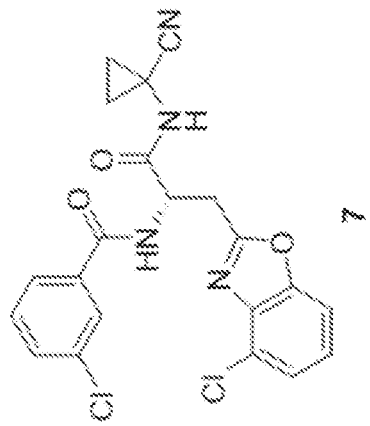
FIG. 20 is a schematic diagram illustrating an exemplary procedure for preparing Compound 7 according to some embodiments of the present disclosure.
Figure 20:
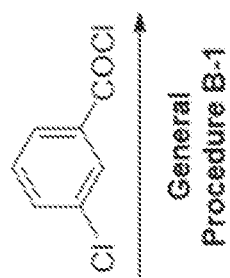
Figure 20:
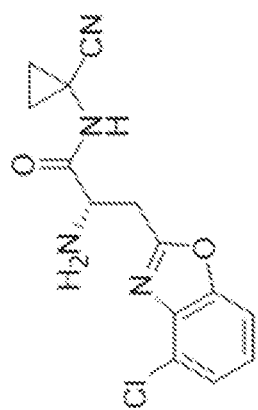
Figure 20:
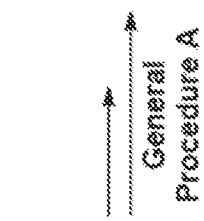
Figure 20:
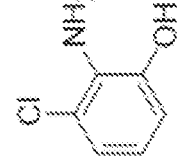

FIG. 20 is a schematic diagram illustrating an exemplary procedure for preparing Compound 7 according to some embodiments of the present disclosure.

Following general procedure A, from 2-amino-3-chlorophenol, the (S)-2-amino-3-(4-chlorobenzo[d]oxazol-2-yl)-N-(1-cyanocyclopropyl)propenamide was obtained as a light-yellow solid. Mass spectrometry was conducted on the resultant compound, and the test results are as follows: Mass(m/z): 305.0 [M+H]$^+$ Following general procedure B-1, from (S)-2-amino-3-(4-chlorobenzo[d]oxazol-2-yl)-N-(1-cyanocyclopropyl)propanamide (50 mg), the desired product Compound 7 was obtained as a white solid (29 mg, 40%). Mass spectrometry was conducted on the resultant compound, and the test results are as follows: Mass(m/z): 443.0 [M+H]$^+$. $^1$H NMR (400 MHz, DMSO-d$_6$) δ 9.11 (s, 1H), 9.06 (d, J=8.0 Hz, 1H), 7.89 (t, J=1.7 Hz, 1H), 7.78 (d, J=7.8 Hz, 1H), 7.64 (m, 2H), 7.51 (t, J=7.9 Hz, 1H), 7.44 (dd, J=8.0, 0.9 Hz, 1H), 7.38 (t, J=8.0 Hz, 1H), 4.97 (dd, J=14.2, 8.1 Hz, 1H), 3.57-3.50 (m, 1H), 3.42-3.36 (m, 1H), 1.46 (m, 2H), 1.17-1.04 (m, 2H).

Example 3.8: Preparation of Compound 8 ((S)-3-chloro-N-(3-(5-chlorobenzo[d]oxazol-2-yl)-1-((1-cyanocyclopropyl)amino)-1-oxopropan-2-yl)benzamide)

Figure 21:
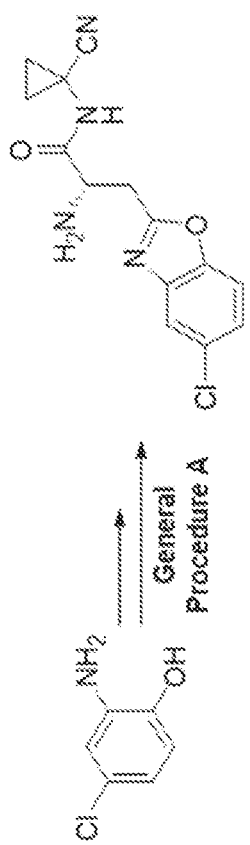
FIG. 21 is a schematic diagram illustrating an exemplary procedure for preparing Compound 8 according to some embodiments of the present disclosure.
Figure 21:
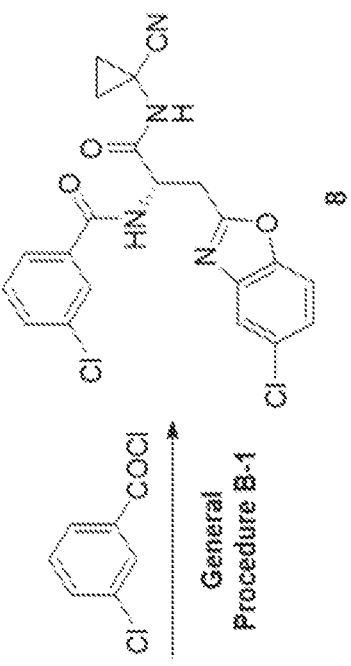

FIG. 21 is a schematic diagram illustrating an exemplary procedure for preparing Compound 8 according to some embodiments of the present disclosure.

Following general procedure A, from 2-amino-4-chlorophenol, the (S)-2-amino-3-(5-chlorobenzo[d]oxazol-2-yl)-N-(1-cyanocyclopropyl)propenamide was obtained as a light-yellow solid. Mass spectrometry was conducted on the resultant compound, and the test results are as follows: Mass(m/z): 305.0 [M+H]$^+$ Following general procedure B-1, from (S)-2-amino-3-(5-chlorobenzo[d]oxazol-2-yl)-N-(1-cyanocyclopropyl)propanamide (60 mg), the desired product Compound 8 was obtained as a white solid (28.9 mg, 33%). Mass spectrometry was conducted on the resultant compound, and the test results are as follows: Mass(m/z): 442.9 [M+H]$^+$. $^1$H NMR (400 MHz, DMSO-d$_6$) δ 9.14 (s, 1H), 9.08 (d, J=7.9 Hz, 1H), 7.92-7.86 (m, 1H), 7.79 (dd, J=4.9, 2.7 Hz, 2H), 7.71 (d, J=8.7 Hz, 1H), 7.62 (dd, J=8.0, 1.1 Hz, 1H), 7.52 (q, J=7.5 Hz, 1H), 7.41 (dd, J=8.7, 2.1 Hz, 1H), 5.04-4.89 (m, 1H), 3.50 (m, 1H), 3.39 (d, J=8.7 Hz, 1H), 1.53-1.41 (m, 2H), 1.17-1.02 (m, 2H).

Example 3.9: Preparation of Compound 9 ((S)-3-chloro-N-(3-(6-chlorobenzo[d]oxazol-2-yl)-1-((1-cyanocyclopropyl)amino)-1-oxopropan-2-yl)benzamide)

Figure 22:
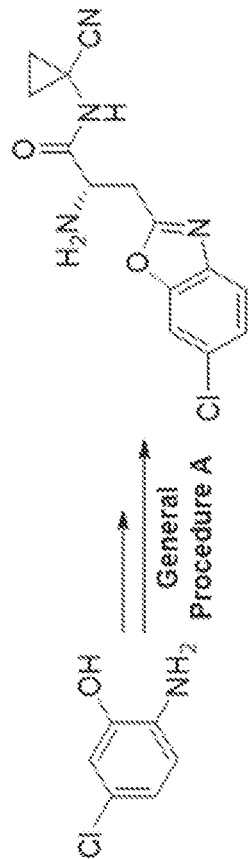
FIG. 22 is a schematic diagram illustrating an exemplary procedure for preparing Compound 9 according to some embodiments of the present disclosure.
Figure 22:
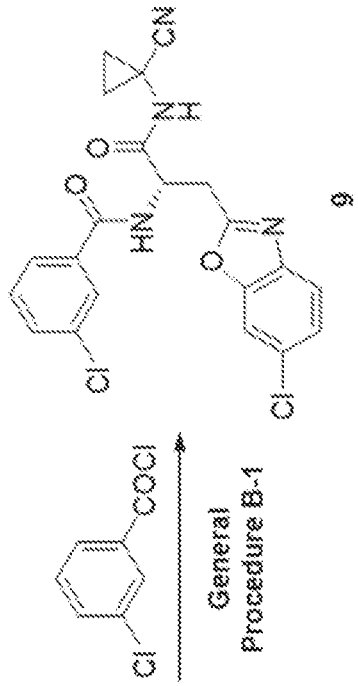

FIG. 22 is a schematic diagram illustrating an exemplary procedure for preparing Compound 9 according to some embodiments of the present disclosure.

Following general procedure A, from 2-amino-5-chlorophenol, the (S)-2-amino-3-(6-chlorobenzo[d]oxazol-2-yl)-N-(1-cyanocyclopropyl)propenamide was obtained as a light-yellow solid. Mass spectrometry was conducted on the resultant compound, and the test results are as follows: Mass(m/z): 305.0 [M+H]$^+$ Following general procedure B-1, from (S)-2-amino-3-(6-chlorobenzo[d]oxazol-2-yl)-N-(1-cyanocyclopropyl)propenamide (55 mg), the desired product Compound 9 was obtained as a white solid (30.1 mg, 42%). Mass spectrometry was conducted on the resultant compound, and the test results are as follows: Mass(m/z): 442.9 [M+H]$^+$. $^1$H NMR (400 MHz, DMSO-d$_6$) δ 9.10 (s, 1H), 9.04 (d, J=7.9 Hz, 1H), 7.88 (m, 2H), 7.78 (d, J=7.8 Hz, 1H), 7.68 (d, J=8.5 Hz, 1H), 7.62 (m, 1H), 7.51 (t, J=7.9 Hz, 1H), 7.39 (dd, J=8.5, 1.9 Hz, 1H), 4.96 (dd, J=14.0, 8.2 Hz, 1H), 3.50 (dd, J=15.6, 5.9 Hz, 1H), 3.37 (d, J=8.7 Hz, 1H), 1.46 (m, 2H), 1.09 (m, 2H).

Example 3.10: Preparation of Compound 10 ((S)-3-chloro-N-(1-((1-cyanocyclopropyl)amino)-1-oxo-3-(5-(trifluoromethyl)benzo[d]oxazol-2-yl)propan-2-yl)benzamide)

Figure 23:
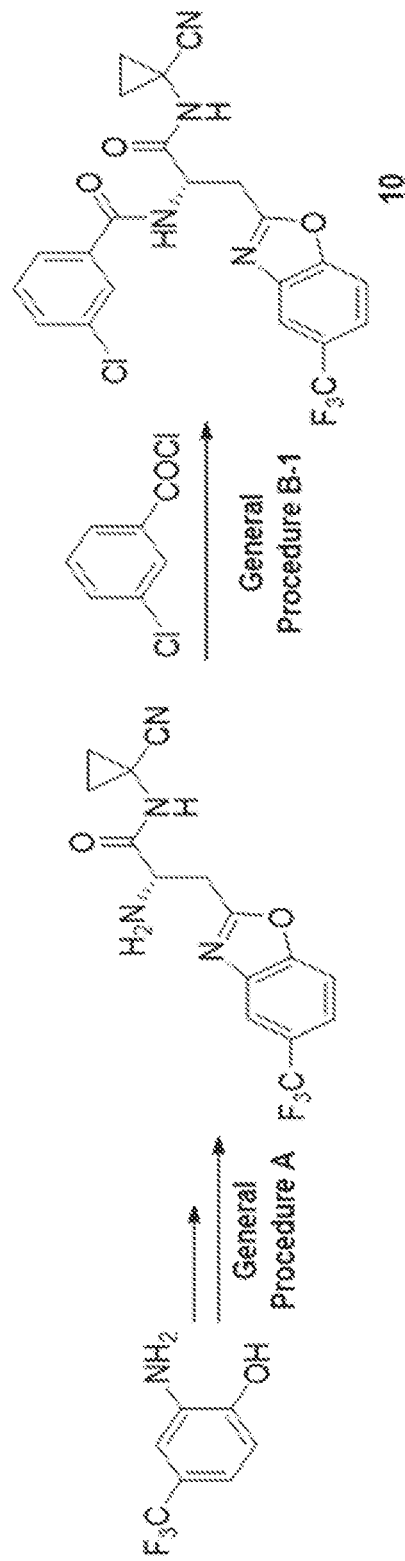
FIG. 23 is a schematic diagram illustrating an exemplary procedure for preparing Compound 10 according to some embodiments of the present disclosure.

FIG. 23 is a schematic diagram illustrating an exemplary procedure for preparing Compound 10 according to some embodiments of the present disclosure.

Following general procedure A, from 2-amino-4-trifluoromethyl-phenol, the (S)-2-amino-N-(1-cyanocyclopropyl)-3-(5-(trifluoromethyl)benzo[d]oxazol-2-yl)propanamide was obtained as a light-yellow solid. Mass spectrometry was conducted on the resultant compound, and the test results are as follows: Mass(m/z): 339.0 [M+H]$^+$ Following general procedure B-1, from (S)-2-amino-N-(1-cyanocyclopropyl)-3-(5-(trifluoromethyl)benzo[d]oxazol-2-yl)propanamide (60 mg), the desired product Compound 10 was obtained as a white solid (30.8 mg, 36%). Mass spectrometry was conducted on the resultant compound, and the test results are as follows: Mass(m/z): 477.0 [M+H]$^+$. $^1$H NMR (400 MHz, DMSO-d$_6$) δ 9.07 (s, 1H), 9.02 (d, J=7.8 Hz, 1H), 8.08-8.04 (m, 1H), 7.89-7.83 (m, 2H), 7.73 (dd, J=6.8, 5.4 Hz, 2H), 7.62-7.56 (m, 1H), 7.47 (t, J=7.9 Hz, 1H), 4.96 (td, J=8.3, 5.9 Hz, 1H), 3.55-3.32 (m, 2H), 1.43 (m, 2H), 1.06 (m, 2H).

Example 3.11: Preparation of Compound 11 ((S)-3-chloro-N-(1-((1-cyanocyclopropyl)amino)-1-oxo-3-(6-(trifluoromethyl)benzo[d]oxazol-2-yl)propan-2-yl)benzamide)

Figure 24:
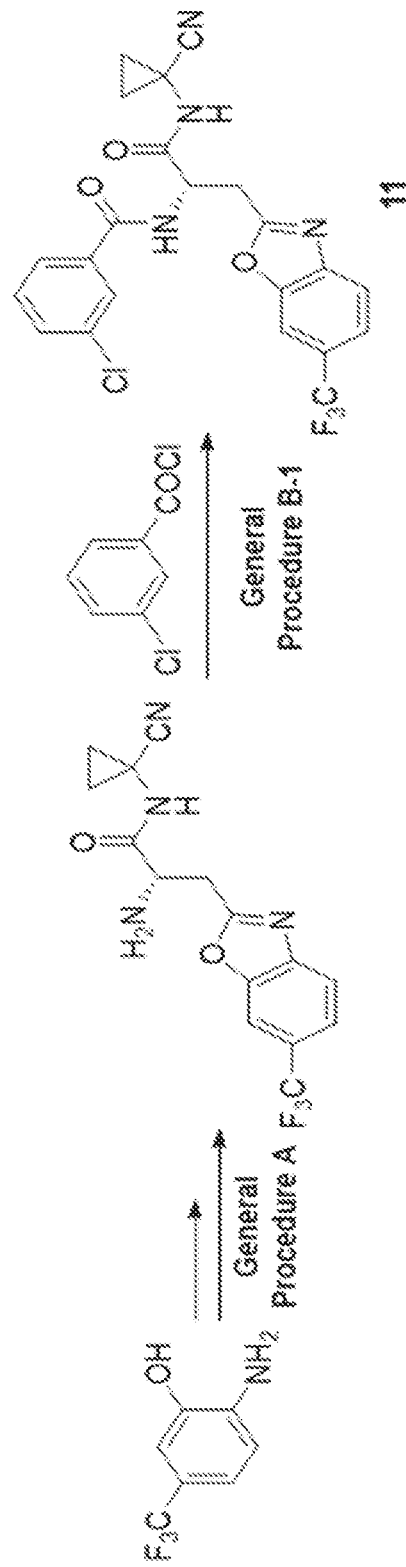
FIG. 24 is a schematic diagram illustrating an exemplary procedure for preparing Compound 11 according to some embodiments of the present disclosure.

FIG. 24 is a schematic diagram illustrating an exemplary procedure for preparing Compound 11 according to some embodiments of the present disclosure.

Following general procedure A, from 2-amino-5-trifluoromethyl-phenol, the (S)-2-amino-N-(1-cyanocyclopropyl)-3-(6-(trifluoromethyl)benzo[d]oxazol-2-yl)propanamide was obtained as a light-yellow solid. Mass spectrometry was conducted on the resultant compound, and the test results are as follows: Mass(m/z): 339.0 [M+H]$^+$ Following general procedure B-1, from (S)-2-amino-N-(1-cyanocyclopropyl)-3-(6-(trifluoromethyl)benzo[d]oxazol-2-yl)propanamide (35 mg), the desired product Compound 11 was obtained as a white solid (25 mg, 51%). Mass spectrometry was conducted on the resultant compound, and the test results are as follows: Mass(m/z): 477.0 [M+H]$^+$. $^1$H NMR (400 MHz, DMSO-d$_6$) δ 9.08 (s, 1H), 9.03 (d, J=7.9 Hz, 1H), 8.16-8.10 (m, 1H), 7.84 (m, 2H), 7.76-7.71 (m, 1H), 7.67 (m, 1H), 7.58 (m, 1H), 7.47 (t, J=7.9 Hz, 1H), 4.96 (td, J=8.3, 6.0 Hz, 1H), 3.52 (m, 1H), 3.41-3.32 (m, 1H), 1.47-1.34 (m, 2H), 1.13-1.05 (m, 2H).

Example 3.12: Preparation of Compound 12 ((S)-3-chloro-N-(1-((1-cyanocyclopropyl)amino)-1-oxo-3-(7-(trifluoromethyl)benzo[d]oxazol-2-yl)propan-2-yl)benzamide)

Figure 25:
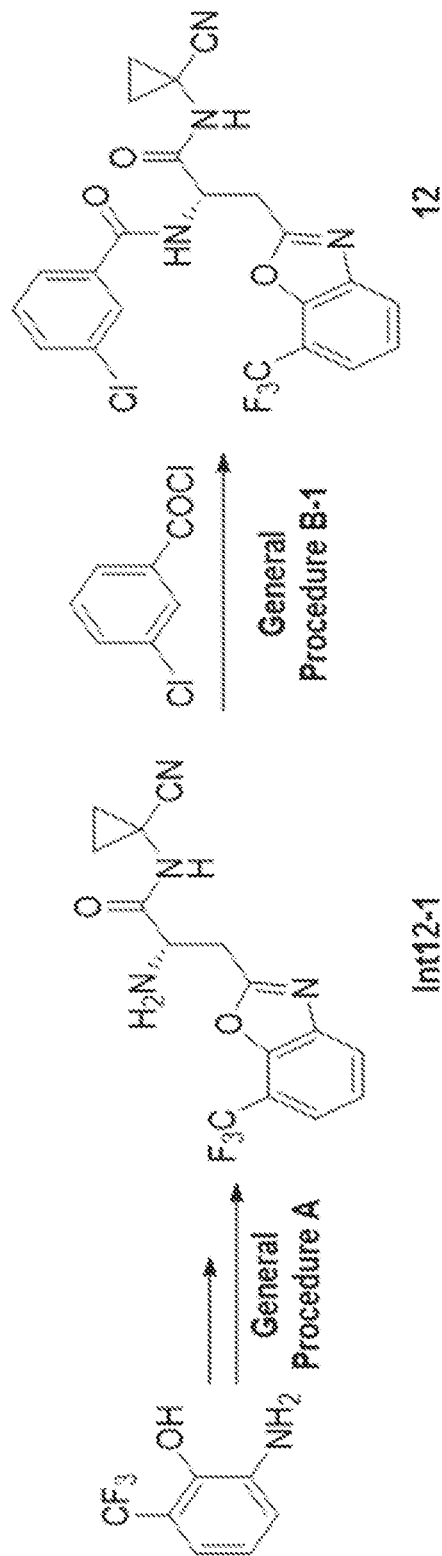
FIG. 25 is a schematic diagram illustrating an exemplary procedure for preparing Compound 12 according to some embodiments of the present disclosure.

FIG. 25 is a schematic diagram illustrating an exemplary procedure for preparing Compound 12 according to some embodiments of the present disclosure.

Following general procedure A, from 2-amino-6-trifluoromethyl-phenol, the (S)-2-amino-N-(1-cyanocyclopropyl)-3-(7-(trifluoromethyl)benzo[d]oxazol-2-yl)propanamide was obtained as a light-yellow solid. Mass spectrometry was conducted on the resultant compound, and the test results are as follows: Mass(m/z): 339.0 [M+H]$^+$.

Following general procedure B-1, from (S)-2-amino-N-(1-cyanocyclopropyl)-3-(7-(trifluoromethyl)benzo[d]oxazol-2-yl)propanamide (60 mg), the desired product Compound 12 was obtained as a white solid (35.4 mg, 42%). Mass spectrometry was conducted on the resultant compound, and the test results are as follows: Mass(m/z): 476.9 [M+H]$^+$. $^1$H NMR (400 MHz, DMSO-d$_6$) δ 9.11 (s, 1H), 9.05 (d, J=8.0 Hz, 1H), 8.01 (d, J=7.8 Hz, 1H), 7.87 (d, J=1.8 Hz, 1H), 7.74 (m, 2H), 7.65-7.59 (m, 1H), 7.52 (m, 2H), 4.99

(dd, J=13.5, 8.7 Hz, 1H), 3.58 (dd, J=15.7, 5.4 Hz, 1H), 3.41 (dd, J=15.7, 9.0 Hz, 1H), 1.48 (m, 2H), 1.14 (m, 2H).

Example 3.13: Preparation of Compound 13 ((S)—N-(3-(benzo[d]oxazol-2-yl)-1-((1-cyanocyclopropyl)amino)-1-oxopropan-2-yl)-3-(tert-butyl)-1-methyl-1H-pyrazole-5-carboxamide)

Figure 26:
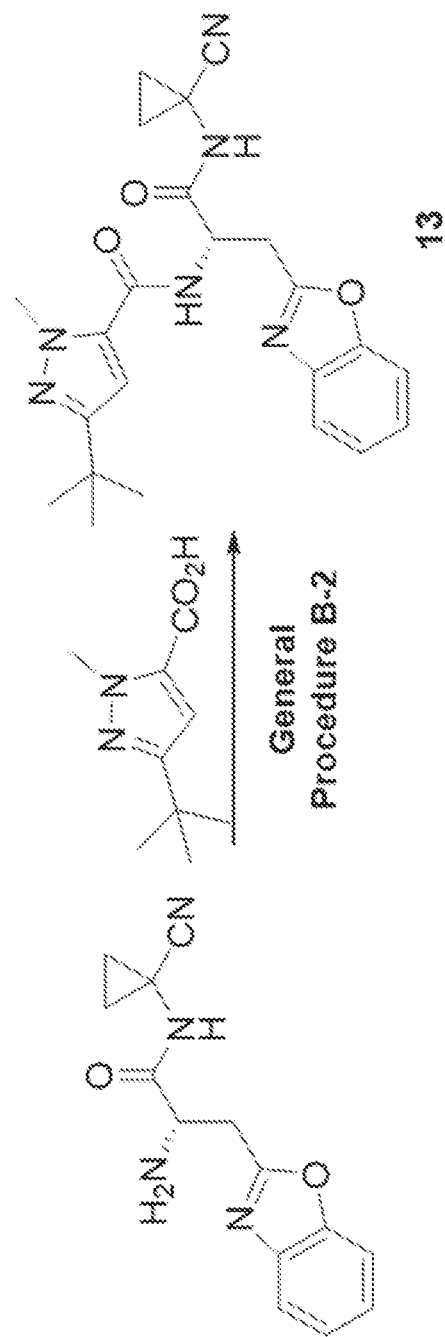
FIG. 26 is a schematic diagram illustrating an exemplary procedure for preparing Compound 13 according to some embodiments of the present disclosure.

FIG. 26 is a schematic diagram illustrating an exemplary procedure for preparing Compound 13 according to some embodiments of the present disclosure.

Following general procedure B-2, from (S)-2-amino-3-(benzo[d]oxazol-2-yl)-N-(1-cyanocyclopropyl)propenamide (50 mg), the desired product Compound 13 was purified by prep-HPLC [(Gemini-C18, 150×21.2 mm, Sum; ACN-H$_2$O (0.1% FA); 15%-80%)] and obtained as a white solid (15 mg, 19%). Mass spectrometry was conducted on the resultant compound, and the test results are as follows: Mass(m/z): 435.1 [M+H]$^+$. $^1$H NMR (400 MHz, CDCl$_3$) δ 8.19 (s, 1H), 7.99 (d, J=6.9 Hz, 1H), 7.67 (m, 1H), 7.54 (s, 1H), 7.38 (m, 2H), 6.55 (s, 1H), 5.06 (td, J=7.2, 4.0 Hz, 1H), 4.13 (s, 3H), 3.68 (dd, J=16.9, 3.9 Hz, 1H), 3.32 (dd, J=16.9, 7.4 Hz, 1H), 1.55 (s, 2H), 1.34 (d, J=7.1 Hz, 9H), 1.22 (m, 2H).

Example 3.14: Preparation of Compound 14 ((S)—N-(3-(benzo[d]oxazol-2-yl)-1-((1-cyanocyclopropyl)amino)-1-oxopropan-2-yl)-6-methylpicolinamide)

Figure 27:
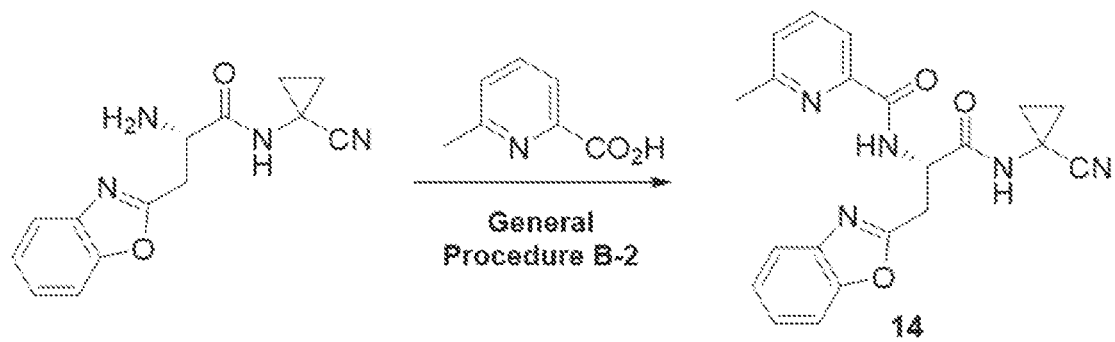
FIG. 27 is a schematic diagram illustrating an exemplary procedure for preparing Compound 14 according to some embodiments of the present disclosure.

FIG. 27 is a schematic diagram illustrating an exemplary procedure for preparing Compound 14 according to some embodiments of the present disclosure.

Following general procedure B-2, from (S)-2-amino-3-(benzo[d]oxazol-2-yl)-N-(1-cyanocyclopropyl)propenamide (50 mg), the desired product Compound 14 was purified by prep-HPLC [(Gemini-C18, 150×21.2 mm, Sum; ACN-H$_2$O (0.1% FA); 15%-80%)] and obtained as a white solid (6.1 mg, 9%). Mass spectrometry was conducted on the resultant compound, and the test results are as follows: Mass(m/z): 390.1 [M+H]$^+$. $^1$H NMR (400 MHz, DMSO-d$_6$) δ 9.18 (s, 1H), 8.97 (d, J=8.3 Hz, 1H), 7.84 (t, J=7.6 Hz, 1H), 7.78 (d, J=7.3 Hz, 1H), 7.62 (m, 2H), 7.45 (d, J=7.5 Hz, 1H), 7.35-7.26 (m, 2H), 4.95 (dd, J=14.5, 6.4 Hz, 1H), 3.52-3.39 (m, 2H), 2.52 (s, 3H), 1.47-1.38 (m, 2H), 1.11-0.99 (m, 2H).

Example 3.15: Preparation of Compound 15 ((S)—N-(3-(benzo[d]oxazol-2-yl)-1-((cyanomethyl)amino)-1-oxopropan-2-yl)-1,3-dicyclopropyl-1H-pyrazole-5-carboxamide)

Figure 28:
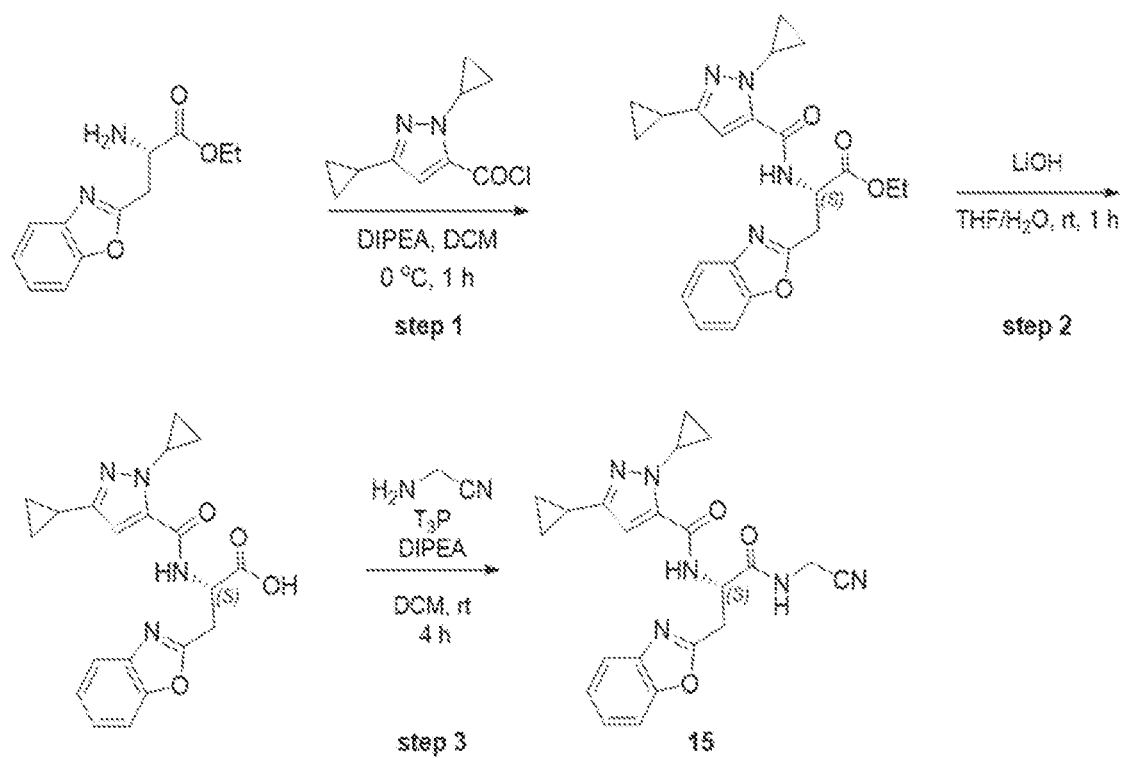
FIG. 28 is a schematic diagram illustrating an exemplary procedure for preparing Compound 15 according to some embodiments of the present disclosure.

FIG. 28 is a schematic diagram illustrating an exemplary procedure for preparing Compound 15 according to some embodiments of the present disclosure.

Step 1. Preparation of ethyl (S)-3-(benzo[d]oxazol-2-yl)-2-(1,3-dicyclopropyl-1H-pyrazole-5-carboxamido) propanoate To a solution of 1,3-dicyclopropyl-1H-pyrazole-5-carbonyl chloride (150 mg, 0.73 mmol) and ethyl (2S)-2-amino-3-(1,3-benzoxazol-2-yl) propanoate (170 mg, 0.73 mmol) in DCM (30 mL) was added DIPEA (282 mg, 2.2 mmol). The reaction mixture was stirred at 0° C. for 1 hour. The solvent was removed under reduced pressure and the residue was purified by Prep-Thin Layer Chromatography (TLC) (PE/EA=3/1) to give the product (170 mg, 56%) as a white solid. Mass spectrometry was conducted on the resultant compound, and the test results are as follows: Mass(m/z): 408.9 [M+H]$^+$.

Step 2. Preparation of (S)-3-(benzo[d]oxazol-2-yl)-2-(1,3-dicyclopropyl-1H-pyrazole-5 carboxamido) propanoic acid To a solution of ethyl (S)-3-(benzo[d]oxazol-2-yl)-2-(1,3-dicyclopropyl-1H-pyrazole-5-carboxamido) propanoate (170 mg, 0.42 mmol) in THF/H$_2$O (5:1, 12 mL) was added LiOH.H$_2$O (175 mg, 4.2 mmol). The reaction mixture was stirred at rt for 1 hour. The reaction solution was adjusted pH to 5-6 by using 1 N aq. HCl. Then the mixture was extracted with EA (20 mL×2). The combined organic layer was washed with brine (10 mL), then dried over with anhydrous Na$_2$SO$_4$. The mixture was filtered, the filtrate was concentrated under vacuum to give the desired product (150 mg, 90%) as yellow oil. Mass spectrometry was conducted on the resultant compound, and the test results are as follows: Mass(m/z): 381.2 [M+H]$^+$.

Step 3. Preparation of (S)—N-(3-(benzo[d]oxazol-2-yl)-1-((cyanomethyl)amino)-1-oxopropan-2-yl)-1,3-dicyclopropyl-1H-pyrazole-5-carboxamide To a solution of (S)-3-(benzo[d]oxazol-2-yl)-2-(1,3-dicyclopropyl-1H-pyrazole-5-carboxamido) propanoic acid (150 mg, 0.39 mmol) and 2-aminoacetonitrile hydrochloride (40 mg, 0.44 mmol) in DCM (15 mL) was added DIPEA (255 mg, 2.0 mmol). After stirring for 10 min at 0° C., T3P (50% in EA, 753 mg, 1.2 mmol) was added and the mixture was stirred at rt for 4 hrs. The solvent was removed under reduced pressure and the residue was purified by Combi-flash (PE/EA=0~ 50%) to give the desired product Compound 15 (35.7 mg, 22%) as a white solid. Mass spectrometry was conducted on the resultant compound, and the test results are as follows: Mass(m/z): 419.2 [M+H]$^+$. $^1$H NMR (400 MHz, DMSO-d$_6$) δ 8.89-8.75 (m, 2H), 7.73-7.62 (m, 2H), 7.43-7.28 (m, 2H), 6.47 (s, 1H), 5.10-5.01 (m, 1H), 4.28-4.13 (m, 3H), 3.54 (dd, J=15.6, 5.2 Hz, 1H), 3.37 (s, 1H), 3.30 (s, 1H), 1.86-1.77 (m, 1H), 1.03-0.76 (m, 6H), 0.59-0.50 (m, 2H).

Example 3.16: Preparation of Compound 16 ((S)—N-(3-(benzo[d]oxazol-2-yl)-1-((1-cyanocyclopropyl)amino)-1-oxopropan-2-yl)-1-cyclopropyl-3-methyl-1H-pyrazole-4-carboxamide)

Figure 29:
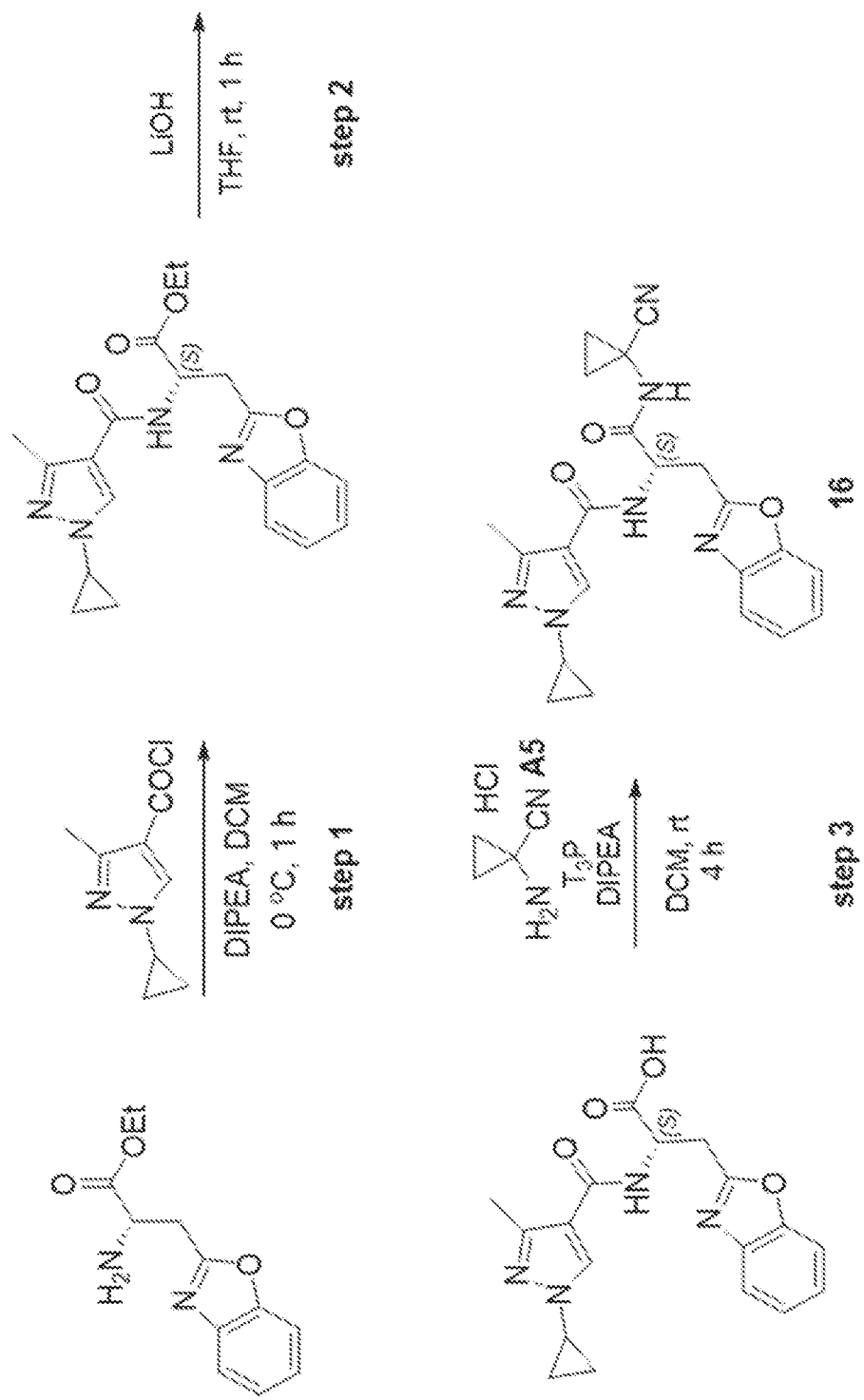
FIG. 29 is a schematic diagram illustrating an exemplary procedure for preparing Compound 16 according to some embodiments of the present disclosure.

FIG. 29 is a schematic diagram illustrating an exemplary procedure for preparing Compound 16 according to some embodiments of the present disclosure.

Step 1. Preparation of ethyl (S)-3-(benzo[d]oxazol-2-yl)-2-(1-cyclopropyl-3-methyl-1H-pyrazole-4-carboxamido) propanoate To a solution of ethyl (S)-2-amino-3-(benzo[d]oxazol-2-yl)propanoate (190 mg, 0.81 mmol) and DIPEA (410 mg, 4.06 mmol) in DCM (5 mL) was added 1-cyclopropyl-3-methyl-1H-pyrazole-4-carbonyl chloride (150 mg, 0.81 mmol). The reaction mixture was stirred at 25° C. for 16 hrs. The mixture was concentrated under reduced pressure to give the crude product as yellow oil (210 mg, 54%). Mass spectrometry was conducted on the resultant compound, and the test results are as follows: Mass(m/z): 383.1 [M+H]$^+$.

Step 2. Preparation of (S)-3-(benzo[d]oxazol-2-yl)-2-(1-cyclopropyl-3-methyl-1H-pyrazole-4-carboxamido)propanoic acid A solution of ethyl (S)-3-(benzo[d]oxazol-2-yl)-2-(1-cyclopropyl-3-methyl-1H-pyrazole-4-carboxamido)propanoate (230 mg, 0.6 mmol) in THF (2 mL) and 1 N aq.LiOH (2 mL) was stirred at 25° C. for 2 hours. After completion, the mixture was concentrated under vacuum. The residue was dissolved in water (10 mL), adjusted pH to 7 with 1N aq. HCl, and extracted with ethyl acetate (10 mL×2). The combined organic layer was washed with brine (10 mL), dried over $Na_2SO_4$, filtered, and concentrated under vacuum to give the desired product as yellow oil (140 mg, 52.56%). Mass spectrometry was conducted on the resultant compound, and the test results are as follows: Mass(m/z): 355.1 [M+H]$^+$.

Step 3. Preparation of (S)—N-(3-(benzo[d]oxazol-2-yl)-1-((1-cyanocyclopropyl)amino)-1-oxopropan-2-yl)-1-cyclopropyl-3-methyl-1H-pyrazole-4-carboxamide A solution of (S)-3-(benzo[d]oxazol-2-yl)-2-(1-cyclopropyl-3-methyl-1H-pyrazole-4-carboxamido)propanoic acid (140 mg, 0.39 mmol), 1-aminocyclopropane-1-carbonitrile (70 mg, 0.59 mmol), T3P (50% in EA, 754 mg, 2.37 mmol), and DIPEA (255 mg, 1.97 mmol) in DCM (5 mL) was stirred at 25° C. for 16 hours. The residue was diluted with NaHCO$_3$(10 mL) and extracted with DCM (10 mL×2). The combined organic layer was washed with brine (10 mL), dried over $Na_2SO_4$, filtered, and concentrated under vacuum, and the residue was purified by Prep-HPLC [Gemini-C18, 150×21.2 mm, 5um; ACN-H$_2$O (0.1% TFA), 30-50] to give the desired product Compound 16 as a white solid (38.4 mg, 22%). Mass spectrometry was conducted on the resultant compound, and the test results are as follows: Mass(m/z): 419.1 [M+H]$^+$. $^1$HNMR (400 MHz, DMSO-d$_6$) δ 8.05 (s, 1H), 7.67-7.46 (m, 2H), 7.45-7.30 (m, 2H), 4.98 (dd, J=7.8, 6.2 Hz, 1H), 3.62-3.46 (m, 2H), 3.37 (dd, J=15.4, 7.8 Hz, 1H), 3.28 (dt, J=3.2, 1.6 Hz, 3H), 1.44 (dd, J=6.2, 3.4 Hz, 2H), 1.15 (dd, J=18.2, 1.6 Hz, 2H), 1.02-0.99 (m, 4H).

Figure 30:
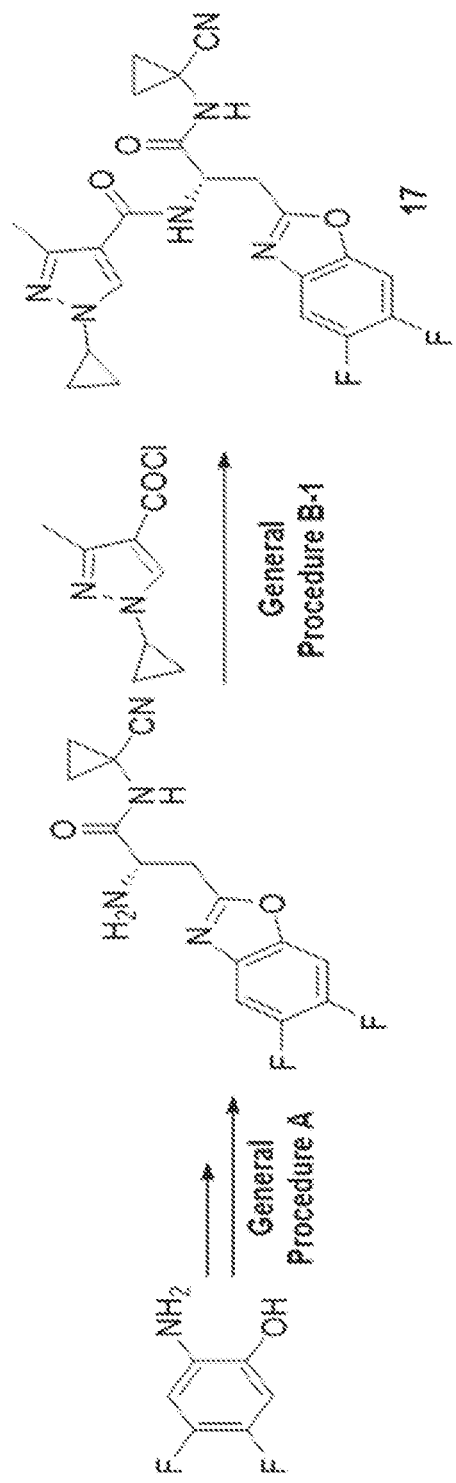
FIG. 30 is a schematic diagram illustrating an exemplary procedure for preparing Compound 17 according to some embodiments of the present disclosure.

Example 3.17: Preparation of Compound 17 ((S)—N-(1-((1-cyanocyclopropyl)amino)-3-(5,6-difluorobenzo[d]oxazol-2-yl)-1-oxopropan-2-yl)-1-cyclopropyl-3-methyl-1H-pyrazole-4-carboxamide FIG. 30 is a schematic diagram illustrating an exemplary procedure for preparing Compound 17 according to some embodiments of the present disclosure.

Following general procedure A, from 2-amino-4,5-difluorophenol, the (S)-2-amino-N-(1-cyanocyclopropyl)-3-(5,6-difluorobenzo[d]oxazol-2-yl)propanamide was obtained as a light-yellow solid. Mass spectrometry was conducted on the resultant compound, and the test results are as follows: Mass(m/z): 306.8 [M+H]$^+$.

Following general procedure B-1, from(S)-2-amino-N-(1-cyanocyclopropyl)-3-(5,6-difluorobenzo [d]oxazol-2-yl) propanamide (83 mg), the desired product Compound 17 was obtained as a white solid (10 mg, 8%). Mass spectrometry was conducted on the resultant compound, and the test results are as follows: Mass(m/z): 454.8 [M+H]$^+$. $^1$H NMR (400 MHz, MeOD) δ 8.10 (s, 1H), 7.61 (ddd, J=17.4, 9.6, 7.2 Hz, 2H), 5.02 (d, J=6.2 Hz, 1H), 3.61 (d, J=5.4 Hz, 1H), 3.55 (dd, J=15.4, 6.2 Hz, 1H), 3.40 (dd, J=15.6, 7.8 Hz, 1H), 2.33 (s, 3H), 1.50 (d, J=2.2 Hz, 2H), 1.23 (dd, J=8.2, 2.2 Hz, 2H), 1.06 (d, J=5.6 Hz, 4H).

Example 3.18: Preparation of Compound 18 ((S)—N-(3-(benzo[d]oxazol-2-yl)-1-((1-cyanocyclopropyl)amino)-1-oxopropan-2-yl)-1-cyclopropyl-3-(trifluoromethyl)-1H-pyrazole-4-carboxamide)

Figure 31:
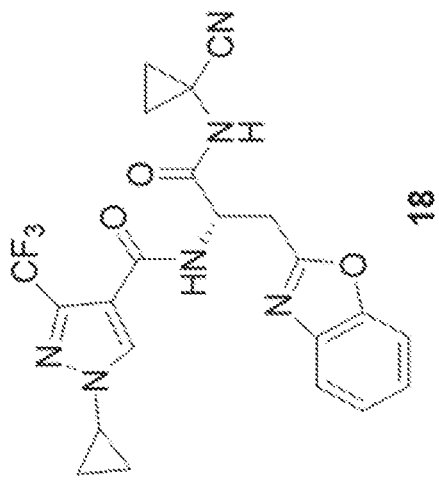
FIG. 31 is a schematic diagram illustrating an exemplary procedure for preparing Compound 18 according to some embodiments of the present disclosure.
Figure 31:
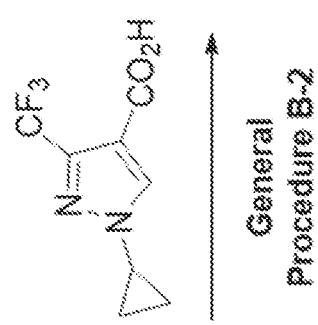
Figure 31:
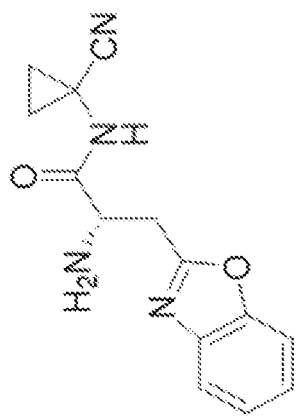

FIG. 31 is a schematic diagram illustrating an exemplary procedure for preparing Compound 18 according to some embodiments of the present disclosure.

Following general procedure B-2, from (S)-2-amino-3-(benzo[d]oxazol-2-yl)-N-(1-cyanocyclopropyl)propenamide (81 mg), the desired product Compound 18 was obtained as a white solid (38 mg, 22%). Mass spectrometry was conducted on the resultant compound, and the test results are as follows: Mass(m/z): 473.1 [M+H]$^+$. $^1$HNMR (400 MHz, DMSO-d$_6$) δ 8.24 (s, 1H), 7.60 (s, 1H), 7.54 (d, J=0.8 Hz, 1H), 7.39-7.27 (m, 2H), 4.97 (d, J=1.0 Hz, 1H), 3.80-3.67 (m, 1H), 3.49 (d, J=6.4 Hz, 1H), 3.40 (d, J=7.8 Hz, 1H), 1.44 (d, J=3.0 Hz, 2H), 1.18-1.04 (m, 6H).

Example 3.19: Preparation of Compound 19 ((S)—N-(3-(benzo[d]oxazol-2-yl)-1-((1-cyanocyclopropyl)amino)-1-oxopropan-2-yl)-1-cyclopropyl-3-(difluoromethyl)-1 H-pyrazole-4-carboxamide)

Figure 32:
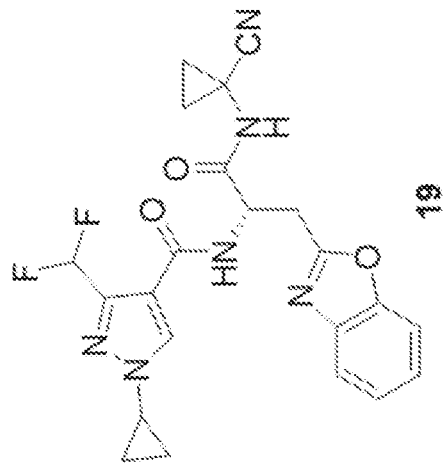
FIG. 32 is a schematic diagram illustrating an exemplary procedure for preparing Compound 19 according to some embodiments of the present disclosure.
Figure 32:
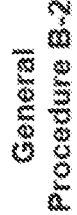
Figure 32:
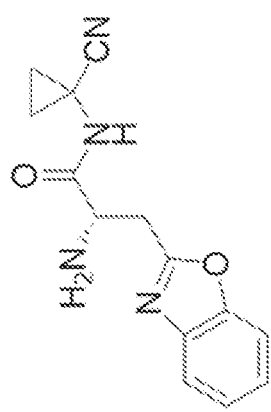

FIG. 32 is a schematic diagram illustrating an exemplary procedure for preparing Compound 19 according to some embodiments of the present disclosure.

Following general procedure B-2, from (S)-2-amino-3-(benzo[d]oxazol-2-yl)-N-(1-cyanocyclopropyl)propenamide (50 mg), the desired product Compound 19 was obtained as a white solid (14.5 mg, 17%). Mass spectrometry was conducted on the resultant compound, and the test results are as follows: Mass(m/z): 455.1 [M+H]$^+$. NMR (400 MHz, DMSO-d$_6$) δ 8.22 (s, 1H), 7.62-7.51 (m, 2H), 7.38-7.29 (m, 2H), 7.02 (t, J=54.0 Hz, 1H), 4.99 (s, 1H), 3.76-3.68 (m, 1H), 3.50 (d, J=6.2 Hz, 1H), 3.40 (d, J=7.8 Hz, 1H), 1.44 (s, 2H), 1.19-1.02 (m, 6H).

Example 3.20: Preparation of Compound 20 ((S)-3-(tert-butyl)-N-(3-(7-chlorobenzo[d]oxazol-2-yl)-1-((1-cyanocyclopropyl)amino)-1-oxopropan-2-yl)-1-cyclopropyl-1H-pyrazole-5-carboxamide)

Figure 33:
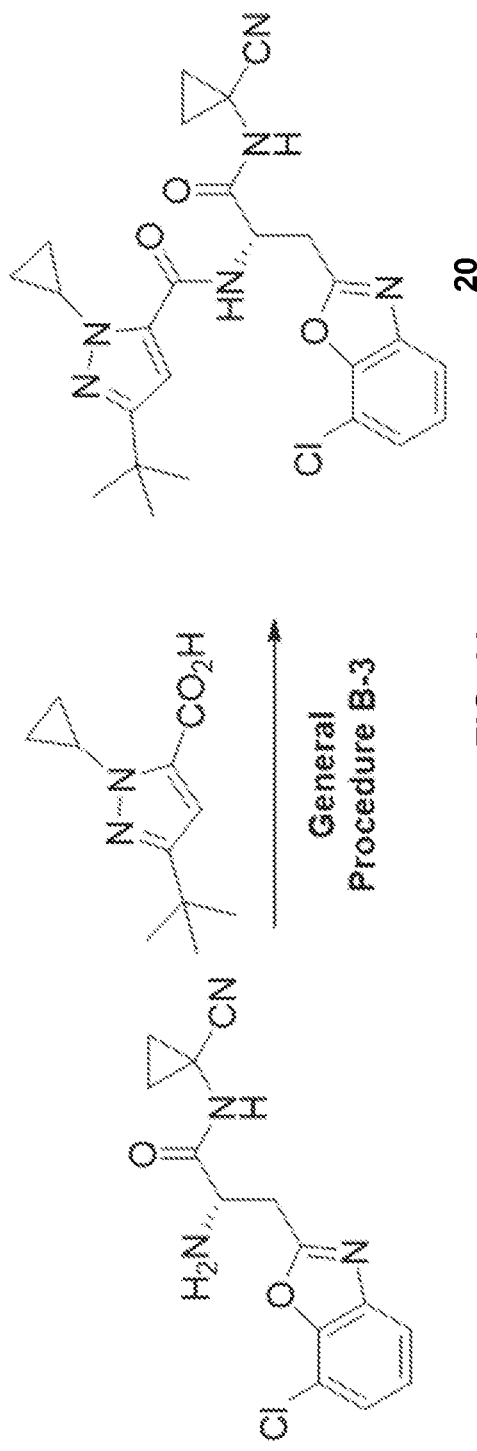
FIG. 33 is a schematic diagram illustrating an exemplary procedure for preparing Compound 20 according to some embodiments of the present disclosure.

FIG. 33 is a schematic diagram illustrating an exemplary procedure for preparing Compound 20 according to some embodiments of the present disclosure.

Following general procedure B-3, from (2S)-2-amino-3-(7-chloro-5-fluoro-1,3-benzoxazol-2-yl)-N-(1-cyanocyclopropyl)propenamide (200 mg), the desired product Compound 20 was obtained as a white solid (37 mg, 19%). Mass spectrometry was conducted on the resultant compound, and the test results are as follows: Mass(m/z): 495.2 [M+H]$^+$. $^1$H NMR (400 MHz, MeOD) δ 7.58 (dd, J=7.8, 1.2 Hz, 1H), 7.39 (dd, J=8.0, 1.2 Hz, 1H), 7.33 (t, J=7.8 Hz, 1H), 6.62 (s, 1H), 5.05 (dd, J=8.6, 5.6 Hz, 1H), 3.98-3.91 (m, 1H), 3.62 (dd, J=15.6, 5.8 Hz, 1H), 3.45 (dd, J=15.4, 8.6 Hz, 1H), 1.49 (t, J=5.6 Hz, 2H), 1.28 (s, 1H), 1.25 (s, 9H), 1.23 (d, J=2.6 Hz, 1H), 1.06 (dd, J=6.4, 3.8 Hz, 1H), 1.00-0.95 (m, 1H), 0.92-0.82 (m, 2H).

Example 3.21: Preparation of Compound 21 ((S)-3-(tert-butyl)-N-(3-(7-chloro-5-fluorobenzo[d]oxazol-2-yl)-1-((1-cyanocyclopropyl)amino)-1-oxopropan-2-yl)-1-cyclopropyl-1 H-pyrazole-5-carboxamide)

Figure 34:
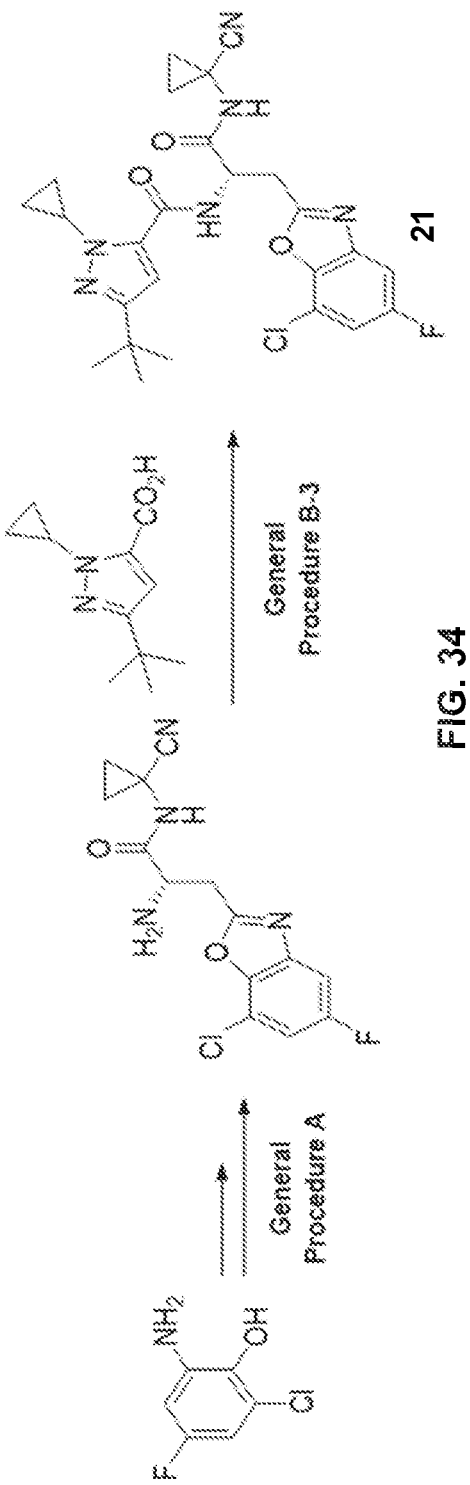
FIG. 34 is a schematic diagram illustrating an exemplary procedure for preparing Compound 21 according to some embodiments of the present disclosure.

FIG. 34 is a schematic diagram illustrating an exemplary procedure for preparing Compound 21 according to some embodiments of the present disclosure.

Following general procedure A, from 2-amino-6-chloro-4-fluorophenol, the (2S)-2-amino-3-(7-chloro-5-fluoro-1,3-benzoxazol-2-yl)-N-(1-cyanocyclopropyl)propanamide was obtained as a yellow oil. Mass spectrometry was conducted on the resultant compound, and the test results are as follows: Mass(m/z): 323.2 [M+H]$^+$.

Following general procedure B-3, from (2S)-2-amino-3-(7-chloro-5-fluoro-1,3-benzoxazol-2-yl)-N-(1-cyanocyclopropyl)propenamide (49 mg), the desired product Compound 21 was obtained as a white solid (4.7 mg, 3%). Mass spectrometry was conducted on the resultant compound, and the test results are as follows: Mass (m/z):513.0 [M+H]$^+$. $^1$H NMR (400 MHz, DMSO-d$_6$) δ 9.12 (s, 1H), 8.80 (d, J=8.0 Hz, 1H), 7.64 (dd, J=8.4, 2.2 Hz, 1H), 7.55 (dd, J=9.4, 2.0 Hz, 1H), 6.69 (s, 1H), 4.92 (d, J=5.8 Hz, 1H), 4.19 (dd, J=7.4, 3.8 Hz, 1H), 3.53 (dd, J=15.4, 5.4 Hz, 1H), 1.48 (t, J=4.1 Hz, 2H), 1.37-1.08 (m, 12H), 1.04 (dd, J=10.0, 6.2 Hz, 1H), 0.94 (dd, J=9.8, 5.8 Hz, 1H), 0.90-0.75 (m, 2H).

Example 3.22: Preparation of Compound 22 ((S)-3-(tert-butyl)-N-(3-(7-chloro-5-fluorobenzo[d]oxazol-2-yl)-1-((1-cyanocyclopropyl)amino)-1-oxopropan-2-yl)-1-(oxetan-3-yl)-1H-pyrazole-5-carboxamide)

Figure 35:
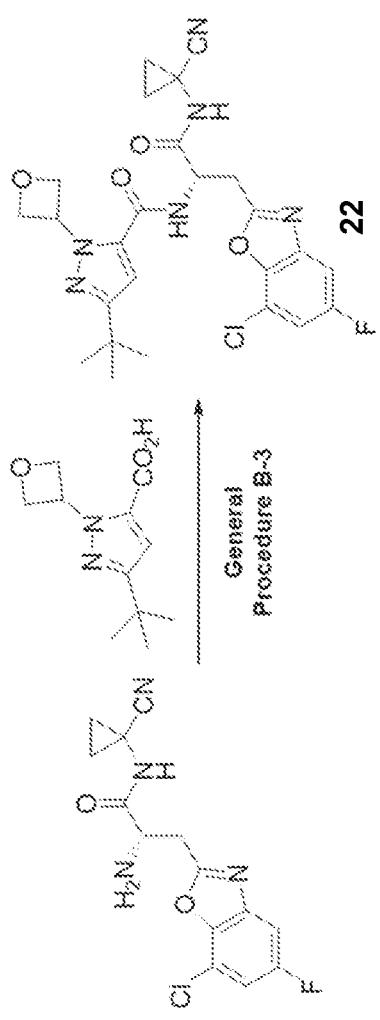
FIG. 35 is a schematic diagram illustrating an exemplary procedure for preparing Compound 22 according to some embodiments of the present disclosure.

FIG. 35 is a schematic diagram illustrating an exemplary procedure for preparing Compound 22 according to some embodiments of the present disclosure.

Following general procedure B-3, from (2S)-2-amino-3-(7-chloro-5-fluoro-1,3-benzoxazol-2-yl)-N-(1-cyanocyclopropyl)propenamide 100 mg), the desired product Compound 22 was obtained as a white solid (6 mg, 4%). Mass spectrometry was conducted on the resultant compound, and the test results are as follows: Mass (m/z): 529.2[M+H]$^+$. $^1$HNMR (400 MHz, DMSO-d$_6$) δ 9.15 (s, 1H), 8.96 (d, J=4.8 Hz, 1H), 7.65-7.55 (m, 2H), 6.85 (s, 1H), 5.88-5.79 (m, 1H), 4.75-4.95 (m, 5H), 3.55-3.48 (m, 1H), 1.55-1.42 (m, 2H), 1.38-1.55 (m, 10H), 1.19-1.05 (m, 2H).

Example 3.23: Preparation of Compound 23 ((S)—N-(3-(4-(1H-pyrazol-4-yl)benzo[d]oxazol-2-yl)-1-((1-cyanocyclopropyl)amino)-1-oxopropan-2-yl)-3-chlorobenzamide)

Figure 36:
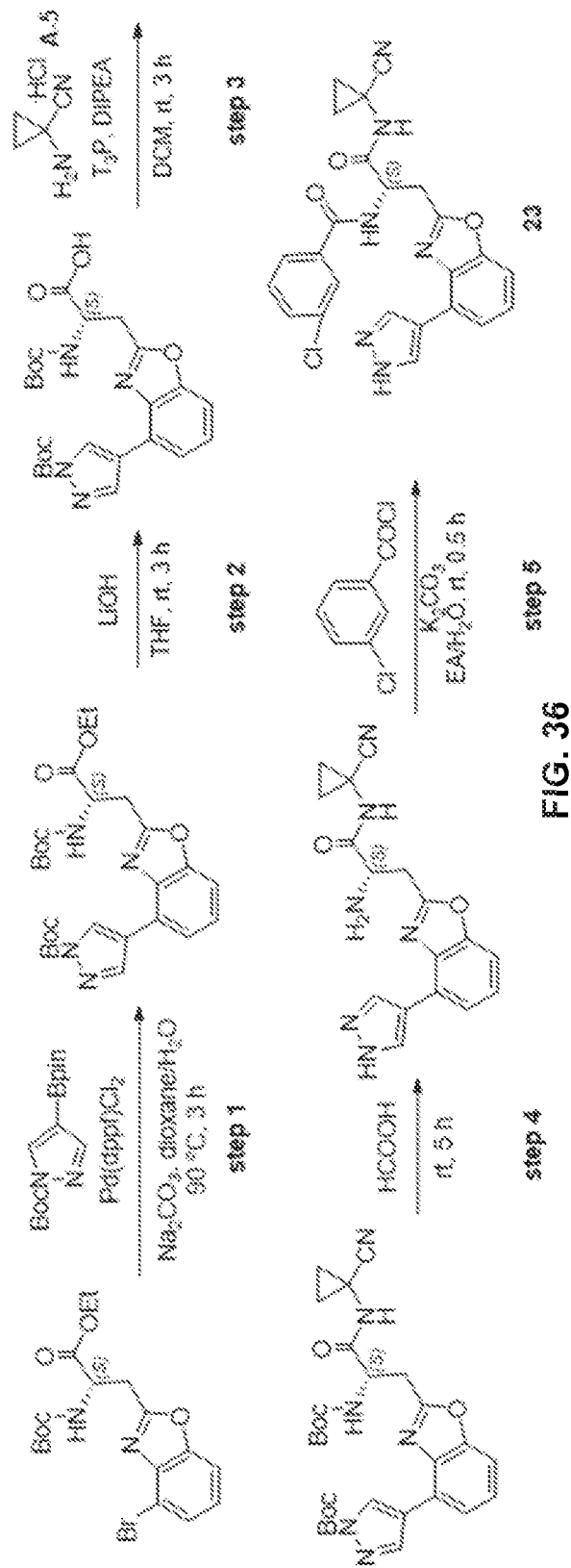
FIG. 36 is a schematic diagram illustrating an exemplary procedure for preparing Compound 23 according to some embodiments of the present disclosure.

FIG. 36 is a schematic diagram illustrating an exemplary procedure for preparing Compound 23 according to some embodiments of the present disclosure.

Step 1. Preparation of tert-butyl (S)-4-(2-(2-((tert-butoxycarbonyl)amino)-3-ethoxy-3-oxopropyl)benzo[d] oxazol-4-yl)-1H-pyrazole-1-carboxylate A solution of ethyl (S)-3-(4-bromobenzo[d]oxazol-2-yl)-2-((tert-butoxycarbonyl)amino)propanoate (450 mg, 1.09 mmol), tert-butyl 4-(4,4,5,5-tetramethyl-1,3,2-dioxaborolan-2-yl)-1H-pyrazole-1-carboxylate (384 mg, 1.31 mmol), PdCl$_2$(dppf) (70.65 mg, 0.10 mmol), Na$_2$CO$_3$ (231 mg, 2.18 mmol) in 1,4-dioxane/H$_2$O (12 mL/2 mL) was stirred at 90° C. for 1 h. The reaction mixture was quenched with water and extracted with EA (60 mL×3). The combined organic layer was dried over Na$_2$SO$_4$ and concentrated under vacuum to give a crude product, which was purified by flash chromatography (MeOH in DCM, 2% to 10%) to obtain the desired product (200 mg, 74%) as a pale solid. Mass spectrometry was conducted on the resultant compound, and the test results are as follows: Mass(m/z): 501.1 [M+H]$^+$.

Step 2. Preparation of (S)-3-(4-(1-(tert-butoxycarbonyl)-1H-pyrazol-4-yl)benzo[d]oxazol-2-yl)-2-((tert-butoxy carbonyl)amino)propanoic acid A solution of tert-butyl (S)-4-(2-(2-((tert-butoxycarbonyl)amino)-3-ethoxy-3-oxopropyl)benzo[d]oxazol-4-yl)-1H-pyrazole-1-carboxylate (350 mg, 0.7 mmol), LiOH (19.06 mg, 0.80 mmol) in THF/H$_2$O (15 mL/4 mL) was stirred at 25° C. for 1 h. The reaction mixture was quenched with water and extracted with EA (60 mL×3). The combined organic layer was dried over Na$_2$SO$_4$ and concentrated under vacuum to give the desired product (280 mg, 85%) as a light-yellow solid. Mass spectrometry was conducted on the resultant compound, and the test results are as follows: Mass(m/z): 473.1 [M+H]$^+$.

Step 3. Preparation of tert-butyl (S)-4-(2-(2-((tert-butoxycarbonyl)amino)-3-((1-cyanocyclopropyl)amino)-3-oxopropyl)benzo[d]oxazol-4-yl)-1H-pyrazole-1-carboxylate A solution of (S)-3-(4-(1-(tert-butoxycarbonyl)-1H-pyrazol-4-yl)benzo[d]oxazol-2-yl)-2-((tert-butoxy carbonyl)amino)propanoic acid (280 mg, 0.59 mmol), A-5 (84 mg, 0.71 mmol), DIPEA (228 mg, 1.77 mmol) and T3P (50% in EA, 402 mg, 0.63 mmol) in DCM (5 mL) was stirred at 25° C. under N$_2$ for 3 hrs. The reaction mixture was quenched with water and extracted with DCM (30 mL×3). The combined organic layer was dried over Na$_2$SO$_4$ and concentrated under vacuum to give a crude product, which was purified by flash chromatography (MeOH in DCM, 2% to 10%) to obtain the desired product (130 mg, 41%) as a pale solid. Mass spectrometry was conducted on the resultant compound, and the test results are as follows: Mass(m/z): 537.1 [M+H]$^+$.

Step 4. Preparation of (S)-3-(4-(1H-pyrazol-4-yl)benzo[d]oxazol-2-yl)-2-amino-N-(1-cyanocyclopropyl) propanamide A solution of tert-butyl (S)-4-(2-(2-((tert-butoxycarbonyl)amino)-3-((1-cyanocyclopropyl)amino)-3-oxopropyl)benzo[d]oxazol-4-yl)-1H-pyrazole-1-carboxylate (130 mg, 0.24 mmol) in FA (2 mL) was stirred at 25° C. for 3 hrs. The mixture was concentrated under reduced pressure to give a residue. The residue was quenched with Sat. NaHCO$_3$ and extracted with EtOAc (60 mL×3). The combined organic layer was dried over Na$_2$SO$_4$ and concentrated under vacuum to give the crude desired product (30 mg, 37%) as a light-yellow solid. Mass spectrometry was conducted on the resultant compound, and the test results are as follows: Mass(m/z): 437.1 [M+H]$^+$.

Step 5. Preparation of (S)—N-(3-(4-(1 H-pyrazol-4-yl)benzo[d]oxazol-2-yl)-1-((1-cyanocyclopropyl)amino)-1-oxopropan-2-yl)-3-chlorobenzamide To a solution of (S)-3-(4-(1 H-pyrazol-4-yl)benzo[d]oxazol-2-yl)-2-amino-N-(1-cyanocyclopropyl) propenamide (30 mg, 0.09 mmol) and K$_2$CO$_3$ (24.66 mg, 0.18 mmol) in EA (2 mL) and H$_2$O (3 mL) was added a solution of 3-chlorobenzoyl chloride (18.73 mg, 0.11 mmol) in EA (0.5 mL) dropwise. After the addition, the reaction mixture was stirred at 25° C. for 0.5 h. Then the reaction mixture was quenched with water and extracted with EA (20 mL×3). The combined organic layer was dried over Na$_2$SO$_4$ and concentrated under vacuum to give a crude product, which was purified by prep-HPLC [(Gemini-C18, 150×21.2 mm, 5um; ACN-H$_2$O (0.1% FA); 15%-95%)] to give the desired product Compound 23 (4.1 mg, 10%) as a white solid. Mass spectrometry was conducted on the resultant compound, and the test results are as follows: Mass(m/z): 475.1 [M+H]$^+$. $^1$H NMR (400 MHz, DMSO-d$_6$) δ 13.18 (s, 1H), 9.15 (s, 1H), 9.10 (d, J=7.8 Hz, 1H), 8.43 (s, 2H), 8.19-8.12 (m, 1H), 7.86 (s, 1H), 7.76 (d, J=8.0 Hz, 1H), 7.64 (d, J=6.7 Hz, 1H), 7.58 (d, J=9.1 Hz, 1H), 7.45 (s, 1H), 7.31 (t, J=7.8 Hz, 1H), 5.06 (d, J=4.1 Hz, 1H), 3.55 (d, J=4.2 Hz, 1H), 3.45 (s, 1H), 1.47 (m, 2H), 1.17-1.06 (m, 2H).

Example 3.24: Preparation of Compound 24 ((S)-3-chloro-N-(1-((1-cyanocyclopropyl)amino)-3-(6-(4-methylpiperazin-1-yl)benzo[d]oxazol-2-yl)-1-oxopropan-2-yl)benzamide)

Figure 37:
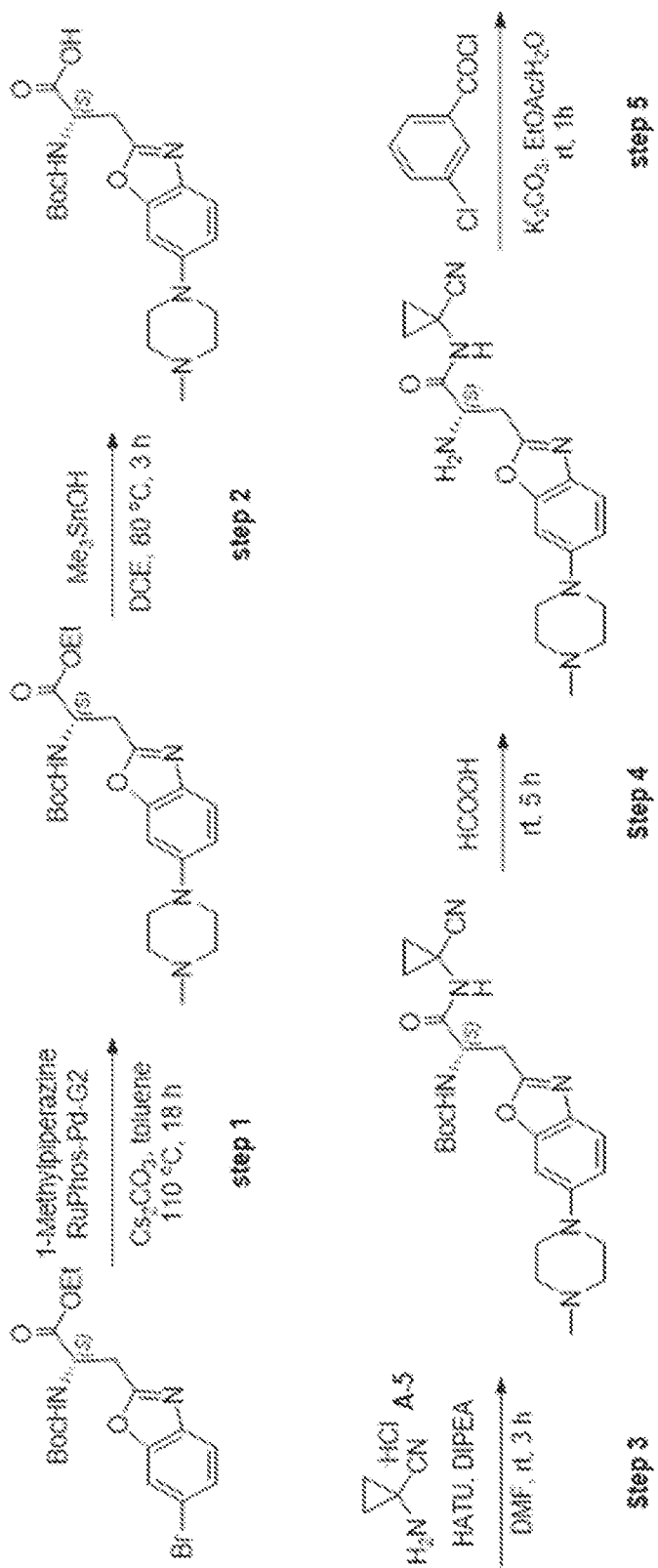
FIG. 37 is a schematic diagram illustrating an exemplary procedure for preparing Compound 24 according to some embodiments of the present disclosure.

FIG. 37 is a schematic diagram illustrating an exemplary procedure for preparing Compound 24 according to some embodiments of the present disclosure.

Step 1. Preparation of ethyl (S)-2-((tert-butoxycarbonyl)amino)-3-(6-(4-methylpiperazin-1-yl)benzo[d]oxazol-2-yl)propanoate Six mixtures of ethyl (S)-3-(6-bromobenzo[d]oxazol-2-yl)-2-((tert-butoxycarbonyl)amino) propanoate (50 mg, 0.73 mmol), 1-methylpiperazine (73 mg, 0.73 mmol), $Cs_2CO_3$ (474.5 mg, 1.46 mmol) and RuPhos-Pd-G2 (57 mg, 0.073 mmol) in toluene (5 mL) under nitrogen were stirred at 110° C. for 18 hrs. The reaction mixtures were cooled to room temperature, combined, concentrated under vacuum to give a crude product. The crude product was then purified on silica gel, eluting with MeOH in DCM (5% to 10%) to give the desired product (180 mg, 57%) as a light brown oil. Mass spectrometry was conducted on the resultant compound, and the test results are as follows: Mass(m/z): 433.1 [M+H]$^+$.

Step 2. Preparation of (S)-2-((tert-butoxycarbonyl)amino)-3-(6-(4-methylpiperazin-1-yl)benzo[d]oxazol-2-yl)propanoic acid A solution of ethyl (S)-2-((tert-butoxycarbonyl)amino)-3-(6-(4-methylpiperazin-1-yl)benzo[d]oxazol-2-yl)propanoate (160 mg, 0.37 mmol) and $Me_3SnOH$ (134 mg, 0.74 mmol) in DCE (6 mL) under nitrogen was heated to 80° C. and stirred for 3 hrs. After concentration, the crude product was then purified on silica gel, eluted with MeOH in DCM (5% to 10%) to give the desired product (80 mg, 53.3%) as a light brown solid. Mass spectrometry was conducted on the resultant compound, and the test results are as follows: Mass(m/z): 405.1 [M+H]$^+$.

Step 3. Preparation of tert-butyl (S)-(1-((1-cyanocyclopropyl)amino)-3-(6-(4-methylpiperazin-1-yl)benzo[d]oxazol-2-yl)-1-oxopropan-2-yl)carbamate A solution of (S)-2-((tert-butoxycarbonyl)amino)-3-(6-(4-methylpiperazin-1-yl)benzo[d] oxazol-2-yl)propanoic acid (70 mg, 0.17 mmol), A-5 (25 mg, 0.21 mmol), HATU (97 mg, 0.26 mmol), and DIPEA (66 mg, 0.51 mmol) in DMF (3 mL) was stirred under nitrogen at 25° C. for 3 hrs. The reaction mixture was quenched with water (10 mL) and extracted with EA (35 mL×3). The combined organic layer was dried over $Na_2SO_4$ and concentrated to dryness and then purified on silica gel, eluted with MeOH in DCM (5% to 10%) to obtain the desired product (60 mg, 75%) as a white solid. Mass spectrometry was conducted on the resultant compound, and the test results are as follows: Mass(m/z): 469.1 [M+H]$^+$.

Step 4. Preparation of (S)-2-amino-N-(1-cyanocyclopropyl)-3-(6-(4-methylpiperazin-1-yl)benzo[d]oxazol-2-yl)propanamide To a solution of tert-butyl (S)-(1-((1-cyanocyclopropyl)amino)-3-(6-(4-methylpiperazin-1-yl)benzo[d]oxazol-2-yl)-1-oxopropan-2-yl)carbamate (60 mg, 0.13 mmol) in FA (2 mL) was stirred under nitrogen at 25° C. for 5 hrs. The mixture was blown by nitrogen to dryness at 20° C. Then the residue was basified with saturated sodium bicarbonate and extracted with EA (20 mL×3). The combined organic layer was concentrated to dryness to give the desired product (30 mg, 63.8%) as a light white solid. Mass spectrometry was conducted on the resultant compound, and the test results are as follows: Mass(m/z): 369.1 [M+H]$^+$.

Step 5. Preparation of (S)-3-chloro-N-(1-((1-cyanocyclopropyl)amino)-3-(6-(4-methylpiperazin-1-yl)benzo[d]oxazol-2-yl)-1-oxopropan-2-yl)benzamide To a solution of (S)-2-amino-N-(1-cyanocyclopropyl)-3-(6-(4-methylpiperazin-1-yl)benzo[d]oxazol-2-yl)propanamide (30 mg, 0.08 mmol) in EA (3 mL) was added $K_2CO_3$ (22 mg, 0.16 mmol) in water (0.5 mL) and then followed by 3-chlorobenzoyl chloride (14 mg, 0.08 mmol) in EA (1 mL) dropwise, after the addition, the reaction mixture was stirred under at 25° C. for 1 h. The reaction mixture was quenched with water (5 mL) and extracted with EA (15 mL×3). The combined organic layer was concentrated to dryness, and the residue was purified by prep-HPLC [(Gemini-C18, 150× 21.2 mm, Sum; ACN-$H_2O$ (0.1% FA); 15%-95%)] to give the desired product Compound 24 (4.9 mg, 12%) as a white solid. Mass spectrometry was conducted on the resultant compound, and the test results are as follows: Mass(m/z): 507.1 [M+H]$^+$. $^1$H NMR (400 MHz, DMSO-d$_6$) δ 9.08 (s, 1H), 9.00 (d, J=7.9 Hz, 1H), 7.89 (t, J=1.8 Hz, 1H), 7.78 (d, J=7.8 Hz, 1H), 7.64-7.59 (m, 1H), 7.51 (t, J=7.9 Hz, 1H), 7.44 (d, J=8.8 Hz, 1H), 7.14 (d, J=2.2 Hz, 1H), 6.97 (dd, J=8.8, 2.3 Hz, 1H), 4.94-4.88 (m, 1H), 3.43 (d, J=5.7 Hz, 1H), 3.26 (d, J=8.8 Hz, 1H), 3.17-3.11 (m, 4H), 2.48-2.43 (m, 4H), 2.22 (s, 3H), 1.46-1.47 (m, 2H), 1.13-1.02 (m, 2H).

Example 3.25: Preparation of Compound 25 ((S)—N-(1-((cyanomethyl)amino)-3-(6-(4-methylpiperazin-1-yl)benzo[d]oxazol-2-yl)-1-oxopropan-2-yl)-1,3-dicyclopropyl-1 H-pyrazole-5-carboxamide)

Figure 38:
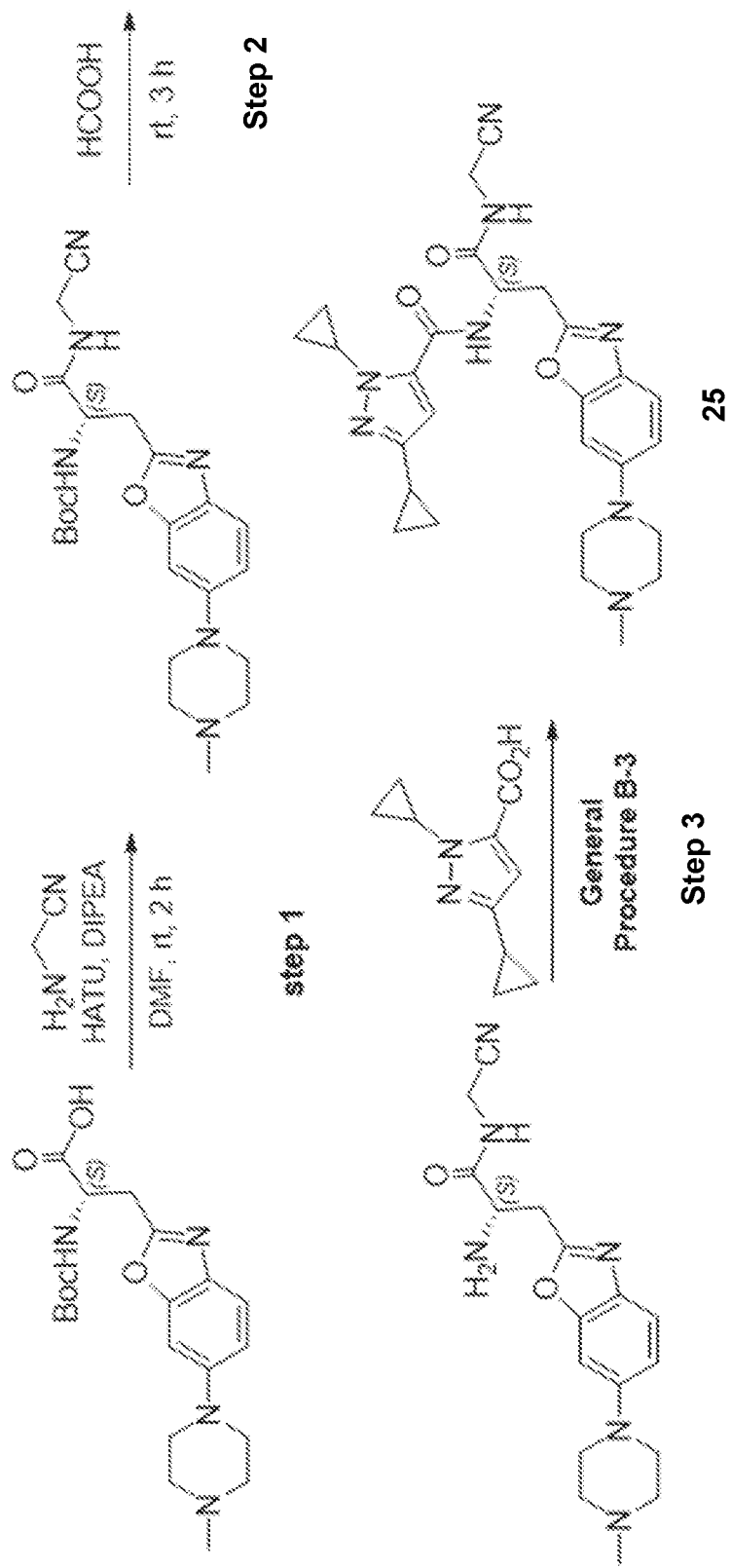
FIG. 38 is a schematic diagram illustrating an exemplary procedure for preparing Compound 25 according to some embodiments of the present disclosure.

FIG. 38 is a schematic diagram illustrating an exemplary procedure for preparing Compound 25 according to some embodiments of the present disclosure.

Step 1. Preparation of tert-butyl (S)-(1-((cyanomethyl)amino)-3-(6-(4-methylpiperazin-1-yl)benzo[d]oxazol-2-yl)-1-oxopropan-2-yl)carbamate To a solution of (S)-2-((tert-butoxycarbonyl)amino)-3-(6-(4-methylpiperazin-1-yl)benzo[d]oxazol-2-yl)propanoic acid (500 mg, 1.24 mmol) in DMF (20 mL) was added DIPEA (798 mg, 6.2 mmol), HATU (1410 mg, 3.72 mmol), and 2-aminoacetonitrile (114 mg, 1.86 mmol). The reaction mixture was stirred at RT for 2 hrs. After the reaction completed, $H_2O$ (30 mL) was added to the reaction mixture, and then extracted with EA (30 mL×3). The combined organic layer was washed with brine (50 mL×3), then dried over anhydrous $Na_2SO_4$. After filtration, the solution was concentrated under vacuum, and the residue was purified by Combi-flash (DCM/MeOH=0~10%) to give the product tert-butyl (S)-(1-((cyanomethyl)amino)-3-(6-(4-methylpiperazin-1-yl)benzo[d]oxazol-2-yl)-1-oxopropan-2-yl)carbamate as yellow oil (310 mg, 56%). Mass spectrometry was conducted on the resultant compound, and the test results are as follows: Mass(m/z): 442.9 [M+H]$^+$.

Step 2. Preparation of (S)-2-amino-N-(cyanomethyl)-3-(6-(4-methylpiperazin-1-yl)benzo[d]oxazol-2-yl)propanamide A solution of tert-butyl (S)-(1-((cyanomethyl)amino)-3-(6-(4-methylpiperazin-1-yl)benzo[d]oxazol-2-yl)-1-oxopropan-2-yl)carbamate (310 mg, 0.7 mmol) in FA (5 mL) was stirred at RT for 3 hrs. The resulting mixture was blown dry with compressed air to give the product (S)-2-amino-N-(cyanomethyl)-3-(6-(4-methylpiperazin-1-yl)benzo[d]oxazol-2-yl)propanamide as brown oil (160 mg, 66%). Mass spectrometry was conducted on the resultant compound, and the test results are as follows: Mass(m/z): 343.1 [M+H]$^+$.

Step 3. Preparation of (S)—N-(1-((cyanomethyl)amino)-3-(6-(4-methylpiperazin-1-yl)benzo[d]oxazol-2-yl)-1-oxopropan-2-yl)-1,3-dicyclopropyl-1H-pyrazole-5-carboxamide Following general procedure B-3, from(S)-2-amino-N-(cyanomethyl)-3-(6-(4-methylpiperazin-1-yl)benzo[d]oxazol-2-yl)propanamide (70 mg), the desired product Compound 25 was obtained as a white solid (5 mg, 4%). Mass spectrometry was conducted on the resultant compound, and the test results are as follows: Mass(m/z): 517.3 [M+H]$^+$. $^1$H NMR (400 MHz, MeOD) δ 7.55 (d, J=8.8 Hz, 1H), 7.26 (d, J=2.2 Hz, 1H), 7.12 (dd, J=8.8, 2.4 Hz, 1H), 6.39 (s, 1H), 5.16 (dd, J=8.8, 5.6 Hz, 1H), 4.21 (s, 2H), 3.93 (ddd, J=11.2, 7.4, 4.0 Hz, 2H), 3.62 (dd, J=15.6, 5.6 Hz, 2H), 3.39 (dd, J=15.4, 8.8 Hz, 2H), 3.00 (s, 3H), 1.87 (ddd, J=13.4, 8.6, 5.0 Hz, 1H), 1.05 (dd, J=9.0, 4.8 Hz, 1H), 0.98-0.78 (m, 6H), 0.65 (dt, J=6.2, 4.2 Hz, 2H).

Example 3.26: Preparation of Compound 26 ((S)-3-(tert-butyl)-N-(1-((1-cyanocyclopropyl)amino)-3-(6-(4-methylpiperazin-1-yl)benzo[d]oxazol-2-yl)-1-oxopropan-2-yl)-1-cyclopropyl-1 H-pyrazole-5-carboxamide)

Figure 39:
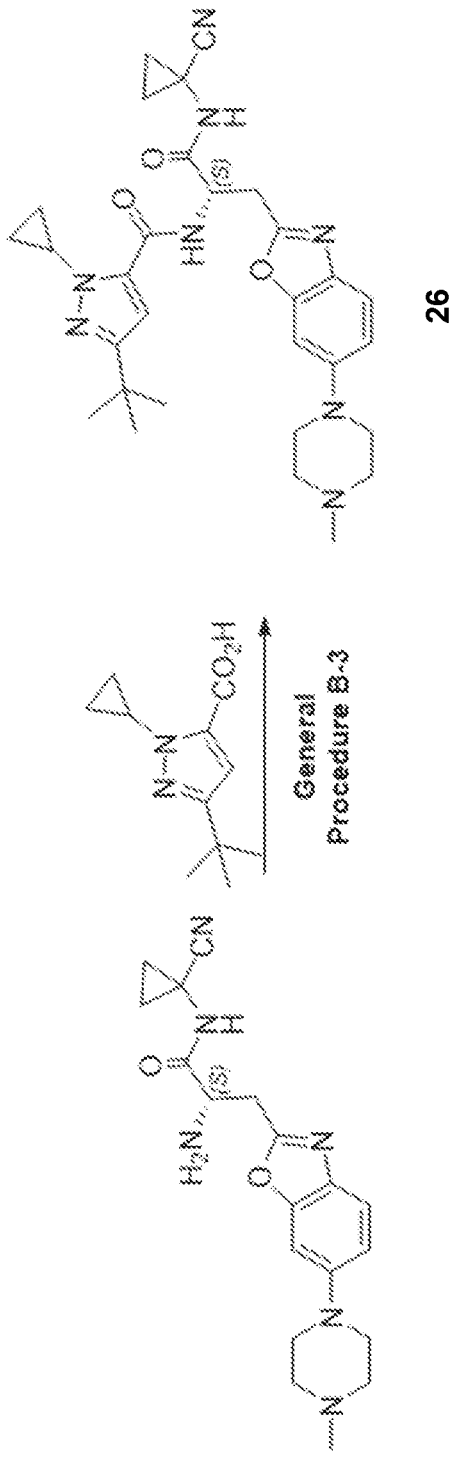
FIG. 39 is a schematic diagram illustrating an exemplary procedure for preparing Compound 26 according to some embodiments of the present disclosure.

FIG. 39 is a schematic diagram illustrating an exemplary procedure for preparing Compound 26 according to some embodiments of the present disclosure.

Following general procedure B-3, from (S)-2-amino-N-(1-cyanocyclopropyl)-3-(6-(4-methylpiperazin-1-yl)benzo[d]oxazol-2-yl)propanamide (80 mg), the desired product Compound 26 was obtained as a white solid (14 mg, 11%). Mass spectrometry was conducted on the resultant compound, and the test results are as follows: Mass(m/z): 559.3 [M+H]$^+$. $^1$H NMR (400 MHz, MeOD) δ 7.43 (d, J=8.8 Hz, 1H), 7.14 (d, J=2.2 Hz, 1H), 7.01 (dd, J=8.8, 2.4 Hz, 1H), 6.50 (s, 1H), 4.91 (dd, J=8.2, 6.0 Hz, 1H), 3.88-3.79 (m, 1H), 3.45 (dd, J=15.4, 6.2 Hz, 2H), 3.29 (d, J=8.2 Hz, 4H), 2.83 (s, 3H), 1.39 (d, J=2.6 Hz, 2H), 1.19 (d, J=1.6 Hz, 2H), 1.15 (s, 9H), 1.14-1.09 (m, 2H), 1.02-0.69 (m, 6H).

Example 3.27: Preparation of Compound 27 ((S)-3-chloro-N-(1-((1-cyanocyclopropyl)amino)-3-(6-(1-methyl-1,2,3,6-tetrahydropyridin-4-yl)benzo[d]oxazol-2-yl)-1-oxopropan-2-yl)benzamide)

Figure 40:
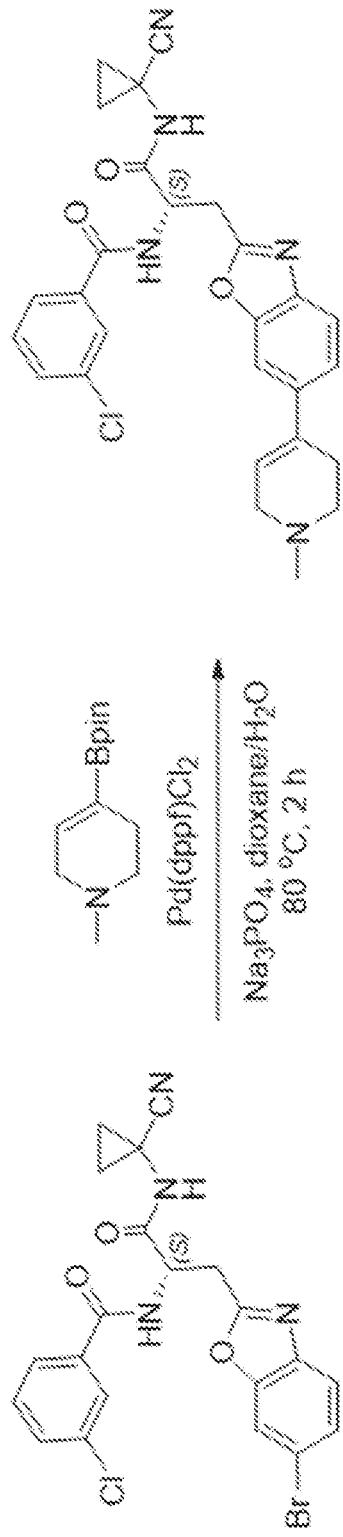
FIG. 40 is a schematic diagram illustrating an exemplary procedure for preparing Compound 27 according to some embodiments of the present disclosure.

FIG. 40 is a schematic diagram illustrating an exemplary procedure for preparing Compound 27 according to some embodiments of the present disclosure.

To a solution of (S)—N-(3-(6-bromobenzo[d]oxazol-2-yl)-1-((1-cyanocyclopropyl)amino)-1-oxopropan-2-yl)-3-chlorobenzamide (100 mg, 0.20 mmol) in dioxane/H$_2$O (10:1, 5 mL) was added 1-methyl-4-(4,4,5,5-tetramethyl-1,3,2-dioxaborolan-2-yl)-3,6-dihydro-2H-pyridine (91 mg, 0.41 mmol), K$_3$PO$_4$ (87 mg, 0.411 mmol), and Pd(dppf)Cl$_2$ (15 mg, 0.02 mmol). The solution was stirred at 80° C. under N$_2$ for 2 hrs. After filtration, the solution was concentrated under vacuum, and the crude product was purified by flash chromatography to give the desired product Compound 27 (18.6 mg, 17.27%) as a white solid. Mass spectrometry was conducted on the resultant compound, and the test results are as follows: Mass (m/z): 504.2 [M+H]$^+$. $^1$H NMR (400 MHz, DMSO-d$_6$) δ 9.09 (s, 1H), 9.03 (d, J=7.8 Hz, 1H), 7.89 (t, J=1.8 Hz, 1H), 7.78 (d, J=7.9 Hz, 1H), 7.67 (d, J=1.3 Hz, 1H), 7.64-7.60 (m, 1H), 7.58 (d, J=8.3 Hz, 1H), 7.52 (d, J=7.9 Hz, 1H), 7.43 (dd, J=8.4, 1.6 Hz, 1H), 6.21 (s, 1H), 4.96 (dd, J=14.0, 8.3 Hz, 1H), 3.51-3.35 (m, 4H), 3.02 (d, J=3.0 Hz, 2H), 2.57 (d, J=4.8 Hz, 2H), 2.28 (s, 3H), 1.47 (d, J=2.8 Hz, 2H), 1.12-1.06 (m, 2H).

Example 3.28: Preparation of Compound 28 ((S)-3-chloro-N-(1-((1-cyanocyclopropyl)amino)-3-(6-(1-(2,2-difluoroethyl)-1,2,3,6-tetrahydropyridin-4-yl)benzo[d]oxazol-2-yl)-1-oxopropan-2-yl)benzamide)

Figure 41:
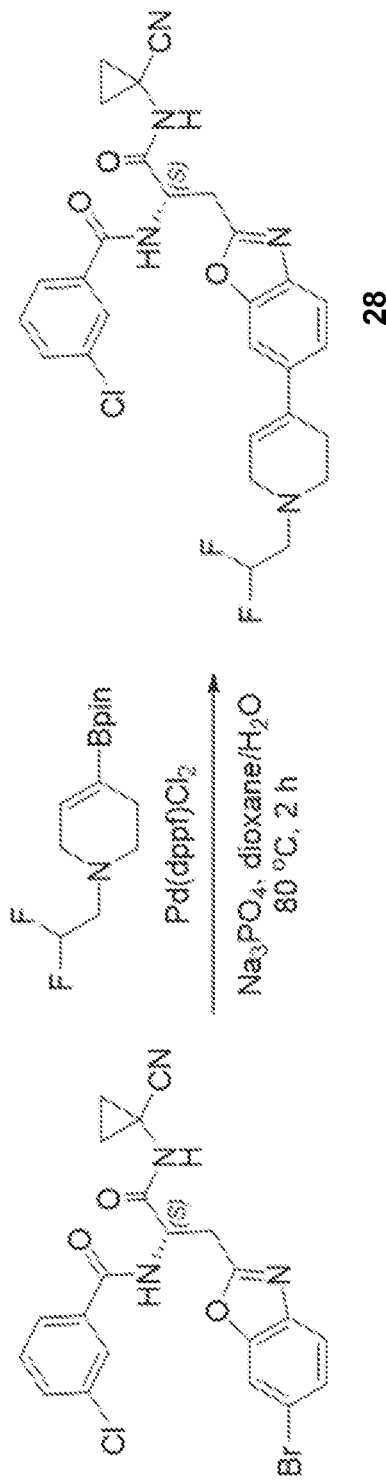
FIG. 41 is a schematic diagram illustrating an exemplary procedure for preparing Compound 28 according to some embodiments of the present disclosure.

FIG. 41 is a schematic diagram illustrating an exemplary procedure for preparing Compound 28 according to some embodiments of the present disclosure.

To a solution of (S)—N-(3-(6-bromobenzo[d]oxazol-2-yl)-1-((1-cyanocyclopropyl)amino)-1-oxopropan-2-yl)-3-chlorobenzamide (130 mg, 0.47 mmol) in dioxane/H$_2$O (10/1, 10 mL) was added 1-(2,2-difluoroethyl)-4-(4,4,5,5-tetramethyl-1,3,2-dioxaborolan-2-yl)-1,2,3,6-tetrahydropyridine (84 mg, 0.57 mmol), K$_3$PO$_4$ (113 mg, 0.94 mmol), and Pd(dppf)Cl$_2$ (20 mg, 0.05 mmol). The reaction mixture was stirred at 100° C. under N$_2$ for 16 hrs. The solvent was removed under reduced pressure and the residue was purified by Combi-flash (DCM/MeOH=0~ 10%) to give the desired product Compound 28 as a yellow solid (35 mg, 13%). Mass spectrometry was conducted on the resultant compound, and the test results are as follows: Mass(m/z): 554.2 [M+H]$^+$. $^1$H NMR (400 MHz, MeOD) δ 7.83 (t, J=1.8 Hz, 1H), 7.75-7.71 (m, 1H), 7.62 (d, J=1.4 Hz, 1H), 7.58-7.53 (m, 2H), 7.49-7.43 (m, 2H), 6.18 (d, J=5.6 Hz, 1H), 6.04 (s, 1H), 5.05 (dd, J=8.2, 6.4 Hz, 1H), 4.91 (d, J=1.8 Hz, 1H), 4.85 (s, 1H), 3.59 (dd, J=15.4, 6.4 Hz, 1H), 3.44 (dd, J=15.4, 8.2 Hz, 1H), 3.33 (d, J=3.4 Hz, 2H), 2.95-2.86 (m, 4H), 1.48 (dd, J=5.2, 2.2 Hz, 2H), 1.19 (dd, J=17.0, 2.4 Hz, 2H).

Example 3.29: Preparation of Compound 29 ((S)-3-(tert-butyl)-N-(1-((1-cyanocyclopropyl)amino)-3-(6-(1-(2,2-difluoroethyl)-1,2,3,6-tetrahydropyridin-4-yl)benzo[d]oxazol-2-yl)-1-oxopropan-2-yl)-1-cyclopropyl-1 H-pyrazole-5-carboxamide)

Figure 42:
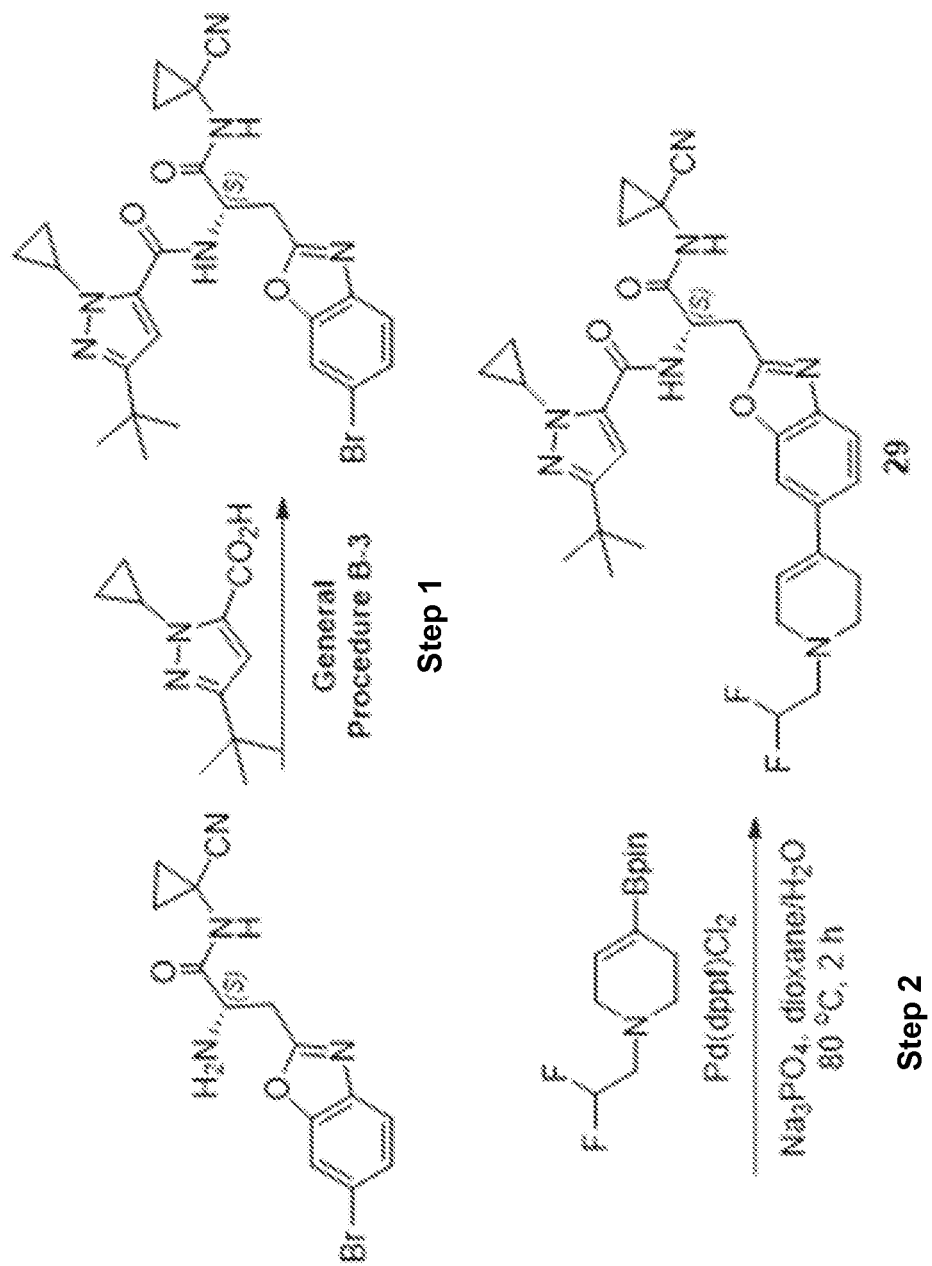
FIG. 42 is a schematic diagram illustrating an exemplary procedure for preparing Compound 29 according to some embodiments of the present disclosure.

FIG. 42 is a schematic diagram illustrating an exemplary procedure for preparing Compound 29 according to some embodiments of the present disclosure.

Step 1. Preparation of (S)—N-(3-(6-bromobenzo[d]oxazol-2-yl)-1-((1-cyanocyclopropyl) amino)-1-oxopropan-2-yl)-3-(tert-butyl)-1-cyclopropyl-1H-pyrazole-5-carboxamide To a solution of (2S)-2-amino-3-(6-bromo-1,3-benzoxazol-2-yl)-N-(1-cyanocyclopropyl)propenamide (1.6 g, 4.58 mmol) and 5-tert-butyl-2-cyclopropyl pyrazole-3-carboxylic acid (954 mg, 4.58 mmol) in DCM (20 mL) was added T3P (50% in EA, 5.83 g, 9.16 mmol) and DIPEA (1.18 g, 9.16 mmol). The reaction mixture was stirred at 25° C. under N$_2$ for 3 hrs. The reaction mixture was concentrated and the residue was purified by silica gel column chromatography (PE:EA=1:1) to give the product as a yellow solid (1.3 g, 47%). Mass spectrometry was conducted on the resultant compound, and the test results are as follows: Mass(m/z): 539.1 541.1[M+H]$^+$.

Step 2. Preparation of (S)-3-(tert-butyl)-N-(1-((1-cyanocyclopropyl)amino)-3-(6-(1-(2,2-difluoroethyl)-1,2,3,6-tetrahydropyridin-4-yl)benzo[d]oxazol-2-yl)-1-oxopropan-2-yl)-1-cyclopropyl-1H-pyrazole-5-carboxamide To a solution of (2S)-3-(6-bromo-1,3-benzoxazol-2-yl)-2-[(5-tert-butyl-2-cyclopropylpyrazol-3-yl)formamido]-N-(1-cyanocyclopropyl)propenamide (150 mg, 0.28 mmol) and 1-(2,2-difluoroethyl)-4-(4,4,5,5-tetramethyl-1,3,2-dioxaborolan-2-yl)-3,6-dihydro-2H-pyridine (114 mg, 0.42 mmol) in dioxane (3 mL) and H$_2$O (0.3 mL) was added K$_3$PO$_4$ (118 mg, 0.56 mmol) and Pd(dppf)Cl$_2$ (20 mg, 0.028 mmol). The reaction mixture was stirred at 90° C. under N$_2$ for 16 hrs. The reaction mixture was concentrated and the residue was purified by Pre-HPLC [Gemini-C18 150×21.2 mm, 5um, mobile phase: ACN-H$_2$O (0.1% FA), gradient: 20-40] to give the desired product Compound 29 as a white solid (30 mg, 19%). Mass spectrometry was conducted on the resultant compound, and the test results are as follows: Mass(m/z): 606.3[M+H]$^+$. $^1$H NMR (400 MHz, DMSO-d$_6$) δ 9.13 (s, 1H), 8.79 (d, J=8.0 Hz, 1H), 7.73 (s, 1H), 7.62 (d, J=8.2 Hz, 1H), 7.47 (d, J=8.4 Hz, 1H), 6.69 (s, 1H), 6.23 (s, 1H), 4.99-4.88 (m, 1H), 4.23-4.15 (m, 1H), 3.49 (dd, J=15.4, 5.8 Hz, 1H), 3.39-3.29 (m, 6H), 3.09-2.56 (m, 4H), 1.53-1.40 (m, 2H), 1.24-1.17 (m, 9H), 1.16-1.07 (m, 2H), 1.06-1.01 (m, 1H), 0.97-0.91 (m, 1H), 0.87-0.78 (m, 2H).

Example 3.30: Preparation of Compound 30 ((S)-3-chloro-N-(1-((1-cyanocyclopropyl)amino)-3-(6-(4-methyl-2-oxopiperazin-1-yl)benzo[d]oxazol-2-yl)-1-oxopropan-2-yl)benzamide)

Figure 43:
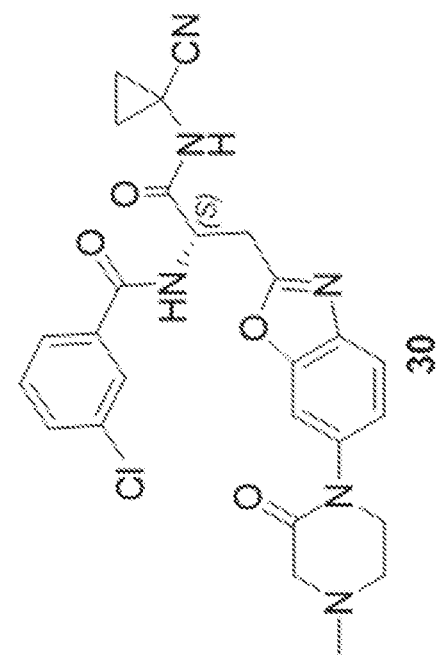
FIG. 43 is a schematic diagram illustrating an exemplary procedure for preparing Compound 30 according to some embodiments of the present disclosure.
Figure 43:
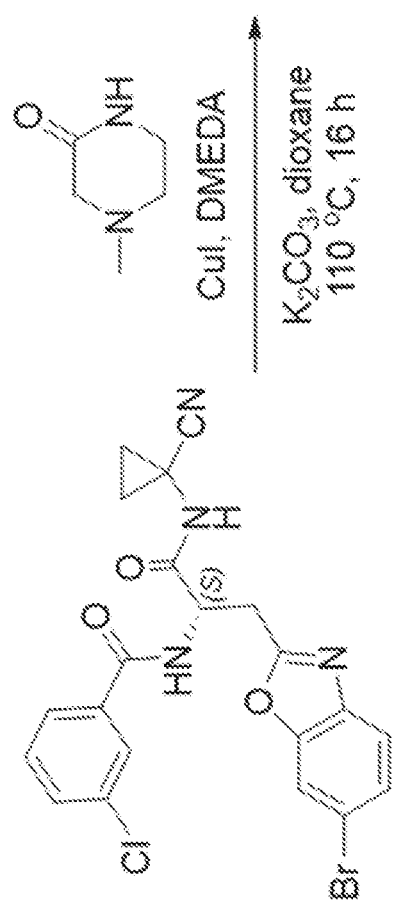

FIG. 43 is a schematic diagram illustrating an exemplary procedure for preparing Compound 30 according to some embodiments of the present disclosure.

To a mixture of (S)—N-(3-(6-bromobenzo[d]oxazol-2-yl)-1-((1-cyanocyclopropyl)amino)-1-oxopropan-2-yl)-3-chlorobenzamide (200 mg, 0.4 mmol) in dioxane (10.0 mL) was added $K_2CO_3$ (113 mg, 0.8 mmol), 4-methylpiperazin-2-one (93 mg, 0.8 mmol), CuI (15 mg, 0.08 mmol), and DMEDA (7 mg, 0.08 mmol). The reaction mixture was degassed with $N_2$ and stirred at 110° C. for 16 hrs. The reaction mixture was concentrated under reduced pressure and the residue was purified by Prep-HPLC [Gemini-C18 150×21.2 mm, 5um; Mobile phase: MeCN/$H_2O$ (0.1% FA); Ratio: 10-25] to give the desired product Compound 30 (12 mg, 6%). Mass spectrometry was conducted on the resultant compound, and the test results are as follows: Mass(m/z): 521.1 [M+H]$^+$. $^1$H NMR (400 MHz, MeOD) δ 7.84 (t, J=1.8 Hz, 1H), 7.75-7.72 (m, 1H), 7.68 (d, J=8.5 Hz, 1H), 7.59 (d, J=1.6 Hz, 1H), 7.57-7.54 (m, 1H), 7.45 (t, J=7.8 Hz, 1H), 7.29 (dd, J=8.4, 1.8 Hz, 1H), 5.06 (dd, J=8.2, 6.2 Hz, 1H), 3.79-3.76 (m, 2H), 3.61 (dd, J=15.4, 6.2 Hz, 1H), 3.47 (dd, J=15.4, 8.2 Hz, 1H), 3.29 (s, 2H), 2.89 (t, J=5.4 Hz, 2H), 2.44 (s, 3H), 1.52-1.44 (m, 2H), 1.26-1.16 (m, 2H).

Example 3.31: Preparation of Compound 31 ((S)—N-(3-(benzo[d]thiazol-2-yl)-1-((1-cyanocyclopropyl)amino)-1-oxopropan-2-yl)-3-chlorobenzamide)

Figure 44:
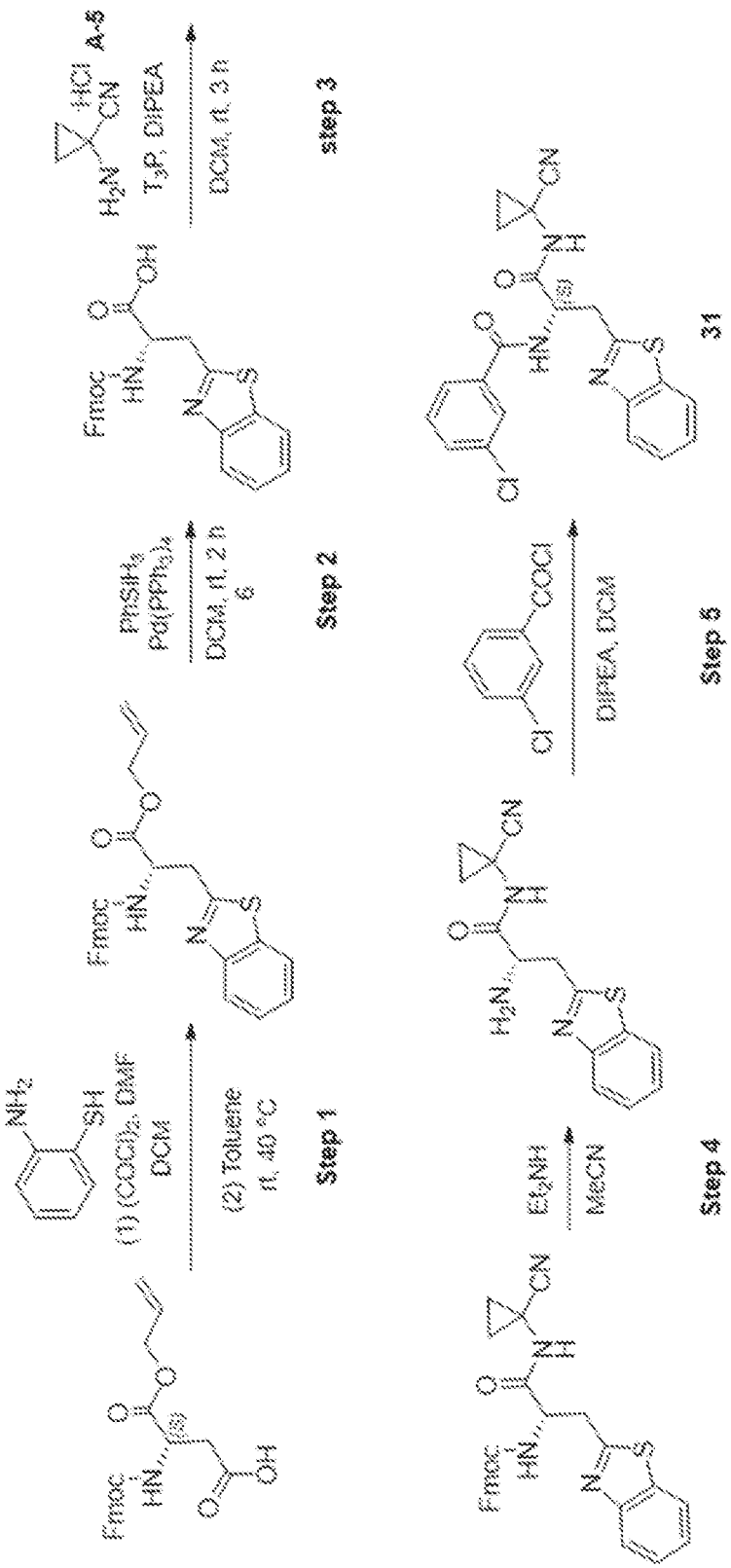
FIG. 44 is a schematic diagram illustrating an exemplary procedure for preparing Compound 31 according to some embodiments of the present disclosure.

FIG. 44 is a schematic diagram illustrating an exemplary procedure for preparing Compound 31 according to some embodiments of the present disclosure.

Step 1. Preparation of allyl (S)-2-((((9H-fluoren-9-yl)methoxy)carbonyl)amino)-3-(benzo[d]thiazol-2-yl)propanoate To a solution of (S)-3-((((9H-fluoren-9-yl)methoxy)carbonyl)amino)-4-(allyloxy)-4-oxobutanoic acid (1 g, 2.53 mmol), (COCl)$_2$ (0.38 g, 3.0 mmol) in DCM (25 mL) was added 1 drop DMF and then the reaction mixture was stirred at 25° C. under $N_2$ for 2 h. Then the solvent was removed under vacuum to give a residue, the residue was dissolved in anhydrous toluene (15 mL). After that, 2-aminobenzenethiol (0.33 g, 2.6 mmol) and DIPEA (0.97 g, 7.5 mmol) was added and the reaction mixture was heated to 40° C. and stirred for 2 hours. After cooled to room temperature, the reaction mixture was removed and then quenched with water (30 mL) and extracted with DCM (120 mL×3). The combined organic layer was dried over $Na_2SO_4$ and concentrated under vacuum to give the crude desired product, which was purified by flash chromatography (EA in PE, 30% to 50%) to give the desired product (0.47 g, 32%) as a white solid. Mass spectrometry was conducted on the resultant compound, and the test results are as follows: Mass(m/z): 485.1 [M+H]$^+$.

Step 2. Preparation of (S)-2-((((9H-fluoren-9-yl)methoxy)carbonyl)amino)-3-(benzo[d]thiazol-2-yl)propanoic acid To a solution of allyl (S)-2-((((9H-fluoren-9-yl)methoxy)carbonyl)amino)-3-(benzo[d]thiazol-2-yl) propanoate (470 mg, 0.96 mmol) in DCM (12 mL) was added phenylsilane (215.43 mg, 2.9 mmol) and followed by tetrakis(triphenylphosphine)palladium (559.23 mg, 0.48 mmol) under nitrogen protection. After the addition, the reaction mixture was stirred at 25° C. for 3 h. The solvent was removed under vacuum to give a crude product, which was purified by flash chromatography (MeOH in DCM, 2%-10%) to obtain the desired product (350 mg, 81%) as a pale solid. Mass spectrometry was conducted on the resultant compound, and the test results are as follows: Mass(m/z): 445.1 [M+H]$^+$.

Step 3. Preparation of (9H-fluoren-9-yl)methyl (S)-(3-(benzo[d]thiazol-2-yl)-1-((1-cyanocyclopropyl)amino)-1-oxopropan-2-yl)carbamate A solution of (S)-2-((((9H-fluoren-9-yl)methoxy)carbonyl)amino)-3-(benzo[d]thiazol-2-yl)propanoic acid (350 mg, 0.78 mmol), 1-aminocyclopropane-1-carbonitrile hydrogen chloride (67.73 mg, 0.82 mmol), DIPEA (203.06 mg, 0.57 mmol) and HATU (358.45 mg, 0.45 mmol) in DMF (5 mL) was stirred at 25° C. under $N_2$ for 3 hrs. The reaction mixture was quenched with water and extracted with EA (30 mL×3). The combined organic layer was dried over $Na_2SO_4$ and concentrated under vacuum to give a crude product, which was purified by flash chromatography (MeOH in DCM, 2% to 10%) to obtain the desired product (90 mg, 20%) as a pale solid. Mass spectrometry was conducted on the resultant compound, and the test results are as follows: Mass(m/z): 509.1 [M+H]$^+$.

Step 4. Preparation of (S)-2-amino-3-(benzo[d]thiazol-2-yl)-N-(1-cyanocyclopropyl)propanamide To a solution of (9H-fluoren-9-yl)methyl (S)-(3-(benzo[d]thiazol-2-yl)-1-((1-cyanocyclopropyl)amino)-1-oxopropan-2-yl)carbamate (90 mg, 0.17 mmol) in MeCN (5 mL) was added $Et_2NH$ (1 mL). The reaction mixture was stirred at 25° C. under $N_2$ for 3 hrs. The mixture was concentrated under reduced pressure to give a residue. The residue was purified by prep-HPLC [(Gemini-C18, 150×21.2 mm, 5um; ACN-$H_2O$ (0.1% FA); 15-90)] to give the desired product (26 mg, 54%) as a white solid. Mass spectrometry was conducted on the resultant compound, and the test results are as follows: Mass(m/z): 287 [M+H]$^+$.

Step 5. Preparation of (S)—N-(3-(benzo[d]thiazol-2-yl)-1-((1-cyanocyclopropyl)amino)-1-oxopropan-2-yl)-3-chlorobenzamide To a solution of (S)-2-amino-3-(benzo[d]thiazol-2-yl)-N-(1-cyanocyclopropyl)propanamide and DIPEA (16.25 mg, 0.12 mmol) in DCM (1 mL) was added a solution of 3-chlorobenzoyl chloride (7.7 mg, 0.04 mmol) in DCM (0.5 mL) dropwise. After the addition, the reaction mixture was stirred at 25° C. for 0.5 h. Then the reaction mixture was quenched with water and extracted with DCM (20 mL×3). The combined organic layer was dried over $Na_2SO_4$ and concentrated under vacuum to give a crude product, which was purified by prep-HPLC [(Gemini-C18, 150×21.2 mm, 5um; ACN-$H_2O$ (0.1% FA); 15%-90%)] to give the desired product Compound 31 (11.2 mg, 31%) as a white solid. Mass spectrometry was conducted on the resultant compound, and the test results are as follows: Mass(m/z): 425.0 [M+H]$^+$. $^1$H NMR (400 MHz, DMSO-$d_6$) δ 8.63 (d, J=6.4 Hz, 1H), 8.24 (s, 1H), 8.01-7.97 (m, 1H), 7.92 (t, J=1.8 Hz, 1H), 7.88 (d, J=7.8 Hz, 1H), 7.80-7.77 (m, 1H), 7.55-7.49 (m, 2H), 7.41 (m, 2H), 5.03 (m, 1H), 3.83 (m, 1H), 3.49-3.43 (m, 1H), 1.53-1.47 (m, 2H), 1.23-1.13 (m, 2H).

Example 3.32: Preparation of Compound 32 ((S)-3-chloro-N-(1-(((1-cyanocyclopropyl)amino)-3-(1-methyl-1 H-benzo[d]imidazol-2-yl)-1-oxopropan-2-yl)benzamide)

Figure 45:
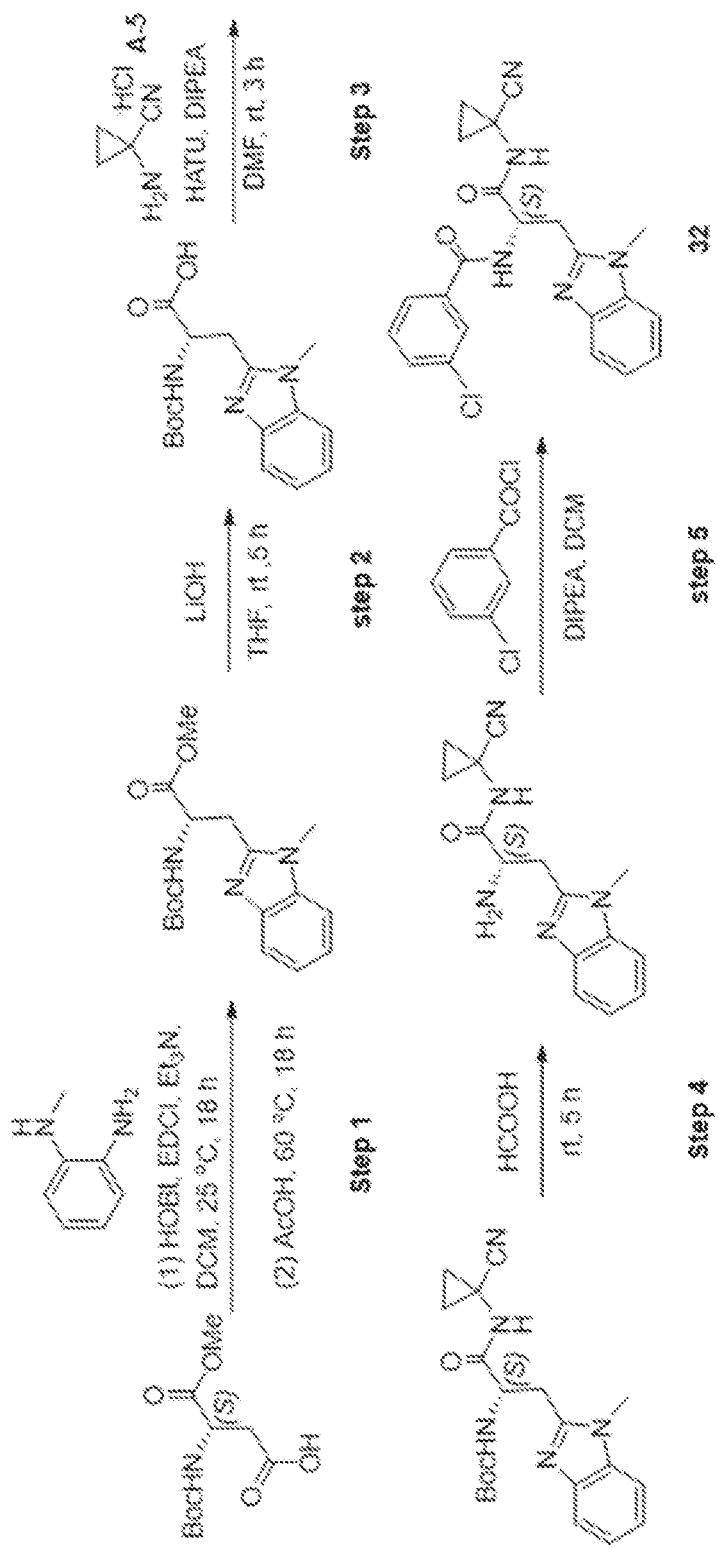
FIG. 45 is a schematic diagram illustrating an exemplary procedure for preparing Compound 32 according to some embodiments of the present disclosure.

FIG. 45 is a schematic diagram illustrating an exemplary procedure for preparing Compound 32 according to some embodiments of the present disclosure.

Step 1. Preparation of methyl (S)-2-((tert-butoxycarbonyl)amino)-3-(1-methyl-1 H-benzo[d]imidazol-2-yl)propanoate A mixture of (S)-3-((tert-butoxycarbonyl)amino)-4-methoxy-4-oxobutanoic acid (1.3 g, 5.26 mmol), $N^1$-methylbenzene-1,2-diamine (284 mg, 5.26 mmol), HOBt (858 mg, 6.31 mmol), EDCl (1.21 g, 6.31 mmol), $Et_3N$ (1.59 g, 15.78 mmol) in DCM (20 mL) under nitrogen was stirred for 18 hrs at 25° C. The reaction mixture was quenched with 15 mL of water and extracted with DCM (30 mL×3). The combined organic layer was dried over $Na_2SO_4$ and concentrated under vacuum, purified on silica gel (EtOAc in PE, 50% to 100%) to give a mixture of NH and NMe-amides, as a light brown oil. This mixture (1.18 mg, 3.4 mmol) in AcOH (10 mL) under nitrogen was heated to 60° C. and stirred for 18 h. The reaction was cooled to room temperature and the solvent was removed to give a residue, the residue was dissolved with EtOAc (30 mL) and basified with Sat. $NaHCO_3$ (20 mL), the organic layer was separated, and the aqueous layer was extracted with EtOAc (30 mL×3). The combined organic layer was washed with brine and dried over anhydrous $Na_2SO_4$. After filtration and concentration, the crude product was then purified on silica gel, eluted with EtOAc in petroleum ether (35% to 100%) to give the desired product (700 mg, 62.5%) as a light-yellow oil. Mass spectrometry was conducted on the resultant compound, and the test results are as follows: Mass(m/z): 334.1 $[M+H]^+$.

Step 2. Preparation of (S)-2-((tert-butoxycarbonyl)amino)-3-(1-methyl-1H-benzo[d]imidazol-2-yl)propanoic acid To a solution of methyl (S)-2-((tert-butoxycarbonyl)amino)-3-(1-methyl-1 H-benzo[d]imidazol-2-yl)propanoate (500 mg, 1.50 mmol) in THF (8 mL) was added a solution of LiOH (72 mg, 3.0 mmol) in water (1.5 mL) slowly. After the addition, the reaction mixture was stirred for 5 hrs. Then the reaction mixture was acidified with HCl (1M) to pH=3 and extracted with EtOAc (30 mL×3). The combined organic layer was washed with brine and dried over anhydrous $Na_2SO_4$. The solvent was removed under vacuum to give the crude product (330 mg, 69%) as a light brown solid. Mass spectrometry was conducted on the resultant compound, and the test results are as follows: Mass(m/z): 320.1 $[M+H]^+$.

Step 3. Preparation of tert-butyl (S)-(1-(((1-cyanocyclopropyl)amino)-3-(1-methyl-1H-benzo[d]imidazol-2-yl)-1-oxopropan-2-yl)carbamate A solution of (S)-2-((tert-butoxycarbonyl)amino)-3-(1-methyl-1H-benzo[d]imidazol-2-yl)propanoic acid (330 mg, 1.03 mmol), A-5 (147 mg, 1.24 mmol), HATU (471 mg, 1.24 mmol), and DIPEA (401.7 mg, 3.09 mmol) in DMF (5 mL) was stirred under nitrogen at 25° C. for 3 hrs. The reaction mixture was quenched with water (10 mL) and extracted with EA (35 mL×3). The combined organic layer was dried over $Na_2SO_4$ and concentrated to dryness and then purified on silica gel, eluted with (EA in PE, 30% to 100%) to obtain the desired product (250 mg, 63.4%) as a white solid. Mass spectrometry was conducted on the resultant compound, and the test results are as follows: Mass(m/z): 384.1 $[M+H]^+$.

Step 4. Preparation of (S)-2-amino-N-(1-cyanocyclopropyl)-3-(1-methyl-1 H-benzo[d]imidazol-2-yl)propanamide A solution of tert-butyl (S)-(1-(((1-cyanocyclopropyl)amino)-3-(1-methyl-1H-benzo[d]imidazol-2-yl)-1-oxopropan-2-yl)carbamate (70 mg, 0.18 mmol) in FA (2 mL) was stirred under nitrogen at 25° C. for 5 hrs. The mixture was blown by nitrogen to dryness at 20° C. Then the residue was basified with saturated sodium bicarbonate and extracted with EA (20 mL×3). And then the combined organic layer was concentrated to dryness to give the desired product (22 mg, 43%) as a pale solid. Mass spectrometry was conducted on the resultant compound, and the test results are as follows: Mass(m/z): 284.1 $[M+H]^+$.

Step 5. Preparation of (S)-3-chloro-N-(1-(((1-cyanocyclopropyl)amino)-3-(1-methyl-1H-benzo[d]imidazol-2-yl)-1-oxopropan-2-yl)benzamide To a solution of (S)-2-amino-N-(1-cyanocyclopropyl)-3-(1-methyl-1H-benzo[d]imidazol-2-yl)propanamide (22 mg, 0.08 mmol) and DIPEA (20.64 mg, 0.16 mmol) in DCM (2 mL) was added a solution of 3-chlorobenzoyl chloride (14 mg, 0.08 mmol) in DCM (0.5 mL) dropwise, after the addition, the reaction mixture was stirred at 25° C. for 1 h. The reaction mixture was quenched with water (5 mL) and extracted with DCM (15 mL×3). The combined organic layer was concentrated to dryness, and the residue was purified by prep-HPLC [(Gemini-C18, 150×21.2 mm, Sum; ACN-$H_2O$ (0.1% FA); 15%-95%)] to give the desired product Compound 32 (4.2 mg, 12.4%) as a white solid. Mass spectrometry was conducted on the resultant compound, and the test results are as follows: Mass(m/z): 422.0 $[M+H]^+$. $^1H$ NMR (400 MHz, DMSO-d) δ 9.01 (s, 1H), 8.98 (d, J=7.6 Hz, 1H), 7.91 (s, 1H), 7.79 (d, J=7.9 Hz, 1H), 7.61 (d, J=9.0 Hz, 1H), 7.51 (t, J=7.8 Hz, 2H), 7.17 (m, 2H), 4.96 (dd, J=14.3, 7.6 Hz, 1H), 3.78 (s, 3H), 3.37 (dd, J=16.5, 6.6 Hz, 2H), 1.47-1.36 (m, 2H), 1.02 (m, 2H).

Figure 46:
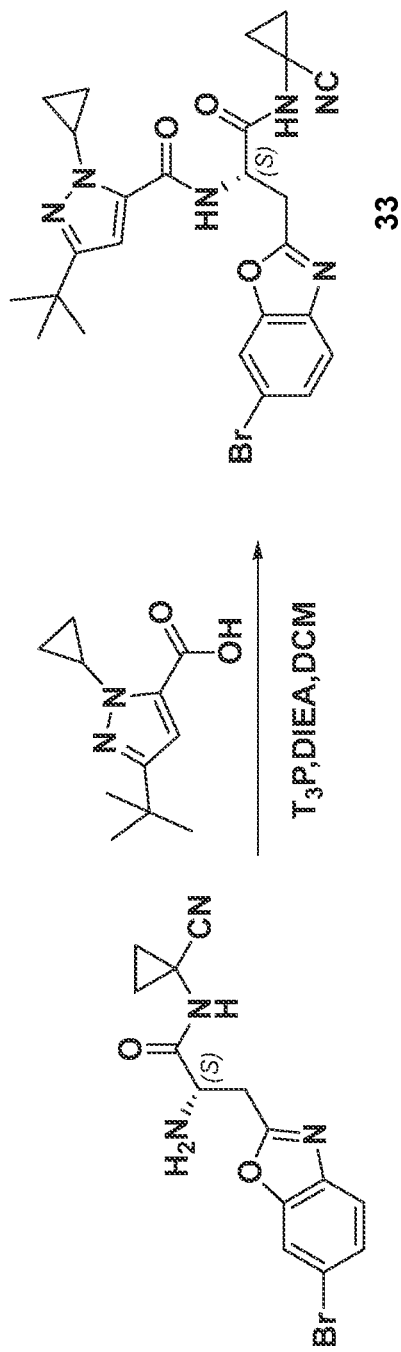
FIG. 46 is a schematic diagram illustrating an exemplary procedure for preparing Compound 33 according to some embodiments of the present disclosure.

Example 3.33: Preparation of Compound 33 (S)—N-(3-(6-bromobenzo[d]oxazol-2-yl)-1-(((1-cyanocyclopropyl)amino)-1-oxopropan-2-yl)-3-(tert-butyl)-1-cyclopropyl-1H-pyrazole-5-carboxamide FIG. 46 is a schematic diagram illustrating an exemplary procedure for preparing Compound 33 according to some embodiments of the present disclosure.

To a solution of (2S)-2-amino-3-(6-bromo-1,3-benzoxazol-2-yl)-N-(1-cyanocyclopropyl)propenamide (1.6 g, 4.58 mmol) and 5-tert-butyl-2-cyclopropyl pyrazole-3-carboxylic acid (954 mg, 4.58 mmol) in DCM (20 mL) was added T3P (50% in EA, 5.83 g, 9.16 mmol) and DIEA (1.18 g, 9.16 mmol). The reaction mixture was stirred at 25° C. under $N_2$ for 3 hrs. The reaction mixture was concentrated and the residue was purified by silica gel column chromatography (PE:EA=1:1) to give the desired product Compound 33 as a yellow solid (1.3 g, 47%). Mass spectrometry was conducted on the resultant compound, and the test results are as follows: Mass(m/z): 539.1 541.1$[M+H]^+$. $^1H$ NMR (400 MHz, DMSO-$d_6$) δ 9.17 (s, 1H), 8.84 (d, J=8.0 Hz, 1H), 8.00 (d, J=1.7 Hz, 1H), 7.64 (d, J=8.4 Hz, 1H), 7.52 (dd, J=8.4, 1.8 Hz, 1H), 6.68 (s, 1H), 4.99-4.88 (m, 1H), 4.26-4.13 (m, 1H), 3.49 (dd, J=15.4, 5.8 Hz, 1H), 3.34-3.29 (m, 1H), 1.55-1.39 (m, 2H), 1.20 (s, 9H), 1.13-0.80 (m, 6H).

Figure 47:
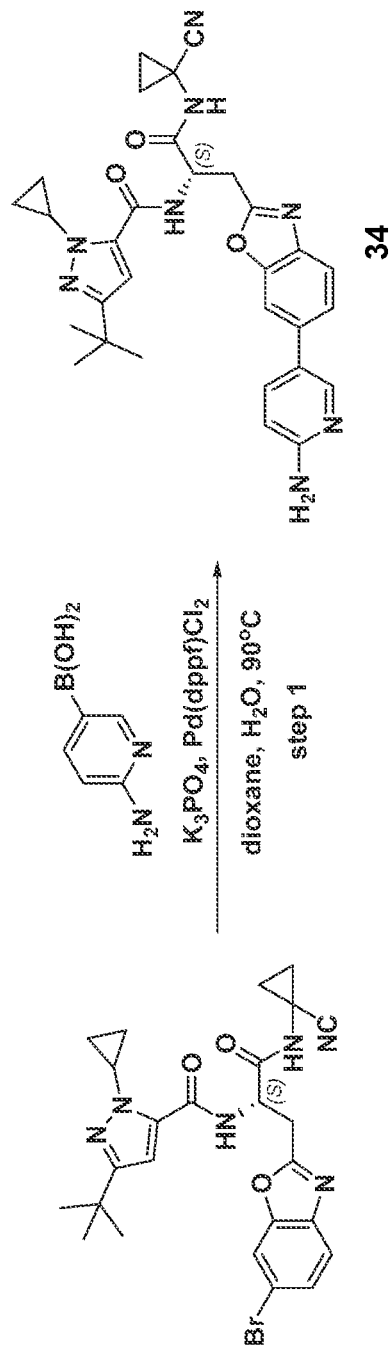
FIG. 47 is a schematic diagram illustrating an exemplary procedure for preparing Compound 34 according to some embodiments of the present disclosure.

Example 3.34: Preparation of Compound 34 (S)—N-(3-(6-(6-aminopyridin-3-yl)benzo[d]oxazol-2-yl)-1-((1-cyanocyclopropyl) amino)-1-oxopropan-2-yl)-3-(tert-butyl)-1-cyclopropyl-1H-pyrazole-5-carboxamide FIG. 47 is a schematic diagram illustrating an exemplary procedure for preparing Compound 34 according to some embodiments of the present disclosure.

To a solution of (S)—N-(3-(6-bromobenzo[d]oxazol-2-yl)-1-((1-cyanocyclopropyl)amino)-1-oxopropan-2-yl)-3-(tert-butyl)-1-cyclopropyl-1H-pyrazole-5-carboxamide (150 mg, 0.28 mmol) and (6-aminopyridin-3-yl)boronic acid (58 mg, 0.42 mmol) in dioxane (3 mL) and H$_2$O (0.3 mL) was added K$_3$PO$_4$ (118 mg, 0.56 mmol) and Pd(dppf)Cl$_2$ (20 mg, 0.028 mmol). The reaction mixture was stirred at 90° C. under N$_2$ for 10 hrs. The reaction mixture was concentrated and the residue was purified by Pre-TLC (DCM: MeOH=20:1) to give the desired product Compound 34 as a brown solid (120 mg, 72%). Mass spectrometry was conducted on the resultant compound, and the test results are as follows: Mass(m/z): 553.3[M+H]$^+$. $^1$H NMR (400 MHz, DMSO-d) δ 9.08 (s, 1H), 8.75 (d, J=8.0 Hz, 1H), 8.25 (d, J=2.2 Hz, 1H), 7.80 (d, J=1.2 Hz, 1H), 7.71 (dd, J=8.6, 2.4 Hz, 1H), 7.62 (d, J=8.2 Hz, 1H), 7.50 (dd, J=8.2, 1.6 Hz, 1H), 6.65 (s, 1H), 6.49 (d, J=8.6 Hz, 1H), 6.07 (s, 2H), 4.96-4.85 (m, 1H), 4.21-4.13 (m, 1H), 3.45 (dd, J=15.6, 5.8 Hz, 1H), 3.30-3.24 (m, 1H), 1.49-1.38 (m, 2H), 1.16 (s, 9H), 1.12-1.05 (m, 2H), 1.01-0.96 (m, 1H), 0.93-0.88 (m, 1H), 0.83-0.76 (m, 2H).

Figure 48:
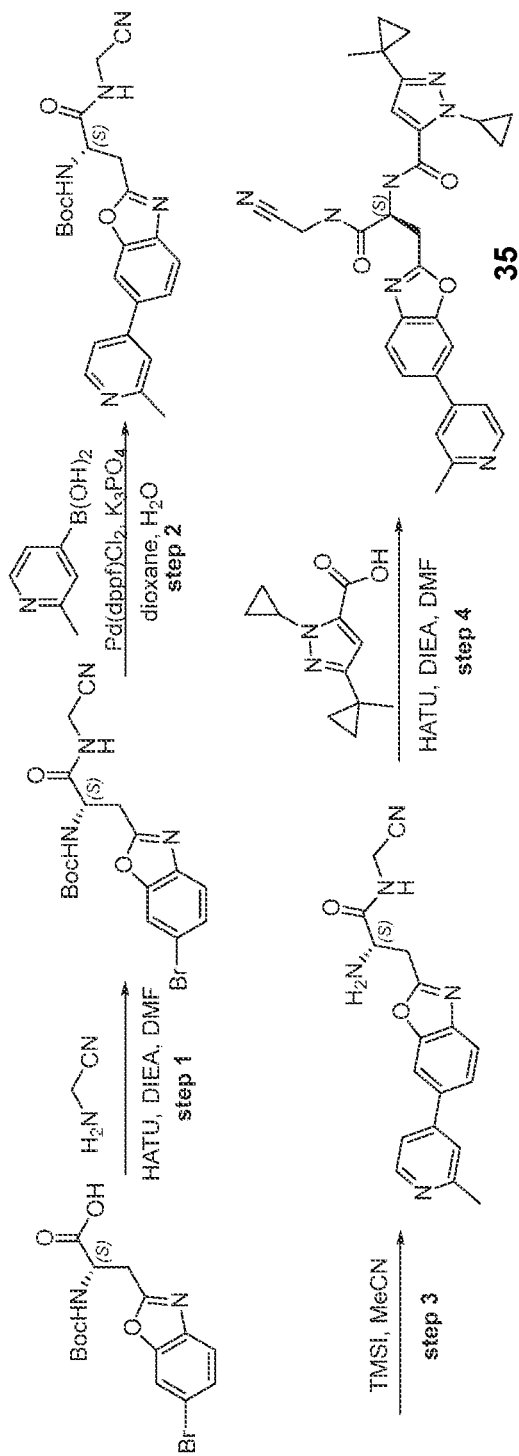
FIG. 48 is a schematic diagram illustrating an exemplary procedure for preparing Compound 35 according to some embodiments of the present disclosure.

Example 3.35: Preparation of Compound 35 (S)—N-(1-((cyanomethyl)amino)-3-(6-(2-methylpyridin-4-yl)benzo[d]oxazol-2-yl)-1-oxopropan-2-yl)-1-cyclopropyl-3-(1-methylcyclopropyl)-1H-pyrazole-5-carboxamide FIG. 48 is a schematic diagram illustrating an exemplary procedure for preparing Compound 35 according to some embodiments of the present disclosure.

Step 1. Preparation of tert-butyl N-[(1S)-2-(6-bromo-1,3-benzoxazol-2-yl)-1-[(cyanomethyl)carbamoyl]ethyl]carbamate To a mixture of (2S)-3-(6-bromo-1,3-benzoxazol-2-yl)-2-{[(tert-butoxy)carbonyl] amino}propanoic acid (2.90 g, 7.5 mmol) in DMF (30.0 mL) was added 2-aminoacetonitrile (0.69 g, 7.5 mmol), DIEA (2.91 g, 22.5 mmol), and HATU (5.70 g, 15 mmol). The reaction was stirred at RT for 2 hrs. Water (100 mL) was added and the reaction mixture was extracted with EA (100 mL×3). The combined organic layers were washed with brine (100 mL×3), dried over Na$_2$SO$_4$, and concentrated under reduced pressure. The residue was purified by flash column (PE:EA=0-50%) to give the desired product tert-butyl N-[(1 S)-2-(6-bromo-1,3-benzoxazol-2-yl)-1-[(cyano methyl)carbamoyl]ethyl]carbamate as a white solid (2.7 g, 76%). Mass spectrometry was conducted on the resultant compound, and the test results are as follows: Mass(m/z): 423.0 [M+H]$^+$.

Step 2. Preparation of tert-butyl (S)-(1-((cyanomethyl)amino)-3-(6-(2-methylpyridin-4-yl)benzo[d]oxazol-2-yl)-1-oxopropan-2-yl)carbamate To a solution of tert-butyl (S)-(3-(6-bromobenzo[d]oxazol-2-yl)-1-((cyanomethyl)amino)-1-oxopropan-2-yl)carbamate (1400 mg, 3.31 mmol) in dioxane/H$_2$O (10/1, 30 mL) was added (2-methylpyridin-4-yl)boronic acid (679 mg, 4.96 mmol), K$_3$PO$_4$ (2103 mg, 9.92 mmol), and 1,1-Bis(diphenylphosphino) ferrocenepalladiumdichloride (242 mg, 0.33 mmol). The reaction mixture was stirred at 90° C. under N$_2$ for 16 hrs. The solvent was removed under reduced pressure and the residue was purified by Combiflash (PE/EA=0~ 80%) to give the product as a brown solid (840 mg, 58%). Mass spectrometry was conducted on the resultant compound, and the test results are as follows: Mass(m/z): 436.1 [M+H]$^+$.

Step 3. Preparation of (S)-2-amino-N-(cyanomethyl)-3-(6-(2-methylpyridin-4-yl)benzo[d]oxazol-2-yl)propanamide To a solution of (S)-(1-((cyanomethyl)amino)-3-(6-(2-methylpyridin-4-yl)benzo[d]oxazol-2-yl)-1-oxopropan-2-yl)carbamate (790 mg, 1.81 mmol) in MeCN (15 mL) was added TMSI (907 mg, 4.54 mmol). The reaction mixture was stirred at RT under N$_2$ for 0.5 hr. H$_2$O (50 mL) was added to the reaction mixture, and then adjusted to pH 8 by using sat. NaHCO$_3$ and extracted with EA (50 mL×3). The combined organic layer was washed with brine (30 mL×2), then dried over with anhydrous Na$_2$SO$_4$ to give the product as a yellow solid (550 mg, 58%). Mass spectrometry was conducted on the resultant compound, and the test results are as follows: Mass(m/z): 336.2 [M+H]$^+$.

Step 4. Preparation of (S)—N-(1-((cyanomethyl)amino)-3-(6-(2-methylpyridin-4-yl)benzo[d]oxazol-2-yl)-1-oxopropan-2-yl)-1-cyclopropyl-3-(1-methylcyclopropyl)-1 H-pyrazole-5-carboxamide To a solution of (S)-2-amino-N-(cyanomethyl)-3-(6-(2-methylpyridin-4-yl)benzo[d]oxazol-2-yl)propanamide (130 mg, 0.39 mmol) in DMF (10 mL) was added 2-cyclopropyl-5-(1-methylcyclopropyl)pyrazole-3-carboxylic acid (80 mg, 0.39 mmol), DIEA (250 mg, 1.94 mmol), and HATU (370 mg, 1.16 mmol). The reaction mixture was stirred at RT under N$_2$ for 2 hrs. After the reaction completed, H$_2$O (30 mL) was added to the reaction mixture, and then extracted with EA (30 mL×3). The combined organic layer was washed with brine (50 mL×2), then dried over with anhydrous Na$_2$SO$_4$. After filtration, the solution was concentrated under vacuum, and the residue was purified by Combiflash (DCM/MeOH=0~ 10%) to give the desired product Compound 35 as a white solid (140 mg, 68%). Mass spectrometry was conducted on the resultant compound, and the test results are as follows: Mass(m/z): 523.9 [M+H]$^+$. $^1$H NMR (400 MHz, DMSO-d$_6$) δ 8.86 (t, J=6.8 Hz, 2H), 8.51 (d, J=5.4 Hz, 1H), 8.14 (s, 1H), 7.78 (s, 2H), 7.67 (s, 1H), 7.58 (d, J=5.2 Hz, 1H), 6.61 (s, 1H), 5.09 (d, J=5.4 Hz, 1H), 4.21 (dd, J=7.6, 3.8 Hz, 1H), 4.17 (dd, J=5.6, 2.0 Hz, 2H), 3.59 (dd, J=15.6, 5.4 Hz, 1H), 3.42-3.36 (m, 1H), 2.54 (s, 3H), 1.33 (s, 3H), 1.01 (dd, J=6.3, 3.8 Hz, 1H), 0.91 (dd, J=10.0, 6.2 Hz, 1H), 0.85-0.74 (m, 4H), 0.68 (dd, J=6.2, 3.8 Hz, 2H).

Figure 49:
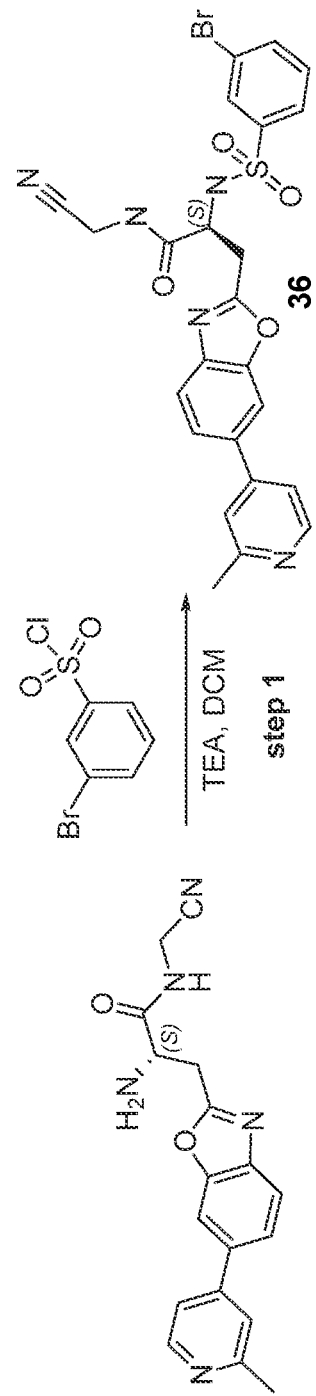
FIG. 49 is a schematic diagram illustrating an exemplary procedure for preparing Compound 36 according to some embodiments of the present disclosure.

Example 3.36: Preparation of Compound 36 (S)-2-((3-bromophenyl)sulfonamido)-N-(cyanomethyl)-3-(6-(2-methylpyridin-4-yl)benzo[d]oxazol-2-yl)propanamide FIG. 49 is a schematic diagram illustrating an exemplary procedure for preparing Compound 36 according to some embodiments of the present disclosure.

To a solution of (S)-2-amino-N-(cyanomethyl)-3-(6-(2-methylpyridin-4-yl)benzo[d]oxazol-2-yl)propanamide (80 mg, 0.24 mmol) in DCM (5 mL) was added 3-bromobenzenesulfonyl chloride (60 mg, 0.24 mmol) and TEA (73 mg, 0.72 mmol) at 0° C. The reaction mixture was stirred at RT under N$_2$ for 3 hrs. The resulting mixture was concentrated. The residue was purified via Prep-TLC (DCM/MeOH=20/1) to give the desired product Compound 36 (S)-2-((3-bromophenyl)sulfonamido)-N-(cyanomethyl)-3-(6-(2-methylpyridin-4-yl)benzo[d]oxazol-2-yl)propanamide as a white solid (20 mg, 15%). Mass spectrometry was conducted on the resultant compound, and the test results are as follows: Mass(m/z): 554.0 [M+H]$^+$. $^1$H NMR (400 MHz, MeOD) δ 8.48 (d, J=5.4 Hz, 1H), 7.88-7.83 (m, 2H), 7.74 (dd, J=8.2, 1.6 Hz, 1H), 7.69-7.62 (m, 3H), 7.59 (d, J=5.4 Hz, 1H), 7.42-7.38 (m, 1H), 7.16 (t, J=7.8 Hz, 1H), 4.49 (dd, J=9.6, 5.0 Hz, 1H), 4.14 (s, 2H), 3.41 (dd, J=15.4, 5.0 Hz, 1H), 3.21 (dd, J=15.4, 9.6 Hz, 1H), 2.63 (s, 3H).).

Figure 50:
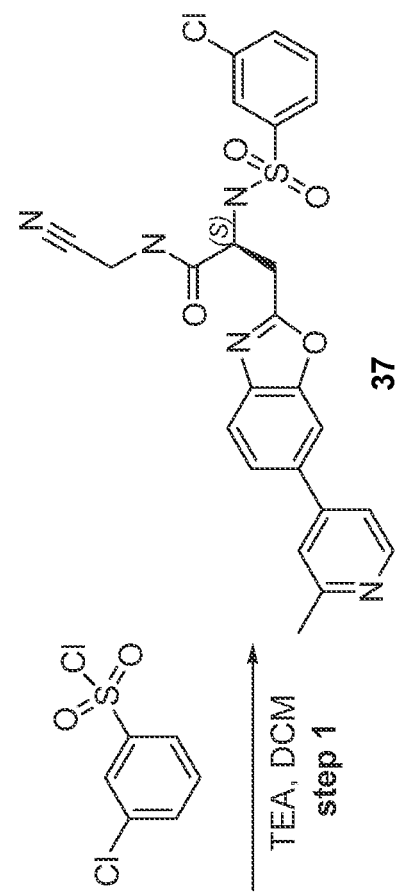
FIG. 50 is a schematic diagram illustrating an exemplary procedure for preparing Compound 37 according to some embodiments of the present disclosure.
Figure 50:
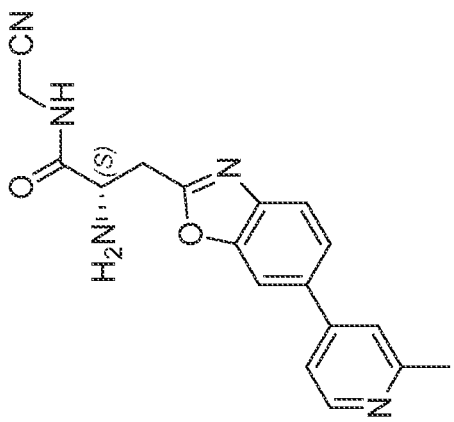

Example 3.37: Preparation of Compound 37 (S)-2-((3-chlorophenyl)sulfonamido)-N-(cyanomethyl)-3-(6-(2-methylpyridin-4-yl)benzo[d]oxazol-2-yl)propanamide FIG. 50 is a schematic diagram illustrating an exemplary procedure for preparing Compound 37 according to some embodiments of the present disclosure.

To a solution of (S)-2-amino-N-(cyanomethyl)-3-(6-(2-methylpyridin-4-yl)benzo[d]oxazol-2-yl)propanamide (80 mg, 0.24 mmol) in DCM (5 mL) was added 3-chlorobenzenesulfonyl chloride (50 mg, 0.24 mmol) and TEA (73 mg, 0.72 mmol) at 0° C. The reaction mixture was stirred at RT under $N_2$ for 3 hrs. The resulting mixture was concentrated. The residue was purified via Prep-TLC (DCM/MeOH=20/1) to give the desired product Compound 37 (S)-2-((3-chlorophenyl)sulfonamido)-N-(cyanomethyl)-3-(6-(2-methylpyridin-4-yl)benzo[d]oxazol-2-yl)propanamide as a white solid (30 mg, 20%). Mass spectrometry was conducted on the resultant compound, and the test results are as follows: Mass(m/z): 510.0 [M+H]$^+$. $^1$H NMR (400 MHz, MeOD) δ 8.48 (d, J=5.4 Hz, 1H), 7.86 (d, J=1.2 Hz, 1H), 7.75-7.69 (m, 2H), 7.66 (d, J=8.4 Hz, 2H), 7.60 (dt, J=10.6, 2.8 Hz, 2H), 7.25 (t, J=4.6 Hz, 2H), 4.49 (dd, J=9.4, 5.0 Hz, 1H), 4.13 (s, 2H), 3.41 (dd, J=15.4, 5.0 Hz, 1H), 3.21 (dd, J=15.4, 9.4 Hz, 2H), 2.63 (s, 3H).

Figure 51:
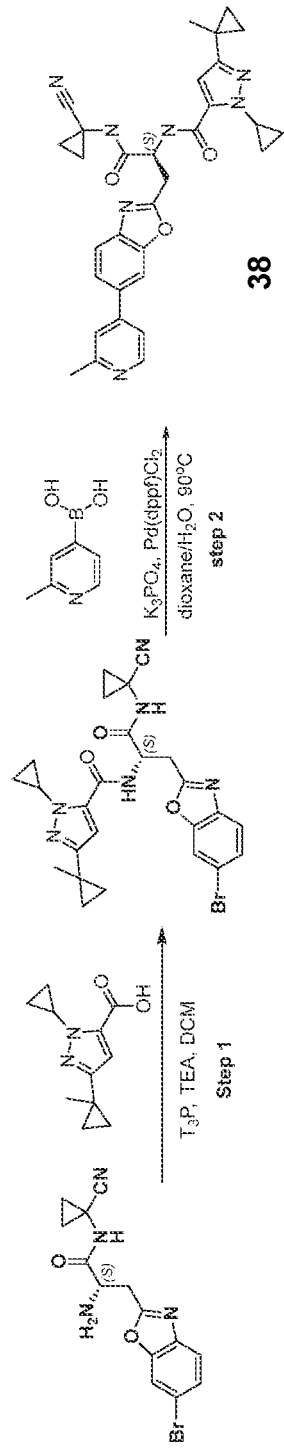
FIG. 51 is a schematic diagram illustrating an exemplary procedure for preparing Compound 38 according to some embodiments of the present disclosure.

Example 3.38: Preparation of Compound 38 (S)—N-(1-((1-cyanocyclopropyl)amino)-3-(6-(2-methylpyridin-4-yl)benzo[d]oxazol-2-yl)-1-oxopropan-2-yl)-1-cyclopropyl-3-(1-methylcyclopropyl)-1H-pyrazole-5-carboxamide FIG. 51 is a schematic diagram illustrating an exemplary procedure for preparing Compound 38 according to some embodiments of the present disclosure.

Step 1. Preparation of (2S)-3-(6-bromo-1,3-benzoxazol-2-yl)-N-(1-cyanocyclopropyl)-2-{[2-cyclopropyl-5-(1-methylcyclopropyl)pyrazol-3-yl]formamido}propenamide To a mixture of (2S)-2-amino-3-(6-bromo-1,3-benzoxazol-2-yl)-N-(1-cyanocyclopropyl) propenamide (454 mg, 1.30 mmol) and 2-cyclopropyl-5-(1-methylcyclopropyl) pyrazole-3-carboxylic acid (295 mg, 1.43 mmol) in DCM (10.0 mL) was added DIEA (504 mg, 3.90 mmol) and T3P (50% in EA, 1.65 g, 2.60 mmol). The reaction was stirred at RT for 16 hrs. The reaction mixture was diluted with water (100 mL) and extracted with EA (100 mL×3). The combined organic layers were washed with NaHCO$_3$(100 mL×3), brine (100 mL), dried over Na$_2$SO$_4$, and concentrated under reduced pressure. The residue was purified by flash column (PE: EA=0-60%) to give the product (2S)-3-(6-bromo-1,3-benzoxazol-2-yl)-N-(1-cyanocyclopropyl)-2-{[2-cyclopropyl-5-(1-methylcyclopropyl)pyrazol-3-yl]formamido}propanamide as a white solid (360 mg, 49%). Mass spectrometry was conducted on the resultant compound, and the test results are as follows: Mass(m/z): 537.1 [M+H]$^+$. $^1$H NMR (400 MHz, MeOD) δ 7.83 (d, J=1.6 Hz, 1H), 7.54 (dt, J=8.4, 5.2 Hz, 2H), 6.51 (s, 1H), 5.04 (dd, J=8.2, 6.2 Hz, 1H), 4.01-3.89 (m, 1H), 3.59 (dd, J=15.4, 6.2 Hz, 1H), 3.43 (dd, J=15.4, 8.2 Hz, 1H), 1.57-1.46 (m, 1H), 1.40 (s, 3H), 1.23 (td, J=12.6, 4.6 Hz, 2H), 1.11-1.05 (m, 1H), 1.02-0.80 (m, 5H), 0.70 (q, J=4.0 Hz, 2H).

Step 2. Preparation of (S)—N-(1-((1-cyanocyclopropyl)amino)-3-(6-(2-methylpyridin-4-yl)benzo[d]oxazol-2-yl)-1-oxopropan-2-yl)-1-cyclopropyl-3-(1-methylcyclopropyl)-1H-pyrazole-5-carboxamide To a solution of (S)—N-(3-(6-bromobenzo[d]oxazol-2-yl)-1-((1-cyanocyclopropyl) amino)-1-oxopropan-2-yl)-1-cyclopropyl-3-(1-methylcyclopropyl)-1H-pyrazole-5-carboxamide (300 mg, 0.56 mmol) in dioxane/H$_2$O (10/1, 15 mL) was added (2-methylpyridin-4-yl)boronic acid (77 mg, 0.56 mmol), K$_3$PO$_4$ (237 mg, 1.12 mmol), and 1,1'-Bis (diphenylphosphino)ferrocenepalladiumdichloride (45 mg, 0.06 mmol). The reaction mixture was stirred at 90° C. under $N_2$ for 16 hrs. The resulting mixture was concentrated. The residue was purified via Prep-TLC (DCM/MeOH=20/1) to give the desired product Compound 38 (S)—N-(1-((1-cyanocyclopropyl)amino)-3-(6-(2-methylpyridin-4-yl)benzo[d]oxazol-2-yl)-1-oxopropan-2-yl)-1-cyclopropyl-3-(1-methylcyclopropyl)-1H-pyrazole-5-carboxamide as a white solid (208 mg, 68%). Mass spectrometry was conducted on the resultant compound, and the test results are as follows: Mass(m/z): 550.2 [M+H]$^+$. $^1$H NMR (400 MHz, MeOD) δ 8.46 (d, J=5.2 Hz, 1H), 8.00 (s, 1H), 7.76 (d, J=0.9 Hz, 2H), 7.65 (s, 1H), 7.56 (d, J=5.2 Hz, 1H), 6.51 (s, 1H), 5.15-5.01 (m, 1H), 3.97-3.94 (m, 1H), 3.65-3.60 (m, 1H), 3.49-3.43 (m, 1H), 2.61 (s, 3H), 1.50 (d, J=3.0 Hz, 2H), 1.38 (s, 3H), 1.26-1.19 (m, 2H), 1.09-1.02 (m, 1H), 0.96-0.93 (m, 1H), 0.90-0.79 (m, 4H), 0.68 (q, J=4.0 Hz, 2H).

Figure 52:
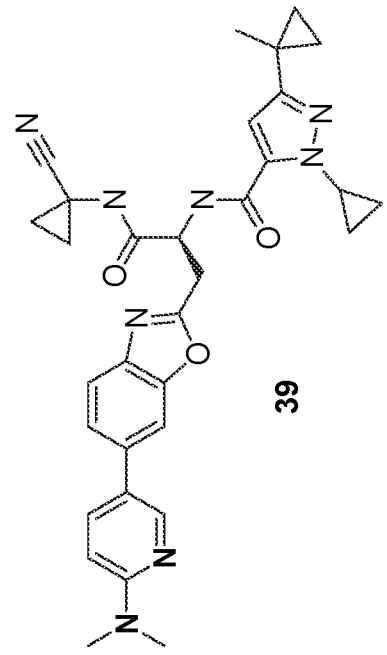
FIG. 52 is a schematic diagram illustrating an exemplary procedure for preparing Compound 39 according to some embodiments of the present disclosure.
Figure 52:
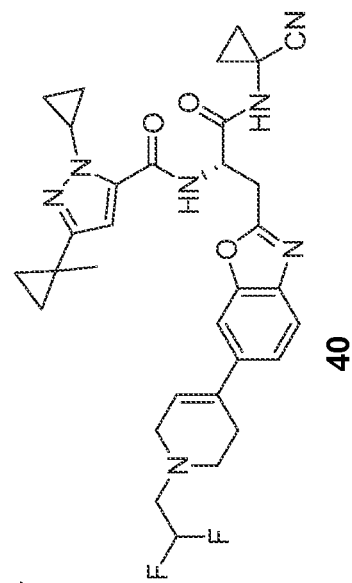

Example 3.39: Preparation of Compound 39 (2S)—N-(1-cyanocyclopropyl)-2-{[2-cyclopropyl-5-(1-methylcyclopropyl)pyrazol-3-yl]formamido}-3-{6-[6-(dimethylamino)pyridin-3-yl]-1,3-benzoxazol-2-yl}propanamide FIG. 52 is a schematic diagram illustrating an exemplary procedure for preparing Compound 39 according to some embodiments of the present disclosure.

To a solution of (S)—N-(3-(6-bromobenzo[d]oxazol-2-yl)-1-((1-cyanocyclopropyl) amino)-1-oxopropan-2-yl)-1-cyclopropyl-3-(1-methylcyclopropyl)-1H-pyrazole-5-carboxamide (80 mg, 0.1489 mmol) in dioxane/H$_2$O (10/1, 2 mL) was added (6-(dimethylamino)pyridin-3-yl)boronic acid (37 mg, 0.223 mmol), K$_3$PO$_4$ (63 mg, 0.297 mmol), and 1,1'-Bis(diphenylphosphino)ferrocenepalladiumdichloride (7 mg, 0.089 mmol). The reaction mixture was stirred at 90° C. under $N_2$ for 16 hrs. The solvent was removed under reduced pressure and the residue was purified by Prep-HPLC [Gemini-C18, 150×21.2 mm, Sum; ACN-H$_2$O (0.1% FA), 25-50] to give the desired product Compound 39 as a white solid (25 mg, 27%). Mass spectrometry was conducted on the resultant compound, and the test results are as follows: Mass(m/z): 579.0 [M+H]$^+$. $^1$H NMR (400 MHz, DMSO-d) δ 9.12 (s, 1H), 8.77 (d, J=7.8 Hz, 1H), 8.48 (d, J=2.2 Hz, 1H), 7.90 (s, 1H), 7.68 (d, J=8.2 Hz, 1H), 7.59 (d, J=8.2 Hz, 1H), 6.75 (d, J=8.6 Hz, 1H), 6.61 (s, 1H), 4.94 (dd, J=14.0, 8.2 Hz, 1H), 4.24-4.12 (m, 1H), 3.48 (dd, J=15.4, 5.6 Hz, 1H), 3.07 (d, J=9.8 Hz, 6H), 1.48 (d, J=2.4 Hz, 2H), 1.34 (s, 3H), 1.23 (s, 1H), 1.11 (q, J=10.6 Hz, 2H), 1.04-0.97 (m, 1H), 0.97-0.89 (m, 1H), 0.85-0.77 (m, 4H), 0.68 (dd, J=6.0, 3.8 Hz, 2H).

Figure 53:
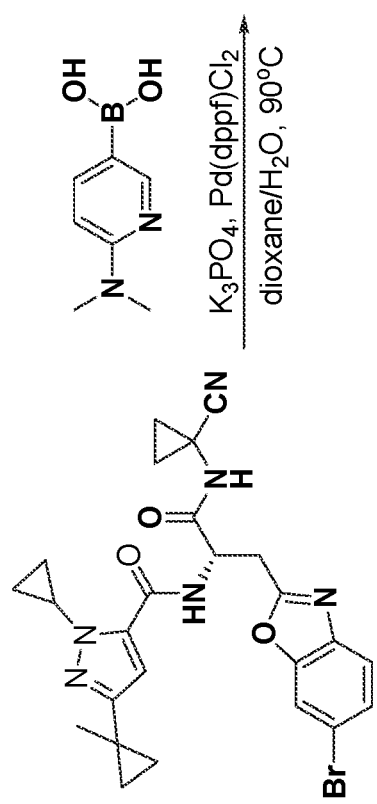
FIG. 53 is a schematic diagram illustrating an exemplary procedure for preparing Compound 40 according to some embodiments of the present disclosure.
Figure 53:
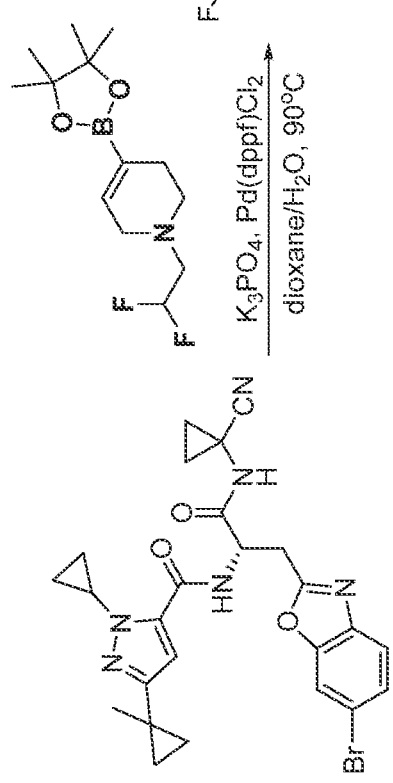

Example 3.40: Preparation of Compound 40 (S)—N-(1-((1-cyanocyclopropyl)amino)-3-(6-(1-(2,2-difluoroethyl)-1,2,3,6-tetrahydropyridin-4-yl)benzo[d]oxazol-2-yl)-1-oxopropan-2-yl)-1-cyclopropyl-3-(1-methylcyclopropyl)-1H-pyrazole-5-carboxamide FIG. 53 is a schematic diagram illustrating an exemplary procedure for preparing Compound 40 according to some embodiments of the present disclosure.

To a solution of (S)—N-(3-(6-bromobenzo[d]oxazol-2-yl)-1-((1-cyanocyclopropyl) amino)-1-oxopropan-2-yl)-1-cyclopropyl-3-(1-methylcyclopropyl)-1H-pyrazole-5-carboxamide (100 mg, 0.18 mmol) in dioxane/H$_2$O (10/1, 10 mL) was added 1-(2,2-difluoroethyl)-4-(4,4,5,5-tetramethyl-1,3,2-dioxaborolan-2-yl)-1,2,3,6-tetrahydro pyridine (51 mg, 0.18 mmol), K$_3$PO$_4$ (76 mg, 0.36 mmol), and 1,1'-Bis(diphenylphosphino)ferrocenepalladiumdichloride (16 mg, 0.02 mmol). The reaction mixture was stirred at 90° C. under N$_2$ for 16 hrs. The resulting mixture was concentrated. The residue was purified by Prep-TLC (DCM/MeOH=10/1) to give the desired product Compound 40 (S)—N-(1-((1-cyanocyclopropyl)amino)-3-(6-(1-(2,2-difluoroethyl)-1,2,3,6-tetrahydropyridin-4-yl)benzo[d]oxazol-2-yl)-1-oxopropan-2-yl)-1-cyclopropyl-3-(1-methylcyclopropyl)-1H-pyrazole-5-carboxamide as a white solid (8 mg, 7%). Mass spectrometry was conducted on the resultant compound, and the test results are as follows: Mass(m/z): 604.1 [M+H]$^+$. $^1$H NMR (400 MHz, MeOD) δ 7.64 (s, 1H), 7.59 (d, J=8.4 Hz, 1H), 7.49 (d, J=8.4 Hz, 1H), 6.51 (s, 1H), 6.20 (d, J=4.2 Hz, 1H), 5.99 (dt, J=55.8, 4.2 Hz, 1H), 5.04 (dd, J=8.2, 6.2 Hz, 1H), 3.94 (td, J=7.4, 3.8 Hz, 1H), 3.59 (dd, J=15.2, 6.2 Hz, 1H), 3.43 (dd, J=15.2, 8.4 Hz, 1H), 3.37-3.34 (m, 2H), 2.99-2.87 (m, 3H), 2.65 (s, 2H), 1.49 (t, J=8.2 Hz, 2H), 1.40 (s, 3H), 1.31 (s, 1H), 1.30-1.15 (m, 2H), 1.06 (dt, J=8.2, 5.2 Hz, 1H), 1.00-0.77 (m, 5H), 0.70 (q, J=3.8 Hz, 2H).

Figure 54:
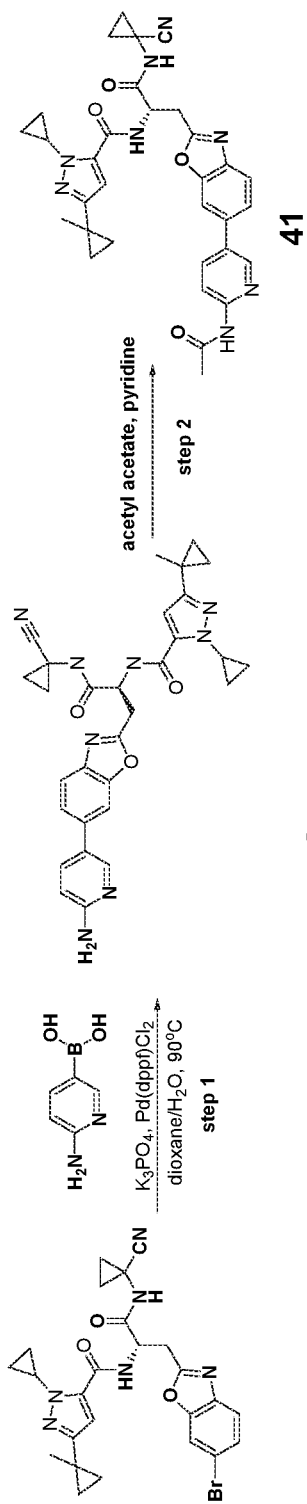
FIG. 54 is a schematic diagram illustrating an exemplary procedure for preparing Compound 41 according to some embodiments of the present disclosure.

Example 3.41: Preparation of Compound 41 (2S)—N-(1-cyanocyclopropyl)-2-{[2-cyclopropyl-5-(1-methylcyclopropyl)pyrazol-3-yl]formamido}-3-[6-(6-acetamidopyridin-3-yl)-1,3-benzoxazol-2-yl]propanamide FIG. 54 is a schematic diagram illustrating an exemplary procedure for preparing Compound 41 according to some embodiments of the present disclosure.

Step 1. Preparation of (S)—N-(3-(6-(6-aminopyridin-3-yl) benzo[d]oxazol-2-yl)-1-((1-cyanocyclopropyl)amino)-1-oxopropan-2-yl)-1-cyclopropyl-3-(1-methylcyclopropyl)-1H-pyrazole-5-carboxamide To a solution of (S)—N-(3-(6-bromobenzo[d]oxazol-2-yl)-1-((1-cyanocyclopropyl) amino)-1-oxopropan-2-yl)-1-cyclopropyl-3-(1-methylcyclopropyl)-1H-pyrazole-5-carboxamide (300 mg, 0.56 mmol) in dioxane/H$_2$O (10/1, 15 mL) was added (6-aminopyridin-3-yl)boronic acid (77 mg, 0.56 mmol), K$_3$P0$_4$ (237 mg, 1.12 mmol), and 1,1'-Bis(diphenylphosphino)ferrocenepalladiumdichloride (45 mg, 0.06 mmol). The reaction mixture was stirred at 90° C. under N$_2$ for 16 hrs. The resulting mixture was concentrated. The residue was purified by Prep-TLC (DCM: MeOH=10:1) to give the product as a white solid (140 mg, 45%). Mass spectrometry was conducted on the resultant compound, and the test results are as follows: Mass(m/z): 551.0 [M+H]$^+$. $^1$H NMR (400 MHz, DMSO-d$_6$) δ 9.12 (s, 1H), 8.76 (d, J=8.0 Hz, 1H), 8.29 (d, J=2.4 Hz, 1H), 7.85 (s, 1H), 7.77 (dd, J=8.6, 2.4 Hz, 1H), 7.66 (d, J=8.2 Hz, 1H), 7.54 (dd, J=8.4, 1.4 Hz, 1H), 6.61 (s, 1H), 6.55 (d, J=8.6 Hz, 1H), 6.17 (s, 2H), 4.93 (dd, J=14.2, 8.4 Hz, 1H), 4.26-4.12 (m, 1H), 3.48 (dd, J=15.6, 5.8 Hz, 1H), 3.29 (s, 1H), 1.51-1.44 (m, 2H), 1.34 (s, 3H), 1.12-1.07 (m, 2H), 1.04-0.98 (m, 1H), 0.95-0.89 (m, 1H), 0.88-0.75 (m, 4H).

Step 2. Preparation of (2S)—N-(1-cyanocyclopropyl)-2-{[2-cyclopropyl-5-(1-methylcyclopropyl)pyrazol-3-yl]formamido}-3-[6-(6-acetamidopyridin-3-yl)-1,3-benzoxazol-2-yl]propanamide To a mixture of (2S)-3-[6-(6-aminopyridin-3-yl)-1,3-benzoxazol-2-yl]-N-(1-cyanocyclopropyl)-2-{[2-cyclopropyl-5-(1-methylcyclopropyl)pyrazol-3-yl]formamido}propenamide (45 mg, 0.081 mmol) in Pyridine (1 mL) was added acetyl acetate (16 mg, 0.163 mmol). The reaction was stirred at RT under N$_2$ for 18 hrs. The solvent was removed under reduced pressure and the residue was purified by Prep-HPLC [Gemini-C18, 150×21.2 mm, Sum; ACN-H$_2$O (0.1% FA), 15-40] to give the desired product Compound 41 as a white solid (15 mg, 29%). Mass spectrometry was conducted on the resultant compound, and the test results are as follows: Mass(m/z): 593.0 [M+H]$^+$. $^1$H NMR (400 MHz, DMSO-d$_6$) δ 10.58 (s, 1H), 9.08 (s, 1H), 8.73 (d, J=8.0 Hz, 1H), 8.65 (d, J=1.8 Hz, 1H), 8.11 (d, J=2.4 Hz, 2H), 8.00 (d, J=1.4 Hz, 1H), 7.67 (dt, J=8.4, 5.0 Hz, 2H), 6.57 (s, 1H), 4.91 (td, J=8.2, 5.8 Hz, 1H), 4.26-4.04 (m, 1H), 3.51-3.42 (m, 1H), 3.30 (dd, J=15.6, 8.8 Hz, 1H), 2.08 (s, 3H), 1.47-1.41 (m, 2H), 1.30 (s, 3H), 1.23-1.19 (m, 3H), 1.14-1.02 (m, 2H), 0.99-0.94 (m, 1H), 0.91-0.86 (m, 1H), 0.84-0.72 (m, 5H), 0.64 (dd, J=6.2, 3.8 Hz, 2H).

Figure 55:
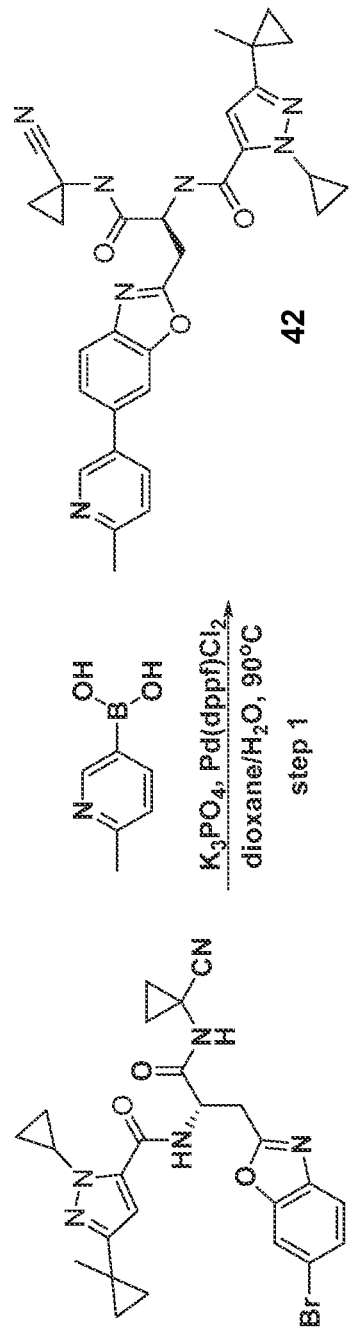
FIG. 55 is a schematic diagram illustrating an exemplary procedure for preparing Compound 42 according to some embodiments of the present disclosure.

Example 3.42: Preparation of Compound 42 (S)—N-(1-((1-cyanocyclopropyl)amino)-3-(6-(6-methylpyridin-3-yl)benzo[d] oxazol-2-yl)-1-oxopropan-2-yl)-1-cyclopropyl-3-(1-methylcyclopropyl)-1H-pyrazole-5-carboxamide FIG. 55 is a schematic diagram illustrating an exemplary procedure for preparing Compound 42 according to some embodiments of the present disclosure.

To a solution of (S)—N-(3-(6-bromobenzo[d]oxazol-2-yl)-1-((1-cyanocyclopropyl) amino)-1-oxopropan-2-yl)-1-cyclopropyl-3-(1-methylcyclopropyl)-1H-pyrazole-5-carboxamide (150 mg, 0.28 mmol) in dioxane/H$_2$O (10:1, 10 mL) was added (6-methylpyridin-3-yl)boronic acid (57 mg, 0.42 mmol), K$_3$PO$_4$ (118 mg, 0.56 mmol), and 1,1'-Bis (diphenylphosphino)ferrocenepalladiumdichloride (20 mg, 0.03 mmol). The reaction mixture was stirred at 90° C. under N$_2$ for 16 hrs. The resulting mixture was concentrated to give the crude product. The residue was purified via Prep-TLC (DCM/MeOH=20/1) to give the desired product Compound 42 (S)—N-(1-((1-cyanocyclopropyl)amino)-3-(6-(6-methylpyridin-3-yl)benzo[d]oxazol-2-yl)-1-oxopropan-2-yl)-1-cyclopropyl-3-(1-methylcyclopropyl)-1H-pyrazole-5-carboxamide as a white solid (70 mg, 45%). Mass spectrometry was conducted on the resultant compound, and the test results are as follows: Mass(m/z): 550.2[M+H]$^+$. $^1$H NMR (400 MHz, DMSO-d$_6$) δ 9.12 (s, 1H), 8.80 (dd, J=14.0, 5.2 Hz, 2H), 8.06-8.00 (m, 2H), 7.76 (d, J=8.4 Hz, 1H), 7.68 (dd, J=8.4, 1.6 Hz, 1H), 7.36 (d, J=8.2 Hz, 1H), 6.61 (s, 1H), 4.95 (d, J=5.8 Hz, 1H), 4.19 (d, J=3.8 Hz, 1H), 3.49 (d, J=5.8 Hz, 1H), 3.37 (d, J=8.8 Hz, 1H), 1.48 (d, J=2.4 Hz, 2H), 1.34 (s, 3H), 1.12 (d, J=10.8 Hz, 2H), 1.00 (s, 1H), 0.93 (s, 1H), 0.80 (dd, J=5.6, 3.8 Hz, 4H), 0.68 (dd, J=6.2, 3.8 Hz, 2H).

Figure 56:
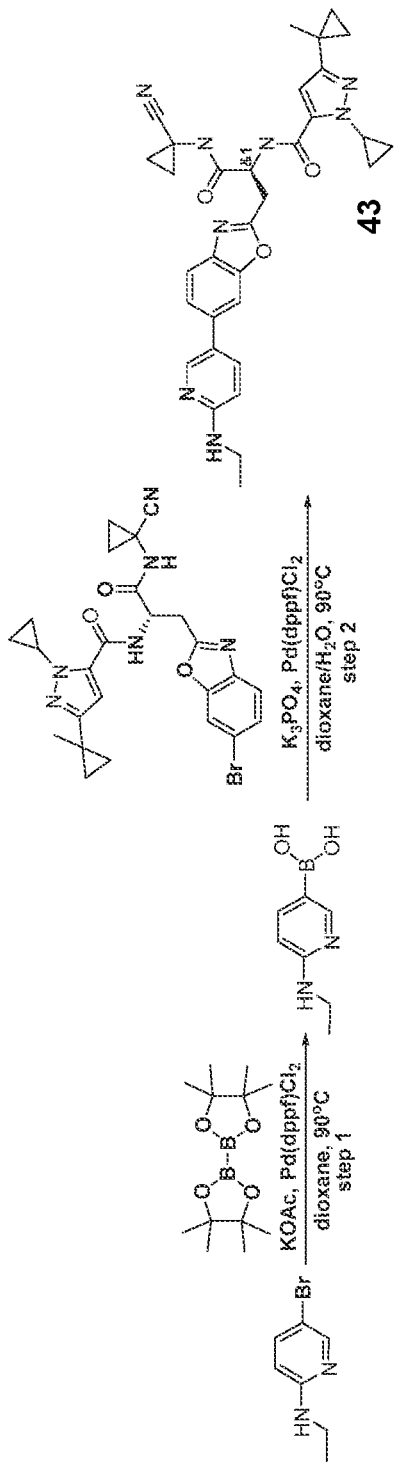
FIG. 56 is a schematic diagram illustrating an exemplary procedure for preparing Compound 43 according to some embodiments of the present disclosure.

Example 3.43: Preparation of Compound 43 (S)—N-(1-((1-cyanocyclopropyl)amino)-3-(6-(6-(ethylamino)pyridin-3-yl)benzo[d] oxazol-2-yl)-1-oxopropan-2-yl)-1-cyclopropyl-3-(1-methylcyclopropyl)-1H-pyrazole-5-carboxamide FIG. 56 is a schematic diagram illustrating an exemplary procedure for preparing Compound 43 according to some embodiments of the present disclosure.

Step 1. Preparation of (6-(ethylamino)pyridin-3-yl)boronic acid

To a solution of 5-bromo-N-ethylpyridin-2-amine (100 mg, 0.5 mmol) in dioxane (10 mL) was added 4,4,4',4',5,5,5',5'-octamethyl-2,2'-bi(1,3,2-dioxaborolane) (190 mg, 0.75 mmol), KOAc (98 mg, 1 mmol), and Pd(dppf)Cl$_2$ (40 mg, 0.05 mmol). The reaction mixture was stirred at 90° C. under N$_2$ for 16 hrs. The solvent was removed under reduced pressure to give the crude product (6-(ethylamino)pyridin-3-yl)boronic acid as yellow oil (90 mg, purity: 60%). Mass spectrometry was conducted on the resultant compound, and the test results are as follows: Mass(m/z): 167.3 [M+H]$^+$.

Step 2. Preparation of (S)—N-(1-((1-cyanocyclopropyl)amino)-3-(6-(6-(ethylamino) pyridine-3-yl)benzo[d]oxazol-2-yl)-1-oxopropan-2-yl)-1-cyclopropyl-3-(1-methyl cyclopropyl)-1H-pyrazole-5-carboxamide To a solution of (S)—N-(3-(6-bromobenzo[d]oxazol-2-yl)-1-((1-cyano cyclopropyl)amino)-1-oxopropan-2-yl)-1-cyclopropyl-3-(1-methylcyclopropyl)-1H-pyrazole-5-carboxamide (100 mg, 0.19 mmol) in dioxane/H$_2$O (10:1, 10 mL) was added (6-(ethylamino)pyridin-3-yl)boronic acid (46 mg, 0.28 mmol), K$_3$PO$_4$ (79 mg, 0.38 mmol), and Pd(dppf)Cl$_2$ (14 mg, 0.02 mmol). The reaction mixture was stirred at 90° C. under N$_2$ for 16 hrs. The solvent was removed under reduced pressure and the residue was purified by Combiflash column (DCM/MeOH=0~10%) to give the desired product Compound 43 (S)—N-(1-((1-cyanocyclopropyl)amino)-3-(6-(6-(ethylamino)pyridin-3-yl) benzo[d]oxazol-2-yl)-1-oxopropan-2-yl)-1-cyclopropyl-3-(1-methylcyclopropyl)-1H-pyrazole-5-carboxamide as a white solid (43 mg, 39%). Mass spectrometry was conducted on the resultant compound, and the test results are as follows: Mass(m/z): 579.2 [M+H]$^+$. $^1$H (400 MHz, MeOD) δ 8.23 (d, J=2.2 Hz, 1H), 7.78-7.72 (m, 2H), 7.67 (d, J=8.4 Hz, 1H), 7.54 (dd, J=8.2, 1.6 Hz, 1H), 6.63 (d, J=8.8 Hz, 1H), 6.52 (s, 1H), 5.06 (dd, J=8.4, 6.0 Hz, 1H), 4.00-3.92 (m, 1H), 3.61 (dd, J=15.2, 6.2 Hz, 1H), 3.45 (dd, J=15.4, 8.4 Hz, 1H), 3.40-3.35 (m, 2H), 1.51 (d, J=2.8 Hz, 2H), 1.39 (s, 3H), 1.28 (d, J=7.2 Hz, 3H), 1.25-1.16 (m, 2H), 1.10-1.03 (m, 1H), 0.97 (dd, J=10.0, 6.0 Hz, 1H), 0.88 (ddd, J=13.6, 8.6, 4.0 Hz, 4H), 0.69 (q, J=4.0 Hz, 2H).

Figure 57:
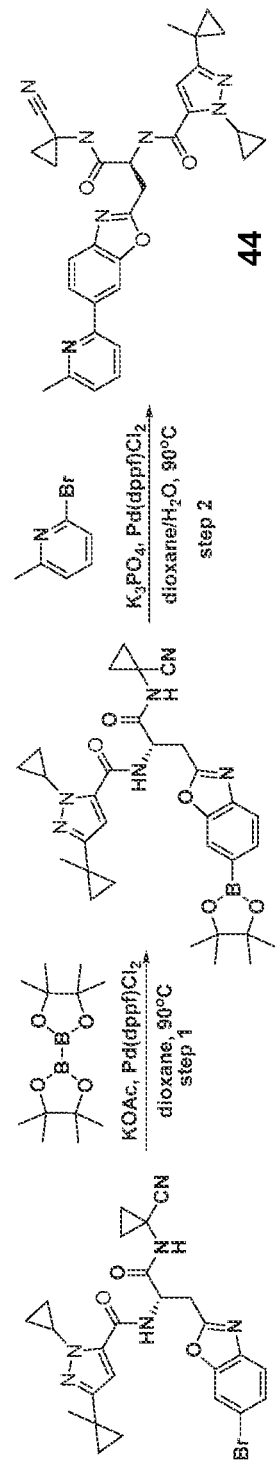
FIG. 57 is a schematic diagram illustrating an exemplary procedure for preparing Compound 44 according to some embodiments of the present disclosure.

Example 3.44: Preparation of Compound 44 (S)—N-(1-((1-cyanocyclopropyl)amino)-3-(6-(6-methylpyridin-2-yl)benzo[d] oxazol-2-yl)-1-oxopropan-2-yl)-1-cyclopropyl-3-(1-methylcyclopropyl)-1H-pyrazole-5-carboxamide FIG. 57 is a schematic diagram illustrating an exemplary procedure for preparing Compound 44 according to some embodiments of the present disclosure.

Step 1. Preparation of (S)—N-(1-((1-cyanocyclopropyl)amino)-1-oxo-3-(6-(4,4,5,5-tetramethyl-1,3,2-dioxaborolan-2-yl)benzo[d]oxazol-2-yl)propan-2-yl)-1-cyclopropyl-3-(1-methylcyclopropyl)-1H-pyrazole-5-carboxamide To a solution of (S)—N-(3-(6-bromobenzo[d]oxazol-2-yl)-1-((1-cyanocyclopropyl)amino)-1-oxopropan-2-yl)-1-cyclopropyl-3-(1-methylcyclopropyl)-1H-pyrazole-5-carboxamide (500 mg, 0.93 mmol) in dioxane (15 mL) was added 4,4,5,5-tetramethyl-2-(4,4,5,5-tetramethyl-1,3,2-dioxaborolan-2-yl)-1,3,2-dioxaborolane (354 mg, 1.39 mmol), KOAc (183 mg, 1.86 mmol), and Pd(dppf)Cl$_2$ (68 mg, 0.09 mmol). The reaction mixture was stirred at 90° C. under N$_2$ for 16 hrs. The solvent was removed under reduced pressure and the residue was purified by Combiflash column (DCM/MeOH=0~5%) to give the product (S)—N-(1-((1-cyanocyclopropyl)amino)-1-oxo-3-(6-(4,4,5,5-tetramethyl-1,3,2-dioxaborolan-2-yl)benzo[d]oxazol-2-yl)propan-2-yl)-1-cyclopropyl-3-(1-methylcyclopropyl)-1H-pyrazole-5-carboxamide as brown oil (400 mg, 73%). Mass spectrometry was conducted on the resultant compound, and the test results are as follows: Mass(m/z): 585.3 [M+H]$^+$.

Step 2. Preparation of (S)—N-(1-((1-cyanocyclopropyl) amino)-3-(6-(6-methylpyridin-2-yl)benzo[d]oxazol-2-yl)-1-oxopropan-2-yl)-1-cyclopropyl-3-(1-methylcyclopropyl)-1H-pyrazole-5-carboxamide To a solution of (S)—N-(1-((1-cyanocyclopropyl)amino)-1-oxo-3-(6-(4,4,5,5-tetramethyl-1,3,2-dioxaborolan-2-yl) benzo[d]oxazol-2-yl)propan-2-yl)-1-cyclopropyl-3-(1-methylcyclopropyl)-1H-pyrazole-5-carboxamide (40 mg, 0.07 mmol) in dioxane/H$_2$O (10:1, 5 mL) was added 2-bromo-6-methylpyridine (13 mg, 0.07 mmol), K$_3$PO$_4$ (33 mg, 0.14 mmol), and Pd(dppf)Cl$_2$ (6 mg, 0.01 mmol). The reaction mixture was stirred at 90° C. under N$_2$ for 16 hrs. The solvent was removed under reduced pressure and the residue was purified by Combiflash column (DCM/MeOH=0~10%) to give the desired product Compound 44 (S)—N-(1-((1-cyanocyclopropyl)amino)-3-(6-(6-methylpyridin-2-yl)benzo[d]oxazol-2-yl)-1-oxopropan-2-yl)-1-cyclopropyl-3-(1-methylcyclopropyl)-1H-pyrazole-5-carboxamide as a yellow solid (4 mg, 10%). Mass spectrometry was conducted on the resultant compound, and the test results are as follows: Mass(m/z): 550.2 [M+H]$^+$. $^1$H NMR (400 MHz, MeOD) δ 8.18 (d, J=1.2 Hz, 1H), 7.97 (dd, J=8.4, 1.6 Hz, 1H), 7.77 (d, J=7.6 Hz, 1H), 7.70 (dd, J=17.6, 8.2 Hz, 2H), 7.24 (d, J=7.6 Hz, 1H), 6.51 (s, 1H), 5.06 (dd, J=8.4, 6.2 Hz, 1H), 3.98-3.92 (m, 1H), 3.60 (s, 1H), 3.48 (d, J=8.4 Hz, 1H), 2.61 (s, 3H), 1.49 (d, J=2.8 Hz, 2H), 1.38 (s, 3H), 1.24-1.18 (m, 2H), 1.07-1.01 (m, 1H), 0.96 (dd, J=10.0, 6.0 Hz, 1H), 0.88 (dt, J=9.8, 5.2 Hz, 4H), 0.68 (q, J=4.0 Hz, 2H).

Figure 58:
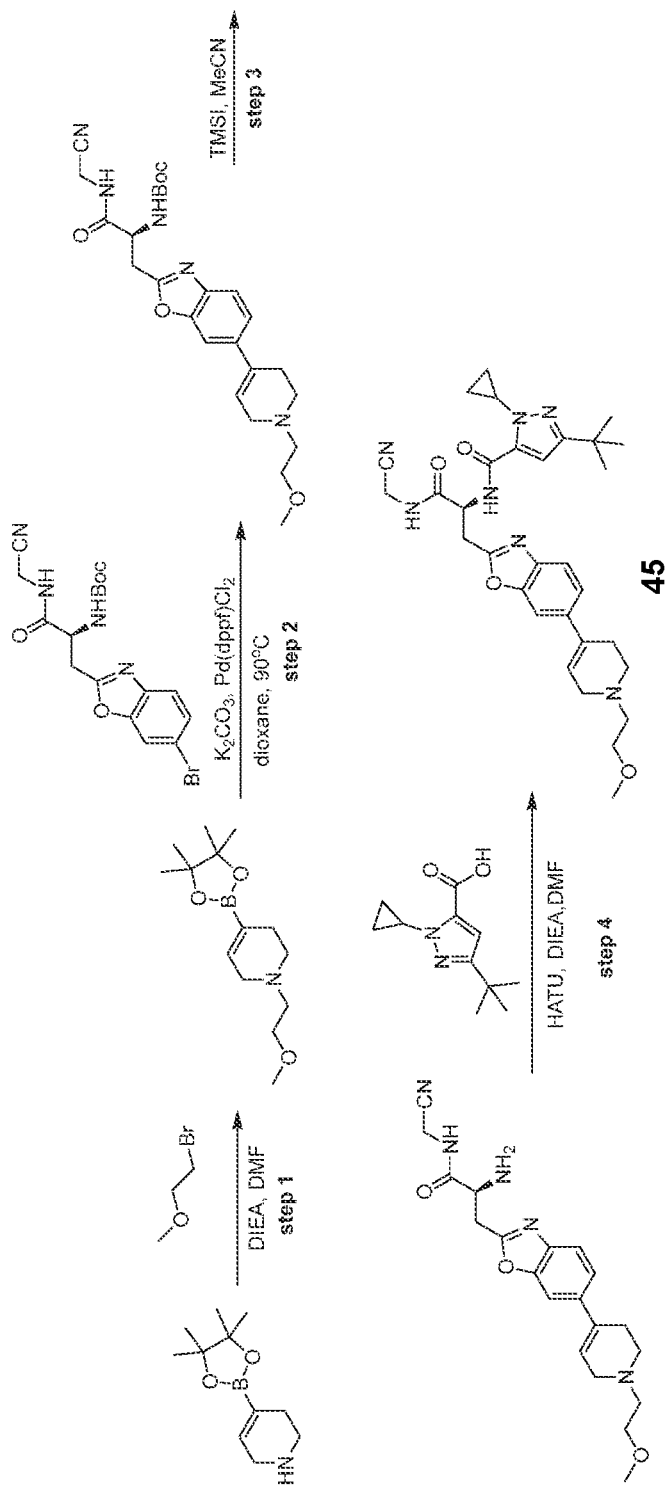
FIG. 58 is a schematic diagram illustrating an exemplary procedure for preparing Compound 45 according to some embodiments of the present disclosure.

Example 3.45: Preparation of Compound 45 (2S)-2-[(5-tert-butyl-2-cyclopropylpyrazol-3-yl)formamido]-N-(cyanomethyl)-3-{6-[1-(2-methoxyethyl)-3,6-dihydro-2H-pyridin-4-yl]-1,3-benzoxazol-2-yl}propanamide FIG. 58 is a schematic diagram illustrating an exemplary procedure for preparing Compound 45 according to some embodiments of the present disclosure.

Step 1. Preparation of 1-(2-methoxyethyl)-4-(4,4,5,5-tetramethyl-1,3,2-dioxaborolan-2-yl)-3,6-dihydro-2H-pyridine To a mixture of 4-(4,4,5,5-tetramethyl-1,3,2-dioxaborolan-2-yl)-1,2,3,6-tetrahydropyridine (1.0 g, 4.07 mmol) in DMF (15.0 mL) was added DIEA (1.58 g, 12.2 mmol) and 1-bromo-2-methoxyethane (623 mg, 4.48 mmol). The reaction was stirred at 60° C. for 16 hrs. The reaction mixture was diluted with water (50 mL) and then extracted with EA (50 mL×3). The combined organic layer was washed with brine (100 mL×3), dried over Na$_2$SO$_4$, and concentrated under reduced pressure. The residue was purified by flash column (DCM:MeOH=15:1) to give the desired product 1-(2-methoxyethyl)-4-(4,4,5,5-tetramethyl-1,3,2-dioxaborolan-2-yl)-3,6-dihydro-2H-pyridine as colorless oil (1.5 g, 96.5%). Mass spectrometry was conducted on the resultant compound, and the test results are as follows: Mass(m/z): 268.2 [M+H]$^+$.

Step 2. Preparation of tert-butyl N-[(1S)-1-[(cyanomethyl)carbamoyl]-2-{6-[1-(2-methoxyethyl)-3,6-dihydro-2H-pyridin-4-yl]-1,3-benzoxazol-2-yl}ethyl]carbamate To a mixture of 1-(2-methoxyethyl)-4-(4,4,5,5-tetramethyl-1,3,2-dioxaborolan-2-yl)-3,6-dihydro-2H-pyridine (196 mg, 0.732 mmol) in 1,4-dioxane/H$_2$O (10:1, 11.0 mL) was added tert-butyl N-[(1S)-2-(6-bromo-1,3-benzoxazol-2-yl)-1-[(cyanomethyl) carbamoyl]ethyl]carbamate (310 mg, 0.732 mmol), K$_2$CO$_3$(304 mg, 2.20 mmol), and Pd(dppf)Cl$_2$ (59.8 mg, 0.0732 mmol). The reaction mixture was stirred under N$_2$ at 90° C. for 6 hrs. The reaction mixture was filtered and the filtrate was concentrated under reduced pressure. The residue was diluted with water (20 mL) and then extracted with EA (20 mL×3). The combined organic layer was washed with brine (50 mL×2), dried over Na$_2$SO$_4$, and concentrated under reduced pressure. The residue was purified by flash column (DCM:MeOH=20:1) to give the product tert-butyl N-[(1 S)-1-[(cyanomethyl)carbamoyl]-2-{6-[1-(2-methoxyethyl)-3,6-dihydro-2H-pyridin-4-yl]-1,3-benzoxazol-2-yl}ethyl]carbamate as a white solid (150 mg, 42%). Mass spectrometry was conducted on the resultant compound, and the test results are as follows: Mass(m/z): 484.2 [M+H]$^+$.

Step 3. Preparation of (2S)-2-amino-N-(cyanomethyl)-3-{6-[1-(2-methoxyethyl)-3,6-dihydro-2H-pyridin-4-yl]-1,3-benzoxazol-2-yl}propanamide To a mixture of tert-butyl N-[(1S)-1-[(cyanomethyl)carbamoyl]-2-{6-[1-(2-methoxyethyl)-3,6-dihydro-2H-pyridin-4-yl]-1,3-benzoxazol-2-yl}ethyl]carbamate (150 mg, 0.310 mmol) in MeCN (5.0 mL) was added TMSI (155 mg, 0.776 mmol). The reaction was stirred at RT for 0.5 hr. The reaction mixture was concentrated under reduced pressure to give the product (2S)-2-amino-N-(cyanomethyl)-3-{6-[1-(2-methoxyethyl)-3,6-dihydro-2H-pyridin-4-yl]-1,3-benzoxazol-2-yl}propanamide as a brown solid (100 mg, 75.7%). Mass spectrometry was conducted on the resultant compound, and the test results are as follows: Mass(m/z): 384.2 [M+H]$^+$.

Step 4. Preparation of (2S)-2-[(5-tert-butyl-2-cyclopropylpyrazol-3-yl)formamido]-N-(cyanomethyl)-3-{6-[1-(2-methoxyethyl)-3,6-dihydro-2H-pyridin-4-yl]-1,3-benzoxazol-2-yl}propanamide To a mixture of (120 mg, 0.248 mmol) in DMF (5.0 mL) was added 5-tert-butyl-2-cyclopropylpyrazole-3-carboxylic acid (62 mg, 0.298 mmol), DIEA (96 mg, 0.745 mmol), and HATU (189 mg, 0.496 mmol). The reaction was stirred at RT for 2 hrs. The reaction mixture was diluted with water (20 mL) and then extracted with EA (20 mL×3). The combined organic layer was washed with brine (50 mL×3), dried over Na$_2$SO$_4$, and concentrated under reduced pressure. The residue was purified by Prep-TLC (DCM:MeOH=15:1) to give the desired product Compound 45 (2S)-2-[(5-tert-butyl-2-cyclopropylpyrazol-3-yl)formamido]-N-(cyanomethyl)-3-{6-[1-(2-methoxyethyl)-3,6-dihydro-2H-pyridin-4-yl]-1,3-benzoxazol-2-yl}propanamide as a white solid (15 mg, 10%). Mass spectrometry was conducted on the resultant compound, and the test results are as follows: Mass(m/z): 547.8 [M+H]+. $^1$H NMR (400 MHz, CDCl$_3$) δ 8.12 (d, J=6.8 Hz, 1H), 8.01 (t, J=5.6 Hz, 1H), 7.57 (d, J=8.2 Hz, 1H), 7.51 (s, 1H), 7.39 (d, J=8.4 Hz, 1H), 6.55 (s, 1H), 6.08 (s, 1H), 5.19 (dd, J=11.0, 6.8 Hz, 1H), 4.18 (t, J=4.6 Hz, 2H), 3.75-3.67 (m, 2H), 3.68 (d, J=4.0 Hz, 1H), 3.53 (s, 2H), 3.39 (s, 3H), 3.33 (dd, J=16.8, 6.8 Hz, 1H), 3.07 (s, 2H), 2.97 (s, 2H), 2.77 (s, 2H), 1.43-1.39 (m, 1H), 1.27 (d, J=12.2 Hz, 9H), 1.01 (d, J=8.0 Hz, 2H), 0.88 (t, J=6.8 Hz, 2H).

Figure 59:
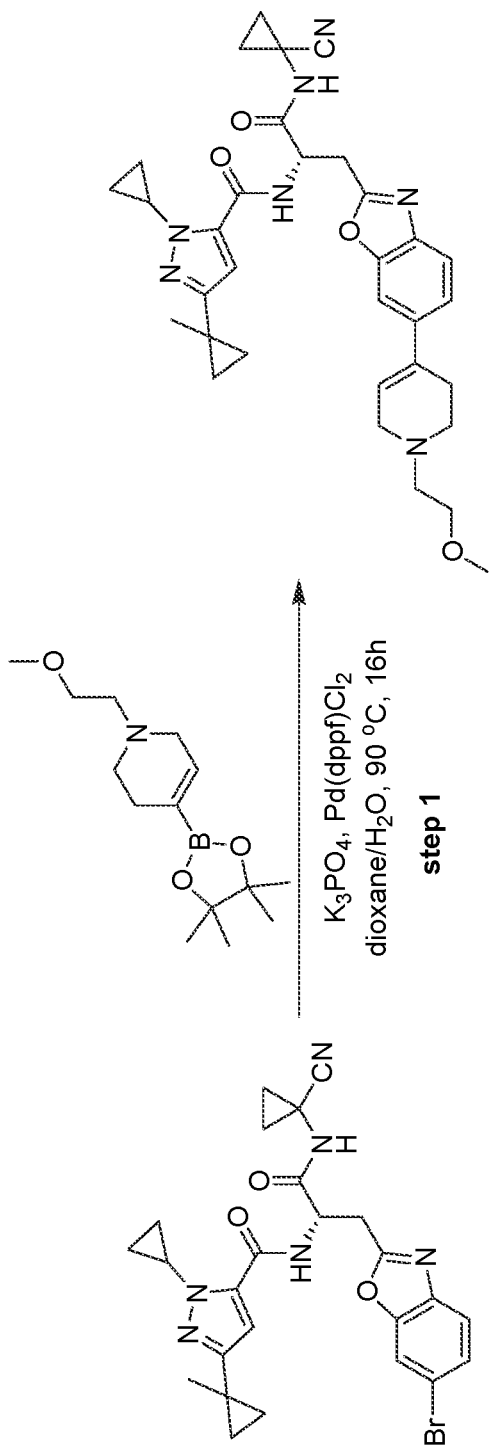
FIG. 59 is a schematic diagram illustrating an exemplary procedure for preparing Compound 46 according to some embodiments of the present disclosure.

Example 3.46: Preparation of Compound 46 (2S)—N-(1-cyanocyclopropyl)-2-{[2-cyclopropyl-5-(1-methylcyclopropyl)pyrazol-3-yl]formamido}-3-{6-[1-(2-methoxyethyl)-3,6-dihydro-2H-pyridin-4-yl]-1,3-benzoxazol-2-yl}propanamide FIG. 59 is a schematic diagram illustrating an exemplary procedure for preparing Compound 46 according to some embodiments of the present disclosure.

To a mixture of (2S)-3-(6-bromo-1,3-benzoxazol-2-yl)-N-(1-cyanocyclopropyl)-2-{[2-cyclopropyl-5-(1-methylcyclopropyl)pyrazol-3-yl]formamido}propanamide (200 mg, 0.372 mmol) and 1-(2-methoxyethyl)-4-(4,4,5,5-tetramethyl-1,3,2-dioxaborolan-2-yl)-3,6-dihydro-2H-pyridine (249 mg, 0.931 mmol) in dioxane/H$_2$O (10:1, 11 mL) was added K$_3$PO$_4$ (158 mg, 0.744 mmol) and Pd(dppf)Cl$_2$ (30 mg, 0.037 mmol). The reaction was stirred at 90° C. under N$_2$ for 16 hrs. The reaction mixture was filtered and the filtrate was extracted with H$_2$O (100 mL) and EtOAc (50×3 mL). The combined organic layers were washed with brine (100 mL), dried over Na$_2$SO$_4$, and concentrated under reduced pressure. The crude product was purified by SFC [Column: chiralpak-AD; mobile phase: CO$_2$-IPA (DEA)] to give the desired product Compound 46 (2S)—N-(1-cyanocyclopropyl)-2-{[2-cyclopropyl-5-(1-methylcyclopropyl)pyrazol-3-yl]form amido}-3-{6-[1-(2-methoxyethyl)-3,6-dihydro-2H-pyridin-4-yl]-1,3-benzoxazol-2-yl}propenamide as a white solid (25 mg, 11%). Mass spectrometry was conducted on the resultant compound, and the test results are as follows: Mass(m/z): 598.2 [M+H]$^+$. 1H NMR (400 MHz, DMSO-d$_6$) δ 9.10 (s, 1H), 8.75 (d, J=8.0 Hz, 1H), 7.70 (s, 1H), 7.61 (d, J=8.4 Hz, 1H), 7.45 (d, J=8.4 Hz, 1H), 6.59 (s, 1H), 6.22 (s, 1H), 4.92 (dd, J=14.0, 8.2 Hz, 1H), 4.20-4.16 (m, 1H), 3.54 (s, 2H), 3.47 (dd, J=15.6, 5.8 Hz, 1H), 3.28 (s, 3H), 3.33 (s, 3H), 2.79 (s, 3H), 2.59 (s, 2H), 1.49-1.45 (m, 2H), 1.34 (s, 3H), 1.14-0.98 (m, 3H), 0.94-0.89 (m, 1H), 0.86-0.77 (m, 4H), 0.68 (dd, J=6.2, 3.8 Hz, 2H).

Figure 60:
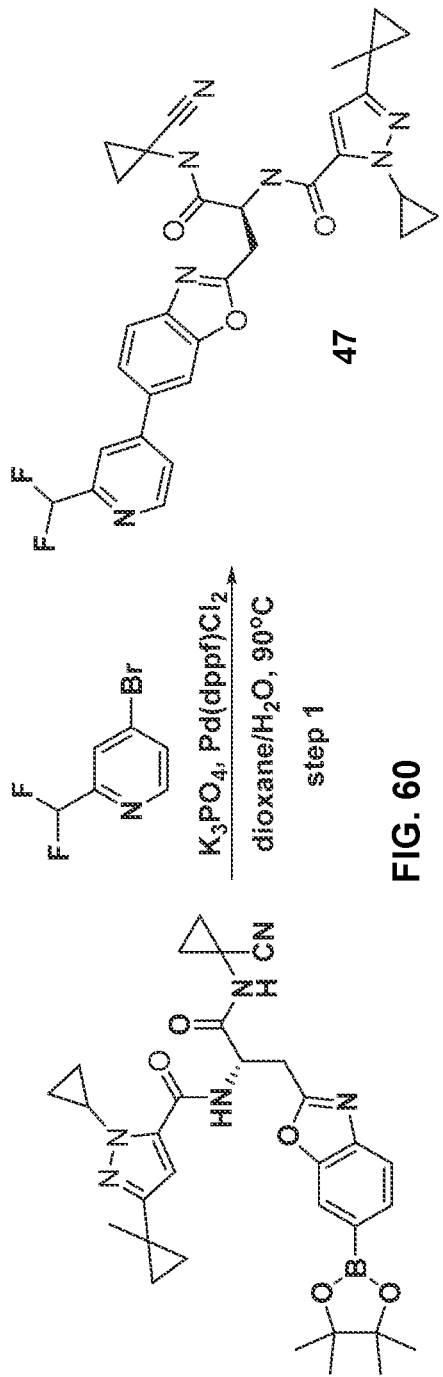
FIG. 60 is a schematic diagram illustrating an exemplary procedure for preparing Compound 47 according to some embodiments of the present disclosure.

Example 3.47: Preparation of Compound 47 (S)—N-(1-((1-cyanocyclopropyl)amino)-3-(6-(2-(difluoromethyl)pyridin-4-yl)benzo[d]oxazol-2-yl)-1-oxopropan-2-yl)-1-cyclopropyl-3-(1-methyl cyclopropyl)-1H-pyrazole-5-carboxamide FIG. 60 is a schematic diagram illustrating an exemplary procedure for preparing Compound 47 according to some embodiments of the present disclosure.

To a solution of (S)—N-(1-((1-cyanocyclopropyl)amino)-1-oxo-3-(6-(4,4,5,5-tetramethyl-1,3,2-dioxaborolan-2-yl) benzo[d]oxazol-2-yl)propan-2-yl)-1-cyclopropyl-3-(1-methylcyclopropyl)-1H-pyrazole-5-carboxamide (100 mg, 0.17 mmol) in dioxane/H$_2$O (10:1, 10 mL) was added 4-bromo-2-(difluoromethyl)pyridine (43 mg, 0.17 mmol), K$_3$PO$_4$ (73 mg, 0.34 mmol), and Pd(dppf)Cl$_2$ (14 mg, 0.02 mmol). The reaction mixture was stirred at 90° C. under N$_2$ for 16 hrs. The solvent was removed under reduced pressure and the residue was purified by Combiflash column (DCM/MeOH=0~10%) to give the desired product Compound 47 (S)—N-(1-((1-cyanocyclopropyl)amino)-3-(6-(2-(difluoromethyl)pyridin-4-yl)benzo[d]oxazol-2-yl)-1-oxopropan-2-y)-1-cyclopropyl-3-(1-methylcyclopropyl)-1H-pyrazole-5-carboxamide as a white solid (7 mg, 7%). Mass spectrometry was conducted on the resultant compound, and the test results are as follows: Mass(m/z): 586.1 [M+H]$^+$. $^1$H NMR (400 MHz, DMSO-d$_6$) δ 9.15 (s, 1H), 8.79 (dd, J=19.8, 6.6 Hz, 2H), 8.26 (s, 1H), 8.06 (s, 1H), 7.98 (d, J=4.8 Hz, 1H), 7.90-7.80 (m, 2H), 7.02 (t, J=54.8 Hz, 1H), 6.61 (s, 1H), 4.97 (d, J=6.0 Hz, 1H), 4.23-4.15 (m, 1H), 3.52 (d, J=5.6 Hz, 1H), 3.41-3.35 (m, 1H), 1.48 (s, 2H), 1.33 (s, 3H), 1.12 (d, J=10.4 Hz, 2H), 1.04-0.89 (m, 2H), 0.86-0.74 (m, 4H), 0.68 (dd, J=6.2, 3.8 Hz, 2H).

Figure 61:
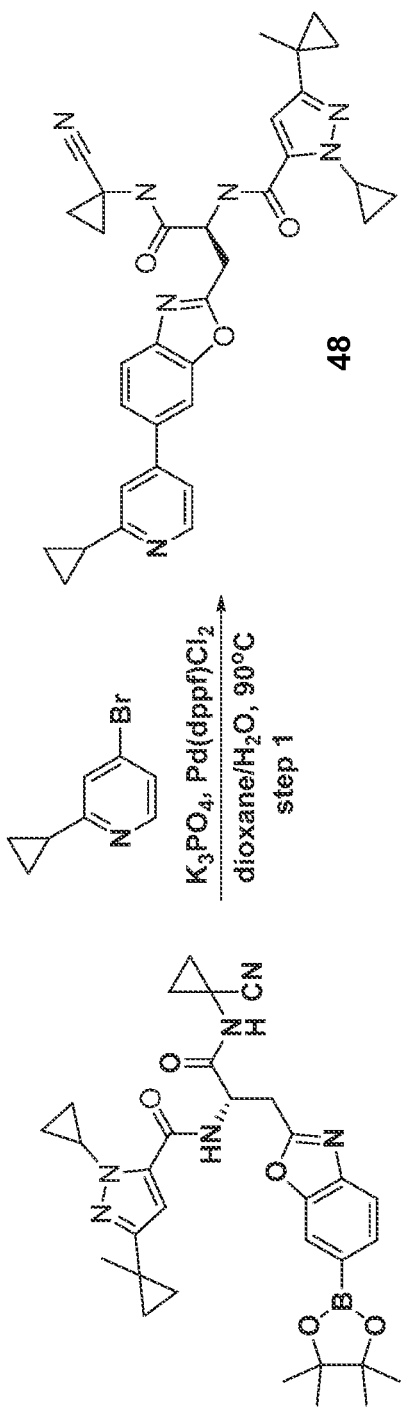
FIG. 61 is a schematic diagram illustrating an exemplary procedure for preparing Compound 48 according to some embodiments of the present disclosure.

Example 3.48: Preparation of Compound 48 (S)—N-(1-((1-cyanocyclopropyl)amino)-3-(6-(2-cyclopropylpyridin-4-yl)benzo[d] oxazol-2-yl)-1-oxopropan-2-yl)-1-cyclopropyl-3-(1-methylcyclopropyl)-1H-pyrazole-5-carboxamide FIG. 61 is a schematic diagram illustrating an exemplary procedure for preparing Compound 48 according to some embodiments of the present disclosure.

To a solution of (S)—N-(1-((1-cyanocyclopropyl)amino)-3-(6-(2-cyclopropyl pyridin-4-yl)benzo[d]oxazol-2-yl)-1-oxopropan-2-yl)-1-cyclopropyl-3-(1-methylcyclopropyl)-1H-pyrazole-5-carboxamide (150 mg, 0.26 mmol) in dioxane/$H_2O$ (10:1, 10 mL) was added 4-bromo-2-cyclopropylpyridine (51 mg, 0.26 mmol), $K_3PO_4$ (109 mg, 0.51 mmol), and Pd(dppf)$Cl_2$ (19 mg, 0.03 mmol). The reaction mixture was stirred at 90° C. under $N_2$ for 16 hrs. The solvent was removed under reduced pressure and the residue was purified by Combiflash column (DCM/MeOH=0~10%) to give the desired product Compound 48 (S)—N-(1-((1-cyanocyclopropyl)amino)-3-(6-(2-cyclopropylpyridin-4-yl)benzo[d]oxazol-2-yl)-1-oxopropan-2-yl)-1-cyclopropyl-3-(1-methylcyclopropyl)-1H-pyrazole-5-carboxamide as a white solid (32 mg, 21%). Mass spectrometry was conducted on the resultant compound, and the test results are as follows: Mass(m/z): 576.3 $[M+H]^+$. $^1$H (400 MHz, MeOD) δ 8.40 (d, J=5.2 Hz, 1H), 7.99 (s, 1H), 7.76 (d, J=1.0 Hz, 2H), 7.54 (d, J=1.2 Hz, 1H), 7.47 (dd, J=5.2, 1.8 Hz, 1H), 6.51 (s, 1H), 5.06 (dd, J=8.4, 6.2 Hz, 1H), 3.98-3.92 (m, 1H), 3.63 (dd, J=15.4, 6.2 Hz, 1H), 3.46 (dd, J=15.4, 8.4 Hz, 1H), 2.21-2.16 (m, 1H), 1.49 (t, J=6.2 Hz, 2H), 1.38 (s, 3H), 1.24-1.18 (m, 2H), 1.09-1.05 (m, 2H), 1.03 (dd, J=4.6, 2.8 Hz, 2H), 0.98-0.78 (m, 6H), 0.68 (q, J=4.0 Hz, 2H).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A compound represented by formula (I-a):

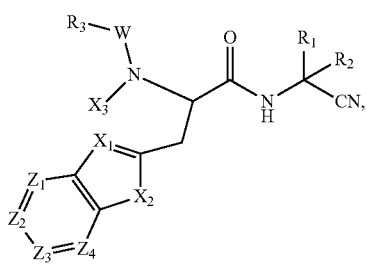

wherein

R₁ and R₂ are independently selected from H, a —CH₂— group, and an alkyl group;

R₁ and R₂ are unconnected or connected via a single bond;

W is CO or SO₂;

R₃ is an alkyl group, a fluoroalkyl group, a cycloalkyl group, an alkoxy group, an aryl group, a heteroaryl group, or a heterocyclic group, and R₃ is optionally substituted by one or more groups selected from halogen, a hydroxyl group, an alkyl group, a fluoroalkyl group, a cycloalkyl group, an aryl group, a heterocyclic group, and an alkoxy group;

X₁ is a CH group or N;

X₂ is O, S, or N—R₄, wherein R₄ is selected from H, an alkyl group, an aryl group, and a heterocyclic group;

X₃ is H, an alkyl group, a cycloalkyl group, an aryl group, a heteroaryl group, or a heterocyclic group, and X₃ is optionally substituted by one or more groups selected from halogen, a hydroxyl group, an alkyl group, a fluoroalkyl group, a cycloalkyl group, and an alkoxy group;

Z₁ is a CH group, C—R₅, or N;

Z₂ is a CH group, C—R₆, or N;

Z₃ is a CH group, C—R₇, or N; and

Z₄ is a CH group, C—R₈, or N, wherein

R₅—R₈ are independently selected from H, halogen, a hydroxyl group, an alkyl group, a fluoroalkyl group, —CN, a cycloalkyl group, an alkoxy group, an aryl group, a heteroaryl group, and a heterocyclic group, and each of R₅-R₈ is optionally substituted by one or more groups selected from halogen, a hydroxyl group, an alkyl group, a fluoroalkyl group, a cycloalkyl group, a heterocyclic group, a cycloalkyl group, an aryl group, and an alkoxy group.

2. The compound of claim 1, wherein the compound is represented by formula (II):

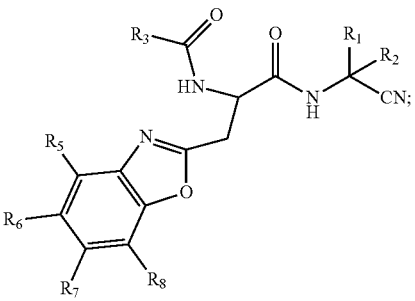

formula (III):

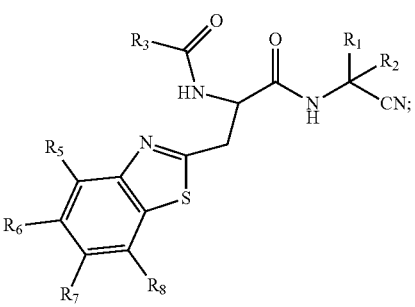

formula (IV):

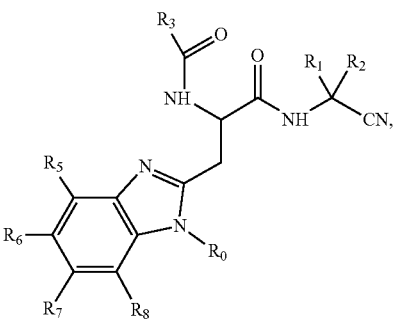

wherein R₀ is H, an alkyl group, a cycloalkyl group, an aryl group, a heteroaryl group, or a heterocyclic group, and R₀ is optionally substituted by one or more groups selected from halogen, a hydroxyl group, an alkyl group, a fluoroalkyl group, a cycloalkyl group, and an alkoxy group; or formula (V):

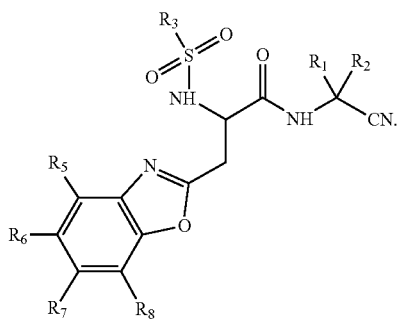

3. The compound of claim 2, wherein $R_5$—$R_8$ are H.
4. The compound of claim 2, wherein
at least one of $R_5$—$R_8$ is halogen or —CN, and
the other of $R_5$-$R_8$ are H.
5. The compound of claim 2, wherein one of $R_5$—$R_8$ is a group represented by
formula (VI-a)

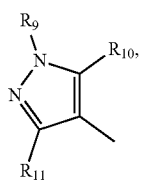

wherein
$R_9$ is H, an alkyl group, a cycloalkyl group, an aryl group, a heteroaryl group, or a heterocyclic group, and
$R_{10}$ and $R_{11}$ are independently selected from H, halogen, a hydroxyl group, an alkyl group, a fluoroalkyl group, a cycloalkyl group, an alkoxy group, an aryl group, a heteroaryl group, and a heterocyclic group;
formula (VI-b)

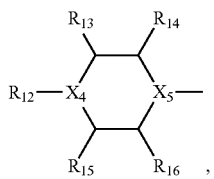

wherein
$X_4$ is S, O, $SO_2$, N, C, or C-$L_1$, wherein $L_1$ is selected from H, halogen, a hydroxyl group, an alkyl group, a fluoroalkyl group, a cycloalkyl group, an alkoxy group, an aryl group, a heteroaryl group, and a heterocyclic group, and $L_1$ is optionally substituted by one or more groups selected from halogen, a hydroxyl group, an alkyl group, a fluoroalkyl group, a cycloalkyl group, an aryl group, a heterocyclic group, and an alkoxy group,
$X_5$ is N or C,
$R_{12}$ does not exist, or is selected from H, halogen, a hydroxyl group, an alkyl group, a fluoroalkyl group, a cycloalkyl group, an alkoxy group, an aryl group, a heteroaryl group, and a heterocyclic group, and is optionally substituted by one or more groups selected from halogen, a hydroxyl group, an alkyl group, a fluoroalkyl group, a cycloalkyl group, an aryl group, a heterocyclic group, and an alkoxy group, and
$R_{13}$—$R_{16}$ are independently selected from H, halogen, a hydroxyl group, an alkyl group, a fluoroalkyl group, a cycloalkyl group, an alkoxy group, an aryl group, a heteroaryl group, and a heterocyclic group, and each of $R_{13}$-$R_{16}$ is optionally substituted by one or more groups selected from halogen, a hydroxyl group, an alkyl group, a fluoroalkyl group, a cycloalkyl group, an aryl group, a heterocyclic group, and an alkoxy group;
formula (VI-c)

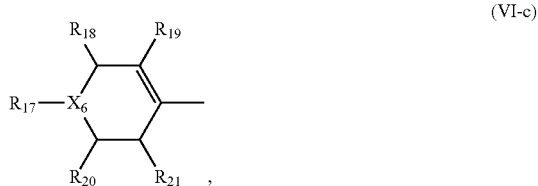

wherein:
$X_6$ is S, O, $SO_2$, N, C, or C-$L_2$, wherein $L_2$ is selected from H, halogen, a hydroxyl group, an alkyl group, a fluoroalkyl group, a cycloalkyl group, an alkoxy group, an aryl group, a heteroaryl group, and a heterocyclic group, and $L_2$ is optionally substituted by one or more groups selected from halogen, a hydroxyl group, an alkyl group, a fluoroalkyl group, a cycloalkyl group, an aryl group, a heterocyclic group, and an alkoxy group,
$R_{17}$ does not exist, or is selected from H, halogen, a hydroxyl group, an alkyl group, a fluoroalkyl group, a cycloalkyl group, an alkoxy group, an aryl group, a heteroaryl group, and a heterocyclic group, and is optionally substituted by one or more groups selected from halogen, a hydroxyl group, an alkyl group, a fluoroalkyl group, a cycloalkyl group, an aryl group, a heterocyclic group, and an alkoxy group, and
$R_{18}$—$R_{21}$ are independently selected from H, halogen, a hydroxyl group, an alkyl group, a fluoroalkyl group, a cycloalkyl group, an alkoxy group, an aryl group, a heteroaryl group, and a heterocyclic group, and each of $R_{18}$-$R_{21}$ is optionally substituted by one or more groups selected from halogen, a hydroxyl group, an alkyl group, a fluoroalkyl group, a cycloalkyl group, an aryl group, a heterocyclic group, and an alkoxy group;
formula (VI-d)

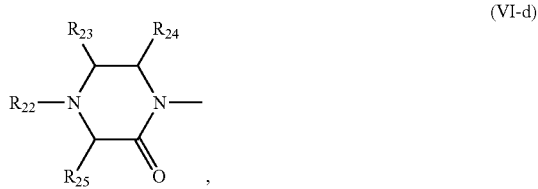

wherein
$R_{22}$ is H, an alkyl group, a cycloalkyl group, an aryl group, a heteroaryl group, or a heterocyclic group, and
$R_{22}$ is optionally substituted by one or more groups selected from halogen, a hydroxyl group, an alkyl group, a fluoroalkyl group, a cycloalkyl group, and an alkoxy group, and $R_{23}$—$R_{25}$ are independently selected from H, halogen, a hydroxyl group, an alkyl group, a fluoroalkyl group, a cycloalkyl group, an alkoxy group, an aryl group, a heteroaryl group, and a heterocyclic group;

formula (VI-e)

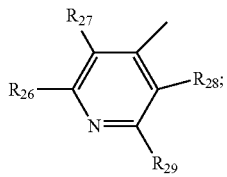

(VI-e)

formula (VI-f)

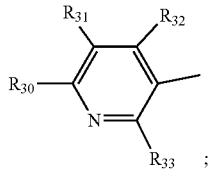

(VI-f)

formula (VI-g)

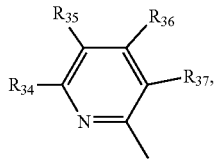

(VI-g)

$R_{26}$—$R_{37}$ are independently selected from H, halogen, a hydroxyl group, an alkyl group, a fluoroalkyl group, a cycloalkyl group, an alkoxy group, an aryl group, a heteroaryl group, a heterocyclic group, and N—$R_{38}$, wherein $R_{38}$ is selected from H, an alkyl group, an aryl group, a heterocyclic group, and a ketone group.

6. The compound of claim 5, wherein $R_5$-$R_{10}$ are H.

7. The compound of claim 5, wherein
$X_4$ and $X_5$ are both N,
$R_{12}$ is a methyl group, and
$R_{13}$-$R_{16}$ are H.

8. The compound of claim 5, wherein
$X_6$ is N,
$R_{13}$-$R_{21}$ are H, and
$R_{17}$ is a methyl group, —CH$_2$—CHF$_2$, or —C$_2$H$_4$—OCH$_3$.

9. The compound of claim 5, wherein $R_{22}$ is a methyl group, and $R_{23}$—$R_{25}$ are H.

10. The compound of claim 5, wherein
$R_{27}$—$R_{29}$ are H, and
$R_{26}$ is a methyl group, —CHF$_2$, or a cyclopropyl group.

11. The compound of claim 5, wherein
$R_{31}$-$R_{33}$ are H, and
$R_{30}$ is a methyl group, —NH$_2$, —NC$_2$H$_6$, —NHCOCH$_3$, or —NHCH$_3$.

12. The compound of claim 5, wherein
$R_{35}$—$R_{37}$ are H, and
$R_{34}$ is a methyl group.

13. The compound of claim 2, wherein $R_3$ is benzene halide.

14. The compound of claim 2, wherein $R_3$ is a group represented by formula (VII-a)

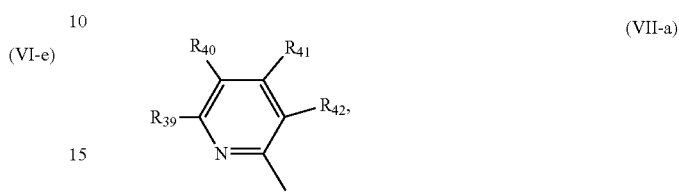

(VII-a)

wherein $R_{39}$—$R_{42}$ are independently selected from H, halogen, a hydroxyl group, an alkyl group, a fluoroalkyl group, a cycloalkyl group, an alkoxy group, an aryl group, a heteroaryl group, a heterocyclic group, and N—$R_{49}$, wherein $R_{49}$ is selected from H, an alkyl group, an aryl group, a heterocyclic group, and a ketone group; or formula (VII-b)

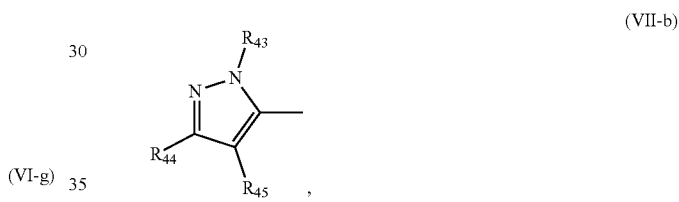

(VII-b)

wherein
$R_{43}$ is H, an alkyl group, a cycloalkyl group, an aryl group, a heteroaryl group, or a heterocyclic group, and
$R_{44}$ and $R_{45}$ are independently selected from H, halogen, a hydroxyl group, an alkyl group, a fluoroalkyl group, a cycloalkyl group, an alkoxy group, an aryl group, a heteroaryl group, and a heterocyclic group, and each of $R_{44}$ and $R_{45}$ is optionally substituted by one or more groups selected from halogen, a hydroxyl group, an alkyl group, a fluoroalkyl group, a cycloalkyl group, an aryl group, a heterocyclic group, and an alkoxy group; or formula (VII-c)

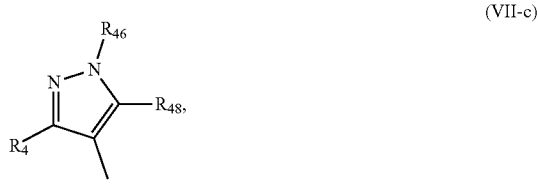

(VII-c)

wherein
$R_{46}$ is H, an alkyl group, a cycloalkyl group, an aryl group, a heteroaryl group, or a heterocyclic group, and
$R_{47}$ and $R_{48}$ are independently selected from H, halogen, a hydroxyl group, an alkyl group, a fluoroalkyl group, a cycloalkyl group, an alkoxy group, an aryl group, a heteroaryl group, and a heterocyclic group, and each of $R_{47}$ and $R_{48}$ is optionally substituted by one or more groups selected from halogen, a hydroxyl group, an alkyl group, a fluoroalkyl group, a cycloalkyl group, an aryl group, a heterocyclic group, and an alkoxy group.

15. The compound of claim 14, wherein
$R_{40}$—$R_{42}$ are H, and
$R_{39}$ is a methyl group.

16. The compound of claim 14, wherein
$R_{45}$ is H,
$R_{43}$ is a methyl group, a cyclopropyl group, or

and
$R_{44}$ is a tert-butyl group, a cyclopropyl group, or

17. The compound of claim 14, wherein
$R_{43}$ is H,
$R_{46}$ is a methyl group, a —CHF$_2$, or —CF$_3$, and
$R_{47}$ is a cyclopropyl group.

18. The compound of claim 2, wherein $R_1$ and $R_2$ are H, or —CH$_2$— groups connected via a single bond.

19. A compound selected from Table 1:

TABLE 1

Compound 1

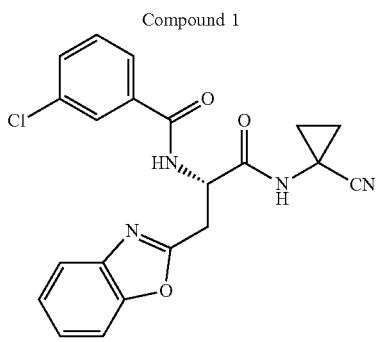

Compound 2

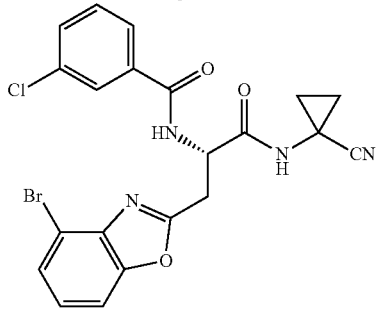 [SMILES: N#CC1(NC(=O)[C@H](Cc2nc3c(Br)cccc3o2)NC(=O)c2cccc(Cl)c2)CC1]

Compound 3

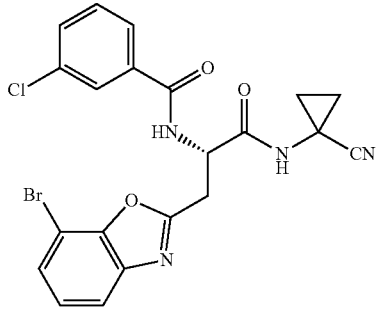

TABLE 1-continued
Compound 4
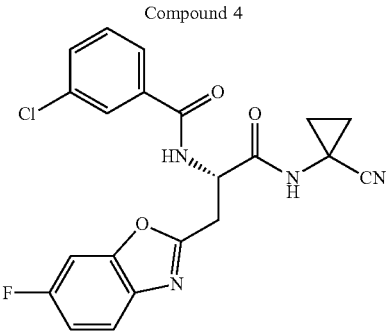
Compound 5
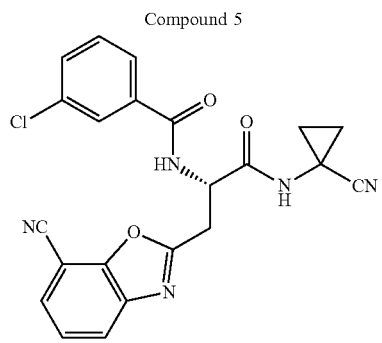
Compound 6
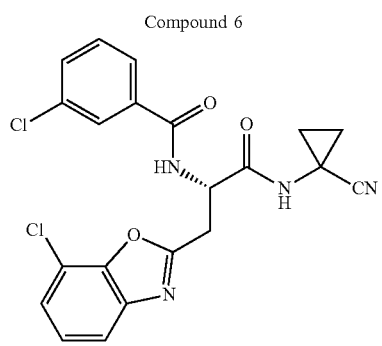
Compound 7
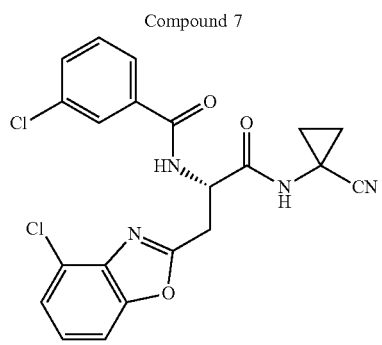

TABLE 1-continued
Compound 8
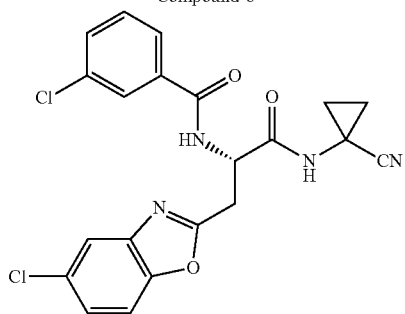
Compound 9
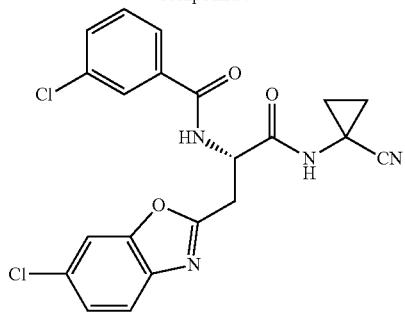
Compound 10
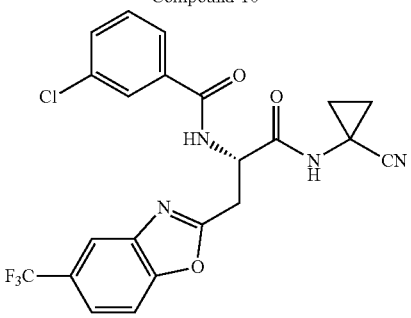
Compound 11
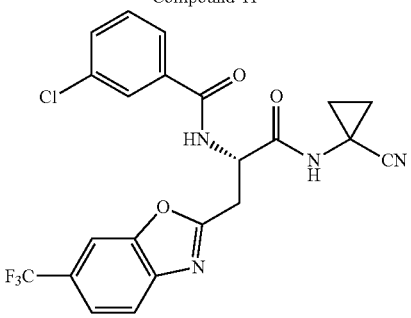

TABLE 1-continued
Compound 12
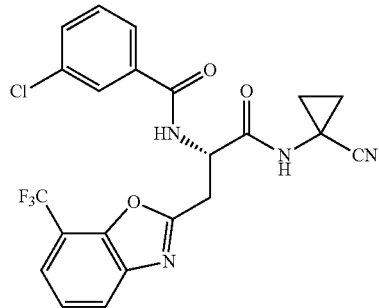 [SMILES: N#Cc1cccc2nc(C[C@H](NC(=O)c3cccc(Cl)c3)C(=O)NC3(C#N)CC3)oc12]
Compound 13
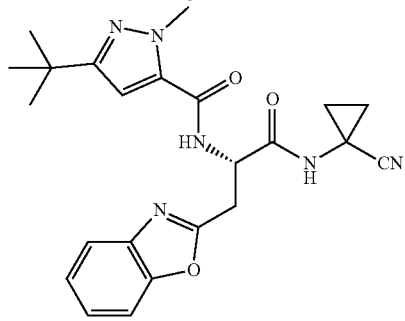 [SMILES: Cn1nc(C(C)(C)C)cc1C(=O)N[C@@H](Cc1nc2ccccc2o1)C(=O)NC1(C#N)CC1]
Compound 14
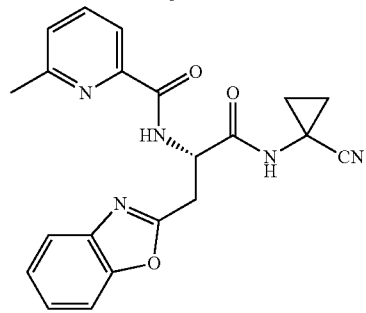
Compound 15
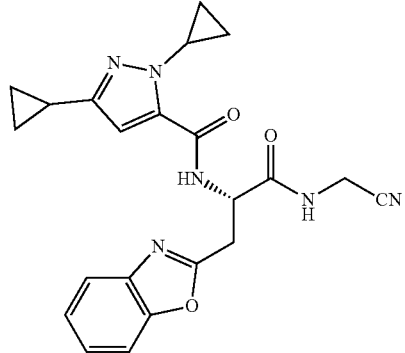 [SMILES: N#CCNC(=O)[C@H](Cc1nc2ccccc2o1)NC(=O)c1cc(C2CC2)nn1C1CC1]

TABLE 1-continued
Compound 16
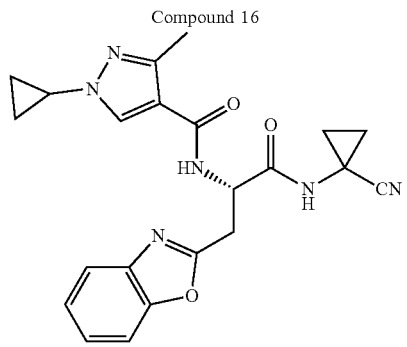
Compound 17
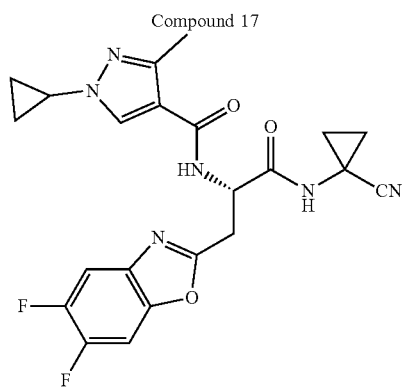
Compound 18
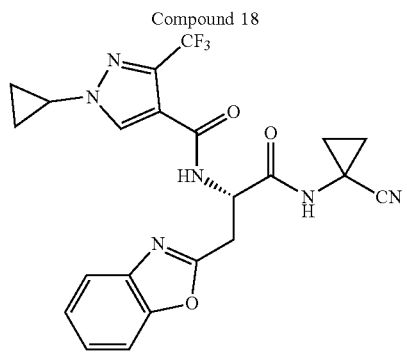
Compound 19
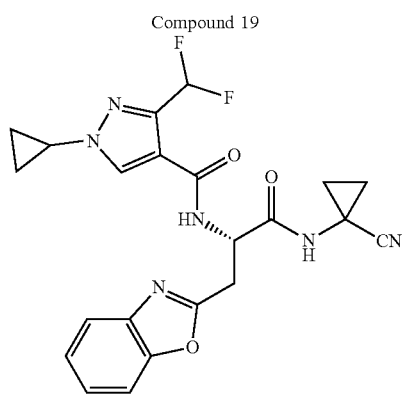

TABLE 1-continued
Compound 20
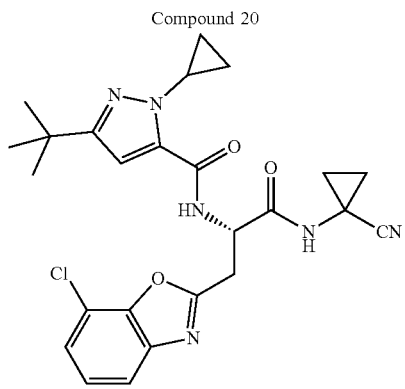
Compound 21
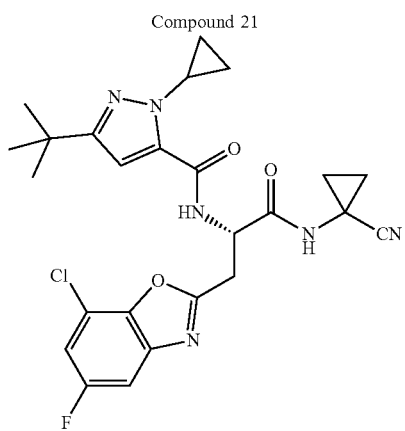
Compound 22
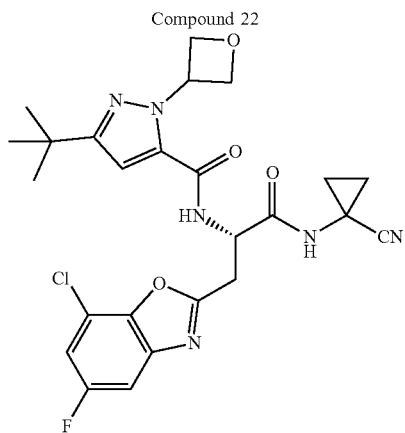
Compound 23
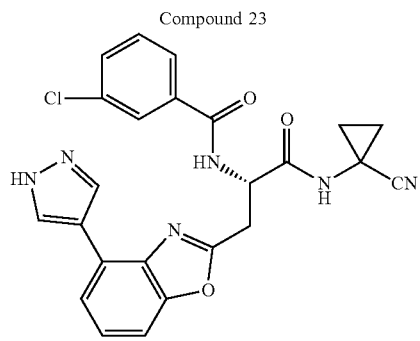

TABLE 1-continued
Compound 24
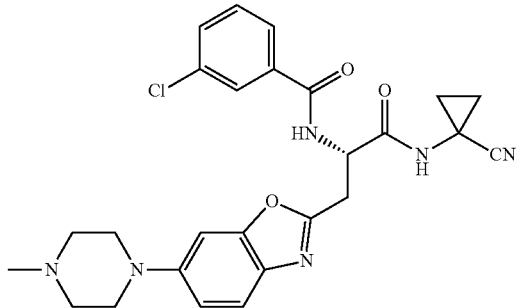 [SMILES: CN1CCN(c2ccc3nc(C[C@H](NC(=O)c4cccc(Cl)c4)C(=O)NC4(C#N)CC4)oc3c2)CC1]
Compound 25
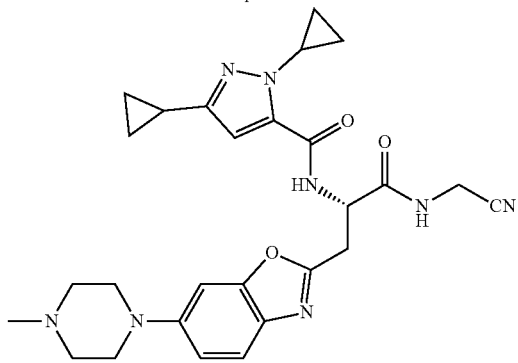
Compound 26
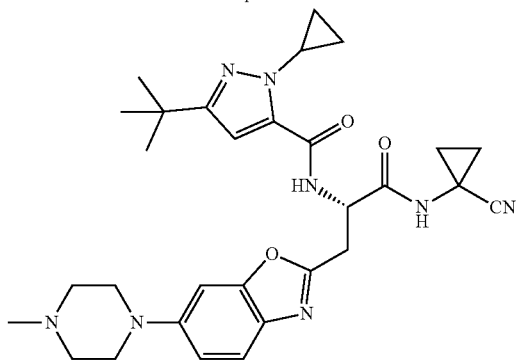
Compound 27
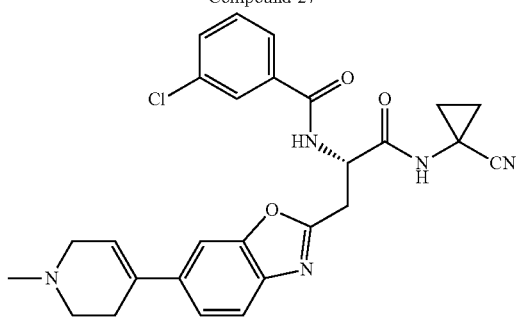

TABLE 1-continued
Compound 28
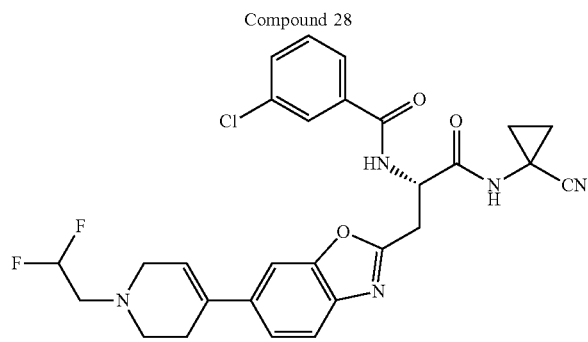
Compound 29
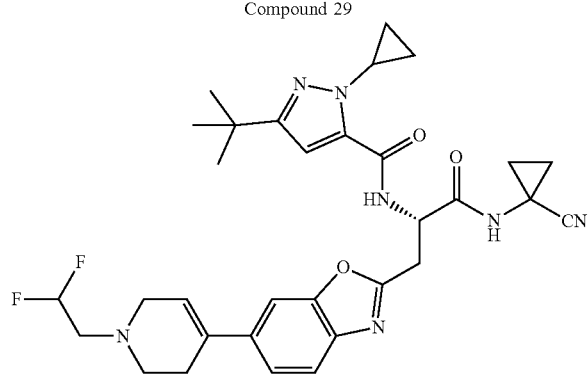
Compound 30
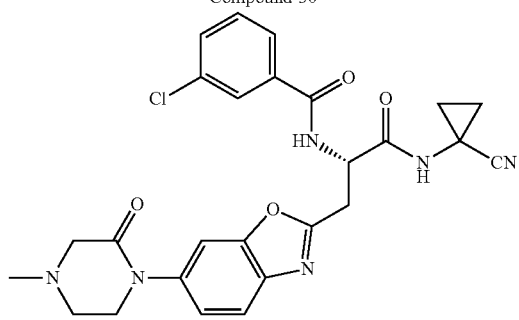
Compound 31
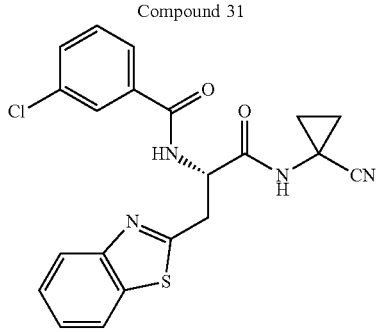

TABLE 1-continued
Compound 32
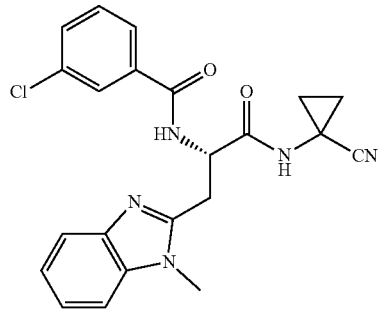 [SMILES: Cn1c(C[C@H](NC(=O)c2cccc(Cl)c2)C(=O)NC2(C#N)CC2)nc2ccccc21]
Compound 33
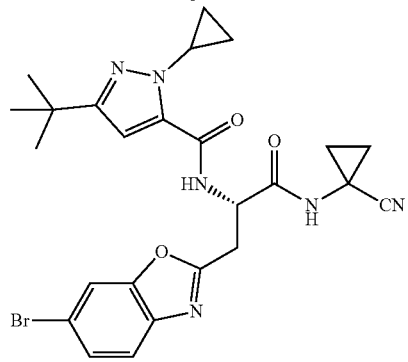
Compound 34
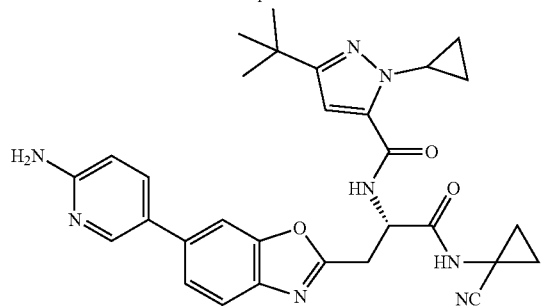
Compound 35
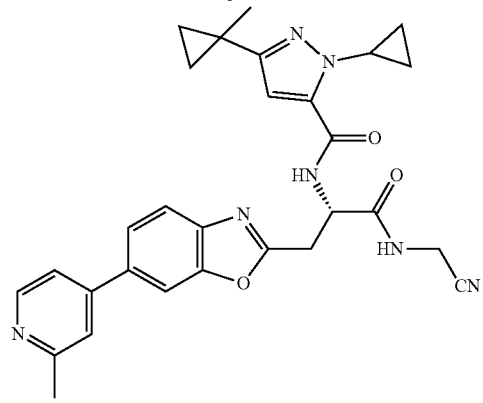

119
120
TABLE 1-continued
Compound 36
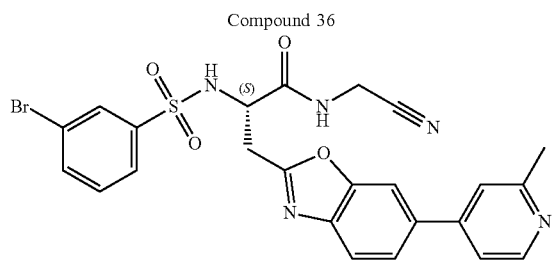
Compound 37
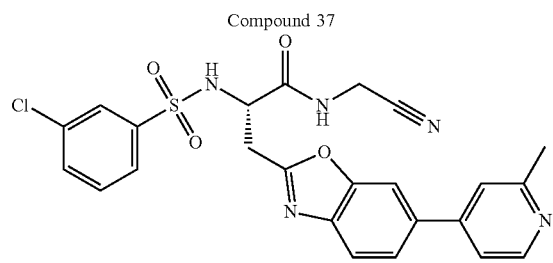
Compound 38
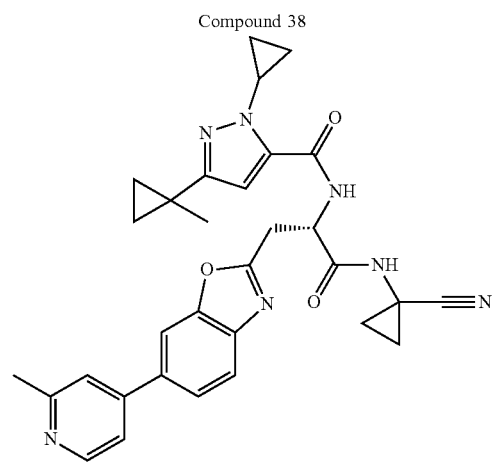
Compound 39
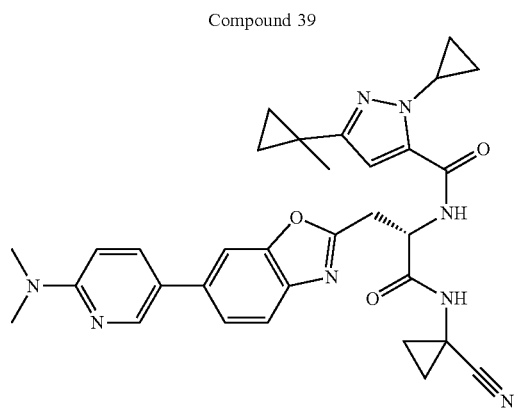

TABLE 1-continued
Compound 40
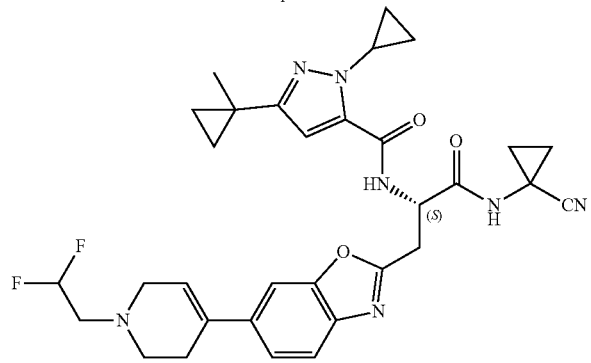
Compound 41
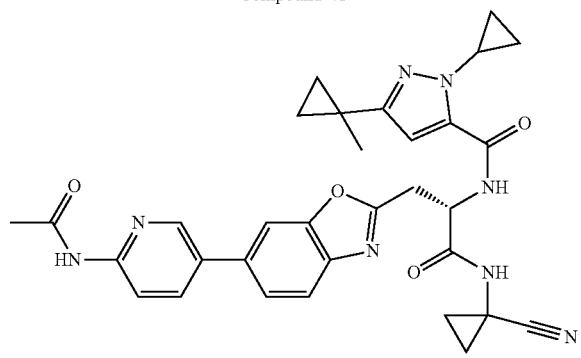
Compound 42
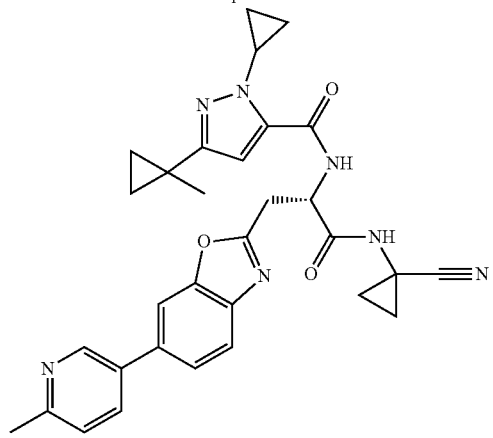

TABLE 1-continued
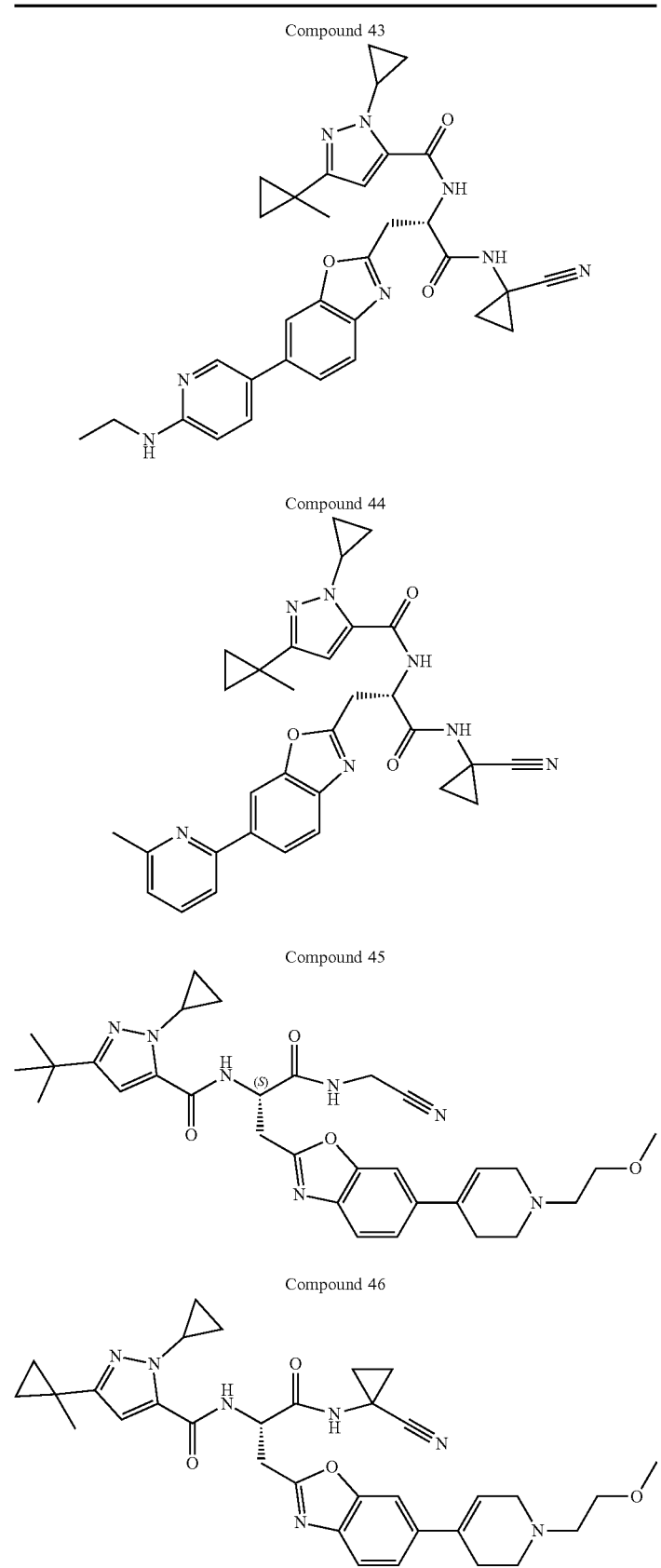

TABLE 1-continued

Compound 47

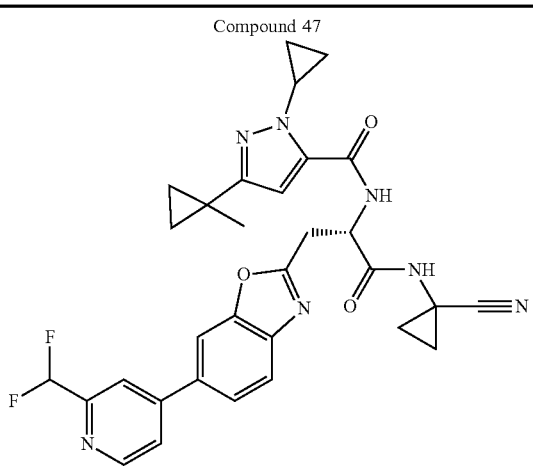

Compound 48

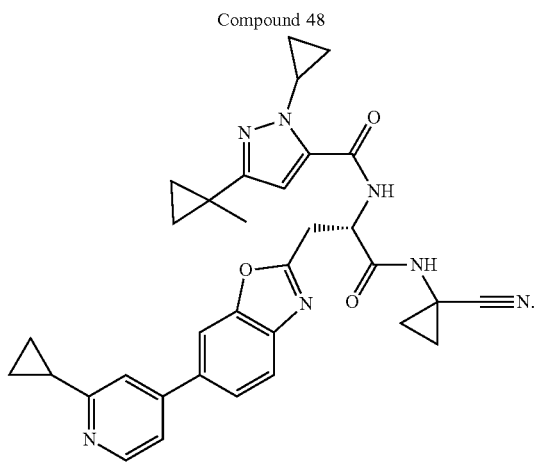

20. A method of treating a disease in a subject, comprising:
administering a composition to a subject suffering from the disease, the composition including a compound represented by formula (I-a):

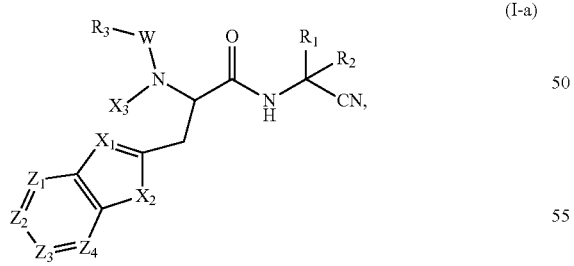

an enantiomer thereof, a diastereomer thereof, a racemate thereof, a solvate thereof, or a pharmaceutically acceptable salt thereof, in a pharmaceutically effective amount, wherein
$R_1$ and $R_2$ are independently selected from H, a —$CH_2$— group, and an alkyl group;
$R_1$ and $R_2$ are unconnected or connected via a single bond;
W is CO or $SO_2$;
$R_3$ is an alkyl group, a fluoroalkyl group, a cycloalkyl group, an alkoxy group, an aryl group, a heteroaryl group, or a heterocyclic group, and $R_3$ is optionally substituted by one or more groups selected from halogen, a hydroxyl group, an alkyl group, a fluoroalkyl group, a cycloalkyl group, an aryl group, a heterocyclic group, and an alkoxy group;
$X_1$ is a CH group or N;
$X_2$ is O, S, or N—$R_4$, wherein $R_4$ is selected from H, an alkyl group, an aryl group, and a heterocyclic group;
$X_3$ is H, an alkyl group, a cycloalkyl group, an aryl group, a heteroaryl group, or a heterocyclic group, and $X_3$ is optionally substituted by one or more groups selected from halogen, a hydroxyl group, an alkyl group, a fluoroalkyl group, a cycloalkyl group, and an alkoxy group;
$Z_1$ is a CH group, C—$R_5$, or N;
$Z_2$ is a CH group, C—$R_6$, or N;
$Z_3$ is a CH group, C—$R_7$, or N; and
$Z_4$ is a CH group, C—$R_8$, or N, wherein
$R_5$–$R_8$ are independently selected from H, halogen, a hydroxyl group, an alkyl group, a fluoroalkyl group, —CN, a cycloalkyl group, an alkoxy group, an aryl group, a heteroaryl group, and a heterocyclic group, and
each of $R_5$-$R_8$ is optionally substituted by one or more groups selected from halogen, a hydroxyl group, an alkyl group, a fluoroalkyl group, a cycloalkyl group, a heterocyclic group, a cycloalkyl group, an aryl group, and an alkoxy group, wherein the disease is a severe acute respiratory syndrome (SARS), a coronavirus disease 19 (COVID-19), long-term effects of coronavirus (long COVID), post-acute sequelae of COVID-19 (PASC), respiratory syncytial virus (RSV) infection, ebola virus infection, middle east respiratory syndrome (MERS), herpes simplex virus infection, acute respiratory distress syndrome (ARDS), ARDS-induced multiple organ failures, acute kidney injury (AKI), liver injury, liver fibrosis, cancer, osteoporosis, inflammation, atherosclerosis, a renal disease, a bone disease, or diabetes.

* * * * *

SEQUENCE LISTING

```
Sequence total quantity: 2
SEQ ID NO: 1           moltype = DNA  length = 19
FEATURE                Location/Qualifiers
source                 1..19
                       mol_type = other DNA
                       organism = synthetic construct
SEQUENCE: 1
tctcgtctgg atcaggcgg                                                19

SEQ ID NO: 2           moltype = DNA  length = 24
FEATURE                Location/Qualifiers
source                 1..24
                       mol_type = other DNA
                       organism = synthetic construct
SEQUENCE: 2
tgctcttcca ctccatcctc ttgg                                          24
```